US012746042B2

(12) United States Patent
Jackson et al.

(10) Patent No.: US 12,746,042 B2
(45) Date of Patent: Sep. 29, 2026

(54) BONE ANCHOR ASSEMBLY WITH BONE DEBRIS SWEEP RING IN RECEIVER SUB-ASSEMBLY

(71) Applicant: Roger P. Jackson, Prairie Village, KS (US)

(72) Inventors: Roger P. Jackson, Prairie Village, KS (US); James L. Surber, Kansas City, KS (US); Nathaniel D. Ginzton, Boise, ID (US); Jurell D. Baker, Plymouth, MN (US)

( * ) Notice: Subject to any disclaimer, the term of this patent is extended or adjusted under 35 U.S.C. 154(b) by 116 days.

(21) Appl. No.: 18/794,410

(22) Filed: Aug. 5, 2024

(65) Prior Publication Data

US 2025/0032156 A1 Jan. 30, 2025

Related U.S. Application Data

(63) Continuation of application No. 18/156,195, filed on Jan. 18, 2023, now Pat. No. 12,053,209.

(60) Provisional application No. 63/339,358, filed on May 6, 2022, provisional application No. 63/300,557, filed on Jan. 18, 2022.

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC ............ A61B 17/7032; A61B 17/7035; A61B 17/7037; A61B 17/8685
See application file for complete search history.

(56) References Cited

U.S. PATENT DOCUMENTS

| | | | |
|---|---|---|---|
| 5,690,630 | A | 11/1997 | Errico et al. |
| 5,891,145 | A | 4/1999 | Morrison et al. |
| 6,063,090 | A | 5/2000 | Schläpfer |
| 6,074,391 | A | 6/2000 | Metz-Stavenhagen et al. |
| 6,146,383 | A | 11/2000 | Studer et al. |
| 6,280,442 | B1 | 8/2001 | Barker et al. |
| 6,835,196 | B2 | 12/2004 | Biedermann et al. |
| 7,186,255 | B2 | 3/2007 | Baynham et al. |
| 7,306,606 | B2 | 12/2007 | Sasing |
| 7,445,627 | B2 | 11/2008 | Hawkes et al. |

(Continued)

*Primary Examiner* — Eduardo C Robert
*Assistant Examiner* — Michelle C Green
(74) *Attorney, Agent, or Firm* — Polsinelli PC

(57) ABSTRACT

A bone anchor assembly includes a bone anchor with a capture portion having a horizontal capture recess and an anchor portion opposite the capture portion, and a receiver with a central bore having a seat surface proximate a bottom opening and a channel for receiving a rod. The assembly also includes a ring retainer with a center aperture having a lower internal recess and an upper internal recess, an open sweep ring in the lower internal recess for sweeping the capture recess of bone debris when the capture portion is uploaded into the center aperture of the ring retainer, and an open capture ring in the upper internal recess for snapping into the swept capture recess of the bone anchor to capture and hold the capture portion of the bone anchor to the ring retainer. The ring retainer is positionable within the central bore of the receiver with its outer surface in frictional engagement with the seat surface to secure the captured bone anchor to the receiver.

21 Claims, 75 Drawing Sheets

(56) References Cited

U.S. PATENT DOCUMENTS

| | | | | |
|---|---|---|---|---|
| 7,479,156 | B2 | 1/2009 | Lourdel et al. | |
| 7,604,655 | B2 | 10/2009 | Warnick | |
| 7,625,396 | B2 | 12/2009 | Jackson | |
| 7,662,172 | B2 | 2/2010 | Warnick | |
| 7,722,654 | B2 | 5/2010 | Taylor et al. | |
| 7,776,067 | B2 | 8/2010 | Jackson | |
| 7,789,896 | B2 | 9/2010 | Jackson | |
| 7,789,900 | B2 | 9/2010 | Levy et al. | |
| 7,833,250 | B2 | 11/2010 | Jackson | |
| 7,857,834 | B2 | 12/2010 | Boschert | |
| 7,875,065 | B2 | 1/2011 | Jackson | |
| 7,896,902 | B2 | 3/2011 | Jeon et al. | |
| 7,967,850 | B2 | 6/2011 | Jackson | |
| 8,034,089 | B2 | 10/2011 | Matthis et al. | |
| 8,097,025 | B2 | 1/2012 | Hawkes et al. | |
| 8,133,262 | B2 | 3/2012 | Whipple | |
| 8,308,782 | B2 | 11/2012 | Jackson | |
| 8,361,123 | B2 | 1/2013 | Fanger et al. | |
| 8,361,129 | B2 | 1/2013 | Chao | |
| 8,366,753 | B2 | 2/2013 | Jackson | |
| 8,556,938 | B2 | 10/2013 | Jackson et al. | |
| 8,657,858 | B2 | 2/2014 | Garamszegi et al. | |
| 8,876,869 | B1 | 11/2014 | Schafer et al. | |
| 8,888,827 | B2 | 11/2014 | Harper et al. | |
| 8,951,290 | B2 | 2/2015 | Hammer et al. | |
| 8,986,349 | B1 | 3/2015 | German et al. | |
| 9,044,272 | B2 | 6/2015 | Shaffrey et al. | |
| 9,060,814 | B2 | 6/2015 | Doubler et al. | |
| 9,119,674 | B2 | 9/2015 | Matthis et al. | |
| 9,358,047 | B2 | 6/2016 | Mishra et al. | |
| 9,439,680 | B2 | 9/2016 | Biedermann et al. | |
| 9,453,526 | B2 | 9/2016 | Black et al. | |
| 9,492,204 | B2 | 11/2016 | Biedermann et al. | |
| 9,615,858 | B2 | 4/2017 | Doubler et al. | |
| 9,655,656 | B2 | 5/2017 | Whipple | |
| 9,707,013 | B2 | 7/2017 | Rezach et al. | |
| 9,724,145 | B2 | 8/2017 | Spratt et al. | |
| 9,763,702 | B2 | 9/2017 | Schlaepfer et al. | |
| 9,775,660 | B2 * | 10/2017 | Spratt ................ | A61B 17/8685 |
| 9,924,975 | B2 | 3/2018 | Jackson et al. | |
| 10,052,136 | B2 | 8/2018 | Nelson | |
| 10,188,432 | B2 | 1/2019 | Jackson et al. | |
| 10,285,738 | B1 | 5/2019 | Doubler et al. | |
| 10,335,204 | B2 | 7/2019 | Matthis et al. | |
| 10,363,070 | B2 | 7/2019 | Jackson et al. | |
| 10,695,100 | B2 | 6/2020 | May et al. | |
| 10,966,760 | B2 | 4/2021 | Armstrong et al. | |
| 11,020,150 | B1 * | 6/2021 | Doubler ............. | A61B 17/7032 |
| 11,109,895 | B2 | 9/2021 | May et al. | |
| 11,219,470 | B2 | 1/2022 | Avidano et al. | |
| 11,234,745 | B2 | 2/2022 | Jackson | |
| 11,439,437 | B1 | 9/2022 | Roberts et al. | |
| 11,690,652 | B1 | 7/2023 | Cummins et al. | |
| 12,310,631 | B2 | 5/2025 | Mickiewicz et al. | |
| 2006/0058788 | A1 | 3/2006 | Hammer et al. | |
| 2006/0161153 | A1 | 7/2006 | Hawkes et al. | |
| 2007/0118117 | A1 * | 5/2007 | Altarac .............. | A61B 17/7037 606/270 |
| 2007/0118123 | A1 | 5/2007 | Strausbaugh et al. | |
| 2007/0270807 | A1 | 11/2007 | Armstrong et al. | |
| 2008/0004625 | A1 | 1/2008 | Runco et al. | |
| 2008/0015579 | A1 * | 1/2008 | Whipple ............ | A61B 17/7037 606/250 |
| 2009/0204155 | A1 | 8/2009 | Aschmann | |
| 2010/0010540 | A1 | 1/2010 | Park | |
| 2010/0152787 | A1 | 6/2010 | Walsh et al. | |
| 2011/0040335 | A1 | 2/2011 | Stihl et al. | |
| 2011/0040338 | A1 | 2/2011 | Jackson | |
| 2011/0270321 | A1 | 11/2011 | Prevost et al. | |
| 2012/0046700 | A1 * | 2/2012 | Jackson ............. | A61B 17/7037 606/305 |
| 2012/0310284 | A1 | 12/2012 | Gerchow | |
| 2013/0144346 | A1 * | 6/2013 | Jackson ............. | A61B 17/7032 606/305 |
| 2013/0218213 | A1 | 8/2013 | Lemoine | |
| 2014/0025119 | A1 | 1/2014 | Biedermann et al. | |
| 2014/0121703 | A1 | 5/2014 | Jackson et al. | |
| 2014/0343617 | A1 * | 11/2014 | Hannen .............. | A61B 17/8605 606/306 |
| 2015/0320465 | A1 * | 11/2015 | Butler ................ | A61B 17/8605 29/428 |
| 2017/0333085 | A1 * | 11/2017 | Jackson ............. | A61B 17/7038 |
| 2018/0243010 | A1 | 8/2018 | Murabayashi et al. | |
| 2019/0183536 | A1 * | 6/2019 | May ................... | A61B 17/7032 |
| 2022/0061892 | A1 * | 3/2022 | Jackson ............. | A61B 17/7035 |
| 2022/0313332 | A1 * | 10/2022 | Jackson ............. | A61B 17/8685 |

* cited by examiner

BONE ANCHOR ASSEMBLY WITH BONE DEBRIS SWEEP RING IN RECEIVER SUB-ASSEMBLY

CROSS-REFERENCE TO RELATED APPLICATIONS

This application is a continuation of U.S. Application Ser. No. 18/156,195, filed Jan. 18, 2023, now U.S. Pat. No. 12,053,209, which claims the benefit of U.S. Provisional Application No. 63/300,557, filed Jan. 18, 2022, and U.S. Provisional Application No. 63/339,358, filed May 6, 2022, each of which is incorporated by reference in its entirety herein and for all purposes.

FIELD

The present disclosure relates generally to spinal implant assemblies utilizing universal shank heads having a common capture portion geometry, and that are configured for connection with an array or collection of pivoting and non-pivoting but axially rotatable (i.e. monoaxial) receiver sub-assemblies having different functionalities, and their use in surgery involving vertebral body stabilizations with spinal fixation systems.

BACKGROUND

Spinal implants in general, and bone anchors or screws in particular, are used in many types of spinal surgery in order to secure various implants to vertebrae along the spinal column for the purposes of treating spinal disorders, such as degenerative conditions and deformities, and also for stabilizing and/or adjusting spinal alignment. A common mechanism for providing vertebral support is to implant the bone screws into certain bones which then, in turn, support a longitudinal structure such as an elongate rod, or are supported by such a rod. Although both closed-ended and open-ended spinal implants, such as bone screws and hooks, are known, the open-ended spinal implants can be particularly well suited for connections to rods and connector arms because such rods or arms do not need to be passed through a closed bore, but rather can be laid or urged into an open channel within the head or receiver of such a screw, hook, or connector. For example, open-ended bone screws generally comprise an anchor portion, such as a threaded shank, connected to a head or receiver having a pair of upwardly-projecting branches or arms which form a yoke that defines a slot or channel configured to receive the rod. The slot or channel could have different shapes, such as, a U-shape or a square shape. Moreover, the threaded shanks of the bone screws can also be replaced with hooks or other types of bone anchors or connectors to form a variety of different types of spinal implants, also having open ends for receiving rods or portions of other structures, and wherein such implants can facilitate surgical techniques performed with different spinal fixation systems.

Early bone screws used in spinal surgery generally had a yoke-shaped 'head' that was integrally formed or "fixed" with the threaded shank, and therefore immovable. Because the fixed head could not be moved relative to the shank, these fixed bone screws needed to be favorably positioned in the spine. Otherwise, the elongate rod would need to be bent in order for it to be placed within the rod-receiving channels of multiple implants due to their alignment. Given the highly curved shape of the spines of some patients, however, this is sometimes very difficult or impossible to do. Therefore, polyaxial (i.e. multiplanar), uni-planar (i.e. monoplanar), and/or translatable pivotal bone screws or bone anchor assemblies, were developed and are now commonly preferred. Open-ended polyaxial bone screw assemblies typically allow for pivoting and rotation of the connected but completely separate yoke-shaped receiver or receiver sub-assembly about an enlarged spherical 'head' or upper capture portion of the threaded shank or bone anchor in one or more planes, until a desired rotational and pivotal position of the receiver is achieved relative to the shank. This can be accomplished by manipulating the position of the receiver relative to the shank during a final stage of a medical procedure when the elongate rod or other longitudinal connecting member is inserted into the receiver or receiver sub-assembly, followed by a locking set screw, a plug, a closure, or other type of locking mechanism known in the art.

It is understood that spinal fixation systems generally include a variety of components that require some assembly, such as the various types of bone anchors, the rods or connector arms, and the closures or plugs with the receivers or receiver sub-assemblies, with each component having specific features with respect to structure and function. Moreover, the receiver sub-assemblies can further include components in addition to the receiver itself, such as pressure inserts, spring rings, separate retainers, and other components of different types that are operable to connect these receiver sub-assemblies with the heads of the bone anchors. The pressure inserts, rings, retainers, and other components can be pre-assembled together within the receivers to form the receiver sub-assemblies that are ready for further assemblage with the bone anchors, and eventually with the rods or connector arms and the closures or plugs.

Some designs provide for the threaded shanks or other types of bone anchor to be bottom loaded into the receiver sub-assemblies. With bottom loaded bone anchor assemblies, for example, some designs known in the art require a separate retainer to hold the shank within the receiver, with the receiver having a bottom opening large enough to allow for the head or upper capture portion of the threaded shank or bone anchor to be uploaded into the central bore or cavity of the receiver. Other types of bottom loaded bone anchor assemblies do not include the separate retainer, however, and instead include a receiver having a lower portion with a bottom opening that is configured to directly threadably mate with the head or upper capture portion of the shank that can be configured as a threaded spherical head to provide for polyaxial or multiplanar motion.

Further to the above, bottom loaded bone anchor assemblies can also be fully assembled by the spinal company or distributor before being shipped to a hospital, so as to help with inventory management, or can be shipped as a modular array of multiple separate and different shanks and a fewer number of pre-assembled receiver sub-assemblies that can then be fully assembled, for example, at the hospital or surgical center during a surgery, thereby saving costs. Additionally, the modular spinal implants can be fully assembled at the hospital either before insertion into the patient, or after the threaded shank or bone anchor has been inserted into the patient, such as with robotic assistance or directly by a robot. The different techniques or approaches for the insertion and assembly of the modular parts of the bone anchor assemblies can be described as ex-vivo and in-vivo, respectively.

SUMMARY

The present disclosure is generally directed to modular spinal fixation systems with bone anchors comprising a certain type of common or universal shank head configured to connect with a wide array of receiver sub-assemblies having different functionalities. To that purpose, one embodiment of the present disclosure comprises a spinal fixation system for securing an elongate rod to a spine of a patient. The spinal fixation system includes an array of receiver sub-assemblies, with each receiver sub-assembly having a receiver with a base portion that defines a lower section of a central bore centered around a vertical centerline axis and communicating with a bottom of each receiver through a bottom opening, and an upper portion having a channel configured to receive the elongate rod. The central bore includes a seat surface proximate the bottom opening, and extends upward through the channel to a top of the receiver. Each receiver sub-assembly further includes one of a multiplanar pivoting retainer sub-assembly, a monoplanar pivoting retainer sub-assembly, or a non-pivoting or mono-axial retainer sub-assembly positioned therein and configured to engage the seat surface. Furthermore, each retainer sub-assembly also includes an internal capture structure that can be common to all of the retainer sub-assemblies, that defines a center aperture, and which is spaced apart from the seat surface of the receiver. The spinal fixation system also includes a bone anchor having a longitudinal axis, a capture portion that is devoid of outer parallel planar side surfaces and configured for uploading into the center aperture of the internal capture structure through the bottom opening of each of the receivers, an anchor portion opposite the capture portion configured for fixation to the bone, and a neck portion extending between the capture portion and the anchor portion, with the capture portion being configured to engage and be retained by the internal capture structure of each type of retainer sub-assemblies. After the capture portion of the bone anchor is captured by the internal capture structure of one of the retainer sub-assemblies, ex-vivo or in-vivo, the bone anchor is further configured to have frictional axial independent rotation with respect to the receiver sub-assembly, together with one of multiplanar motion, monoplanar motion, or non-pivotal monoaxial motion with respect to the receiver sub-assembly.

Another embodiment of the present disclosure comprises a bone anchor assembly that can have a bone anchor or bone screw including an upper capture portion incorporating a geometry generally configured with lateral facing frusto-conical outer surfaces that are devoid of any parallel planar surfaces and a horizontal capture recess extending into and circumferentially around a mid-portion thereof. The assembly can also include a receiver having a central bore with a seat surface proximate a bottom opening, as well as a ring retainer comprising both a center aperture with a tapered inner surface that is slidably engageable with the frusto-conical outer surfaces of the upper capture portion of the bone anchor, and an internal center aperture recess that extends into and circumferentially around the tapered inner surface thereof. The assembly can further include a capture structure or capture ring having a capture ring aperture that is smaller than the center aperture, and which is positionable within the center aperture recess, so as to form a retainer sub-assembly, prior to the assembly of the ring retainer within the receiver. Upon securing the ring retainer with the enclosed capture ring within the central bore of the receiver and against the seat surface, with the center aperture centered above the receiver bottom opening, the upper capture portion of the bone anchor is uploadable into the center aperture with the frusto-conical outer surfaces of the upper capture portion engaging and continuously expanding the capture ring, and not the ring retainer, until the horizontal capture recess reaches the center aperture recess, at which point the capture ring snaps into the horizontal capture recess to couple the bone anchor to the ring retainer and the receiver. It will be appreciated that the frusto-conical configuration for the outer surfaces is but one possible geometry for the universal shank heads disclosed therein, and that other geometries can include cylindrical shapes with recesses or threads and partial spherical shapes with recesses, threads, or different outer surface radii, for example.

Additional embodiments of the present disclosure will be better understood upon review of the detailed description set forth below taken in conjunction with the accompanying drawing figures, which are briefly described as follows.

BRIEF DESCRIPTION OF THE DRAWINGS

FIG. 120 is a partially cut-away front perspective view of the monoaxial receiver sub-assembly moving downward until the universal capture portion of the bone anchor engages and pushes the capture ring upward to engage the top surface of the recess of the monoaxial ring retainer.

FIG. 121 is a partially cut-away front perspective view of the monoaxial receiver sub-assembly moving further downward as the universal capture portion of the bone anchor drives the capture ring outward within the recess of the monoaxial ring retainer to a maximum expansion configuration.

FIG. 122 is a partially cut-away front perspective view of the monoaxial receiver sub-assembly moving further downward until the capture ring snaps into the retainer recess to capture the universal capture portion within the monoaxial receiver sub-assembly.

FIG. 123 is a partially cut-away front perspective view of the monoaxial bone anchor assembly, fully assembled with the elongate rod and closure and with the bone anchor in a non-articulated position relative to the receiver.

FIG. 124 is a close-up cross-sectional side view of the fully-assembled monoaxial bone anchor assembly of FIG. 96.

FIG. 125 is a partially cut-away front perspective view of a multi-component spinal fixation system having at least three major types of receiver sub-assemblies and a bone anchor having another type a universal shank head that are configured together to provide for bone debris clearance, in accordance with another representative embodiment of the present disclosure.

FIG. 126 is an exploded perspective view of a multiplanar embodiment of a bone anchor assembly with bone debris clearance, in accordance with the representative embodiment of the multi-component spinal fixation system shown in FIG. 125.

FIG. 127 is a perspective view of the bone anchor of the multiplanar bone anchor assembly of FIG. 126.

FIG. 128 is a perspective view of the capture portion of the bone anchor of FIG. 127.

FIG. 129 is a cross-sectional side view of the capture portion of the bone anchor of FIG. 127.

FIG. 130 is a top view of the bone anchor of FIG. 127.

FIG. 131 is a bottom view of the bone anchor of FIG. 127.

Figure 126:
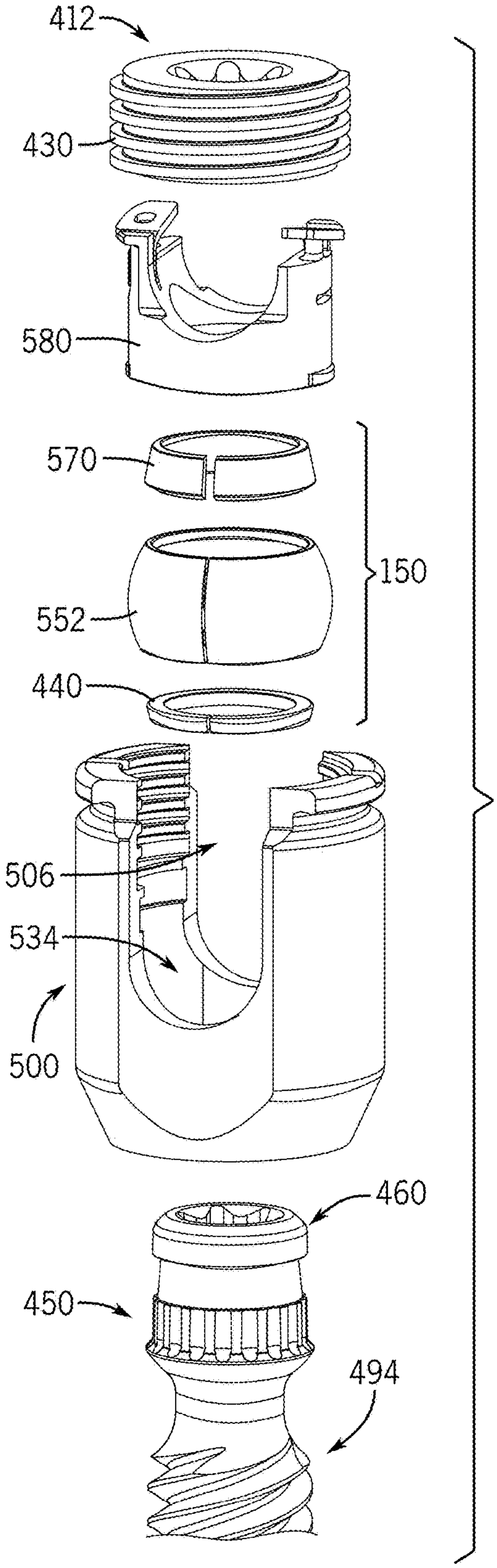
Figure 127:
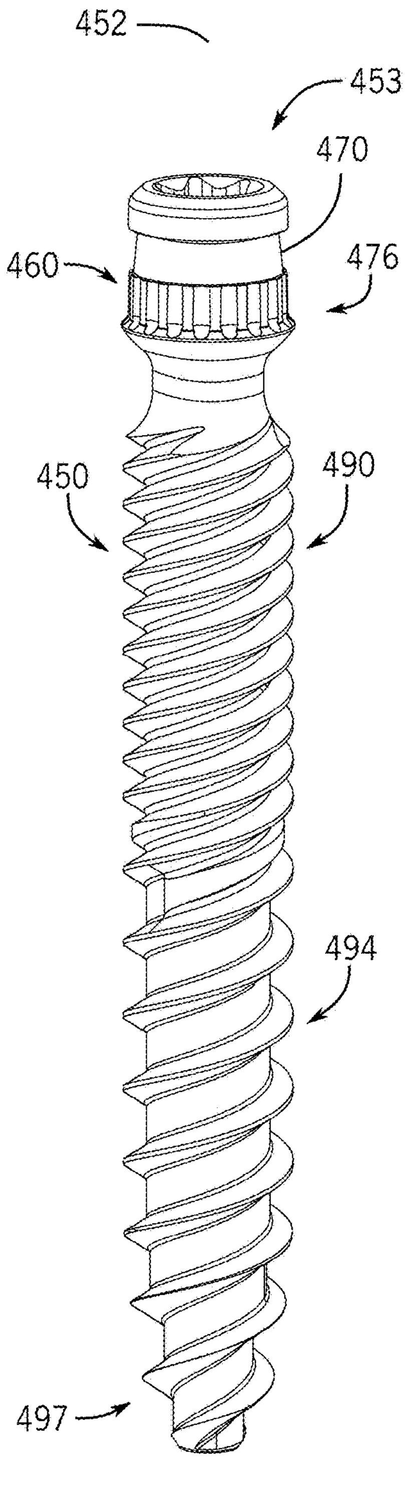
Figure 128:
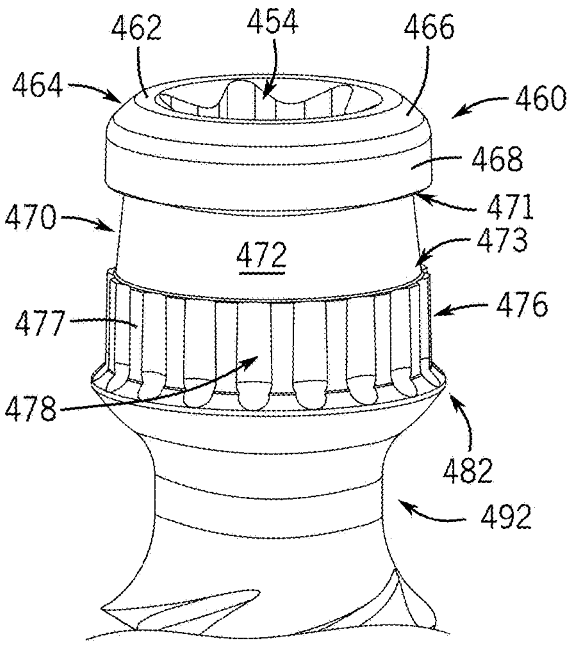
Figure 129:
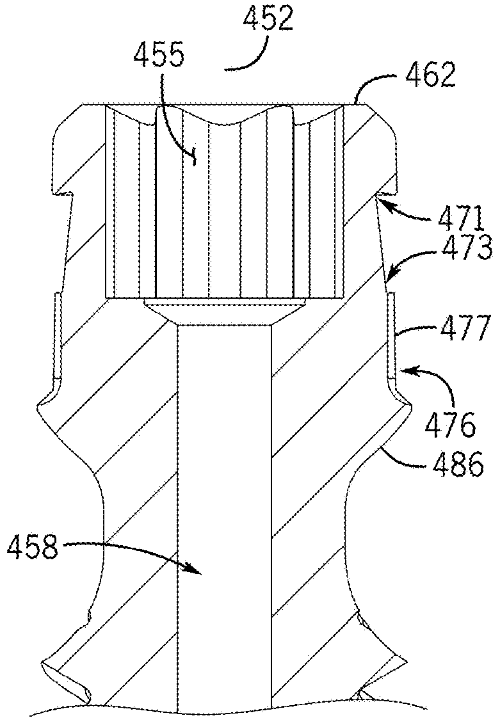
Figure 130:
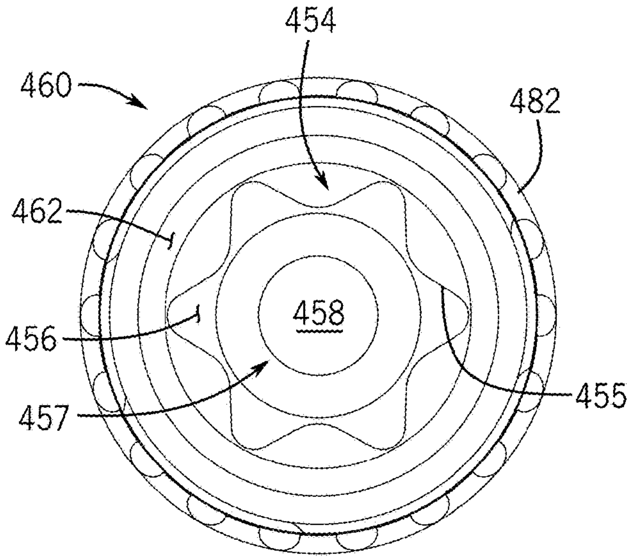
Figure 131:
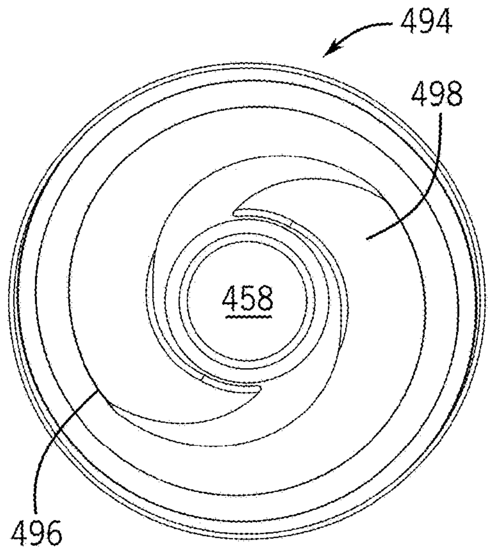
Figure 132:
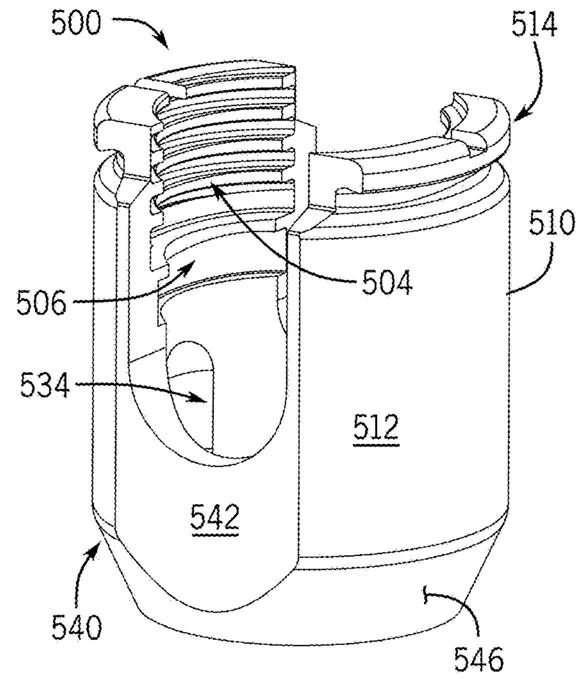

FIG. 132 is a perspective view of the receiver of the multiplanar bone anchor assembly of FIG. 126.

Figure 133:
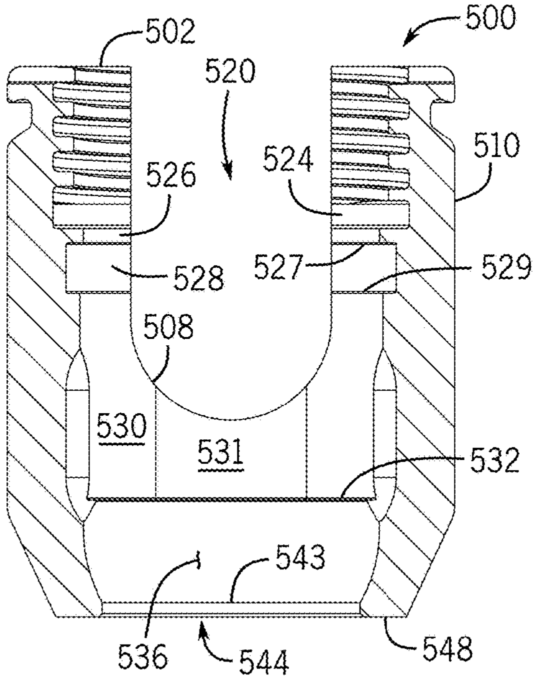

FIG. 133 is a cross-sectional side view of the receiver of FIG. 132.

Figure 134:
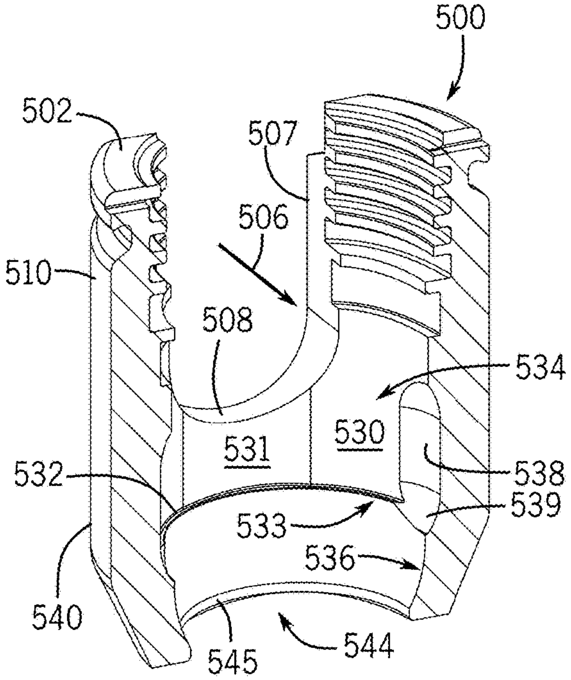

FIG. 134 is a cross-sectional perspective view of the receiver of FIG. 132.

Figure 135:
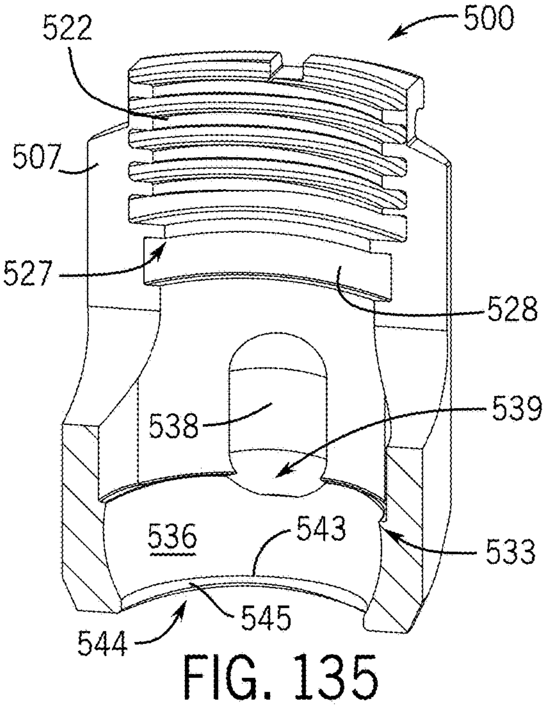

FIG. 135 is another cross-sectional perspective view of the receiver of FIG. 132.

Figure 136:
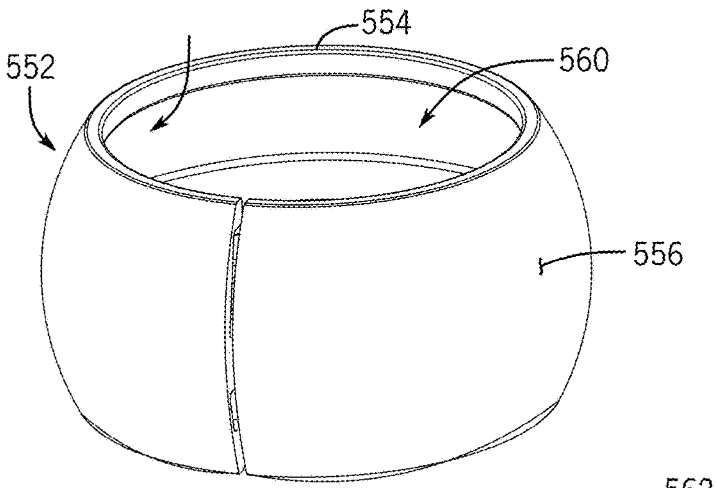

FIG. 136 is a perspective view of the ring retainer of the multiplanar bone anchor assembly of FIG. 126.

Figure 137:
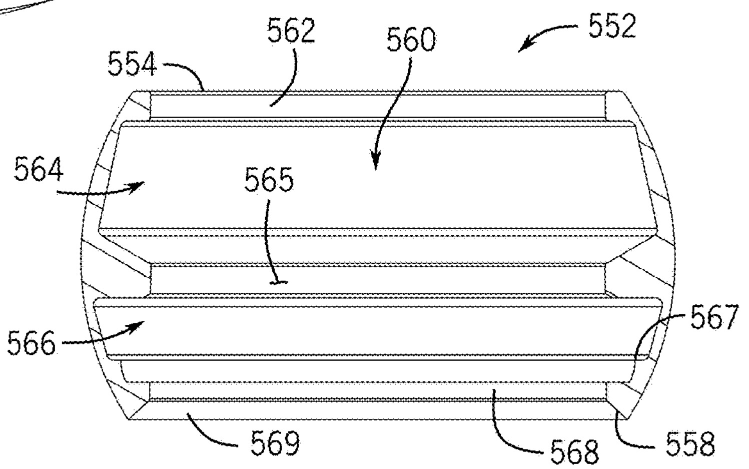

FIG. 137 is a cross-sectional side view of the ring retainer of FIG. 136.

Figure 138:
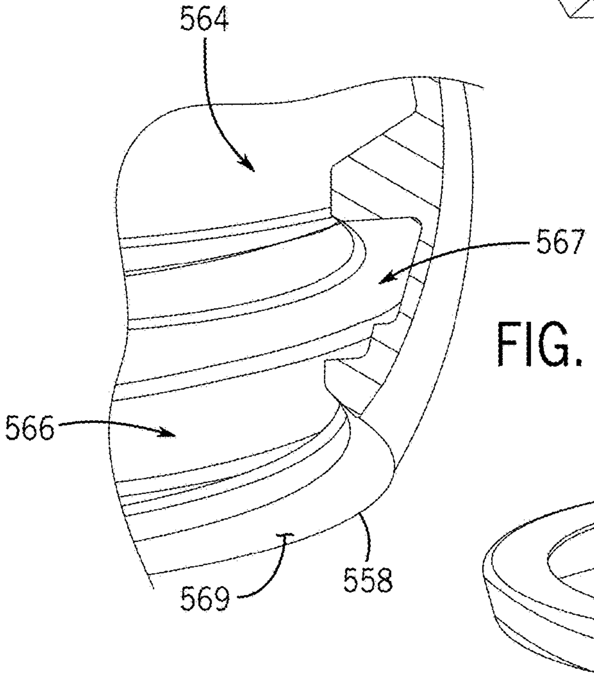

FIG. 138 is a close-up cross-sectional perspective view of the ring retainer of FIG. 136.

Figure 139:
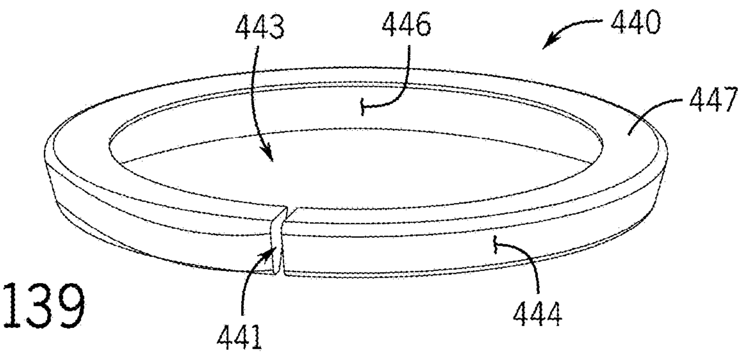

FIG. 139 is a perspective view of the bone sweep ring of the multiplanar bone anchor assembly of FIG. 126.

Figure 140:
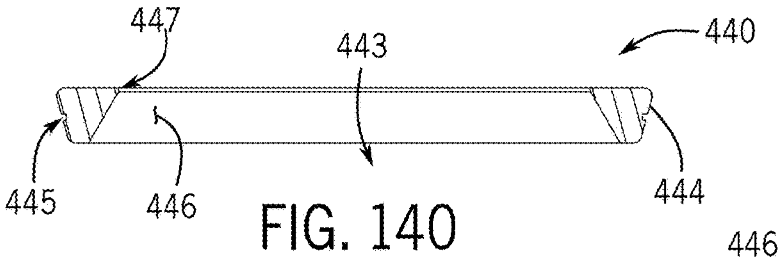

FIG. 140 is a cross-sectional side view of the bone sweep ring of FIG. 139.

Figure 141:
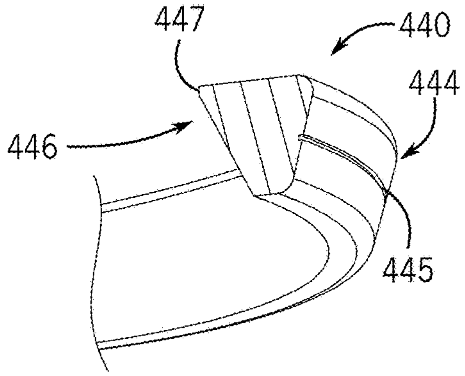

FIG. 141 is a close-up cross-sectional perspective view of the bone sweep ring of FIG. 139.

Figure 142:
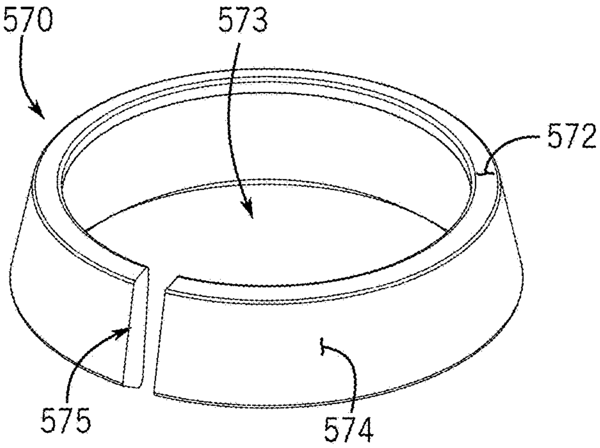

FIG. 142 is a perspective view of the capture ring of the multiplanar bone anchor assembly of FIG. 126.

Figure 143:
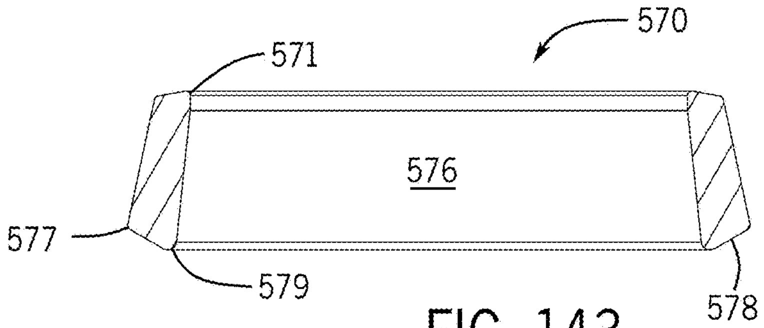

FIG. 143 is a cross-sectional side view of the capture ring of FIG. 142.

Figure 144:
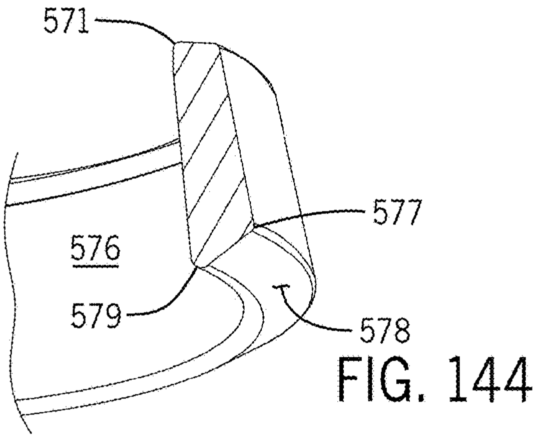

FIG. 144 is a close-up cross-sectional perspective view of the capture ring of FIG. 142.

Figure 145:
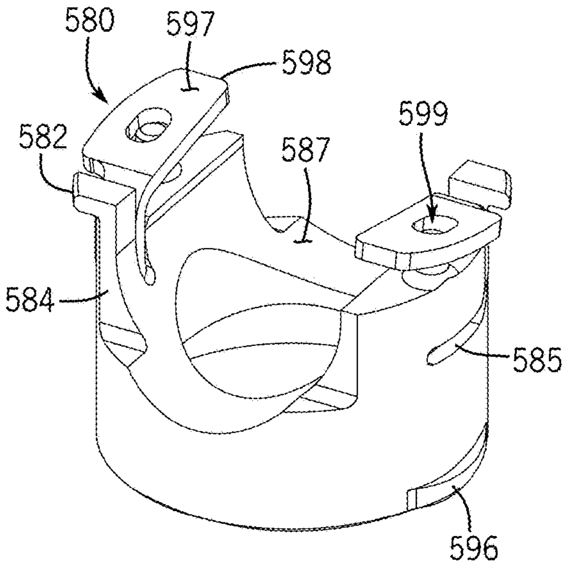

FIG. 145 is a top perspective view of the pressure insert of the multiplanar bone anchor assembly of FIG. 126.

Figure 146:
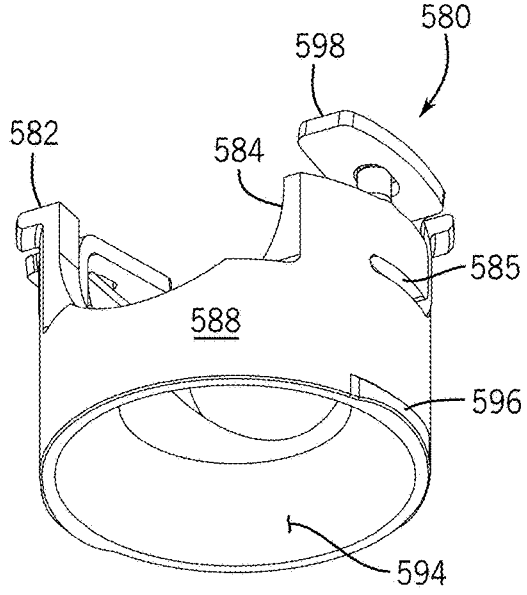

FIG. 146 is a bottom perspective view of the pressure insert of FIG. 145.

Figure 147:
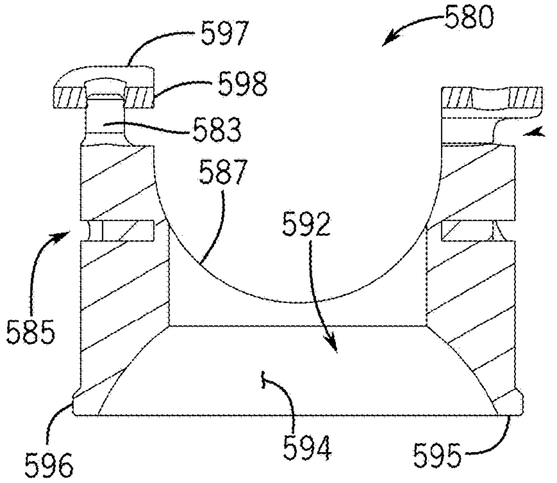

FIG. 147 is a cross-sectional side view of the pressure insert of FIG. 145.

Figure 148:
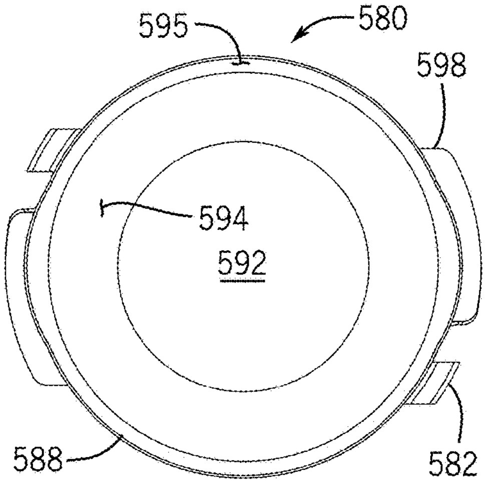

FIG. 148 is a bottom view of the pressure insert of FIG. 145.

Figure 149:
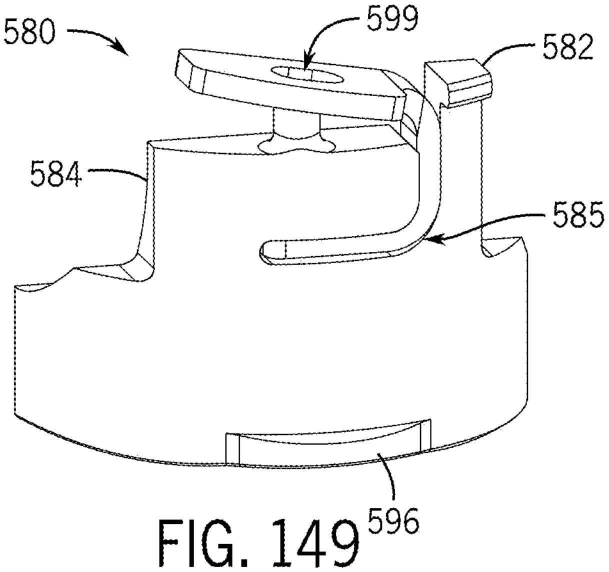

FIG. 149 is a close-up perspective view of an upright arm of the pressure insert of FIG. 145.

Figure 150:
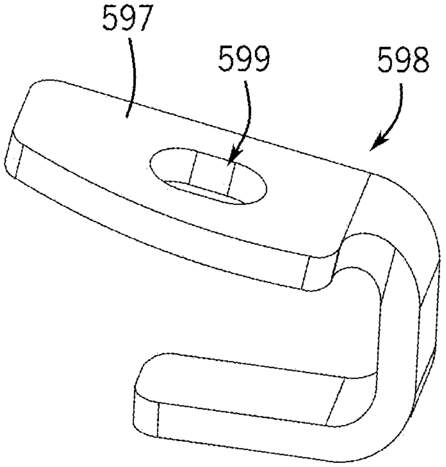

FIG. 150 is a close-up perspective view of the U-shaped non-integral spring element of FIG. 145.

Figure 151:
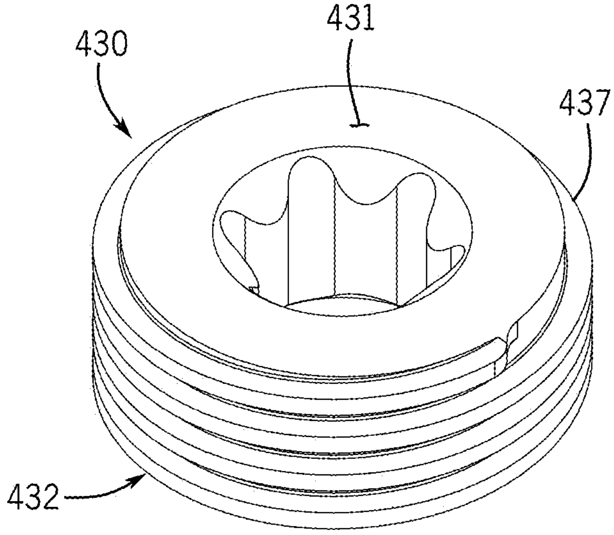

FIG. 151 is a top perspective view of the closure of the pivotal bone anchor assembly of FIG. 126.

Figure 152:
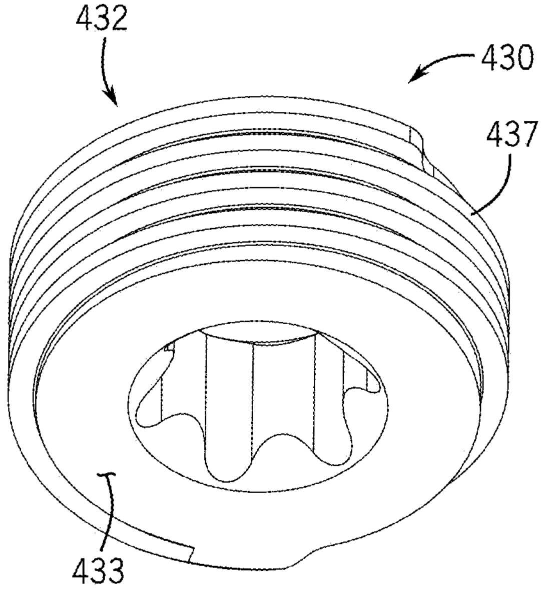

FIG. 152 is a bottom perspective view of the closure of FIG. 151

Figure 153:
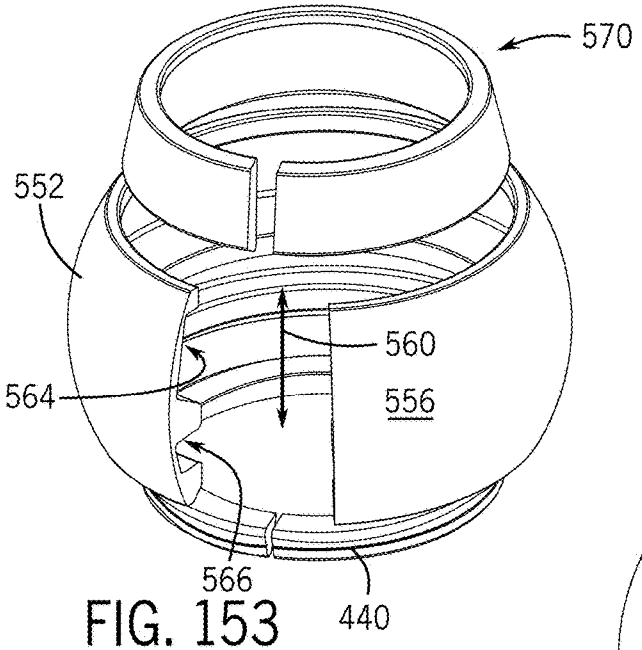

FIG. 153 is a perspective view of the ring retainer of FIG. 136, the bone sweep ring of FIG. 139, and the capture ring of FIG. 142 prior to assembly together into a multiplanar retainer sub-assembly.

Figure 154:
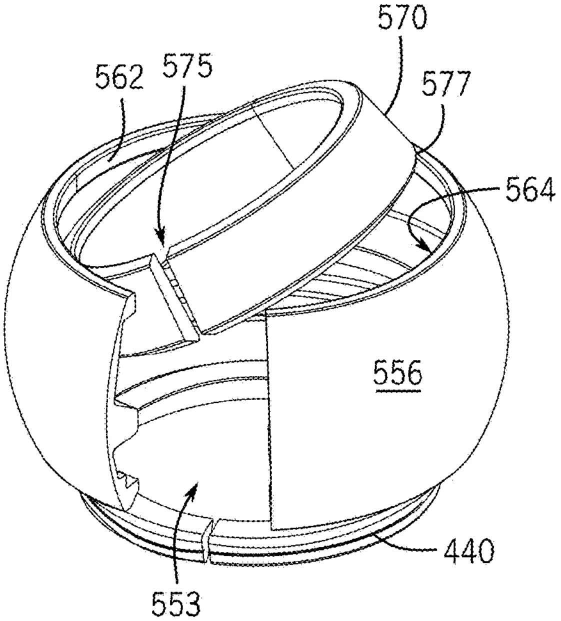

FIG. 154 is a perspective view of the ring retainer, bone sweep ring, and capture ring of FIG. 153 during assembly together into the multiplanar retainer sub-assembly.

Figure 155:
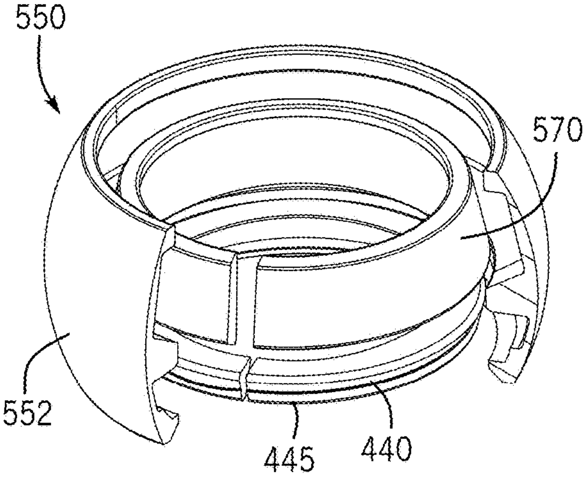

FIG. 155 is partially cut-away perspective view of the ring retainer, bone sweep ring, and capture ring of FIG. 153 after assembly together into the multiplanar retainer sub-assembly.

Figure 156:
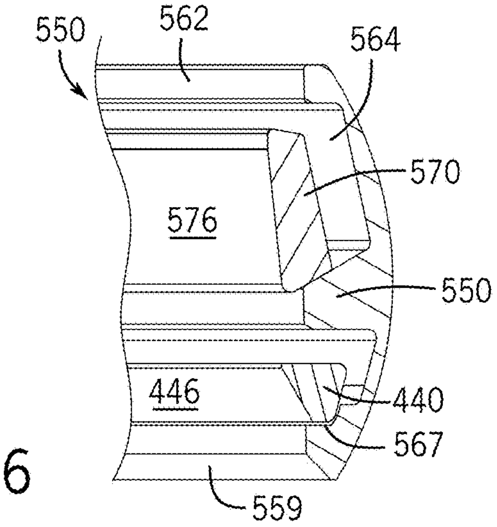

FIG. 156 is a close-up cross-sectional front view of the ring retainer, bone sweep ring, and capture ring of FIG. 153 after assembly together into the multiplanar retainer sub-assembly.

Figure 157:
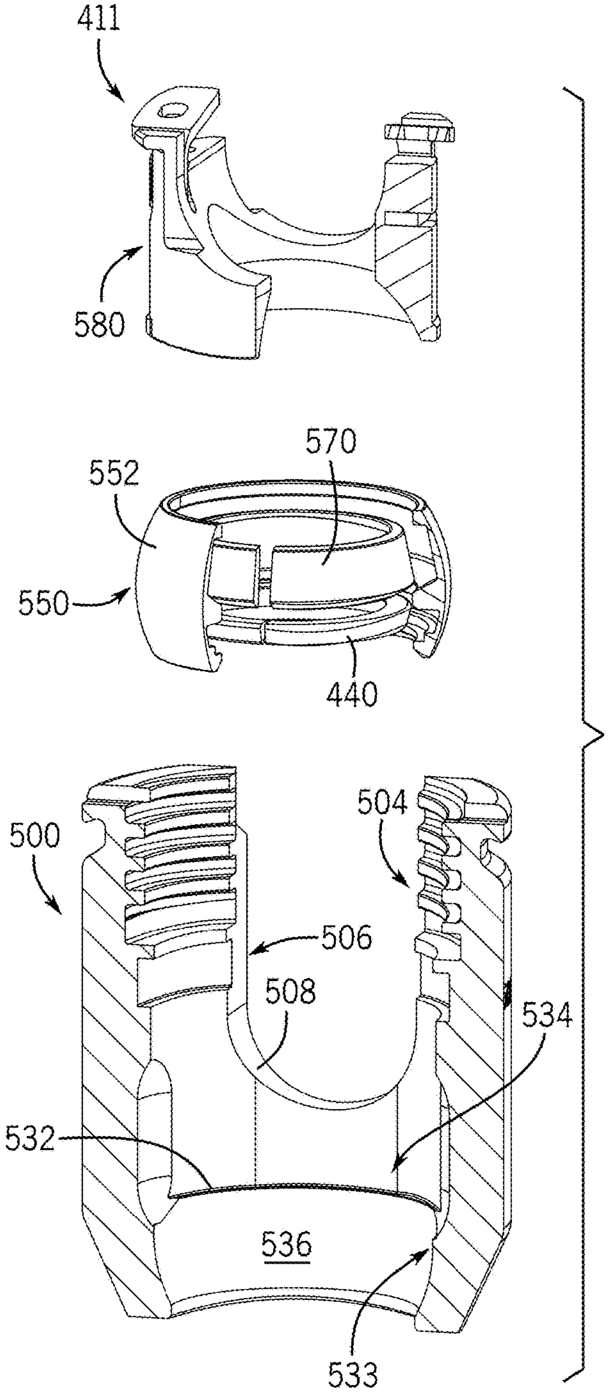

FIG. 157 is an exploded partially cut-away perspective view of the components of a multiplanar receiver sub-assembly with bone debris clearance, prior to their pre-assembly into a shipping configuration with the receiver.

Figure 158:
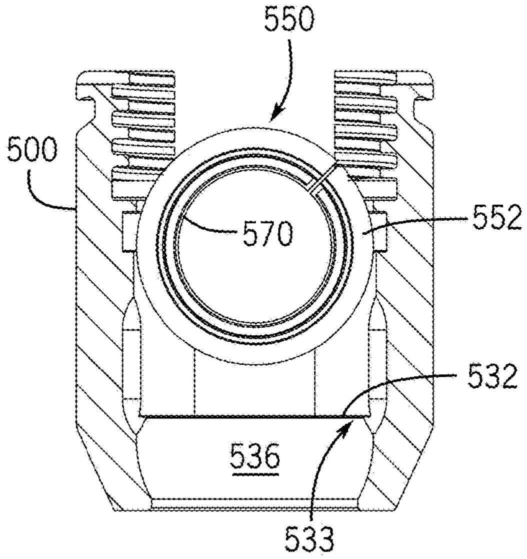

FIG. 158 is a partially cut-away front view of the receiver of FIG. 157 with vertically-oriented multiplanar retainer sub-assembly being downloaded through the open channel of the receiver.

Figure 159:
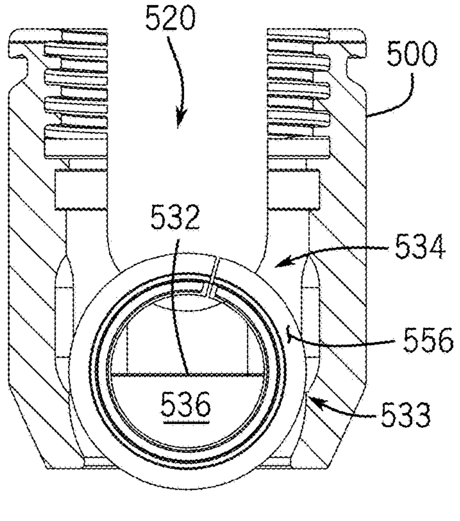

FIG. 159 is a partially cut-away front view of the receiver of FIG. 158 with the vertically-oriented multiplanar retainer sub-assembly contacting the upper edge of the seat surface of the receiver.

Figure 160:
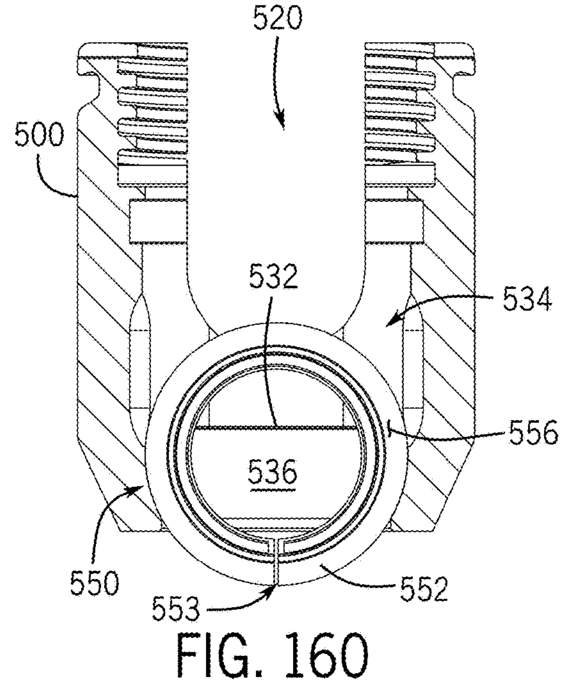

FIG. 160 is a partially cut-away front view of the receiver of FIG. 159 with the vertically-oriented multiplanar retainer sub-assembly being somewhat resiliently compressed and pushed down into a vertical partially-seated engagement with the seat surface of the receiver.

Figure 161:
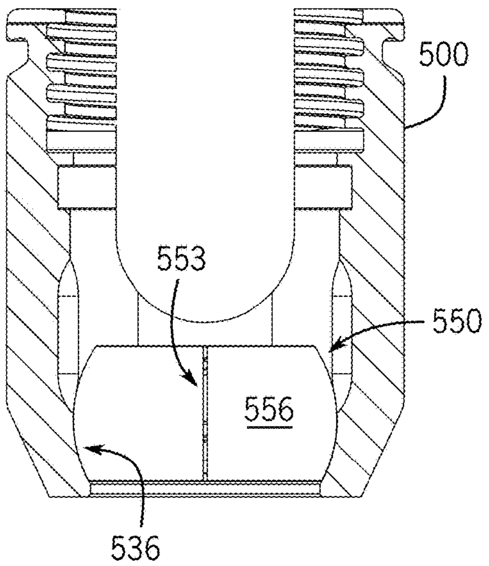

FIG. 161 is a partially cut-away front view of the receiver of FIG. 160 with the multiplanar retainer sub-assembly being rotated to a horizontal fully-seated engagement the seat surface of the receiver.

Figure 162:
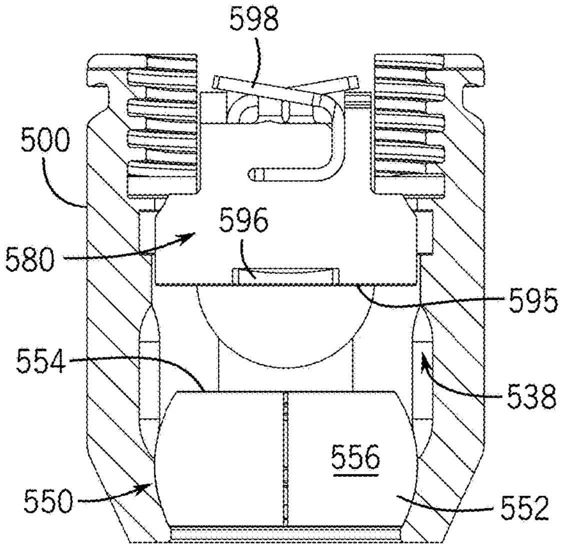

FIG. 162 is a partially cut-away front view of the receiver with the seated multiplanar retainer sub-assembly and with a multiplanar pressure insert being downloaded through the open channel of the receiver.

Figure 163:
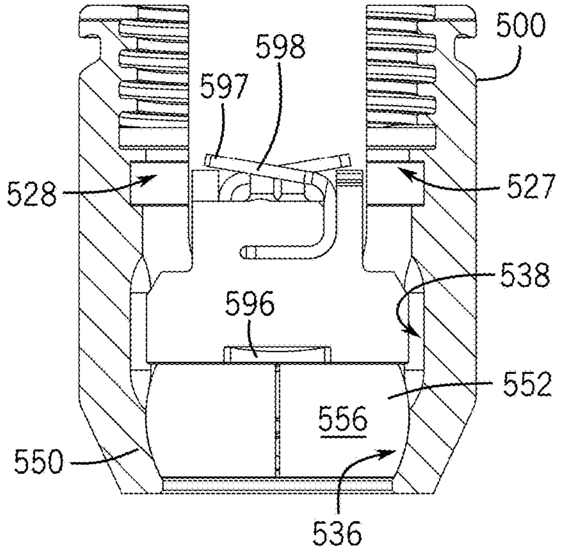

FIG. 163 is a partially cut-away front view of the receiver with the seated multiplanar retainer sub-assembly, with the multiplanar pressure insert being further downloaded into the cavity of the receiver to engage the retainer sub-assembly.

Figure 164:
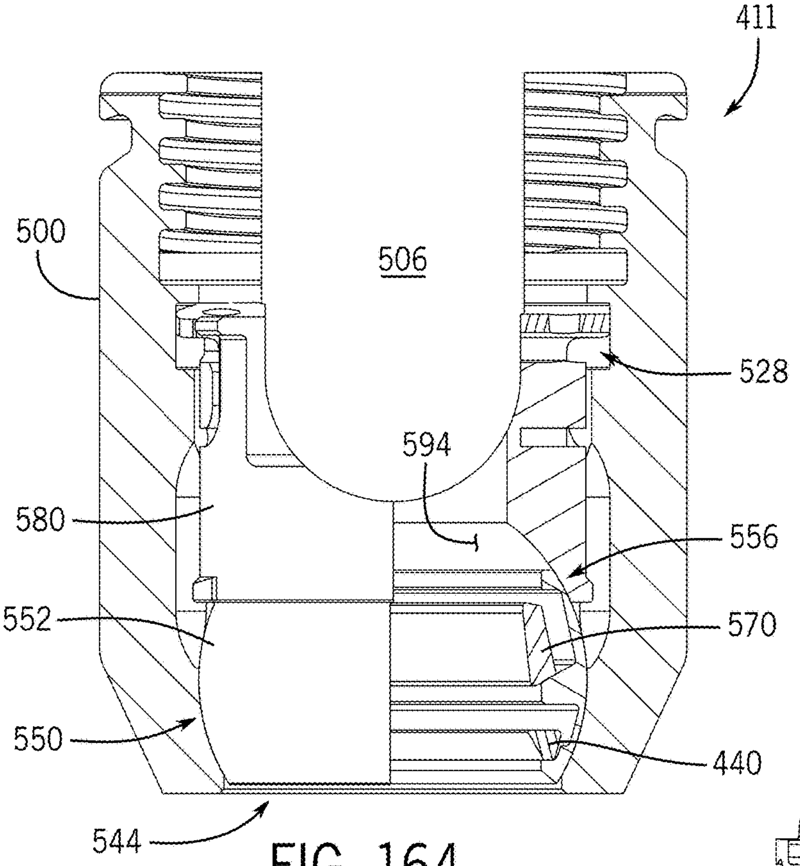

FIG. 164 is a partially cut-away front view of the receiver with the seated multiplanar retainer sub-assembly and the multiplanar pressure insert being fully rotated therein to form a pre-assembled multiplanar receiver sub-assembly with bone debris clearance in the shipping state.

Figure 165:
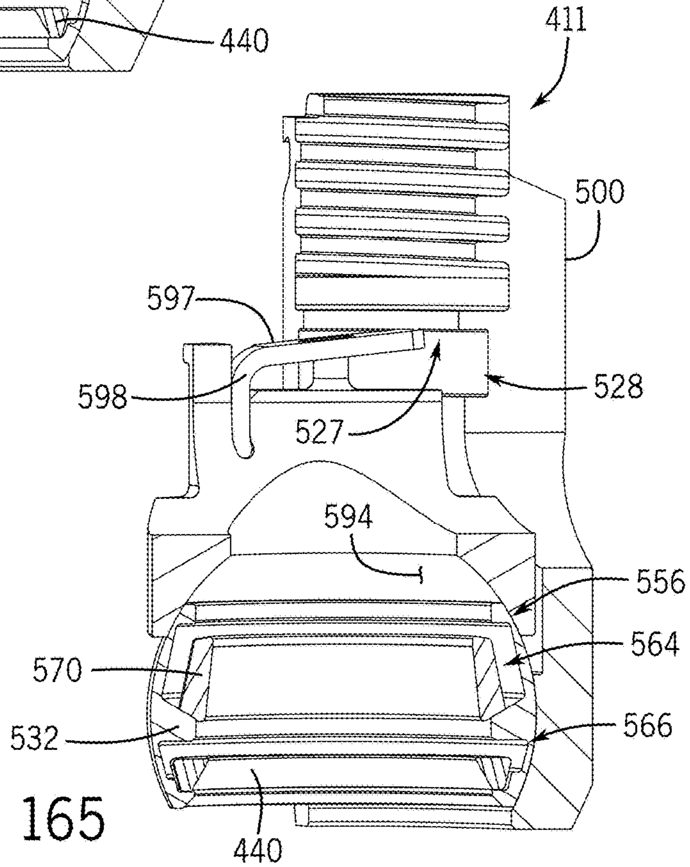

FIG. 165 is a partially cut-away side view of the receiver with the seated multiplanar retainer sub-assembly and the multiplanar pressure insert being fully rotated therein to form a pre-assembled multiplanar receiver sub-assembly with bone debris clearance in the shipping state.

Figure 166:
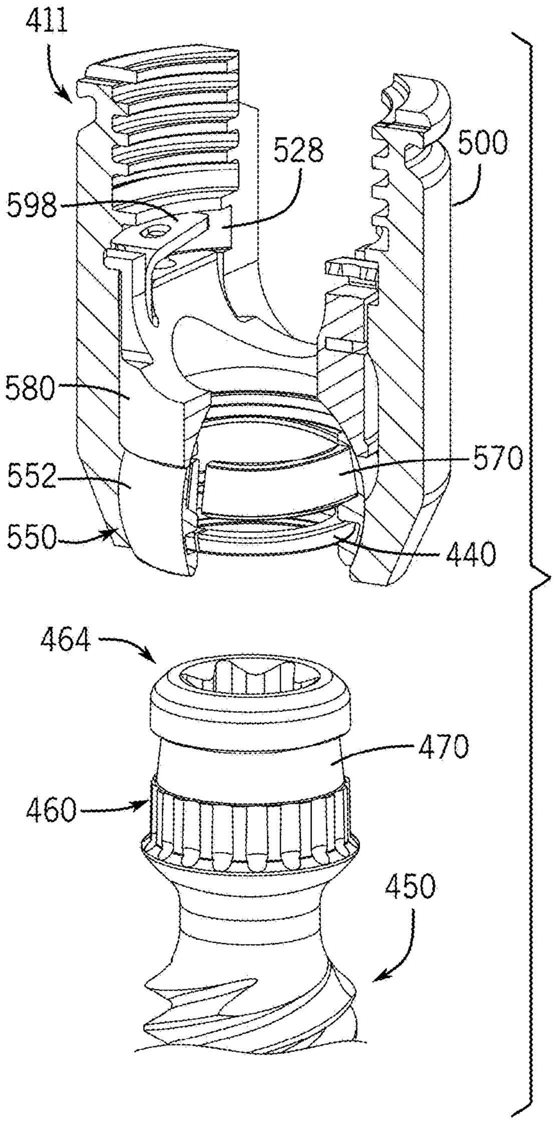

FIG. 166 is a partially cut-away front perspective view of the multiplanar receiver sub-assembly with bone debris clearance positioned above the universal capture portion of a bone anchor.

Figure 167:
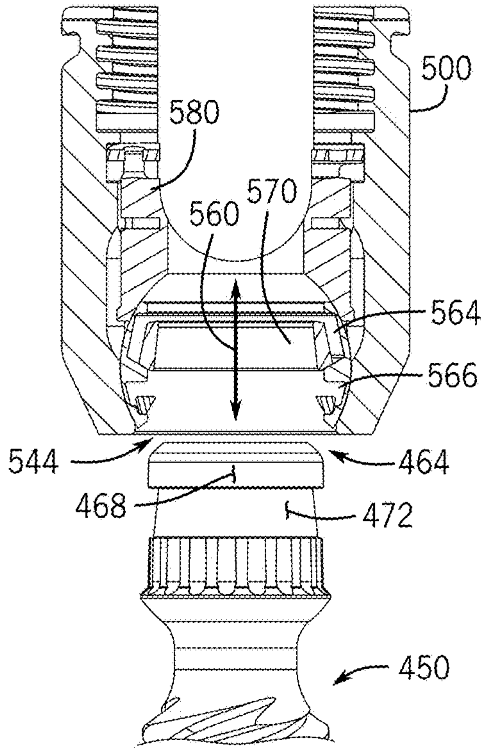

FIG. 167 is a partially cut-away front view of the multiplanar receiver sub-assembly of FIG. 166 moving downward onto the universal capture portion of the bone anchor.

Figure 168:
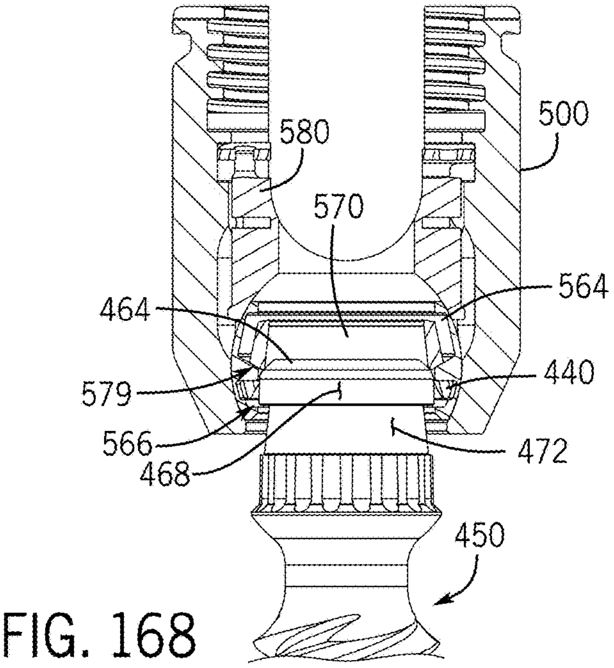

FIG. 168 is a partially cut-away front view of the multiplanar receiver sub-assembly of FIG. 167 moving downward until the universal capture portion engages the capture ring enclosed within the ring retainer and the bone sweep ring begins to scrape the upper slidable surface of the capture portion.

Figure 169:
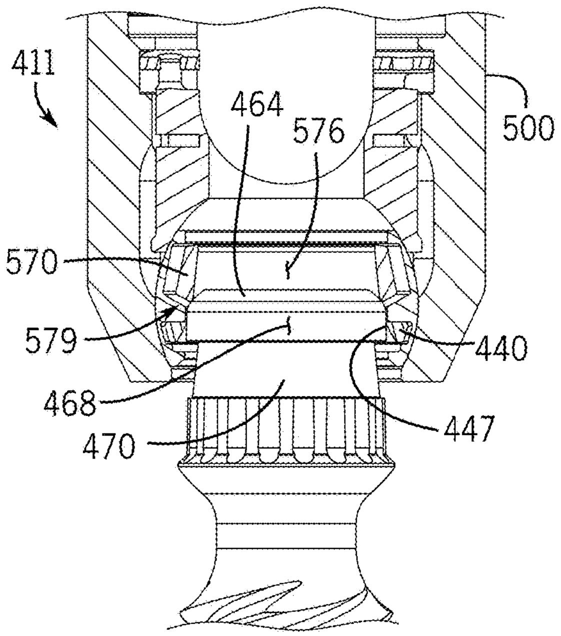

FIG. 169 is a partially cut-away front view of the multiplanar receiver sub-assembly of FIG. 168 moving further downward as the universal capture portion pushes the capture ring upward to engage the top surface of the recess of the ring retainer and the bone sweep ring scrapes the upper slidable surface of the capture portion.

Figure 170:
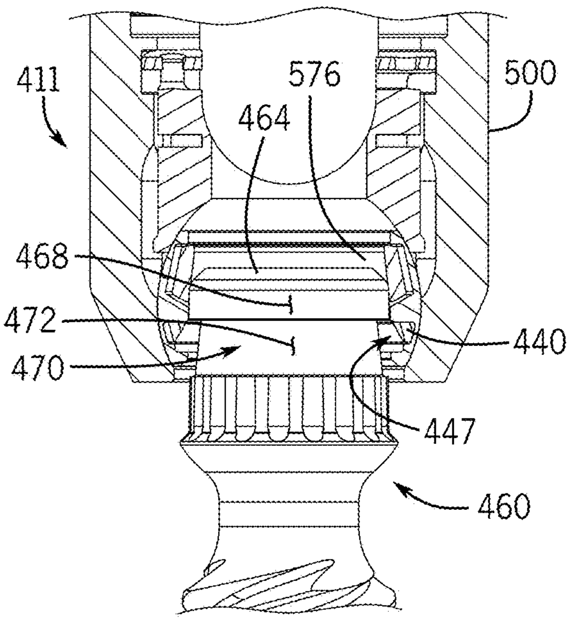

FIG. 170 is a partially cut-away front view of the multiplanar receiver sub-assembly of FIG. 169 moving further downward as the universal capture portion drives the capture ring outward within the recess of the ring retainer and the bone sweep ring scrapes the upper slidable surface of the capture portion.

Figure 171:
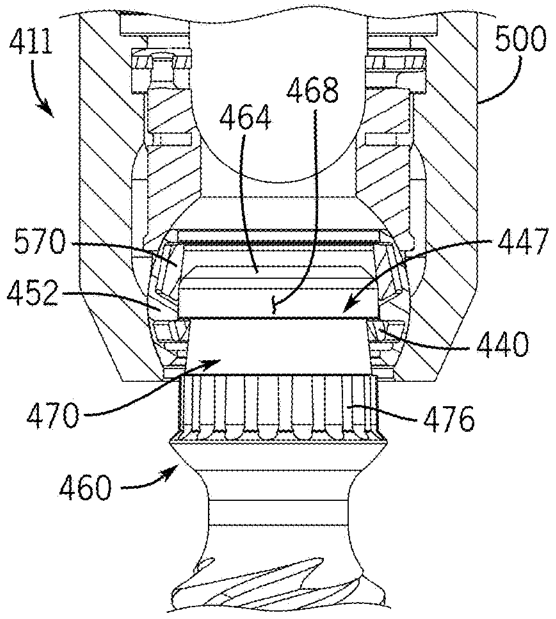

FIG. 171 is a partially cut-away front view of the multiplanar receiver sub-assembly of FIG. 170 moving further downward as the universal capture portion pushes further upward through the capture ring and the bone sweep ring begins to scrape the inner recessed surface of the capture recess.

Figure 172:
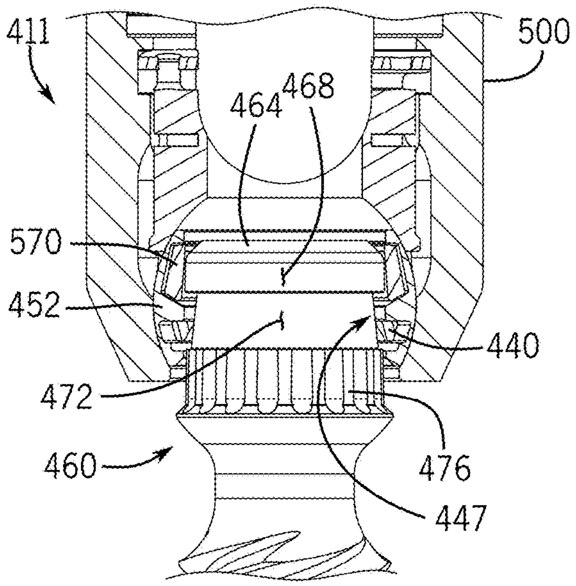

FIG. 172 is a partially cut-away front view of the multiplanar receiver sub-assembly of FIG. 171 moving further downward as the universal capture portion pushes further upward through the capture ring and the bone sweep ring scrapes the inner recessed surface of the capture recess.

Figure 173:
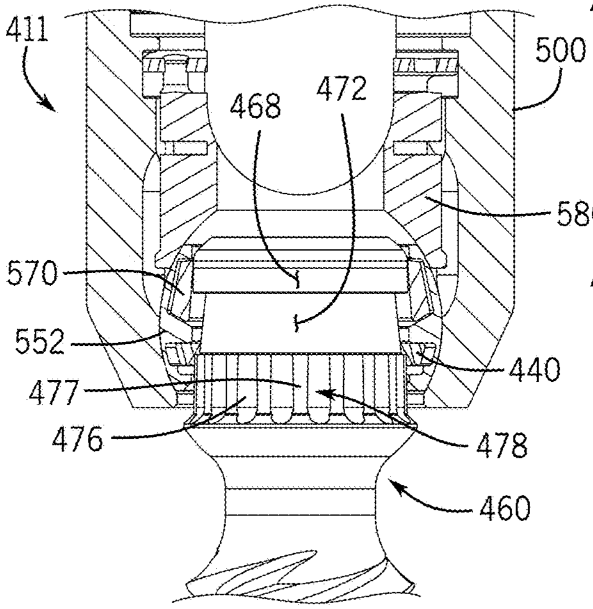

FIG. 173 is a partially cut-away front view of the multiplanar receiver sub-assembly of FIG. 172 moving further downward as the universal capture portion pushes further upward through the capture ring and the bone sweep ring finishes scraping the inner recessed surface of the capture recess.

Figure 174:
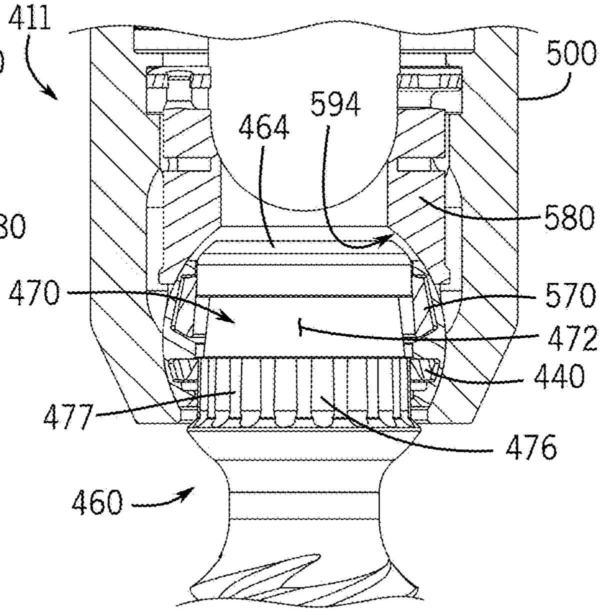

FIG. 174 is a partially cut-away front view of the multiplanar receiver sub-assembly of FIG. 173 moving further downward as the universal capture portion pushes further upward through the capture ring and the bone sweep ring begins to scrape downward across the raised top surfaces of the debris storage pockets.

Figure 175:
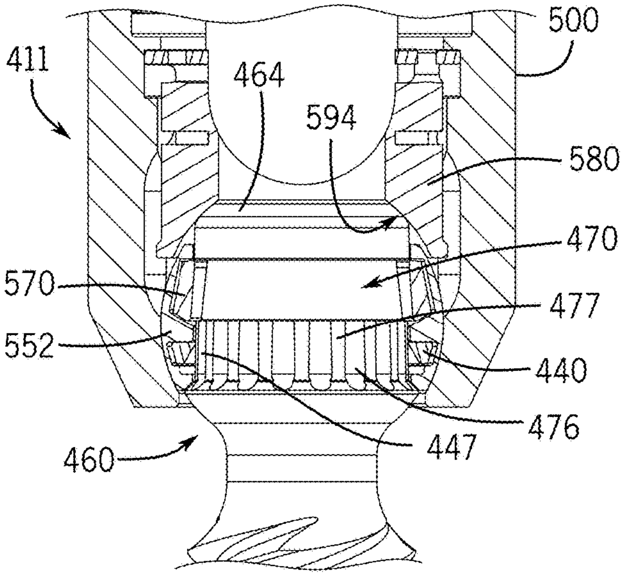

FIG. 175 is a partially cut-away front view of the multiplanar receiver sub-assembly of FIG. 174 moving further downward as the universal capture portion pushes further upward through the seated multiplanar retainer sub-assembly to engage the bottom surface of the pressure insert and the bone sweep ring scrapes downward across the raised top surfaces of the debris storage pockets.

Figure 176:
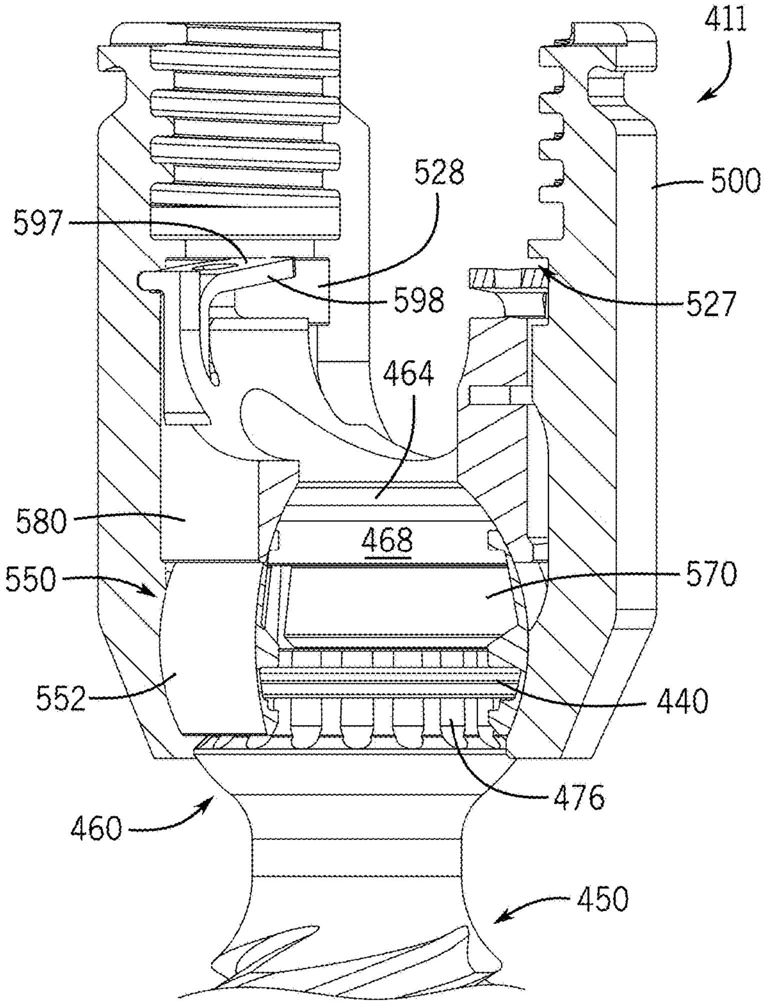

FIG. 176 is a partially cut-away front perspective view of the multiplanar receiver sub-assembly of FIG. 175 moving further downward and the insert moving upward until the capture ring snaps into the retainer recess to capture the universal capture portion within the multiplanar receiver sub-assembly.

Figure 177:
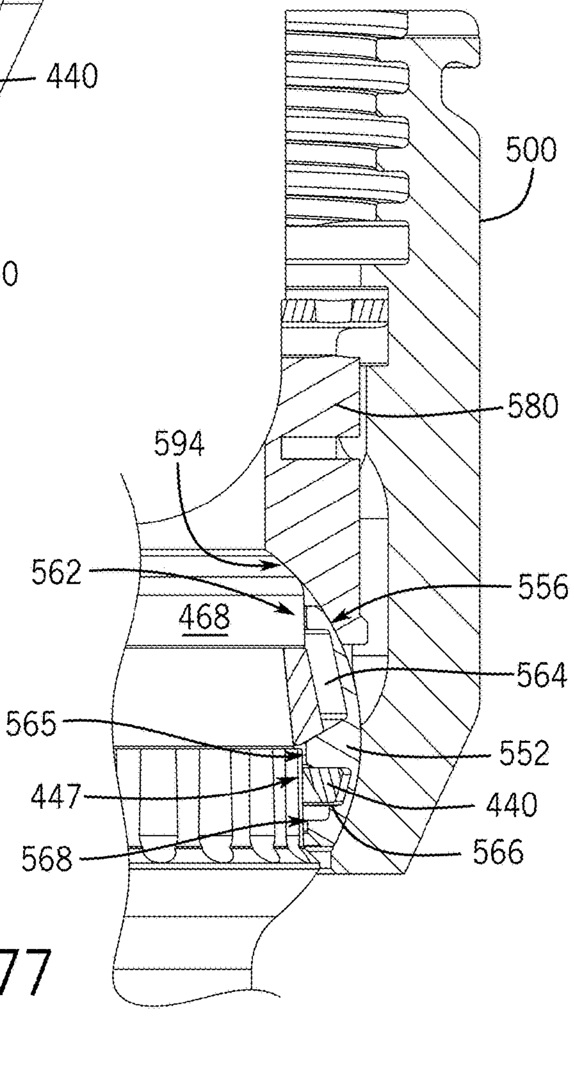

FIG. 177 is a close-up cross-sectional side view of the multiplanar receiver sub-assembly and universal capture portion of FIG. 176.

Figure 178:
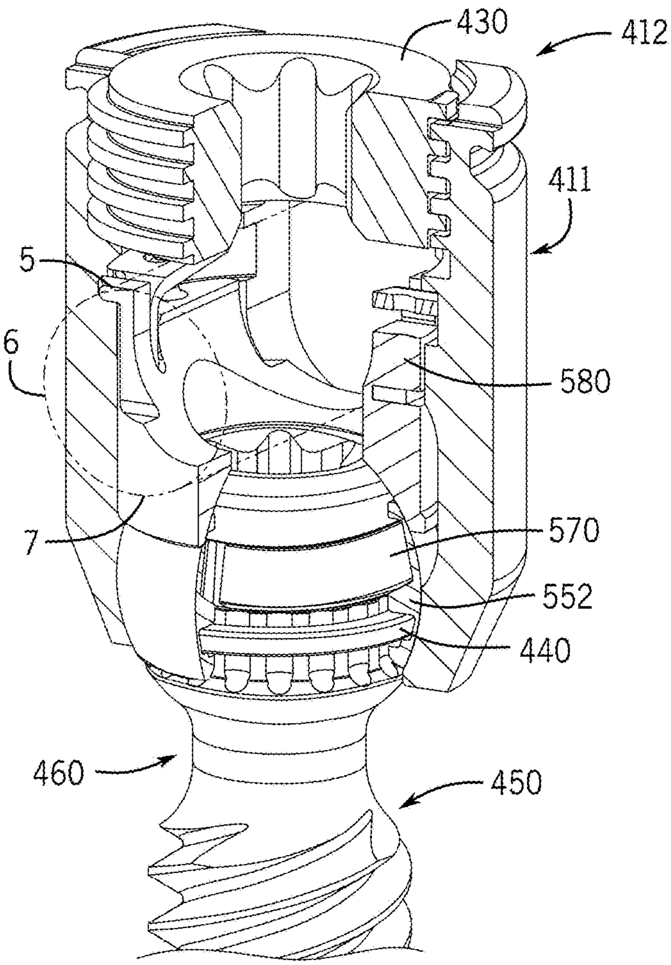

FIG. 178 is a partially cut-away front perspective view of the multiplanar bone anchor assembly with bone debris clearance, fully assembled with the elongate rod and closure and with the bone anchor in a non-articulated position relative to the receiver.

Figure 179:
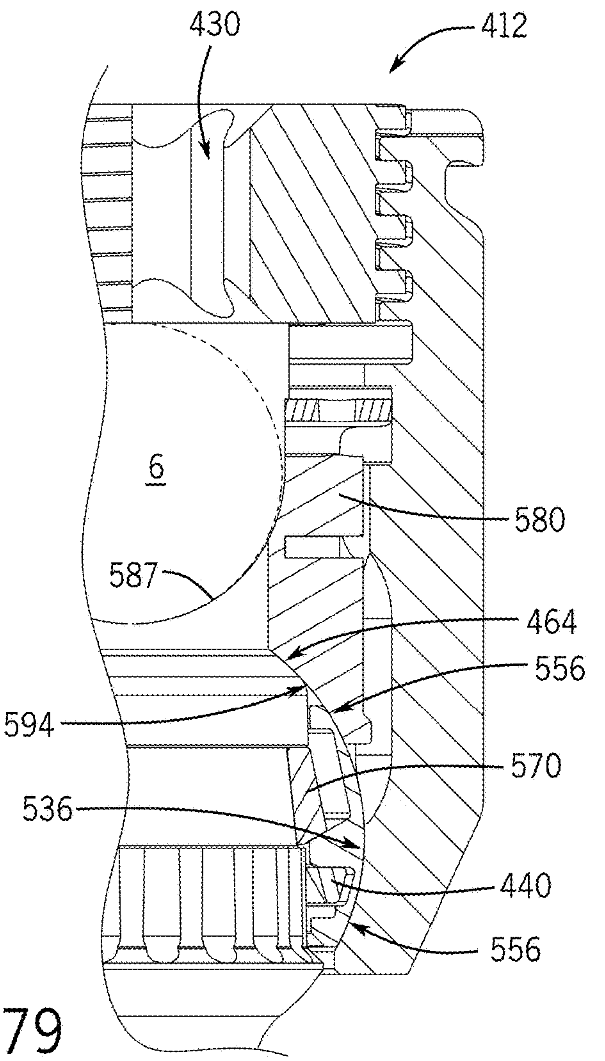

FIG. 179 is a close-up cross-sectional side view of the fully-assembled multiplanar bone anchor assembly of FIG. 178.

Figure 180:
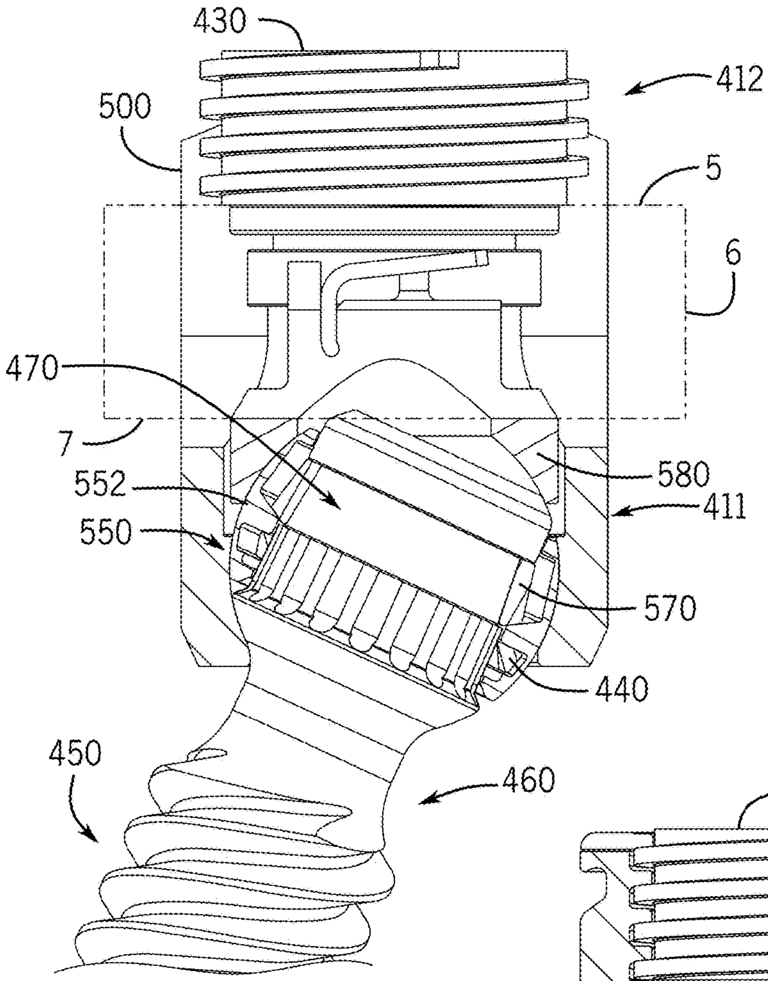

FIG. 180 is a cross-sectional side view of the fully-assembled multiplanar bone anchor assembly of FIG. 178, with the bone anchor in an articulated position relative to the receiver.

Figure 181:
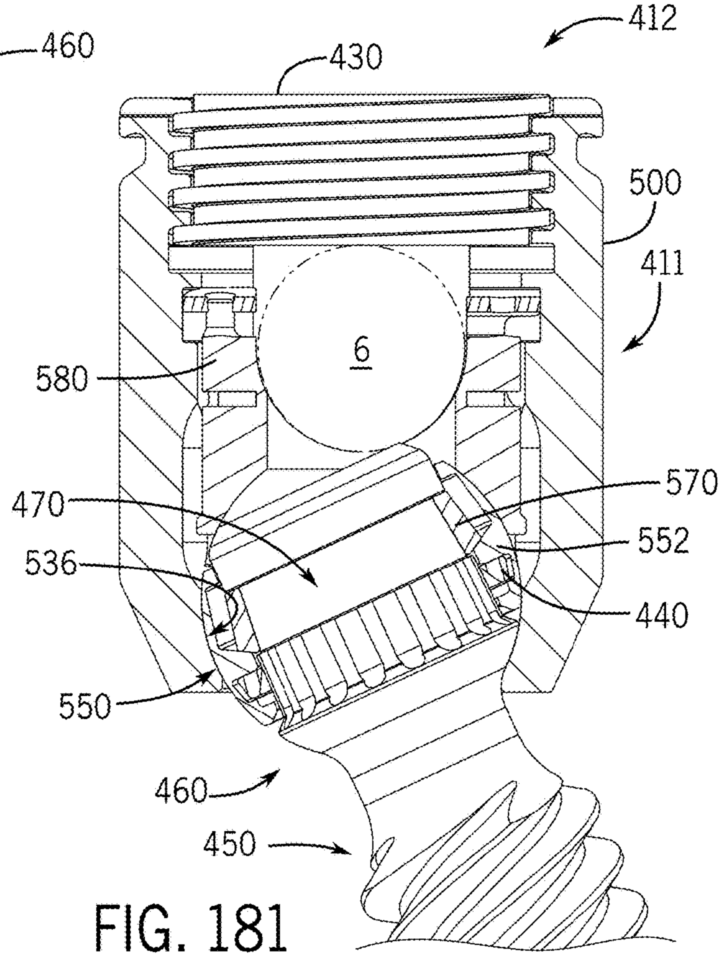

FIG. 181 is a cross-sectional front view of the fully-assembled multiplanar bone anchor assembly of FIG. 178, with the bone anchor in another articulated position relative to the receiver.

Figure 125:
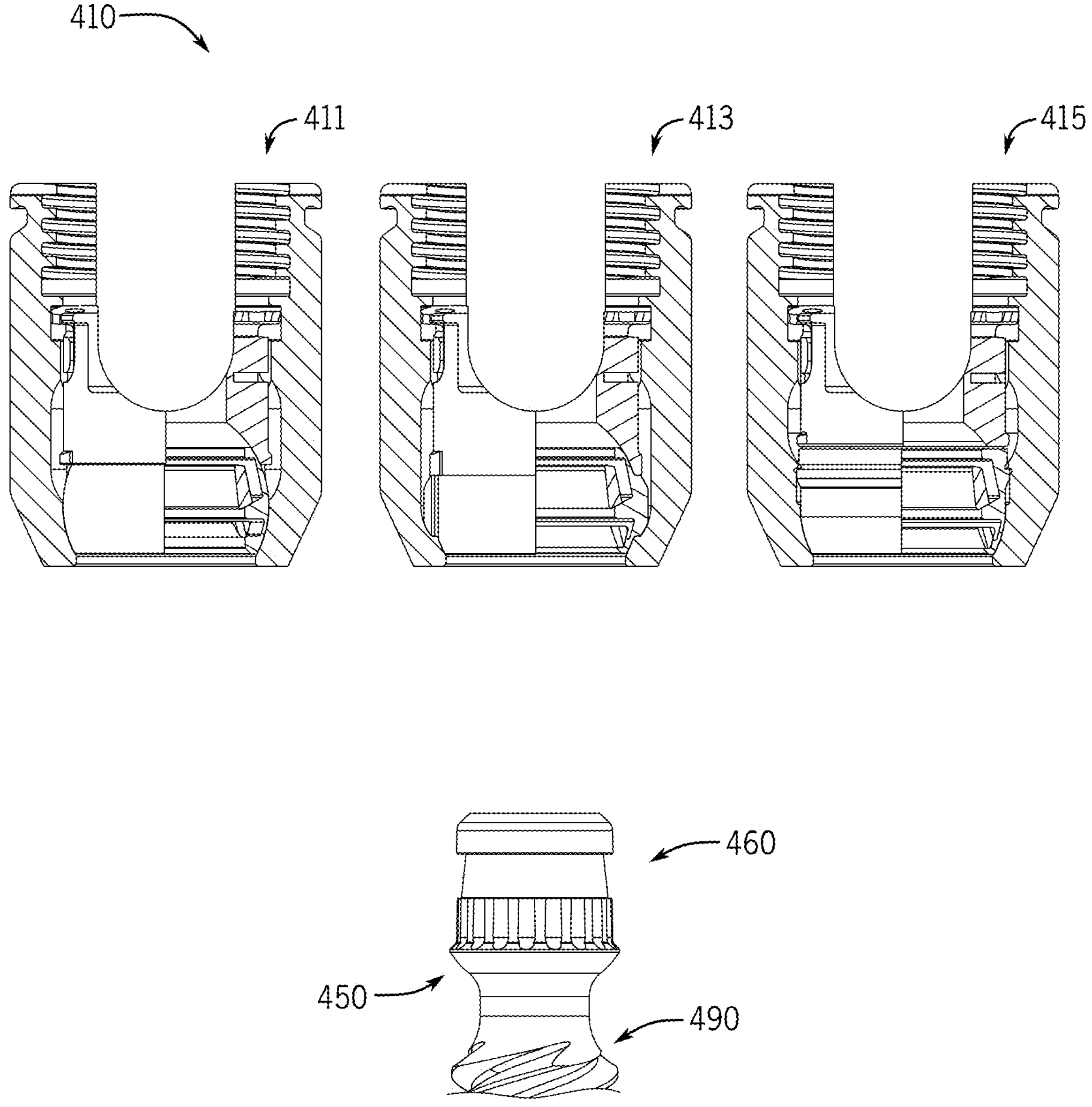
Figure 182:
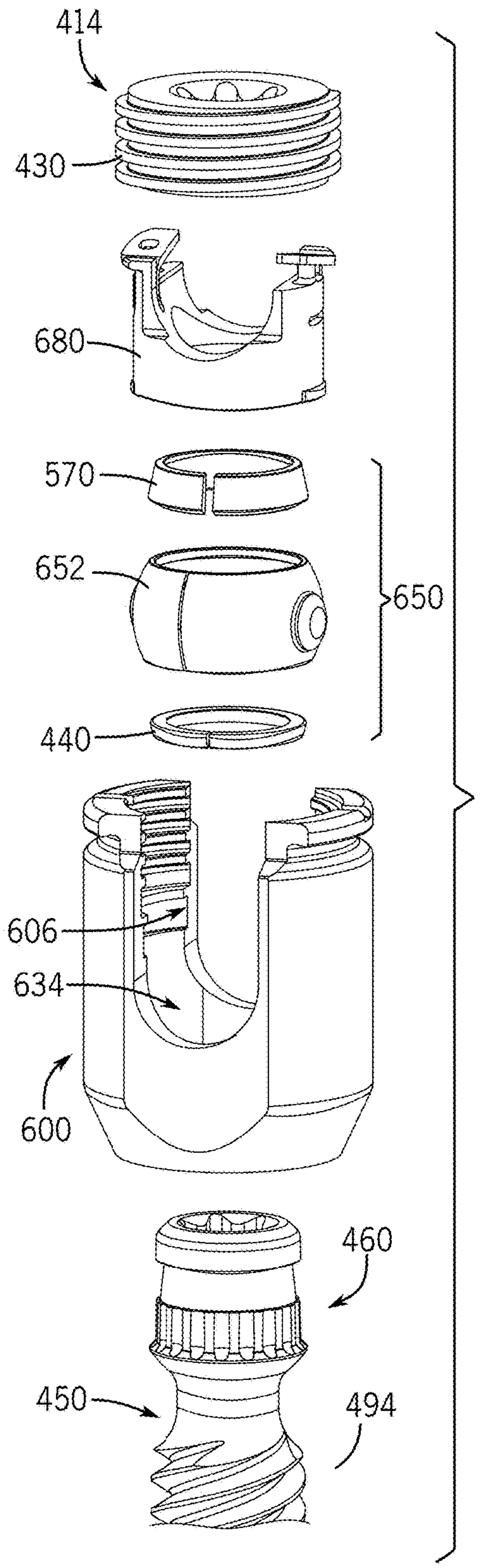

FIG. 182 is an exploded perspective view of a monoplanar embodiment of a bone anchor assembly with bone debris clearance, in accordance with the representative embodiment of the multi-component spinal fixation system shown in FIG. 125.

Figure 183:
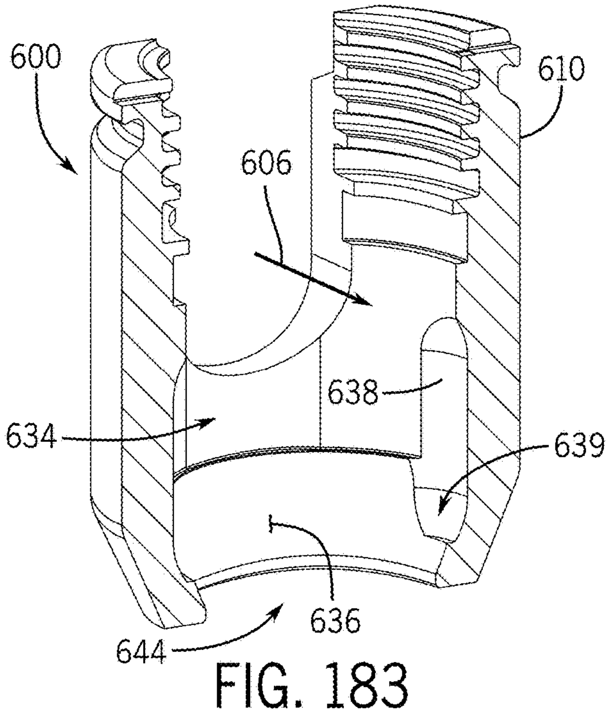

FIG. 183 is a cross-sectional perspective view of the receiver of the monoplanar bone anchor assembly of FIG. 182.

Figure 184:
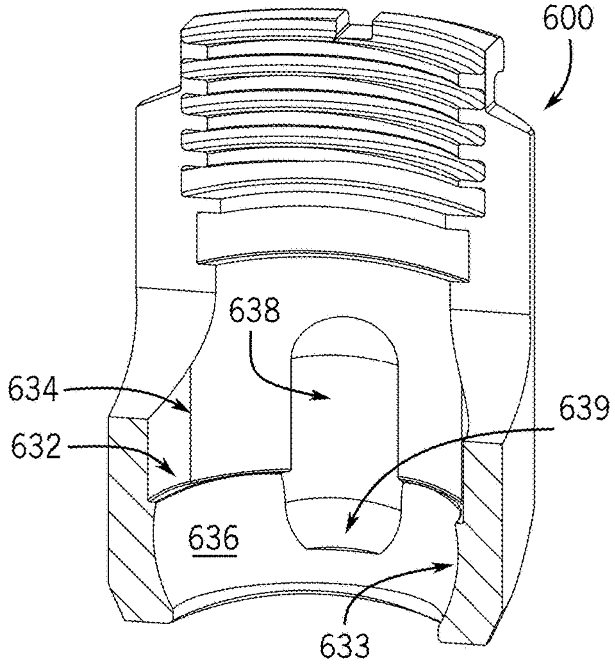

FIG. 184 is another cross-sectional perspective view of the receiver of FIG. 182.

Figure 185:
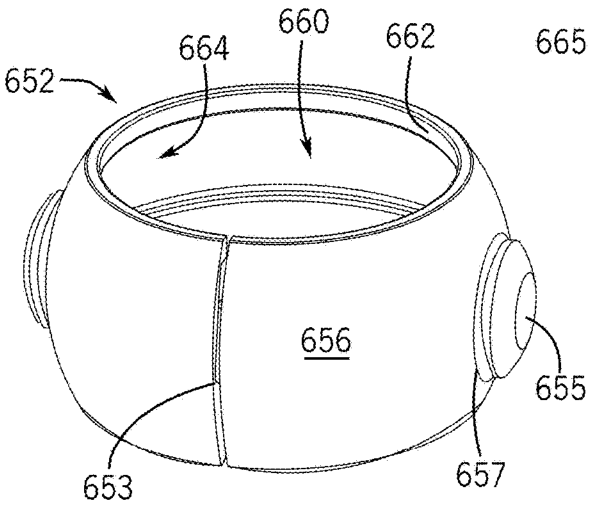

FIG. 185 is a perspective view of the ring retainer of the monoplanar bone anchor assembly of FIG. 182.

Figure 186:
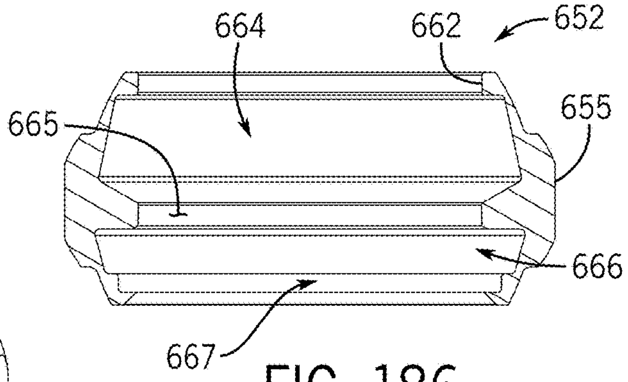

FIG. 186 is a cross-sectional side view of the ring retainer of FIG. 185.

Figure 187:
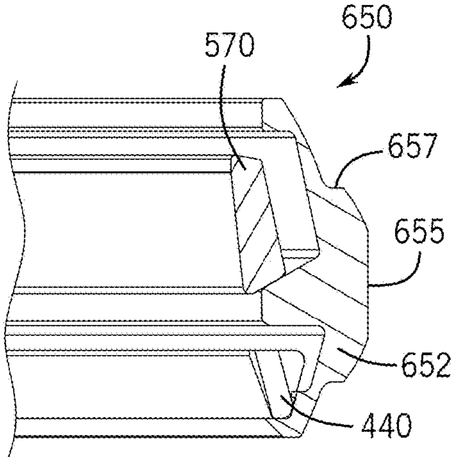

FIG. 187 is a close-up cross-sectional front view of the ring retainer, bone sweep ring, and capture ring of FIG. 182 after assembly together into the monoplanar retainer sub-assembly.

Figure 188:
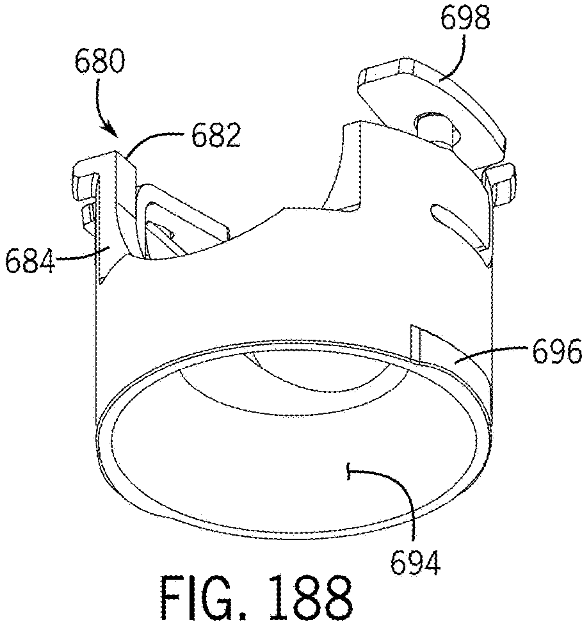

FIG. 188 is a bottom perspective view of the pressure insert of the monoplanar bone anchor assembly of FIG. 182.

Figure 189:
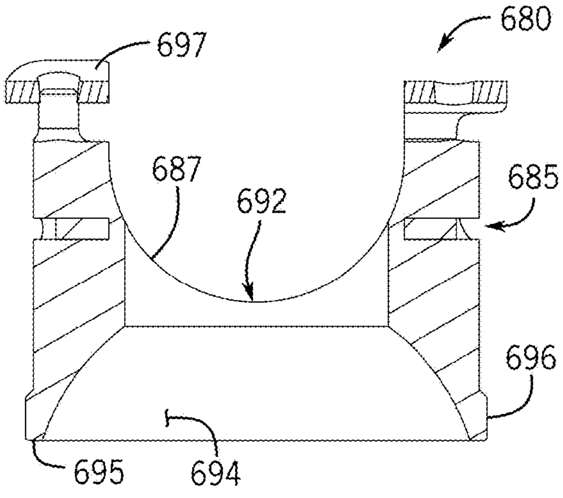

FIG. 189 is a cross-sectional front view of the pressure insert of the monoplanar bone anchor assembly of FIG. 182.

Figure 190:
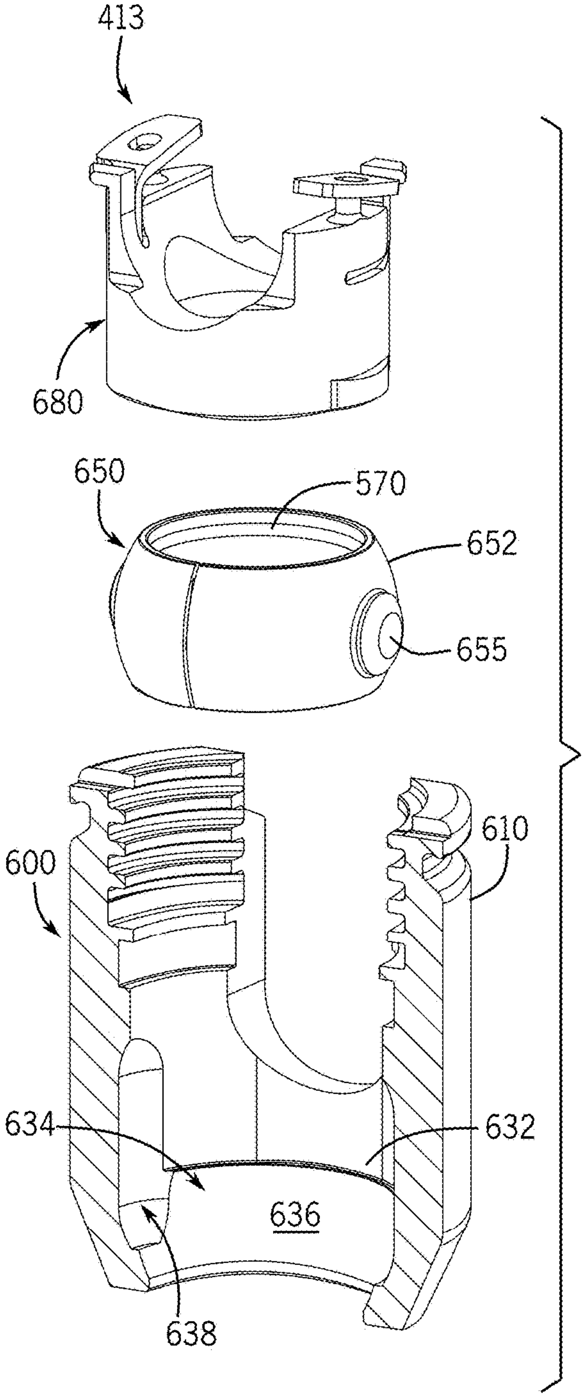

FIG. 190 is an exploded partially cut-away perspective view of the components of a monoplanar receiver sub-assembly with bone debris clearance, prior to their pre-assembly into a shipping configuration with the receiver.

Figure 191:
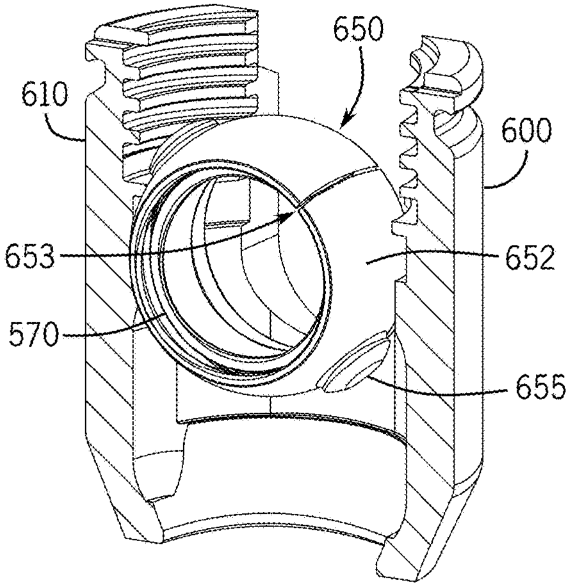

FIG. 191 is a partially cut-away perspective view of the receiver of FIG. 190 with vertically-oriented monoplanar retainer sub-assembly being downloaded through the open channel of the receiver.

Figure 192:
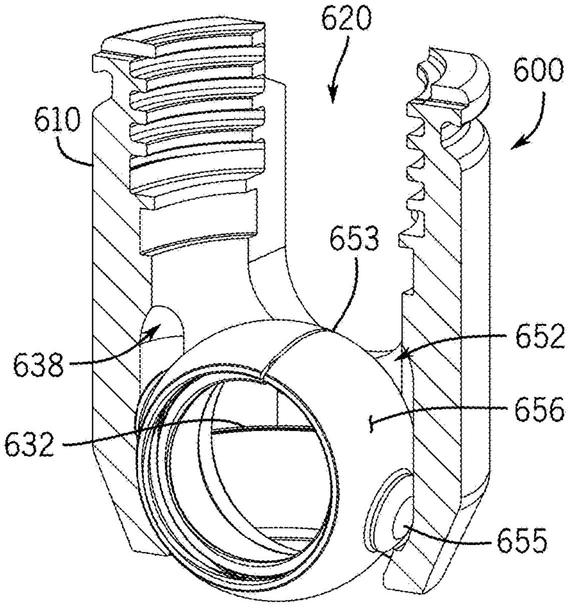

FIG. 192 is a partially cut-away perspective view of the receiver of FIG. 192 with the vertically-oriented multiplanar retainer sub-assembly contacting the upper edge of the seat surface of the receiver.

Figure 193:
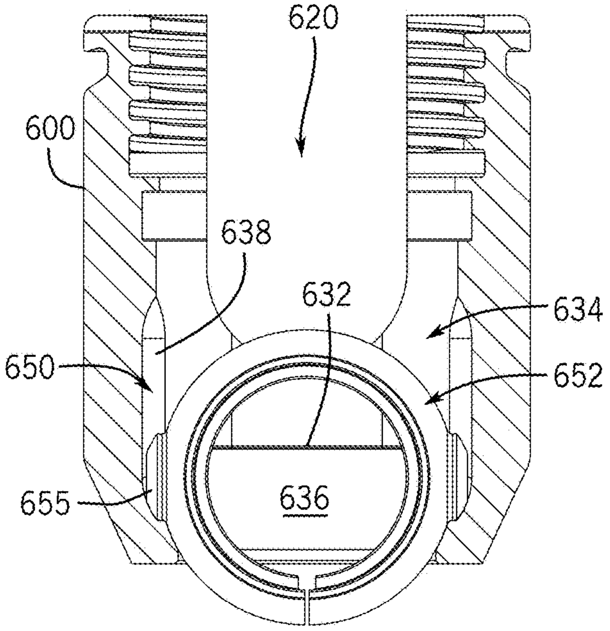

FIG. 193 is a partially cut-away front view of the receiver of FIG. 192 with the vertically-oriented monoplanar retainer sub-assembly being somewhat resiliently compressed and pushed down into a vertical partially-seated engagement with the seat surface of the receiver.

Figure 194:
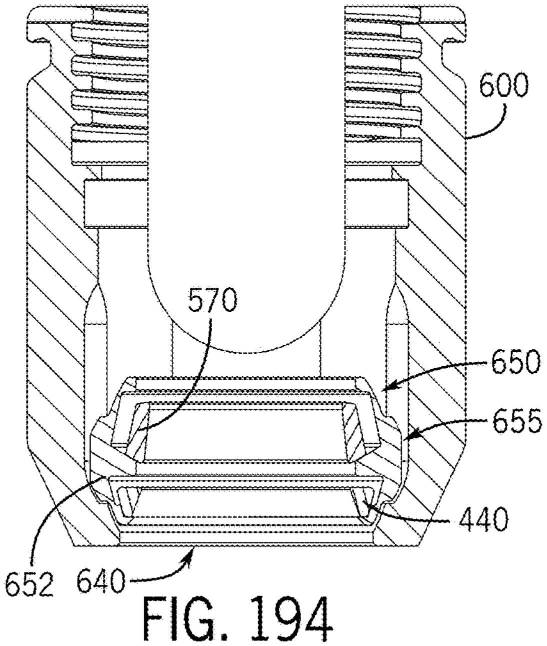

FIG. 194 is a cross-sectional front view of the receiver of FIG. 193 with the monoplanar retainer sub-assembly being rotated to a horizontal fully-seated engagement the seat surface of the receiver.

Figure 195:
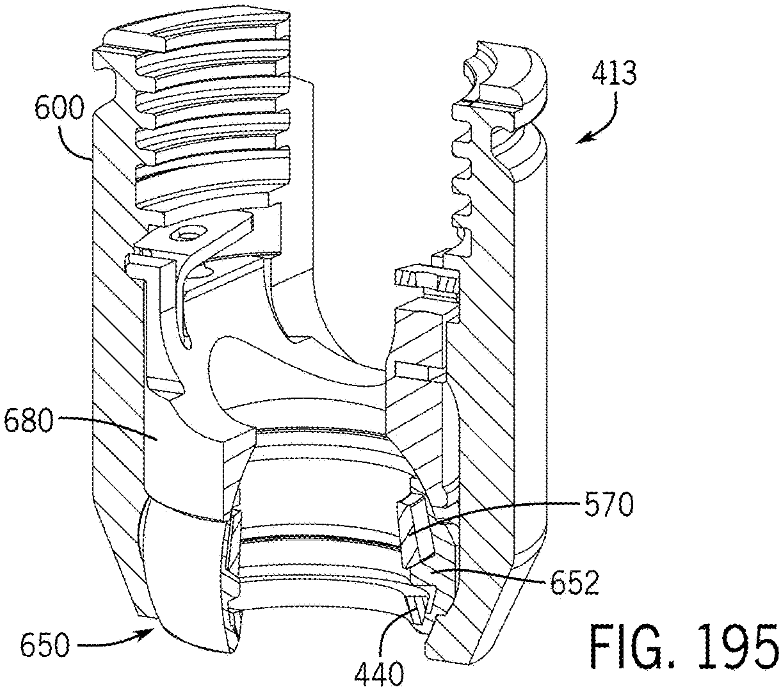

FIG. 195 is a partially cut-away perspective view of the receiver with the seated monoplanar retainer sub-assembly and the monoplanar pressure insert being fully rotated therein to form a pre-assembled monoplanar receiver sub-assembly with bone debris clearance in the shipping state.

Figure 196:
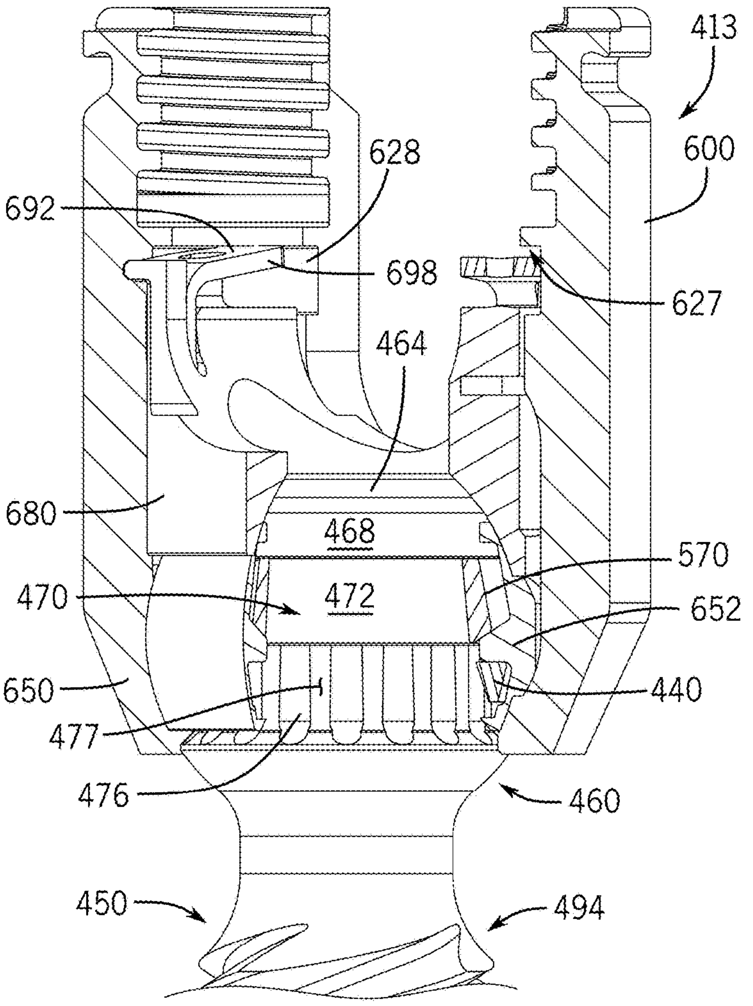

FIG. 196 is a partially cut-away front perspective view of the monoplanar receiver sub-assembly of FIG. 195 with bone debris clearance having the universal capture portion fully captured within the monoplanar retainer sub-assembly.

Figure 197:
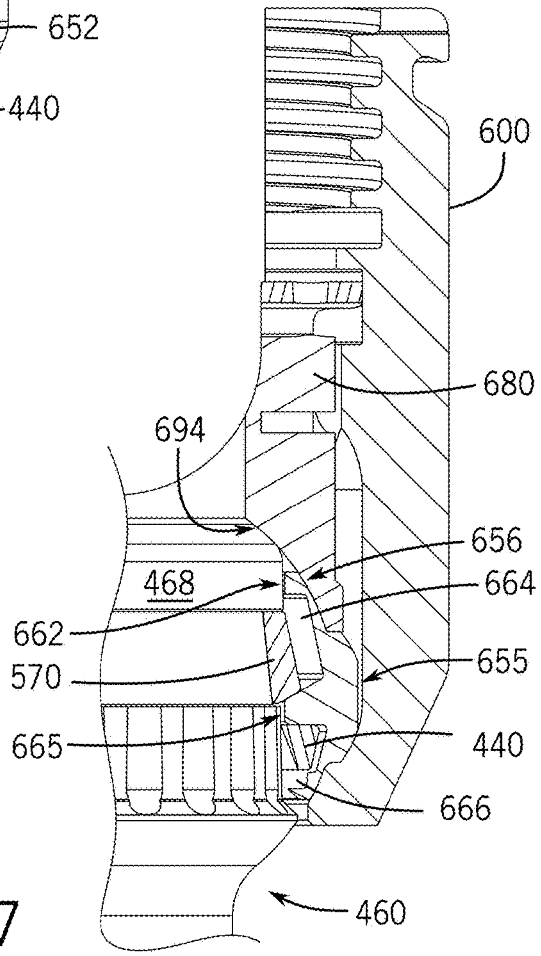

FIG. 197 is a close-up cross-sectional side view of the monoplanar receiver sub-assembly and universal capture portion of FIG. 196.

Figure 198:
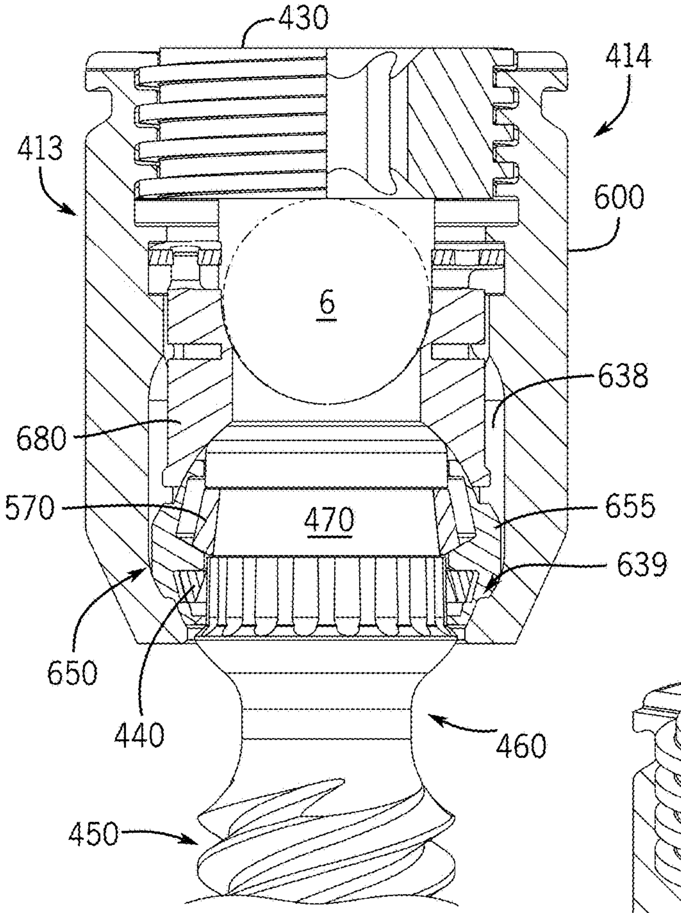

FIG. 198 is cross-sectional front view of the monoplanar bone anchor assembly with bone debris clearance, fully assembled with the elongate rod and closure and with the bone anchor in a non-articulated position relative to the receiver.

Figure 199:
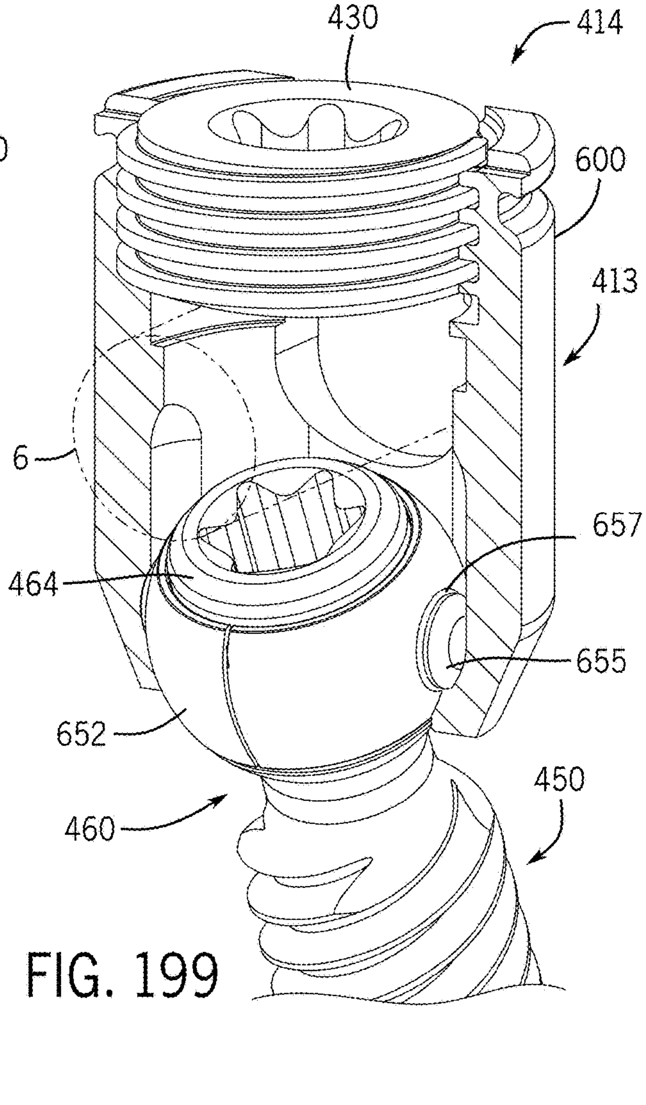

FIG. 199 is a partially cut-away front perspective view of the fully-assembled monoplanar bone anchor assembly of FIG. 198.

Figure 200:
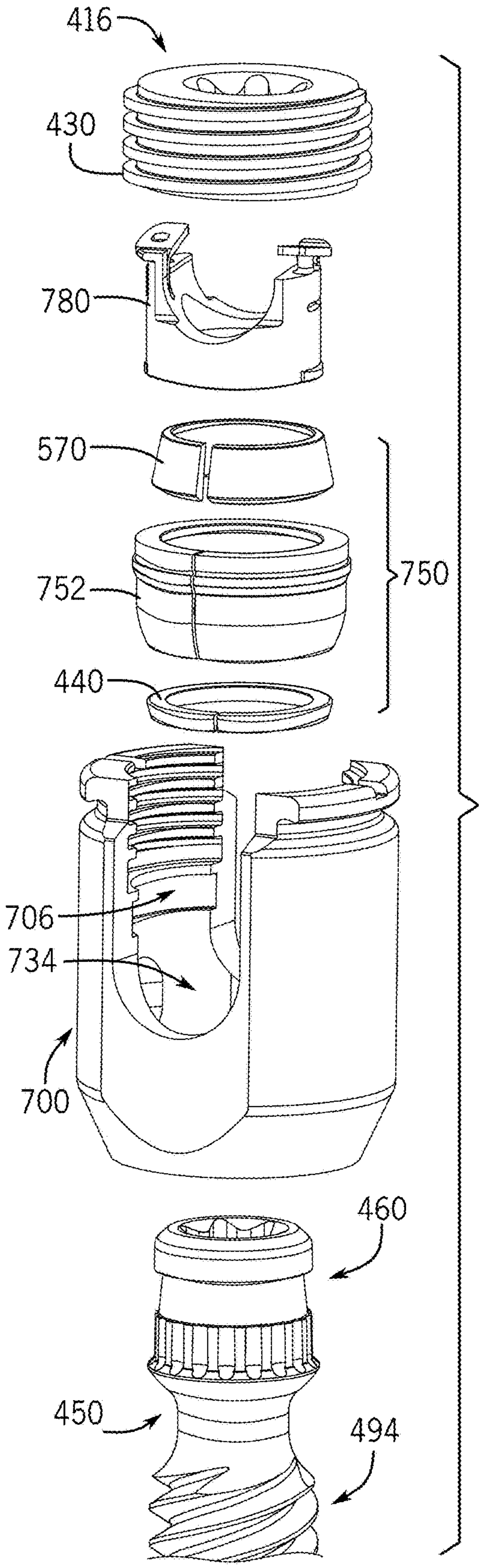

FIG. 200 is an exploded perspective view of a monoaxial embodiment of a bone anchor assembly with bone debris clearance, in accordance with the representative embodiment of the multi-component spinal fixation system shown in FIG. 125.

Figure 201:
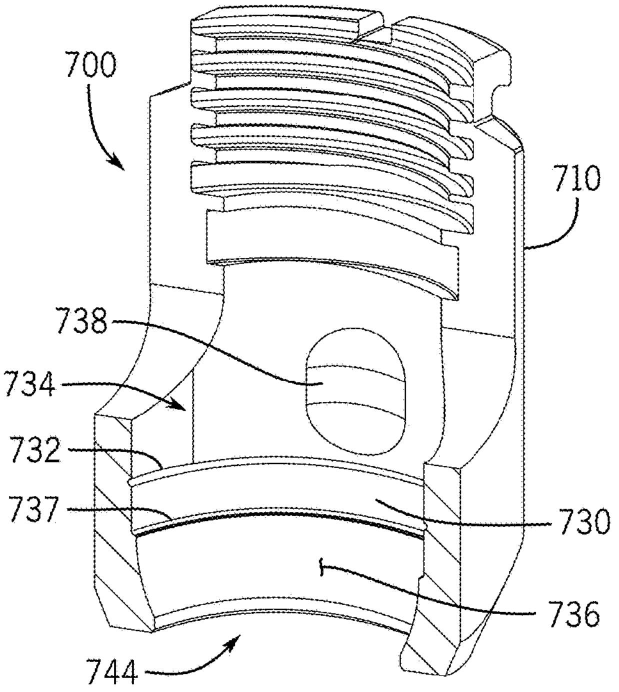

FIG. 201 is a cross-sectional perspective view of the receiver of the monoaxial bone anchor assembly of FIG. 200.

Figure 202:
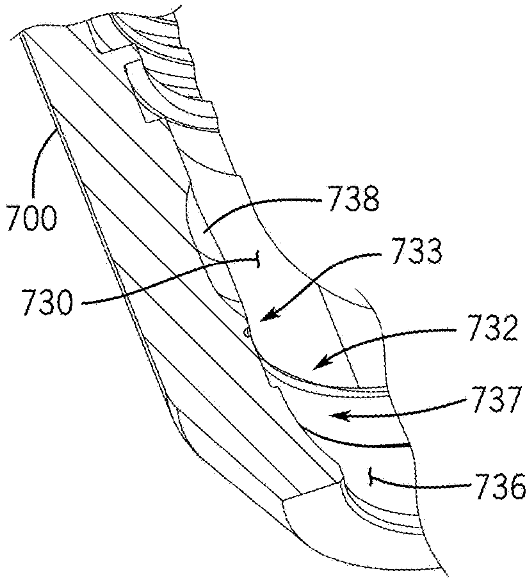

FIG. 202 is a close up perspective view of the cavity of the receiver of FIG. 201.

Figure 203:
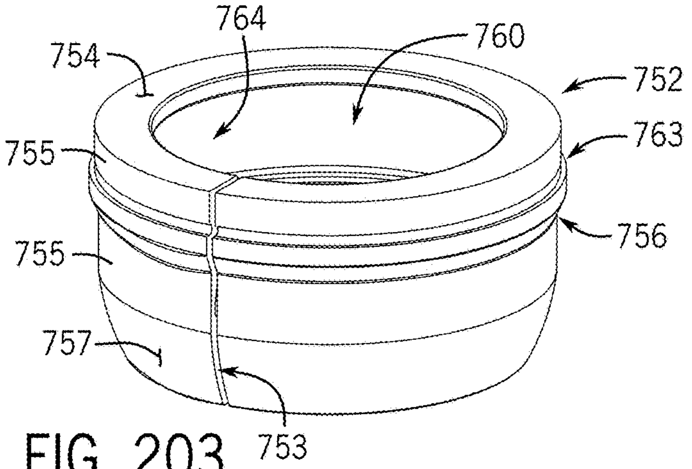

FIG. 203 is a perspective view of the ring retainer of the monoaxial bone anchor assembly of FIG. 200.

Figure 204:
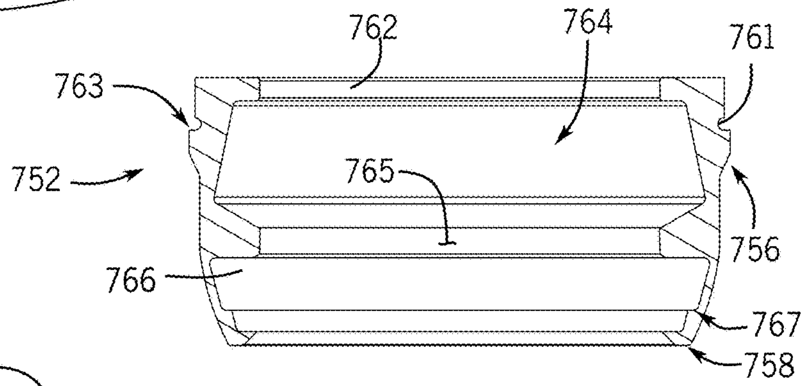

FIG. 204 is a cross-sectional side view of the ring retainer of FIG. 203.

Figure 205:
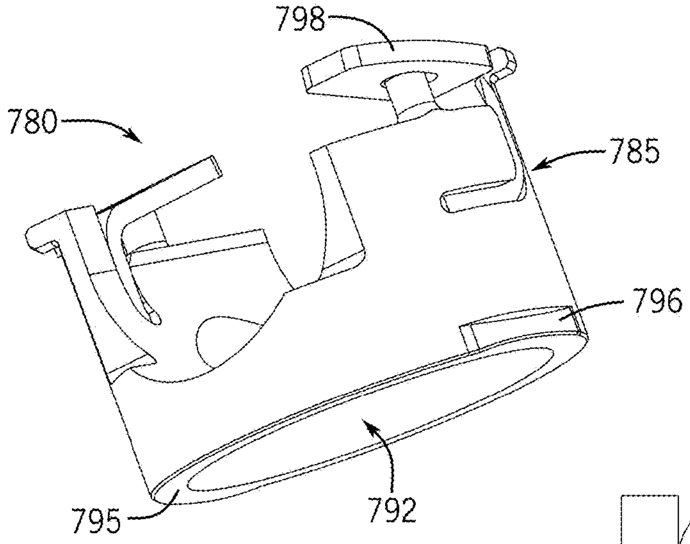

FIG. 205 is a side perspective view of the pressure insert of the monoaxial bone anchor assembly of FIG. 200.

Figure 206:
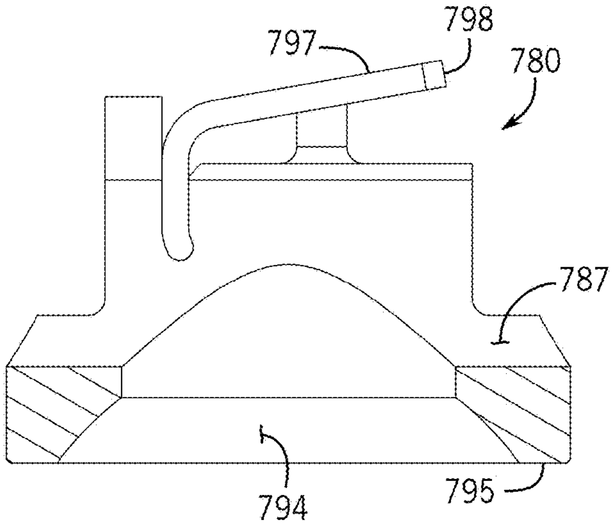

FIG. 206 is a cross-sectional side view of the pressure insert of the monoaxial bone anchor assembly of FIG. 205.

Figure 207:
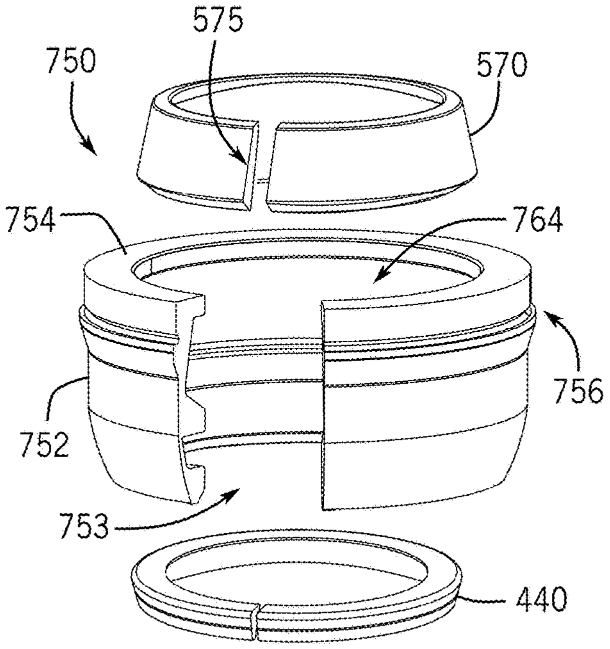

FIG. 207 is a perspective view of the ring retainer, the bone sweep ring, and the capture ring of FIG. 200 prior to assembly together into a monoaxial retainer sub-assembly.

Figure 208:
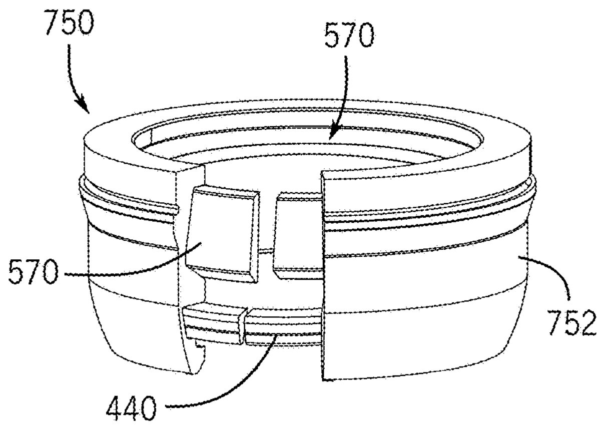

FIG. 208 is partially cut-away perspective view of the ring retainer, bone sweep ring, and capture ring of FIG. 207 after assembly together into the monoaxial retainer sub-assembly.

Figure 209:
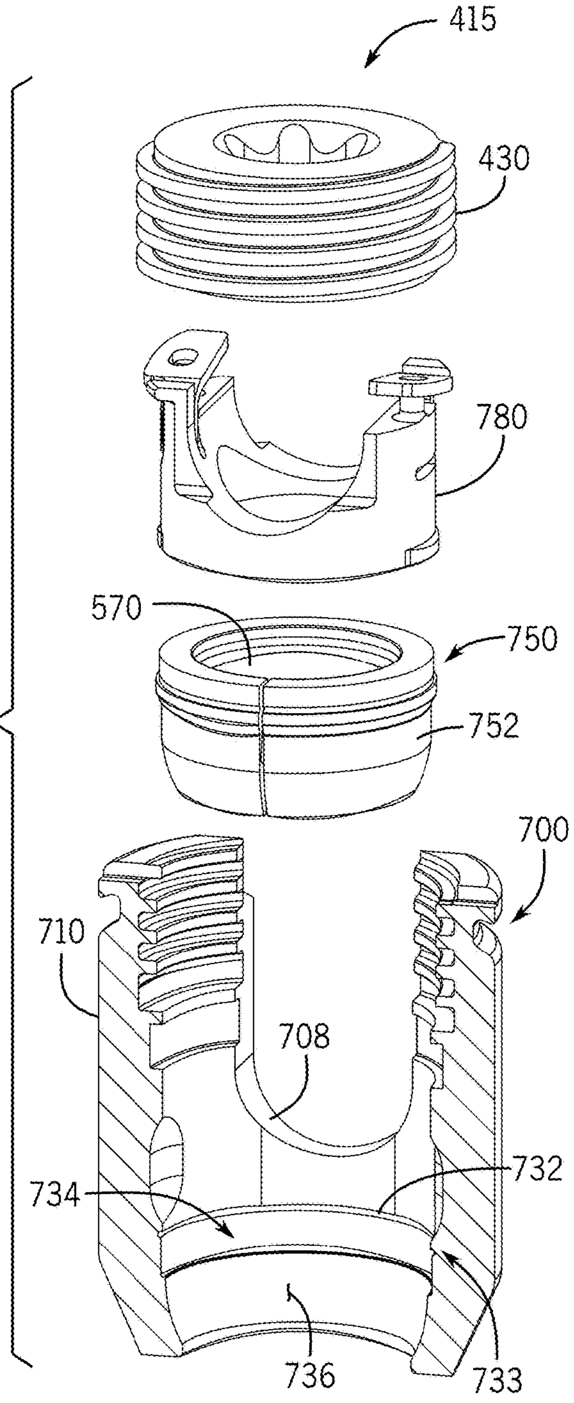

FIG. 209 is an exploded partially cut-away perspective of the components of a monoaxial receiver sub-assembly with bone debris clearance, prior to their pre-assembly into a shipping configuration with the receiver.

Figure 210:
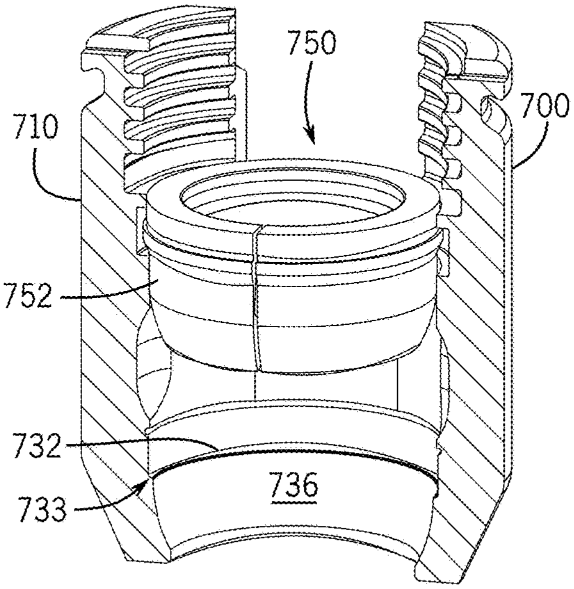

FIG. 210 is a partially cut-away front perspective view of the receiver of FIG. 209 with the horizontally-oriented monoaxial retainer sub-assembly being downloaded through the channel of the receiver.

Figure 211:
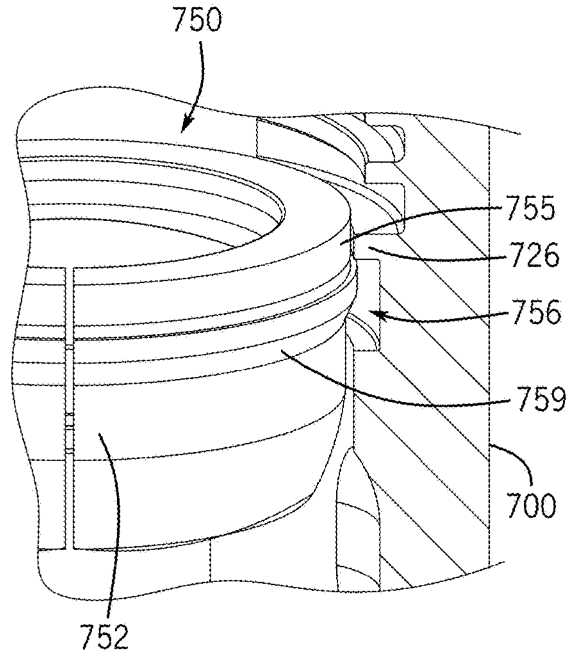

FIG. 211 is a close-up partially cut-away front perspective view of the receiver and the monoaxial retainer sub-assembly of FIG. 210.

Figure 212:
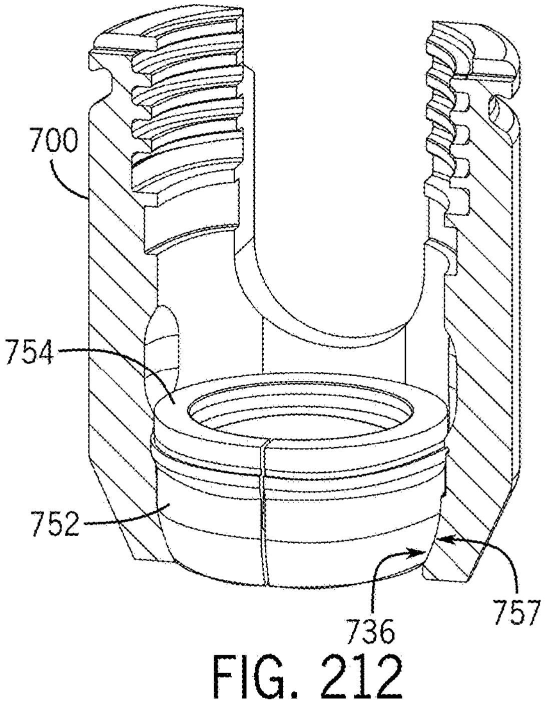

FIG. 212 is a partially cut-away front perspective view of the receiver of FIG. 210 with the monoaxial retainer sub-assembly being pressed down into engagement with the seat surface of the receiver.

Figure 213:
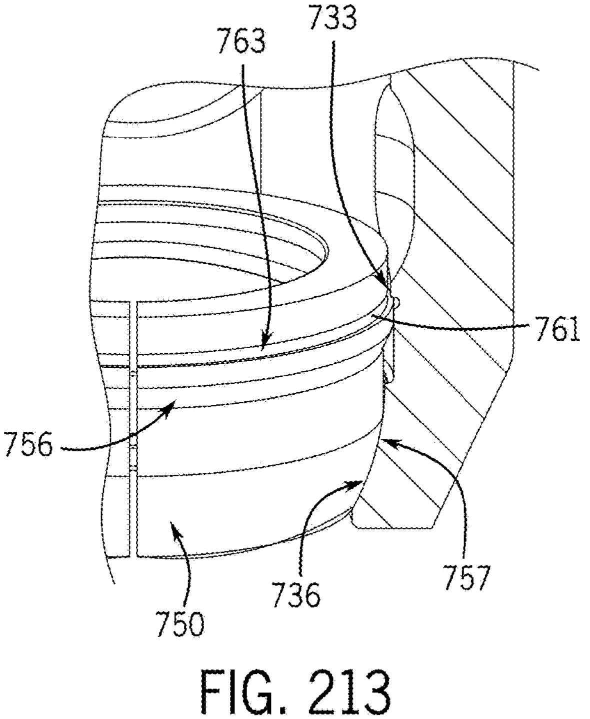

FIG. 213 is a close-up partially cut-away front perspective view of the receiver and the monoaxial retainer sub-assembly of FIG. 212.

Figure 214:
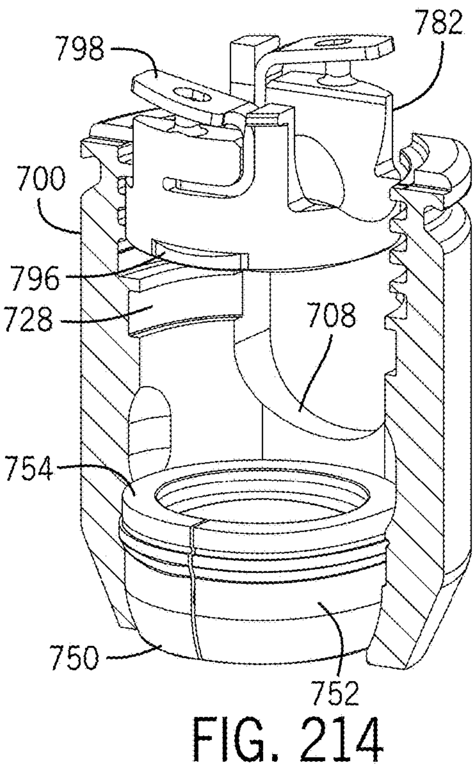

FIG. 214 is a partially cut-away front perspective view of the receiver and seated monoaxial retainer sub-assembly of 212, with the monoaxial pressure insert being downloaded through the open channel of the receiver.

Figure 215:
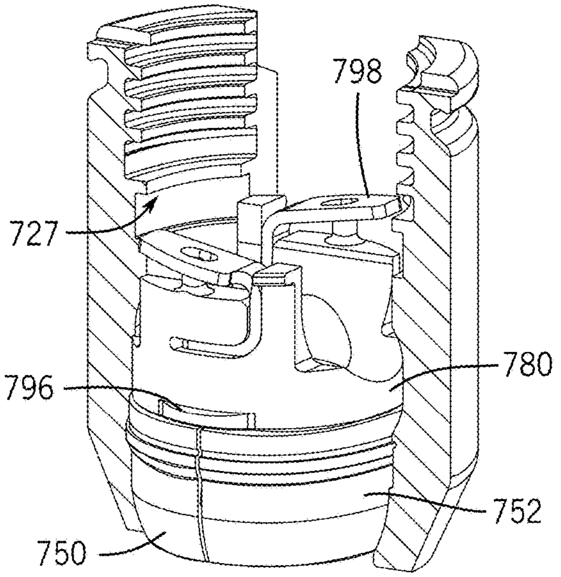

FIG. 215 is a partially cut-away front perspective view of the receiver and seated monoaxial retainer sub-assembly of 214, with the monoaxial pressure insert being further downloaded into the cavity of the receiver to engage the ring retainer.

Figure 216:
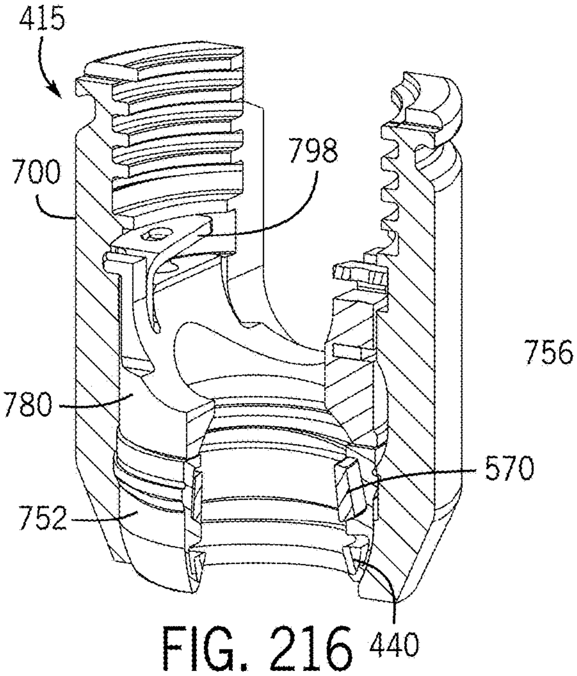

FIG. 216 is a partially cut-away front perspective view of the receiver and seated monoaxial retainer sub-assembly of 215, with the monoaxial pressure insert being fully rotated therein to form a pre-assembled monoaxial receiver sub-assembly in the shipping state position.

Figure 217:
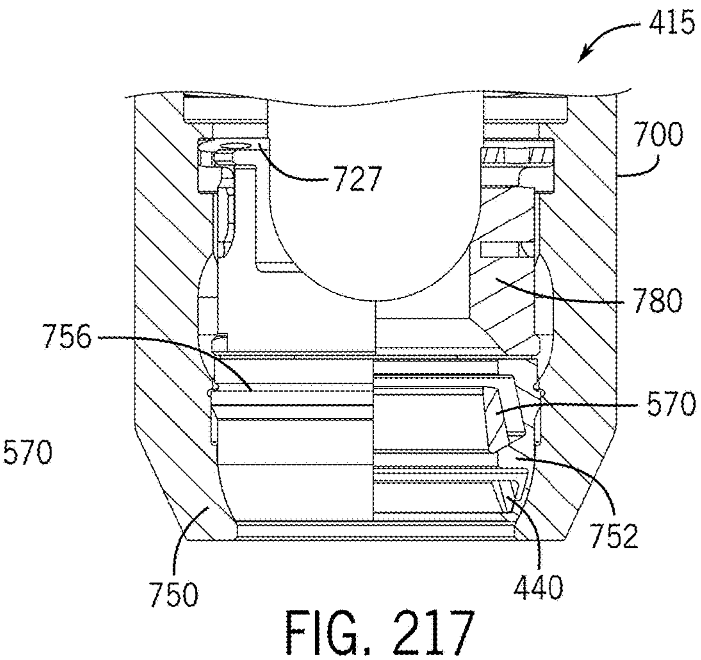

FIG. 217 is a partially cut-away front view of the pre-assembled monoaxial receiver sub-assembly in the shipping state position of FIG. 216.

Figure 218:
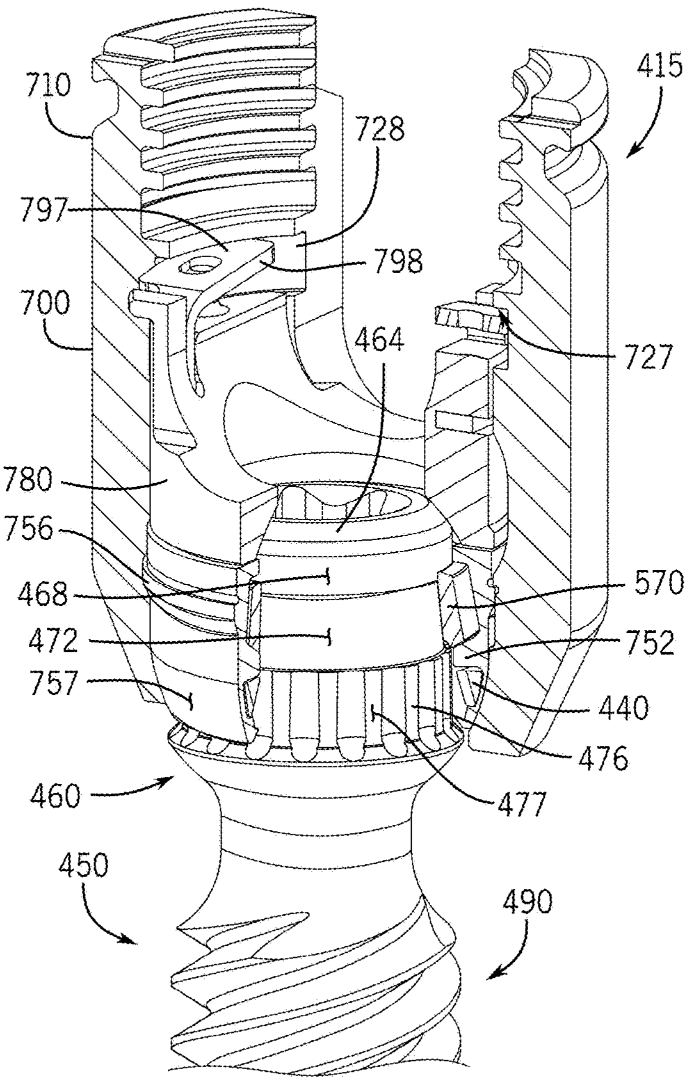

FIG. 218 is a partially cut-away front perspective view of the monoaxial receiver sub-assembly of FIG. 217 with bone debris clearance having the universal capture portion fully captured within the monoaxial retainer sub-assembly.

Figure 219:
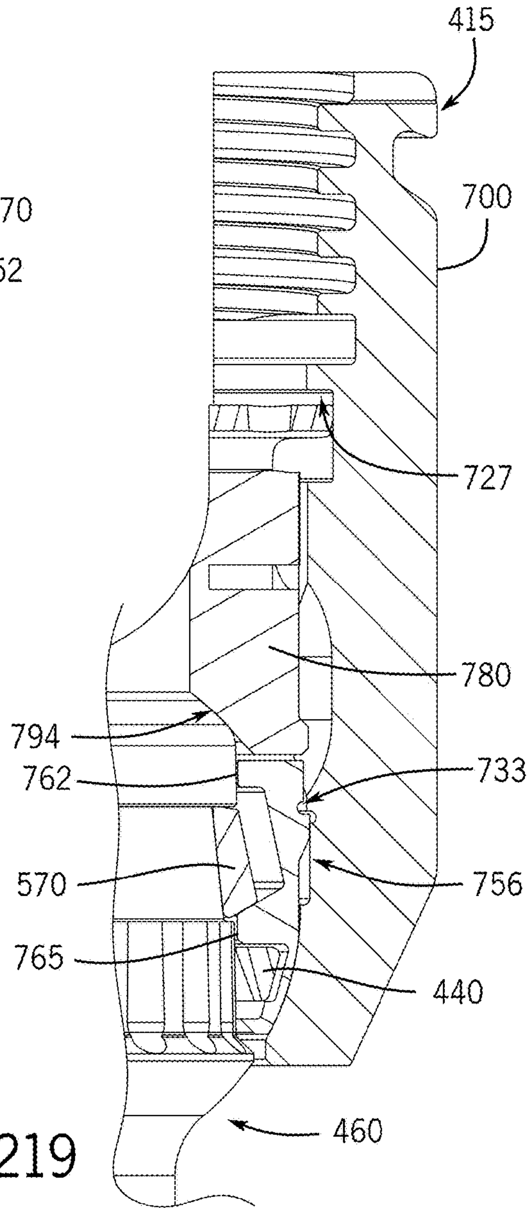

FIG. 219 is a close-up cross-sectional side view of the monoaxial receiver sub-assembly and universal capture portion of FIG. 218.

Figure 220:
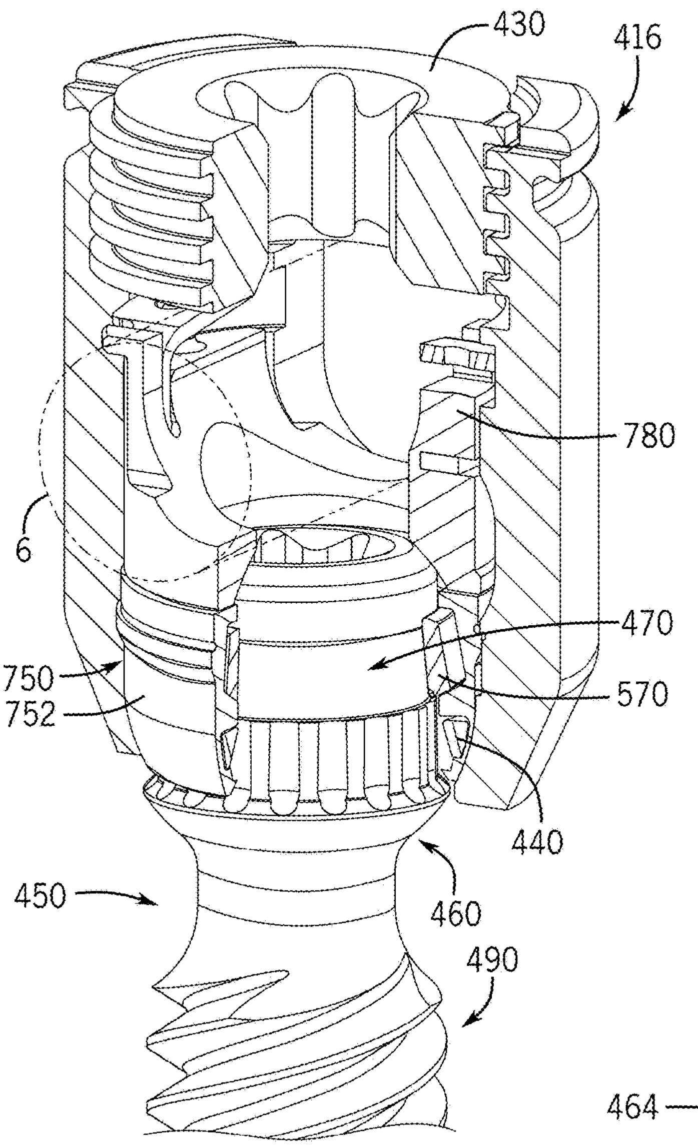

FIG. 220 is a partially cut-away front perspective view of the monoaxial bone anchor assembly with bone debris clearance, fully assembled with the elongate rod and closure and with the bone anchor in a non-articulated position relative to the receiver.

Figure 221:
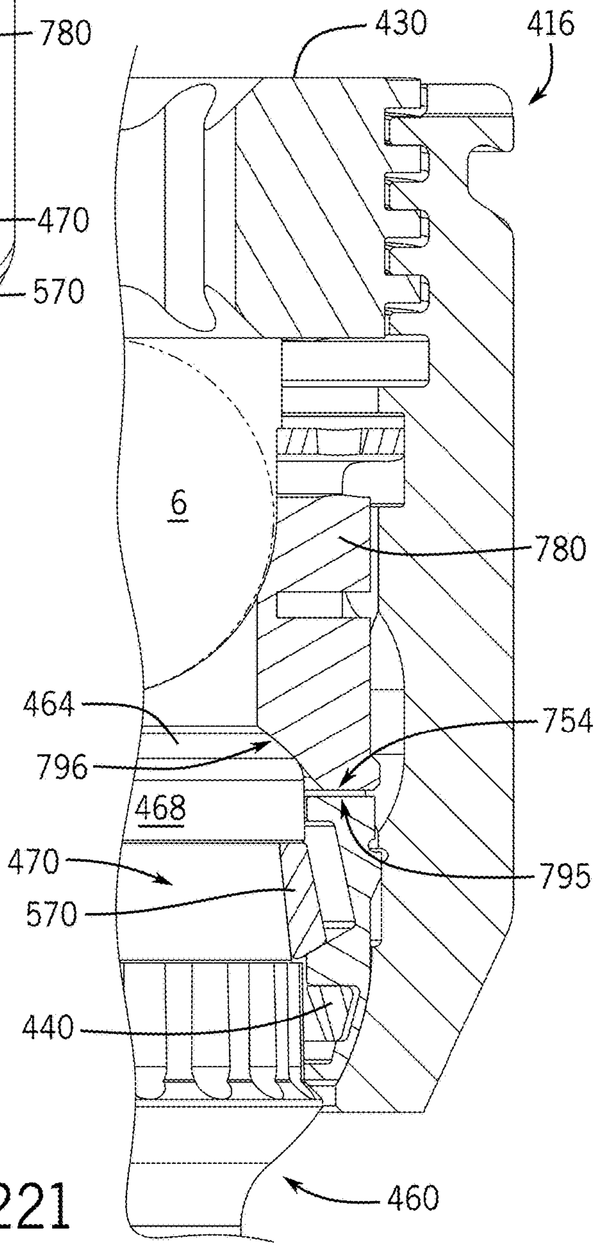

FIG. 221 is a close-up cross-sectional side view of the fully-assembled monoaxial bone anchor assembly of FIG. 220.

Figure 222:
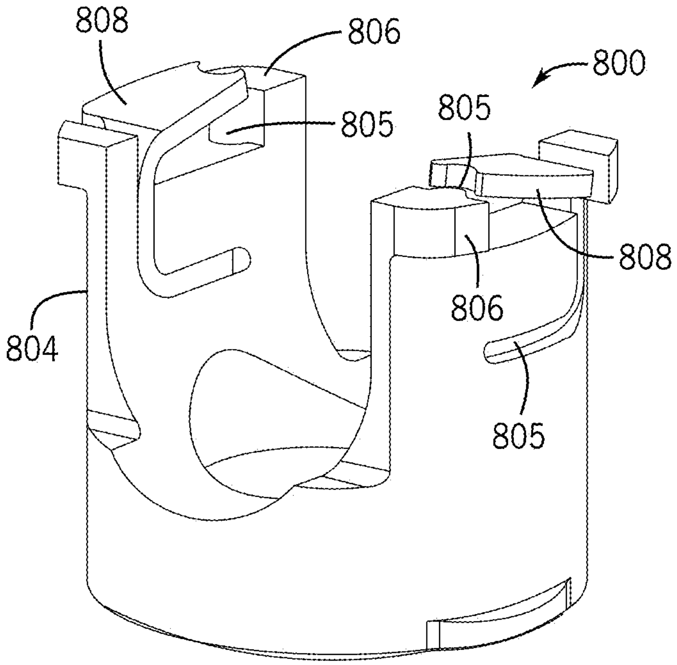

FIG. 222 is a top perspective view of another multipiece pressure insert with non-integral spring elements or clips that could be modified for use with any embodiment of bone anchor assembly described above, in accordance with another representative embodiment of the present disclosure.

Figure 223:
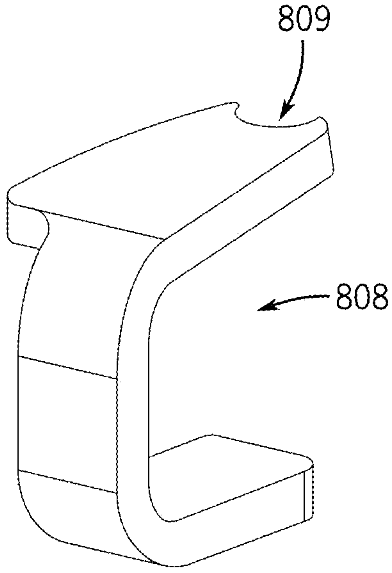

FIG. 223 is a close-up perspective view of the U-shaped non-integral spring element of FIG. 222.

Figure 224:
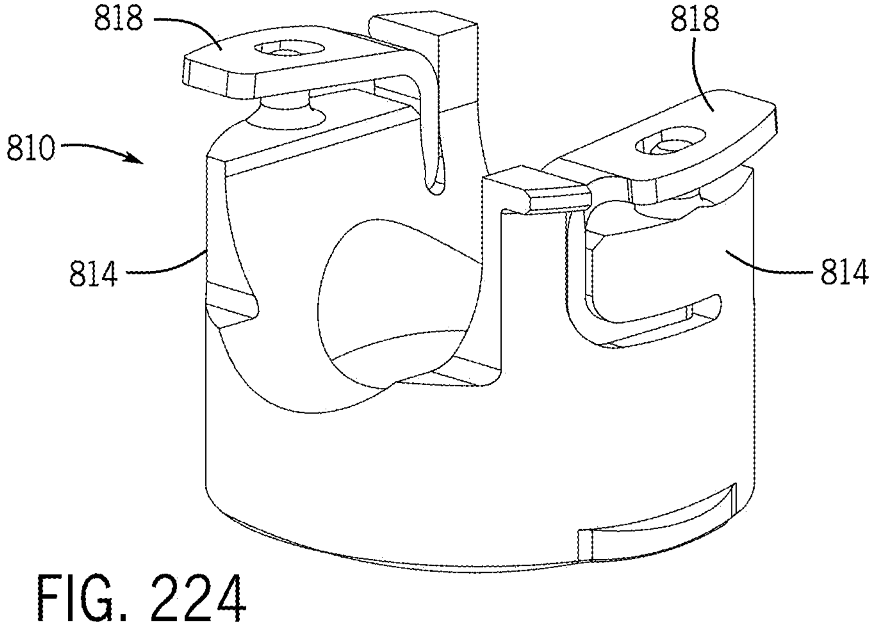

FIG. 224 is a top perspective view of yet another multi-piece pressure insert with non-integral spring elements or clips that could be modified for use with any embodiment of bone anchor assembly described above, in accordance with another representative embodiment of the present disclosure.

Figure 225:
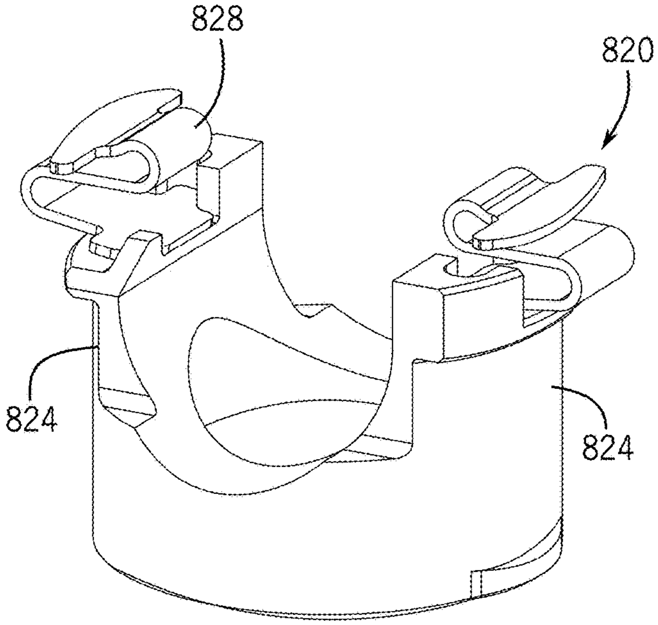

FIG. 225 is a top perspective view of yet another multi-piece pressure insert with non-integral spring elements or clips that could be modified for use with any embodiment of bone anchor assembly described above, in accordance with another representative embodiment of the present disclosure.

Figure 226:
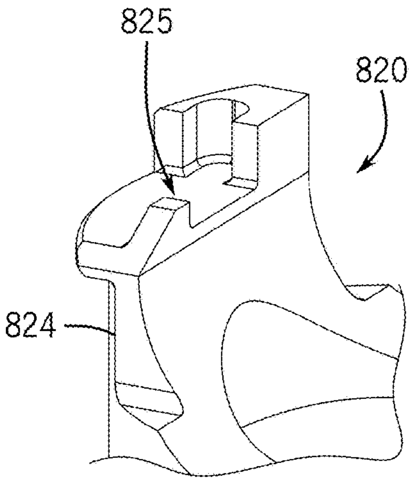

FIG. 226 is a close-up perspective view of an upright arm of the pressure insert of FIG. 225.

Figure 227:
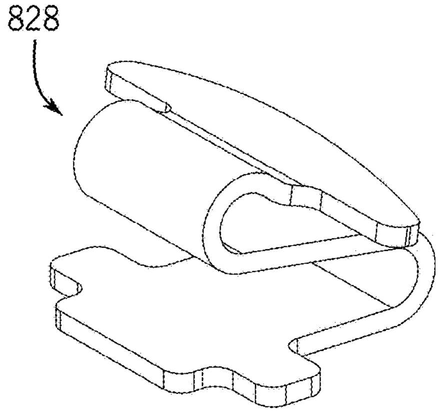

FIG. 227 is a close-up perspective view of the U-shaped non-integral spring element of FIG. 225.

Figure 228:
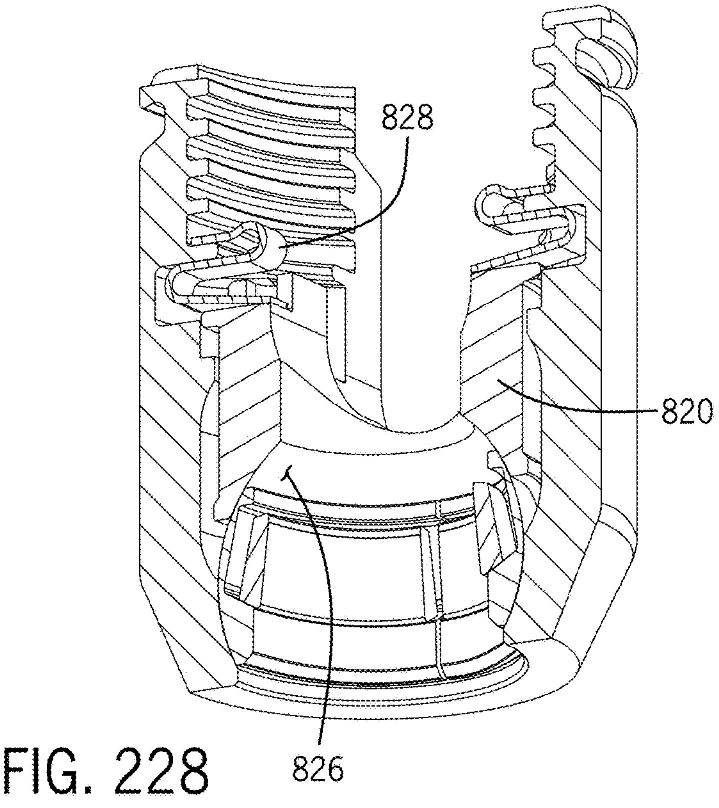

FIG. 228 is a partially cut-away perspective view of a multiplanar bone anchor assembly incorporating the embodiment of the pressure insert shown FIG. 225.

Figure 229:
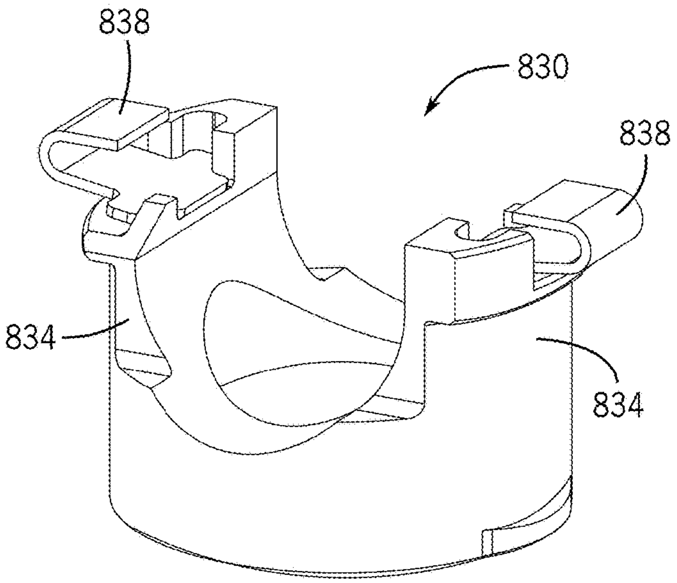

FIG. 229 is a top perspective view of yet another multi-piece pressure insert with non-integral spring elements or clips that could be modified for use with any embodiment of bone anchor assembly described above, in accordance with another representative embodiment of the present disclosure.

Figure 230:
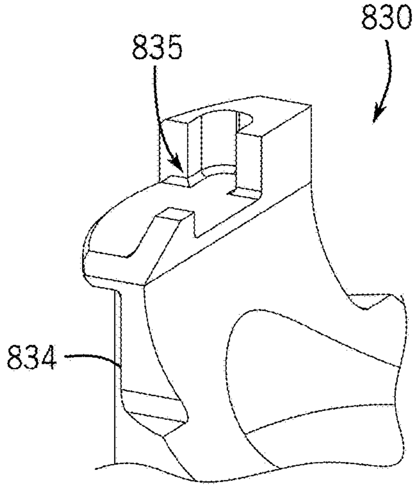

FIG. 230 is a close-up perspective view of an upright arm of the pressure insert of FIG. 229.

Figure 231:
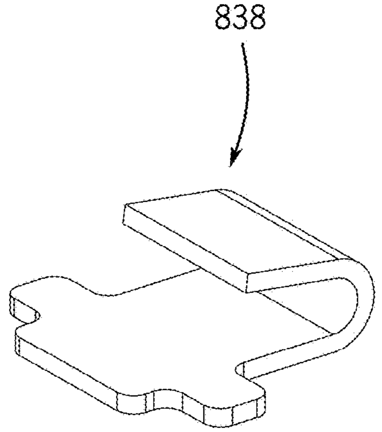

FIG. 231 is a close-up perspective view of the U-shaped non-integral spring element of FIG. 229.

Figure 232:
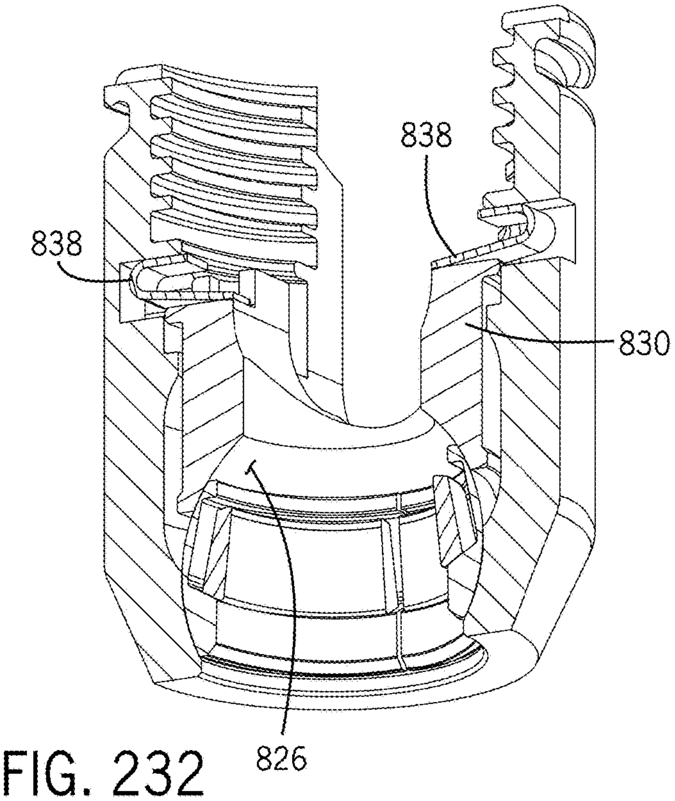

FIG. 232 is a partially cut-away perspective view of a multiplanar bone anchor assembly incorporating the embodiment of the pressure insert shown FIG. 229.

Figure 233:
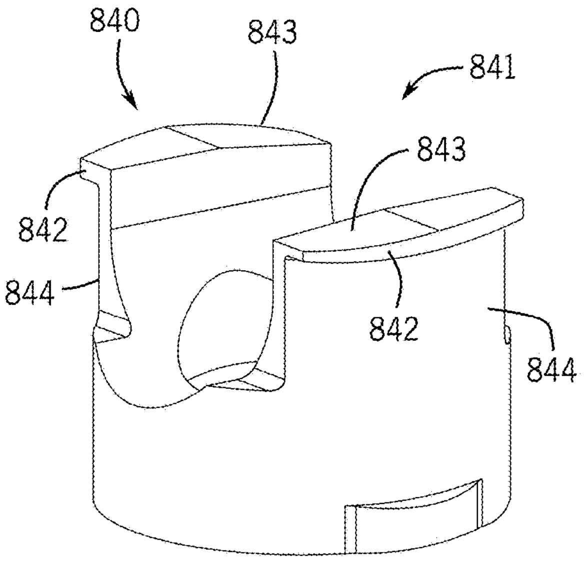

FIG. 233 is a top perspective view of a single piece pressure insert with camming flanges that could be modified for use with any embodiment of bone anchor assembly described above, in accordance with another representative embodiment of the present disclosure.

Figure 234:
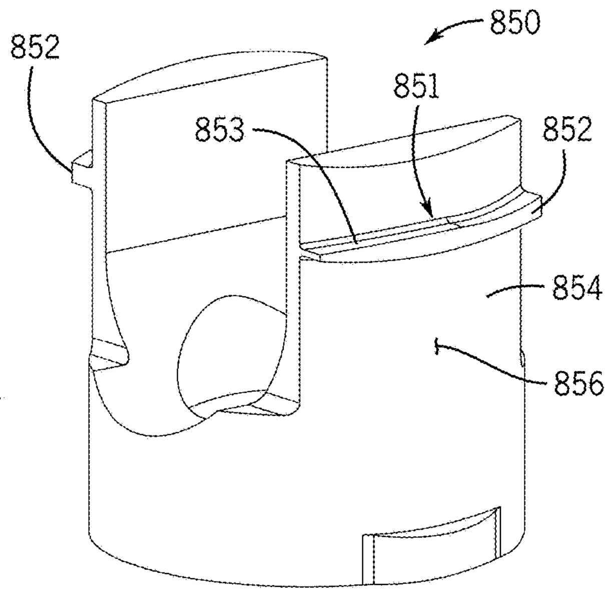

FIG. 234 is a top perspective view of yet another single piece pressure insert with camming flanges that could be modified for use with any embodiment of bone anchor assembly described above, in accordance with another representative embodiment of the present disclosure.

Figure 235:
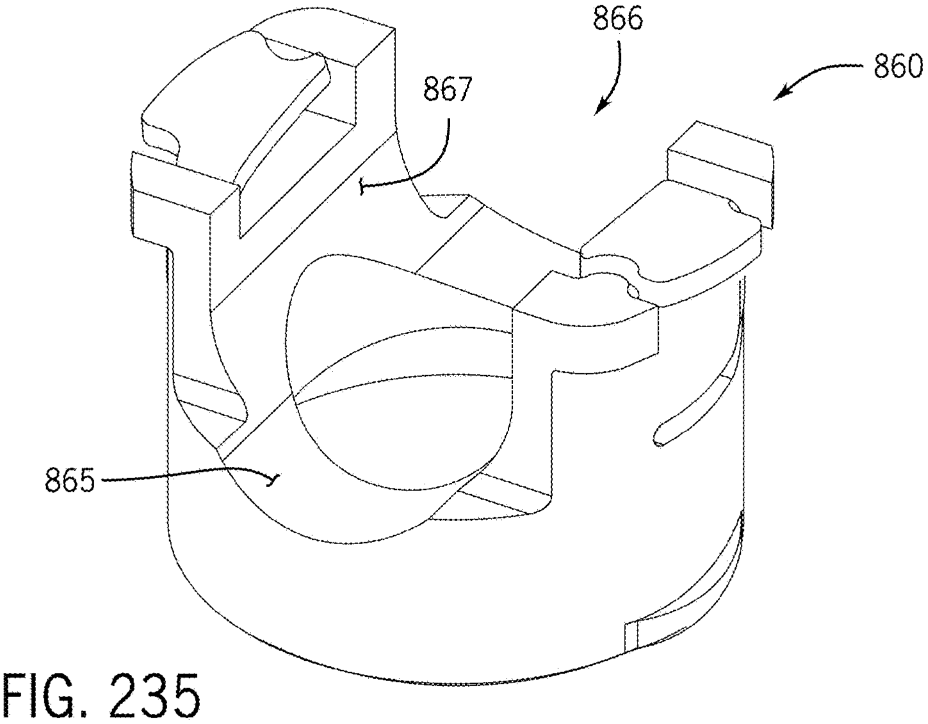

FIG. 235 is a top perspective view of yet another multi-piece pressure insert with an insert rod channel configured to receive rods of differing size that could be modified for use with any embodiment of bone anchor assembly described above, in accordance with another representative embodiment of the present disclosure.

Figure 236:
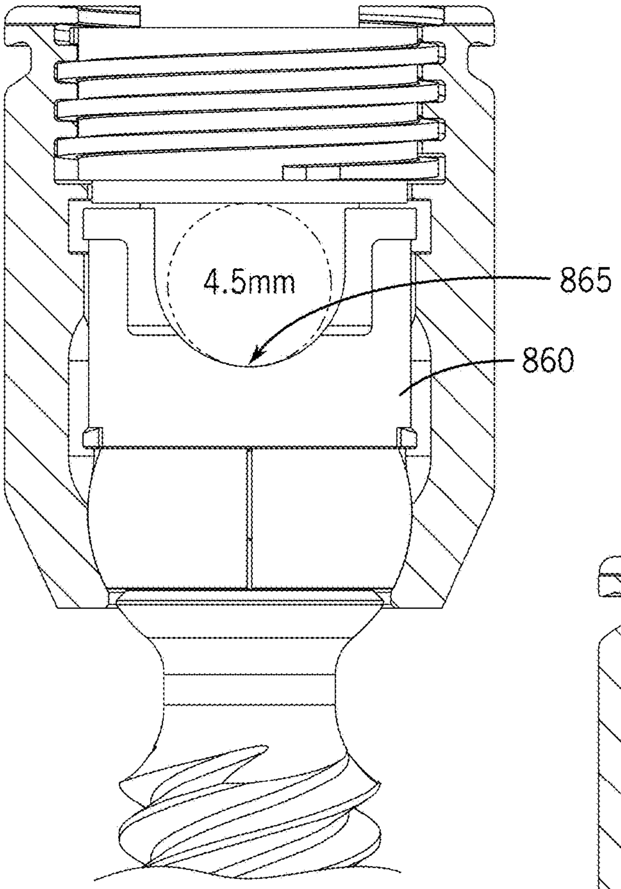
Figure 237:
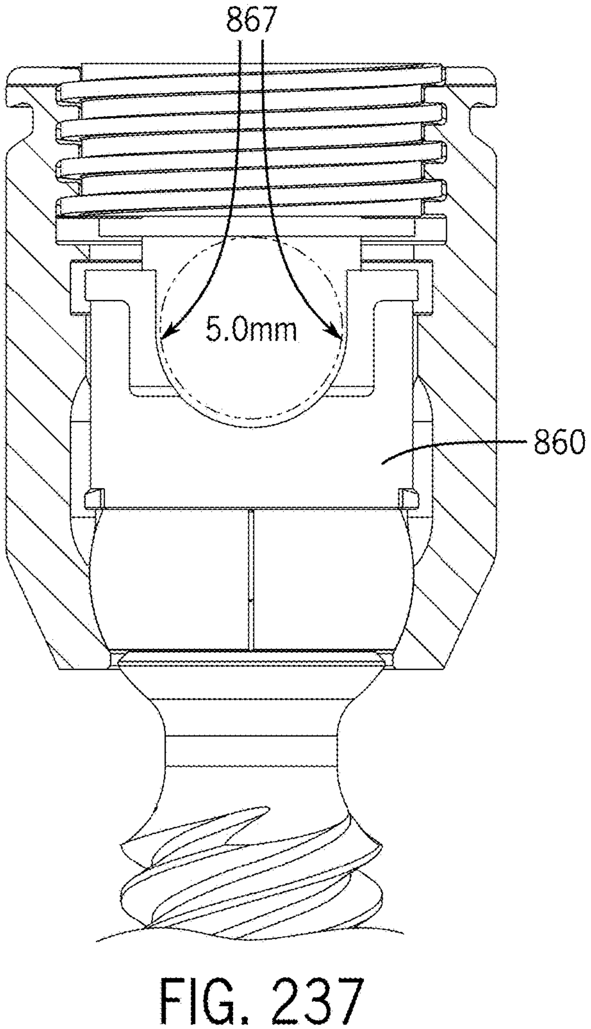

FIGS. 236 and 237 are front views of the multipiece pressure insert of FIG. 235 with rods of differing size received therein.

Figure 238:
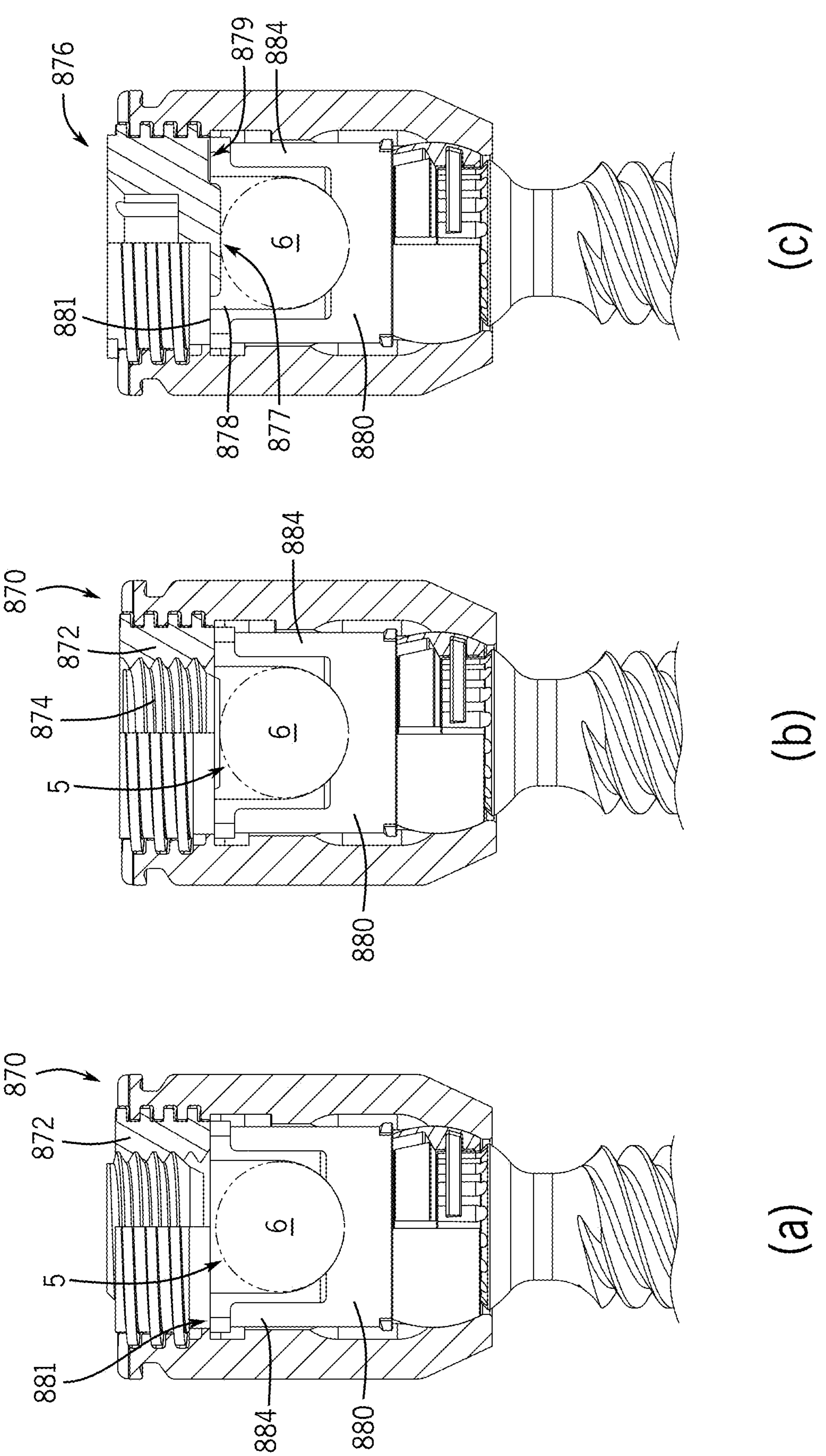

FIG. 238 includes three front views of a bone anchor assembly having a single piece pressure insert configured for use with interchangeable closures, in accordance with another representative embodiment of the present disclosure.

Those skilled in the art will appreciate and understand that the various features and structures or components of the bone anchor assemblies shown in the drawings described above, together with their relative relationships, interconnections and functions, can be interpreted as being drawn to scale. Nevertheless, it is also understood that the representative embodiments of the present disclosure disclosed and claimed herein are not limited to the precise structures and interrelationships of the features and components shown in the drawing figures, and that the dimensions, relative positions, and interconnections between the illustrated features and components may also be expanded, reduced, re-shaped, or otherwise revised or altered as needed to more clearly illustrate the structure of the embodiments depicted therein or the functions of the various features and components, as described below. Again, it is foreseen that some parts and features are interchangeable in their arrangement between the different embodiments disclosed.

DESCRIPTION OF THE INVENTION

The following description, in conjunction with the accompanying drawings, is provided as an enabling teaching of one or more representative universal shank heads that are configured for use with an array or collection of complementary pivotal and non-pivotal receiver sub-assemblies in a modular spinal fixation system, together with methods for assembling and employing the bone anchors and receiver sub-assemblies as portions of the modular spinal fixation system for securing elongate rods to patient bone in spinal surgery. As described below, the individual bone anchor assemblies, the spinal fixation system, and/or the methods of the present disclosure for the representative universal shank head can provide significant advantages and benefits over other pivotal and/or non-pivotal bone anchors and spinal fixation systems known in the art due to, in one aspect, the degree of versatility and adaptability provided by the shank head universality (i.e. a shank head having a common geometry that is connectable with each of the complementary receiver sub-assemblies) that is incorporated into the modular spinal fixation system. The recited advantages are not meant to be limiting in any way, however, as one skilled in the art will appreciate that other advantages and benefits may also be realized upon practicing the present disclosure.

Furthermore, those skilled in the relevant art will recognize that changes can be made to the disclosed embodiment for shank head universality, beyond those described, while still obtaining the beneficial results. It will also be apparent that some of the advantages and benefits of the described embodiment for the invention can be obtained by selecting some of the features (e.g. the structures or components) of the receiver sub-assemblies without utilizing other features, and that features from one sub-assembly embodiment may be interchanged or combined with features from other sub-assemblies in any appropriate combination. For example, any individual feature or collective features of method embodiments may be applied to apparatus, product or system embodiments, and vice versa. Likewise, structural elements or functional features from one embodiment may also be combined with or replaced by structural elements or functional features from one or more additional embodiments in any suitable manner. Those who work in the art will therefore recognize that many modifications and adaptations to the representative embodiments described herein are possible and may even be desirable in certain circumstances, and are to be considered part of the disclosure for the invention. Thus, the present disclosure is provided as an illustration of the principles for one representative embodiment of a universal shank head, since the scope of the invention is to be defined by the claims.

Spinal Fixation System

Figure 1:
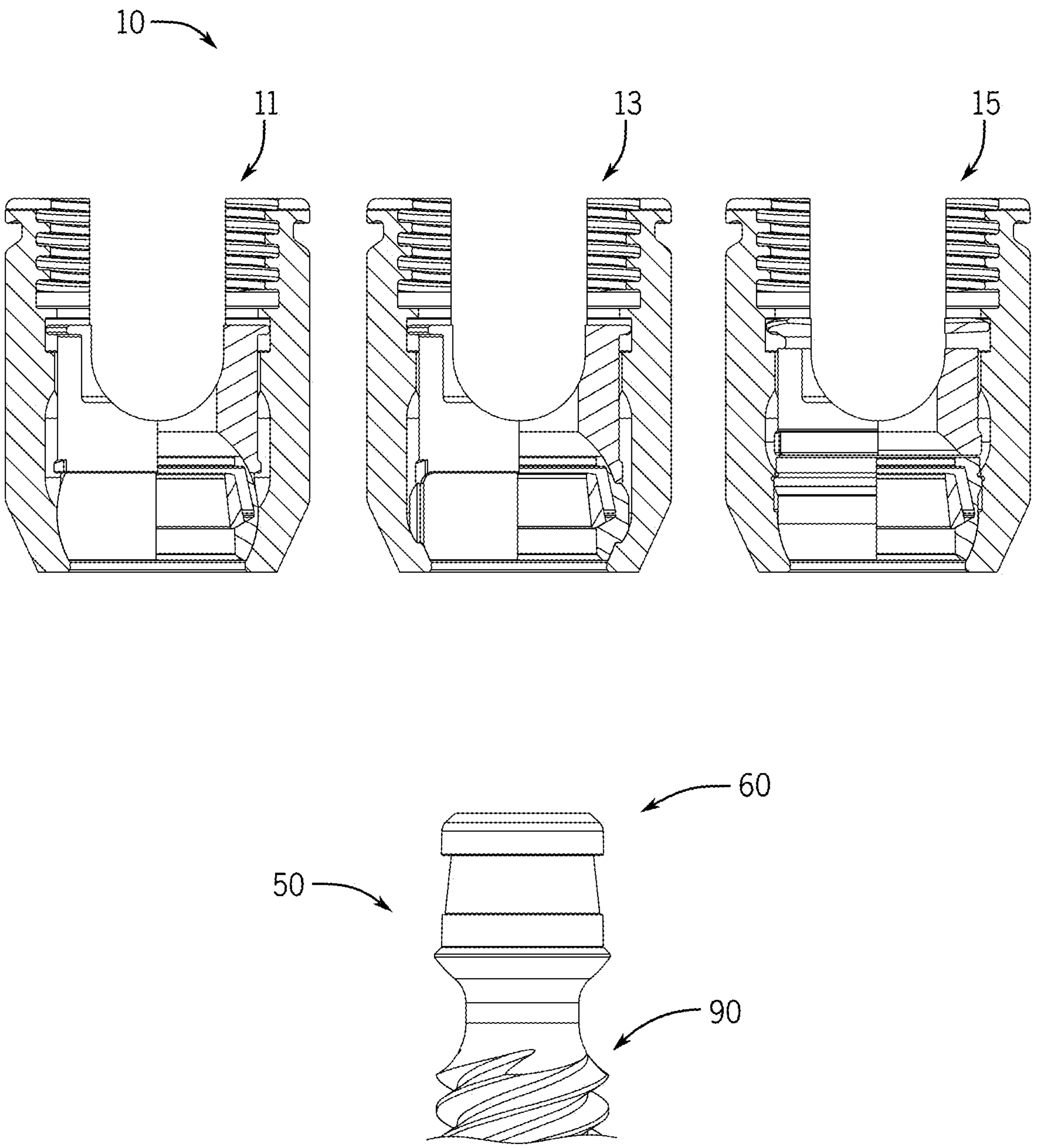
FIG. 1 is a partially cut-away front perspective view of a multi-component spinal fixation system showing three major types of receiver sub-assemblies and a bone anchor having one form of a universal shank head, with each receiver sub-assembly having different functionalities and being attachable to the defined common geometry on the upper capture portion of the bone anchor, in accordance with a representative embodiment of the present disclosure.

As shown in FIG. 1, the present disclosure generally relates to a spinal fixation system 10 and associated methods for performing spinal fixation surgeries with the use of bone anchor assemblies having bone anchors or attachment structures (such as bone screws, hooks, shanks, and other known anchor components) attached to longitudinal connecting members (such as rods, cords, connector arms, and other known longitudinal connecting members) with universal shank heads that can be bottom loaded into receiver sub-assemblies (i.e. housings or heads), and wherein the receiver sub-assemblies and at least some of their associated internal components can pivot and/or rotate axially in different selected directions relative to their bone anchors. More specifically, receivers that are configured to provide different functionalities, such as multiplanar pivotal movement, monoplanar pivotal movement, non-pivotal but axially rotatable (i.e. monoaxial) movement, pre-lock friction fit, provisional independent locking, and the like, can be pre-assembled with their internal components into receiver sub-assemblies that are configured to be snapped onto or otherwise connected on the same type of universal shank head having an upper end capture portion geometry that is common to all of the bone anchors (which may or may not be cannulated). This allows for the bone anchors to be affixed to the bony anatomy either before or after being connected with their respective pivoting or non-pivoting receiver sub-assemblies. For instance, in some cases it may be desirable to implant or attach the bone anchors into or on the spine of the patient independent of their larger and somewhat bulky receiver sub-assemblies, and decide later on in the surgical procedure where each of the multiplanar, uniplanar, or monoaxial receiver sub-assemblies should be placed and utilized on the implanted spinal construct. This type of modular capability can be advantageous for both midline and pedicle screw placement trajectories into the vertebral bodies.

The spinal fixation system 10 of FIG. 1 is directed toward eliminating or at least improving upon shortcomings of the prior art through the introduction of a bone anchor 50 or attachment structure, such a bone screw, comprising a shank body 90 with a threaded portion at a lower end and a universal or common capture portion 60 at an upper end (also known as a “universal” shank head) that can provide the spinal fixation system 10 with enhanced modular capabilities, in that the capture portion 60 is not limited to connection with just one type of receiver sub-assembly. In particular, the type of universal or common capture portion 60 or shank head shown in FIG. 1 is configured to be snapped onto and captured by any of a multiplanar pivotal and independently rotatable receiver sub-assembly 11, a monoplanar pivotal and independently rotatable receiver sub-assembly 13, or an independently rotatable but non-pivotal (i.e. monoaxial) receiver sub-assembly 15, or by any version of receiver sub-assembly providing the same functionalities or that is combined with different or additional functionalities such as a pre-lock friction fit, provisional independent locking, favored angle articulation (i.e. increased articulation in a single plane), and the like.

Additional benefits of the spinal fixation system 10 will also be appreciated by one skilled in the art, including but not limited to increased savings afforded by the more complete modular component designs that allow for common components to be shared between the different types of receiver sub-assemblies, fewer implants needing to be maintained in inventory, accounted for, and being shipped to and from hospitals and surgery centers, reduced overall costs, and other benefits yet to be realized, such as more options to provide for enhanced and efficient spine surgeries with better outcomes. For example, it is also foreseen that the geometry of the universal capture portion 60 or shank head can provide for a more reduced profile and rigid connection with a driving instrument, such as the end of an arm of a navigated robot, so as to better provide for navigated and robotic assisted insertions of the threaded screw shanks into vertebral bodies. Yet another advantage of the universal capture portion 60 or shank head can involve the absence of parallel flat or planar outer side surfaces formed into the shank head that would otherwise require a somewhat restricted or “keyed” type of bottom loaded entry into one or more of the receiver sub-assemblies, and wherein, in some cases, the absence of the parallel flat surfaces can improve the pull-out strength of the bone anchor assembly.

Figure 2:
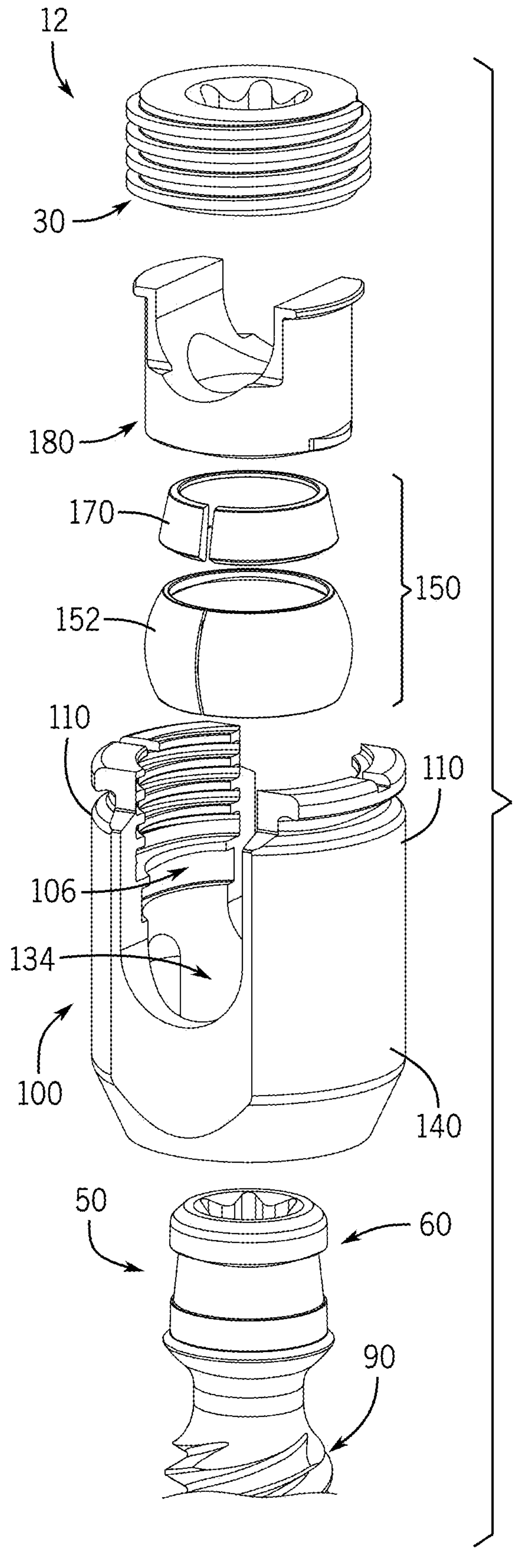
FIG. 2 is an exploded perspective view of a multiplanar embodiment of a bone anchor assembly, in accordance with the representative embodiment of the multi-component spinal fixation system shown in FIG. 1.
Figure 3:
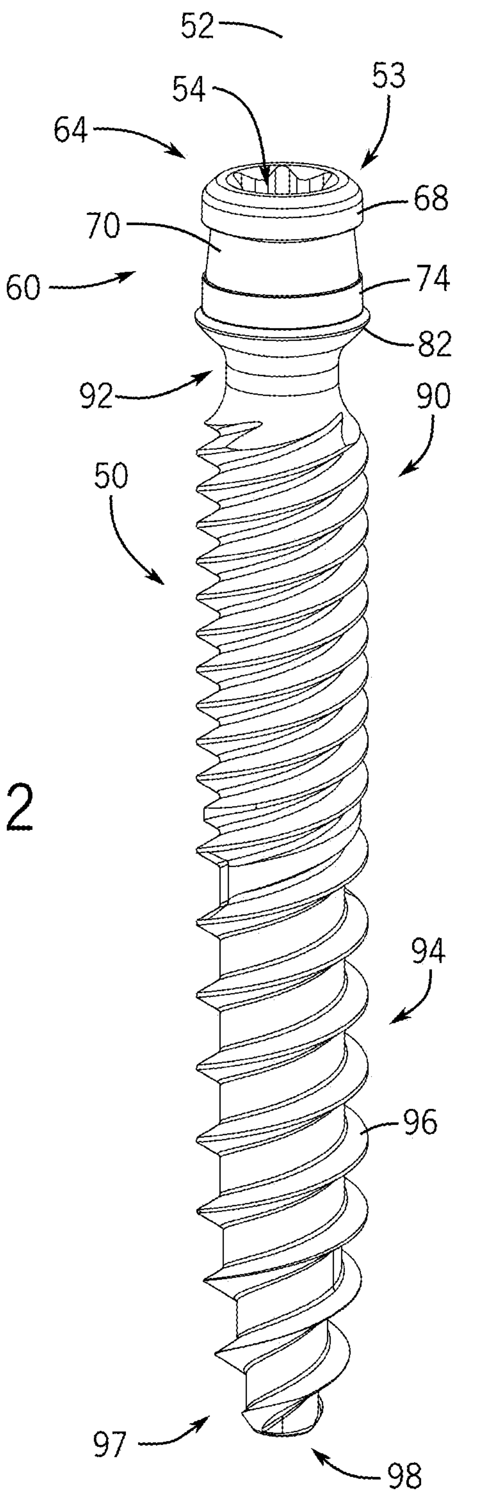
FIG. 3 is a perspective view of the bone anchor of the multiplanar bone anchor assembly of FIG. 2.
Figure 4:
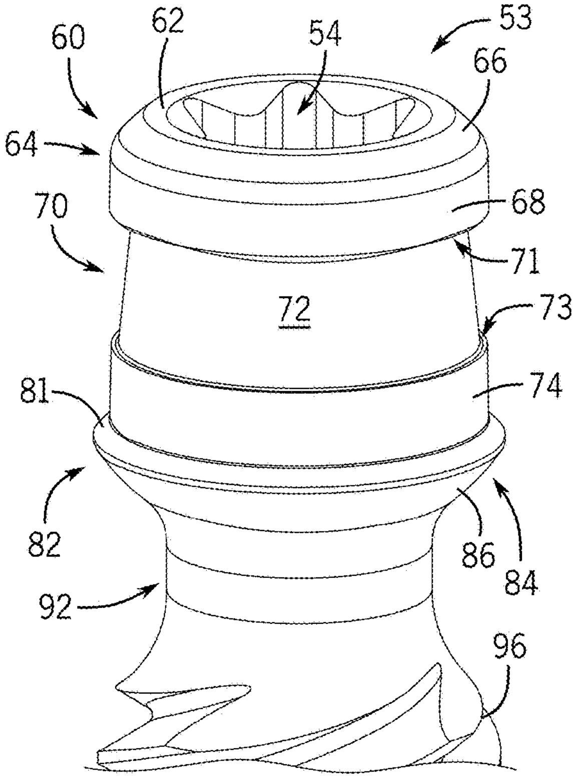
FIG. 4 is a perspective view of the capture portion of the bone anchor of FIG. 3.
Figure 5:
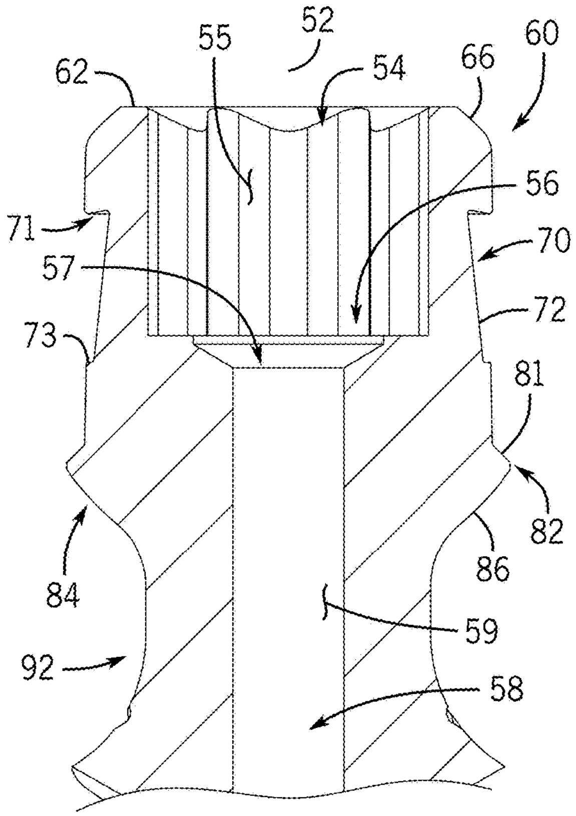
FIG. 5 is a cross-sectional side view of the capture portion of the bone anchor of FIG. 3.
Figure 6:
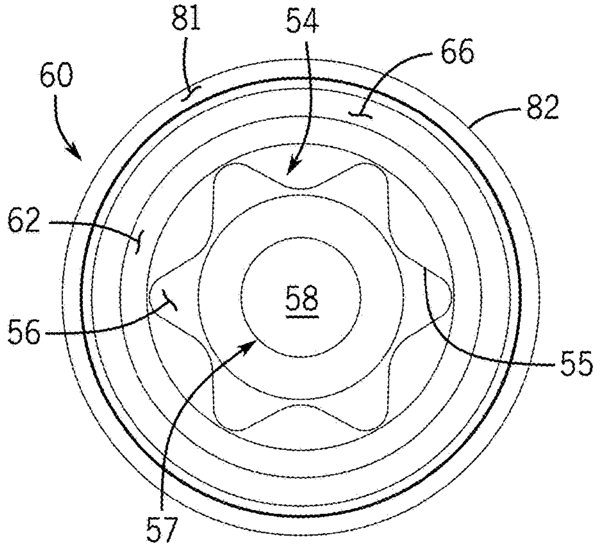
FIG. 6 is a top view of the bone anchor of FIG. 3.
Figure 7:
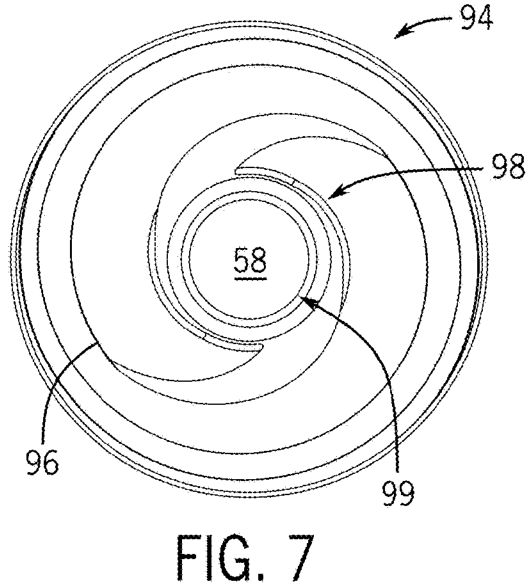
FIG. 7 is a bottom view of the bone anchor of FIG. 3.
Figure 8:
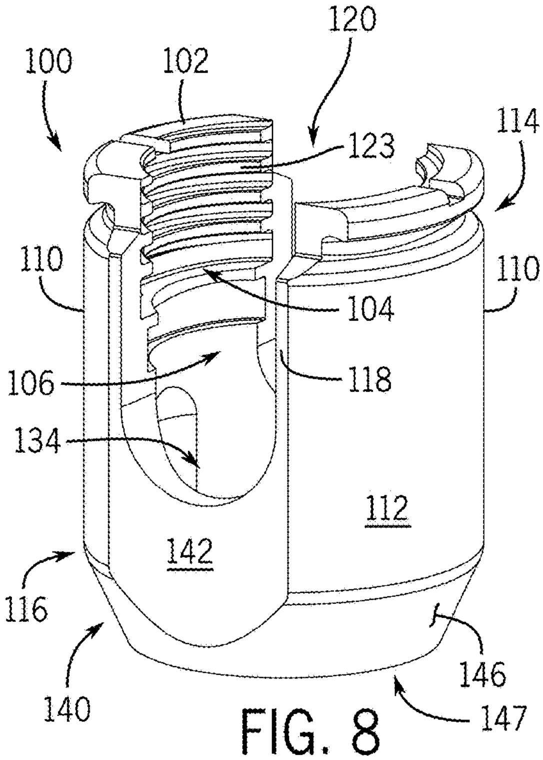
FIG. 8 is a perspective view of the receiver of the multiplanar bone anchor assembly of FIG. 2.
Figure 65:
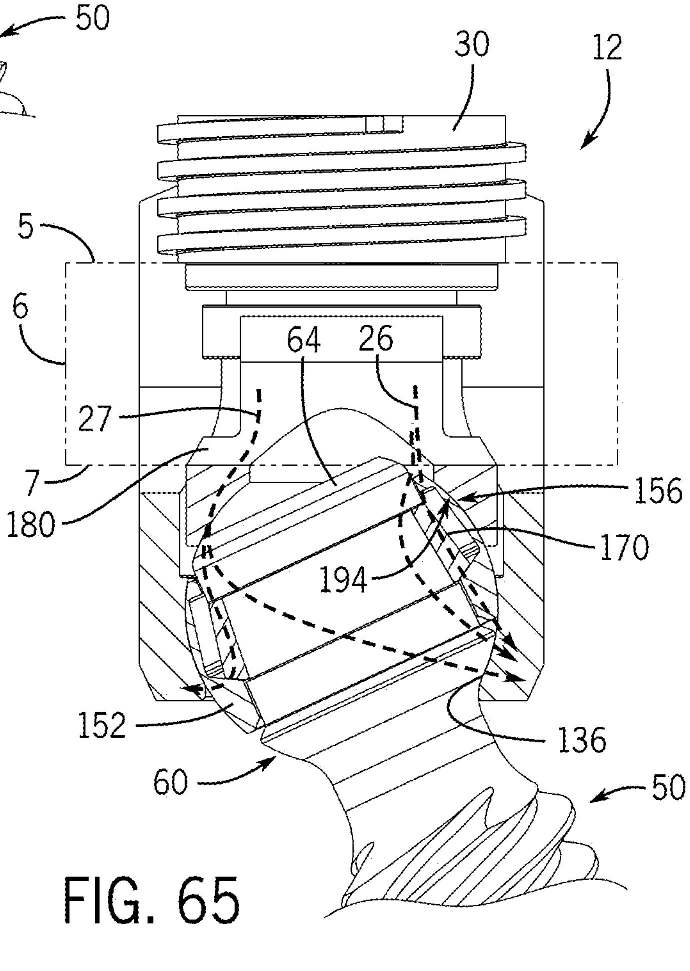
FIG. 65 is a cross-sectional side view of the fully-assembled multiplanar bone anchor assembly of FIG. 62, with the bone anchor in an articulated position relative to the receiver and resultant locking load path.

The representative embodiment of the multiplanar pivotal and rotatable receiver sub-assembly 11 shown in FIG. 1 can be combined with the bone anchor 50 having the universal capture portion 60 to form a multiplanar bone anchor assembly 12 further described in reference to FIGS. 2-65. The multiplanar bone anchor assembly 12 can include components having features or aspects configured to provide for pivotal motion of the bone anchor relative to the receiver sub-assembly around a 360-degree range, and also to provide for independent rotational motion relative to a longitudinal axis of the bone anchor around a 360-degree range, and is hereinafter interchangeably referenced to as a polyaxial, multi-axial, or multiplanar assembly 12.

Similarly, the representative embodiment of the monoplanar pivotal and independently rotatable receiver sub-assembly 13 shown in FIG. 1 can be combined with the same universal bone screw 50 to form a monoplanar bone anchor assembly 14 further described in reference to FIGS. 66-97. The monoplanar bone anchor assembly 14 can include alternative components having features or aspects configured to limit the pivotal motion of the bone anchor relative to the receiver sub-assembly (or vice versa) to a single plane (i.e. sagittal, medial-lateral) while still providing for rotational motion around a 360-degree range, and is hereinafter interchangeably referenced as a uni-planar or monoplanar assembly. Again, as shown in the drawings, the head or capture portion 60 of the universal bone screw 50 can be included into this monoplanar functionality without the use of parallel flat or planar side surfaces formed into the side surfaces of the capture portions.

Likewise, the representative embodiment of the non-pivotal but rotatable, or monoaxial, receiver sub-assembly 15 shown in FIG. 1 can be combined with the same universal bone screw 50 to form a monoaxial bone anchor assembly 16 further described in reference to FIGS. 98-124. The non-pivotal or monoaxial bone anchor assembly 16 can also include alternative components having features or aspects configured to prevent or inhibit pivotal motion of the bone anchor relative to the receiver sub-assembly (or vice versa), with some possible limited toggle, while still providing for rotational motion around a 360-degree range, and is hereinafter interchangeably referenced as a non-pivotal, substantially 'fixed', or monoaxial assembly 16.

Thus, regardless of the type, degree or amount of pivotal motion, each embodiment for the bone anchor assembly generally is configured to provide a spinal fixation system wherein the bone anchor first be coupled to the bone anchor assembly using a common internal capture structure, such as an open capture ring, and then can rotate around its longitudinal or spin axis relative to the receiver sub-assembly (or vice versa) at least prior to a locking the bone anchor assembly with the elongate rod and closure in the final locked position and with at least some degree of a pre-lock friction fit. It will be appreciated that this feature can allow for the rotatable implantation, or screwing in, of the anchor portion of a pre-assembled bone anchor assembly to a desired depth in the bone of a patient without rotation of the receiver sub-assembly, thereby allowing the receiver sub-assembly to be secured by separate tooling, or maintained in a desired alignment, throughout the implantation of the bone anchor. In addition, this feature can allow for the height of the receiver sub-assembly above the bone, or the length of the anchor portion of the bone anchor that is implanted in the bone, to be more precisely controlled, and wherein more aggressive thread forms with larger pitches for faster insertions with fewer rotations can be utilized, especially with robot assisted surgeries. In addition, the upper end capture portion geometry of the screw can further provide for a very strong and secure connection with a driving tool for manual or robotic insertions.

Other than the structural differences between the different embodiments that are generally configured to limit the pivotal motion or to allow for greater pivotal motion, particularly in one direction, it will be further appreciated that the features and aspects of the various embodiments can be substantially the same, and with interchangeability of one or more of the separate components. To that point, the receivers, open or closed, for each embodiment can share the same type of tool attachment structure, for example. Thus, a skilled artisan will recognize that a description of certain aspects of the separate components set forth in reference to the embodiment of the multiplanar assembly illustrated in FIGS. 2-65 may also apply to the same aspects of the components and features illustrated in the embodiment of the monoplanar assembly shown in FIGS. 66-97 and the components illustrated in the embodiment of the monoaxial assembly shown in FIGS. 98-124, unless otherwise indicated. As noted above, such a spinal fixation system allows for the introduction of a bone anchor 50 having the universal capture portion 60 or shank head that is bottom loaded and receivable within any of the representative multiplanar pivotal, monoplanar pivotal, and monoaxial non-pivotal embodiments of the specific receiver sub-assembly and without keyed entry or other alignment limitations, as further disclosed herein. While a frusto-conical version of the capture portion is disclosed to practice the invention, other types of capture portions are also contemplated, such as spherical shapes with opposite dimples or with recesses or threads or different radii (e.g. bi-spheric), as well as cylindrical shapes with recesses or threads, and the like.

Multiplanar Bone Anchor Assembly

Referring now in more detail to the drawing figures, wherein like parts are identified with like reference numerals throughout the several views, FIG. 2 illustrates one representative embodiment of a multiplanar pivotal bone anchor assembly 12 that includes a bone anchor 50, such as a threaded shank, having a universal capture portion 60 or shank head and an anchor portion 94 opposite the capture portion 60 for securement within or attachment to the bone of a patient. The multiplanar assembly 12 also includes a multiplanar receiver 100 or housing having a base portion 140 defining an internal cavity or lower portion of a central bore 120 that is configured to receive the capture portion 60 of the shank 50, and a pair of upright arms 110 defining an open rod channel 106 configured for receiving an elongate rod 6 (see FIGS. 62-65). The multiplanar receiver 100 can be initially pivotably secured to the capture portion 60 with a number of separate internal components that have been pre-assembled into the internal cavity 134 and the rod channel 106 to form a multiplanar receiver sub-assembly 11. These internal components can include, but are not limited to, the pivoting or articulating retainer sub-assembly 150 that includes a ring retainer 152 having a separate open capture ring 170 secured therein (as described in more detail below), and a so called pressure insert, saddle, crown, spacer or compression element 180. After an elongate rod 6 has been positioned within the lower portion of the rod channel 106, a closure 30 can be threadably or otherwise secured into an upper portion of the rod channel to apply pressure to an upper surface of the elongate rod, such as by direct contact therebetween, thereby locking both the elongate rod 6 and the multiplanar assembly 12 into a final locked position. As discussed in more detail below, in one aspect the separate open capture ring 170 can be common to each embodiment of receiver sub-assembly shown in FIG. 1.

As shown in the exploded assembly view of FIG. 2 and isolated views of FIGS. 3-7, the bone anchor 50 has a capture portion 60, or type of universal shank head, at a proximal end 53, and a body 90 extending distally from the capture portion 60 with an attachment or anchor portion 94 at a distal end 97 configured for fixation to the bone of a patient. In one aspect the body 90 of the bone anchor can comprise both the anchor portion 94 as well as a narrow neck portion 92 extending longitudinally between the anchor portion 94 and the capture portion 60. Although shown in the figures as a shank body with bone engagement threads 96, it is foreseen that the anchor portion 94 of the body 90 could also be configured as a hook blade, or another type of bone attachment structure, extending downward from the neck portion 92. As such, the universal capture portion 60 or shank head can be common to all of the bone anchors 50 included in the spinal fixation system 10 described above, regardless of the size or type of the anchor portion extending downward or below the capture portion 60.

At its upper end, the universal capture portion 60 or shank head includes an annular horizontally-planar top surface 62 that surrounds an internal drive feature or drive socket 54. Extending downwardly and outwardly from the top surface 62 is an upper curvate section 64 that is radiused, chamfered or beveled with respect to the horizontal flat top surface 62, and which, in one aspect, can case the entry of the proximal end 53 of the bone anchor 50 into the center aperture of the capture ring 170 positioned within the ring retainer 152. Below the upper curvate section 64 are an upper outer slidable surface 68 and a lower outer slidable surface 74 centered on the bone anchor's longitudinal or spin axis 52, and which are separated by a horizontal capture recess 70 extending into and circumferentially around a mid-portion of the capture portion 60. The capture portion 60 can further include a lower curvate section 84 that curves downwardly and inwardly from the lower outer slidable surface 74 toward the narrow neck portion 92 of the body 90 of the bone anchor. In one aspect the lower curvate section 84 can extend radially outward beyond the lower end portion of the lower outer slidable surface 74 to create an outer lip structure 82 that can be further defined, in part, by an upwardly- and outwardly-facing beveled lip surface 81. As described above, these outer surfaces of the capture portion 60 are generally devoid of parallel flat or planar outer side surfaces or sections that might require a type of keyed entry through the bottom opening of the receiver.

The upper curvate section 64 and the lower curvate section 84 of the capture portion 60 of the bone anchor 50 can further include upper and lower spherical surfaces 66, 86 that together define upper and lower spherical extensions, respectively, of a spherical outer surface of the ring retainer 152, so as to form a substantially spherical capture head when the ring retainer 152 is coupled to the capture portion 60. As described in detail below, the upper spherical extension 66 can be engaged by the complementary-shaped bottom surface of the pressure insert 180 upon assembly of the bone anchor 50 to the multiplanar receiver sub-assembly 11, and the lower spherical extension 86 can engage the complementary-shaped spherical seat surface 136 of the multiplanar receiver 100 upon articulation of the bone anchor 50 relative to the multiplanar receiver sub-assembly 11.

The outer slidable surfaces 68, 74 can be straight cylindrical surfaces or preferably frusto-conical surfaces having a slight taper angle devoid of any flat surfaces, and can have different lengths as measured along the longitudinal axis of the bone anchor 50. When formed as frusto-conical surfaces (as shown), the outer slidable surfaces 68, 74 can be widest toward the lower end of the capture portion 60 (i.e. the end that is closest to the neck 92 or anchor portion 94 of the bone anchor 50), and then can narrow or taper while moving upward toward the upper end 53 and top surface 62 of the capture portion 60. It will be appreciated that the tapered outer slidable surfaces 68, 74 may also facilitate the insertion of the capture portion 60 into the center aperture of the capture ring 170, so as to be easier than the insertion of a capture portion having a straight cylinder shape into a center aperture that can, in some aspects, also be defined by non-tapered inner cylindrical surfaces. Although the upper outer slidable surface 68 and the lower outer slidable surface 74 are shown as having a common straight taper angle extending between the two surfaces of about one degree, it is foreseen that in other embodiments the upper outer slidable surface 68 and the lower outer slidable surface 74 can each define their own tapered surface having a taper angle ranging between about 0.5 degrees to about five degrees, or greater. Moreover, each of the outer slidable surfaces 68, 74 may have a taper angle that is same or different from the other, and may also have an outer diameter at a lower end that is the same or different from the other.

As shown in the drawings, the outer slidable surfaces 68, 74 can bracket the horizontal capture recess 70 extending into and circumferentially around the mid-portion of the capture portion 60, with the capture recess 70 having a height between an upper step surface 71 and a lower step surface 73 that can be significantly greater than its depth. As shown in the illustrated embodiment, for example, the height of the capture recess can be three to four times greater than its depth. In addition, the outwardly-facing inner recessed surface 72 of the capture recess 70 that extends between the upper step surface 71 and the lower step surface 73 can be tapered, with a taper angle ranging between about three degrees and about nine degrees, thereby resulting in the upper step surface 71 having a greater depth or overhang than that of the lower step surface 73. Although shown with an inner recessed surface 72 that is tapered, it is foreseen that the capture recess can have an inner recessed surface with a different profile, including but not limited to a straight cylindrical profile, a curved, curvate or curvilinear profile, a spherical profile, and the like. In one aspect the upper step surface 71 can also have an outwardly- and downwardly-beveled profile to form an undercut or a dove-tail like engagement with a top surface of the capture ring 170 that serves to keep the capture ring 170 in position upon connection with the capture recess 70 of the capture portion 60, as described below.

As described above, the top surface 62 of the capture portion 60 can be an annular planar top surface that surrounds an internal drive feature 54 or drive socket. The illustrated internal drive feature 54 is an aperture formed in the top surface 62, and in one aspect can be a multi-lobular or star-shaped aperture, such as those sold under the trademark TORX, or the like, having internal faces 55 designed to receive a multi-lobular or star-shaped tool for rotating and driving the bone anchor 50 into the vertebra. It is foreseen that such an internal tool engagement structure or drive feature 54 may take a variety of tool-engaging forms and may include one or more apertures of various shapes, such as a pair of spaced apart apertures or a hex shape designed to receive a hex tool (not shown) of an Allen wrench type. The seat or base surface 56 of the drive feature 54 can be disposed perpendicular to the shank axis, with the drive feature otherwise being coaxial with the longitudinal axis 52 of the bone anchor 50. In operation, a driving tool is received in the internal drive feature 54, being seated at the base surface 56 and engaging the internal faces 55 of the drive feature for rotating and driving the anchor portion 94 of the bone anchor into the vertebra, either before or after the bone anchor 50 is attached or coupled to the multiplanar receiver sub-assembly 11. If attached, the threaded anchor portion 94 of the body 90 of the bone anchor can be driven into the vertebra with the driving tool extending downward through both the central bore 120 of the multiplanar receiver 100 and the central aperture of the pressure insert 180 of the multiplanar receiver sub-assembly 11.

In one aspect the bone anchor 50 or shank can be cannulated (and also fenestrated for the application of bone cement, or even expandable) with a narrow bore 58 or aperture extending through the entire length thereof and centered about the longitudinal axis 52 of the shank. The bore 58 can be defined by an inner cylindrical sidewall 59 with a lower circular opening 99 at the shank tip 98 and an upper circular opening 57 communicating with the internal drive socket 54 at the base surface 56, and is coaxial with the body 90 and the capture portion 60 of the bone anchor 50. The bore 58 provides a passage through the shank interior for a length of wire (not shown) inserted into the vertebra prior to the implantation of anchor portion 94 of the bone anchor 50, the wire providing a guide for insertion of the anchor portion 94 into the vertebra. The bore 58 can also provide for a pin to extend therethrough and beyond the shank tip 98, the pin being associated with a tool to facilitate insertion of the body 90 of the bone anchor into the vertebra.

To provide a biologically active interface with the bone, the body 90 of the bone anchor, including both the threaded anchor portion 94 and the neck 42, may be coated, perforated, made porous or otherwise treated or textured. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate (Ca3(PO4)2, tetra-calcium phosphate (Ca4P2O9), amorphous calcium phosphate and hydroxyapatite (Ca10(PO9)6(OH)2). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Figure 9:
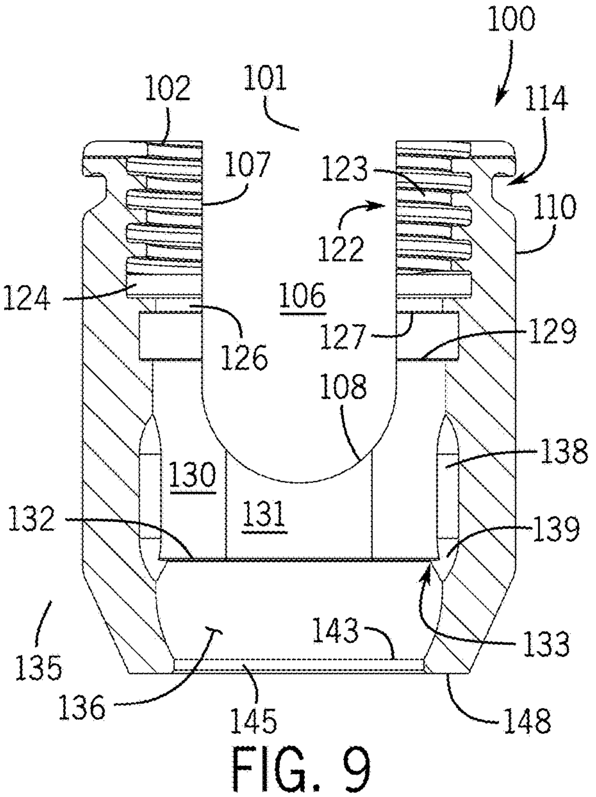
FIG. 9 is a cross-sectional side view of the receiver of FIG. 8.
Figure 10:
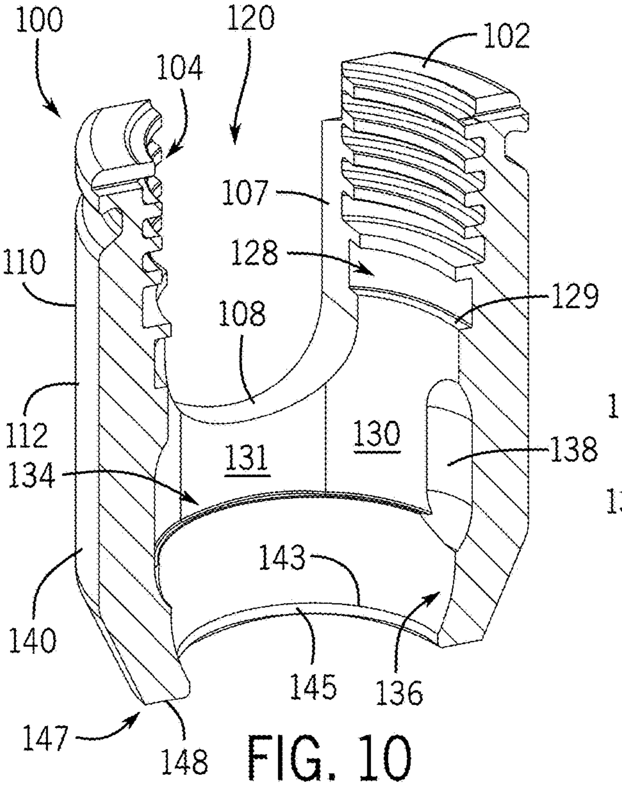
FIG. 10 is a cross-sectional perspective view of the receiver of FIG. 8.
Figure 11:
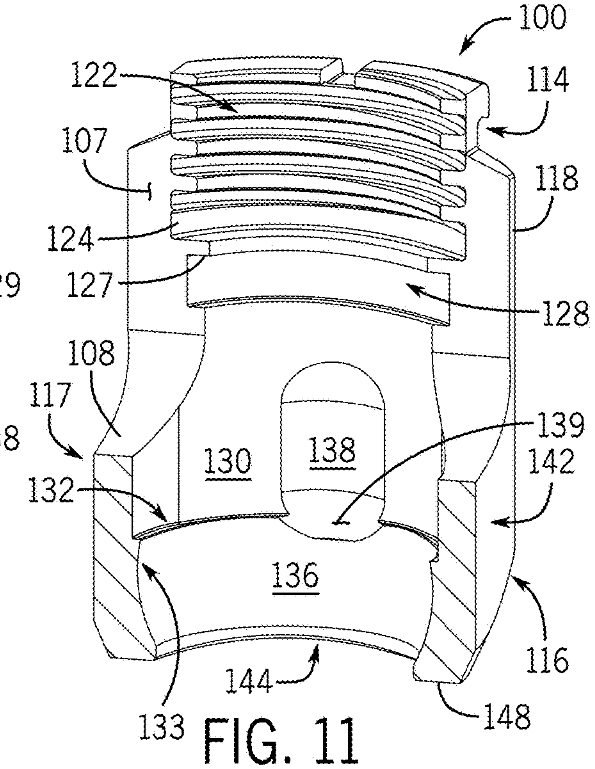
FIG. 11 is another cross-sectional perspective view of the receiver of FIG. 8.
Figure 12:
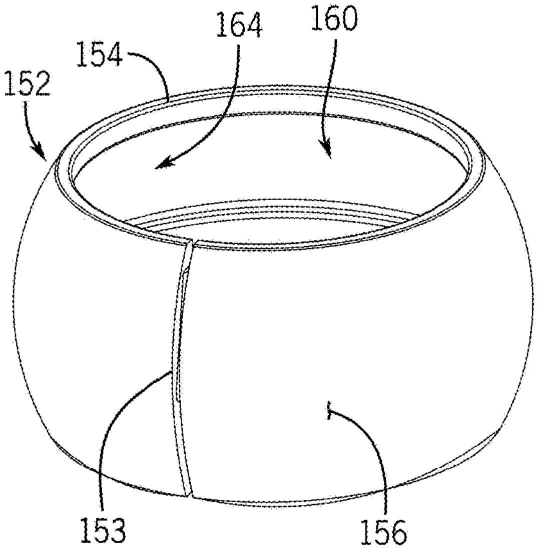
FIG. 12 is a perspective view of the ring retainer of the multiplanar bone anchor assembly of FIG. 2.
Figure 13:
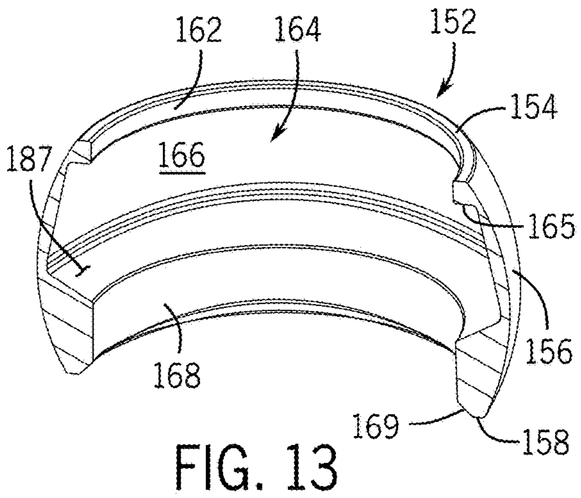
FIG. 13 is a cross-sectional perspective view of the ring retainer of FIG. 12.
Figure 14:
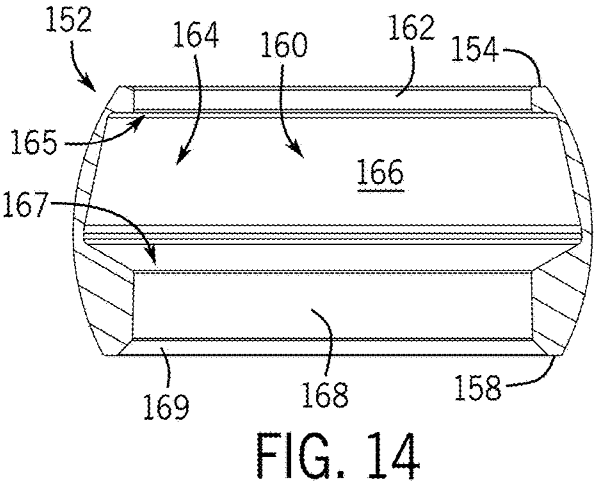
FIG. 14 is a cross-sectional side view of the ring retainer of FIG. 12.
Figure 15:
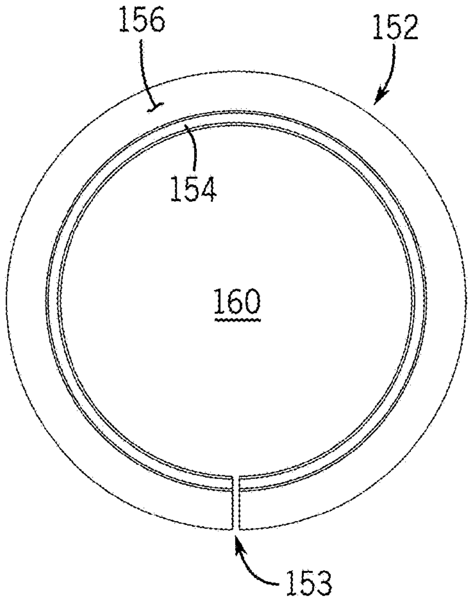
FIG. 15 is a top view of the ring retainer of FIG. 12
Figure 16:
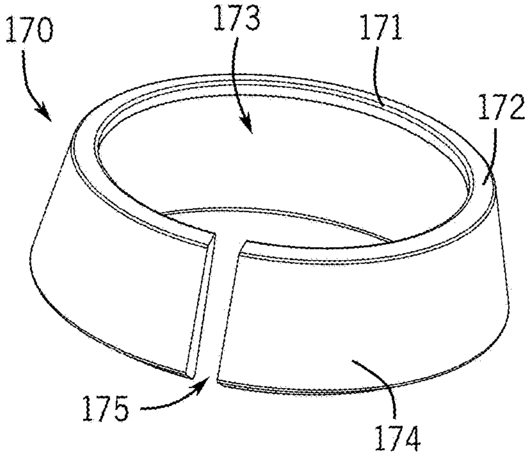
FIG. 16 is a perspective view of the capture ring of the multiplanar bone anchor assembly of FIG. 2.
Figure 17:
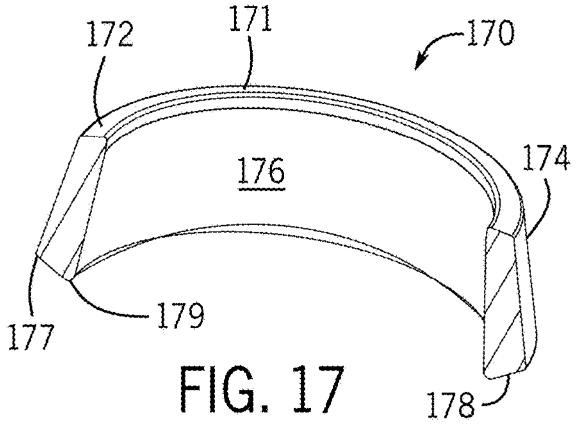
FIG. 17 is a cross-sectional perspective view of the capture ring of FIG. 16.
Figure 18:
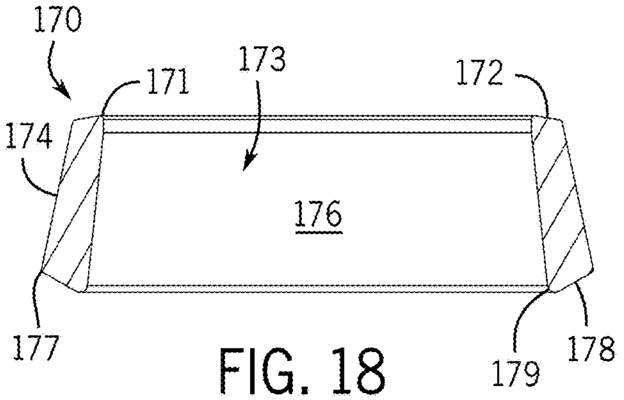
FIG. 18 is a cross-sectional side view of the capture ring of FIG. 16.
Figure 19:
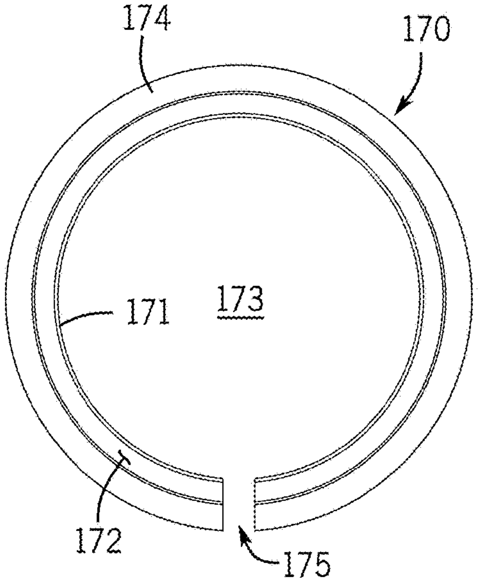
FIG. 19 is a top view of the capture ring of FIG. 16.
Figure 20:
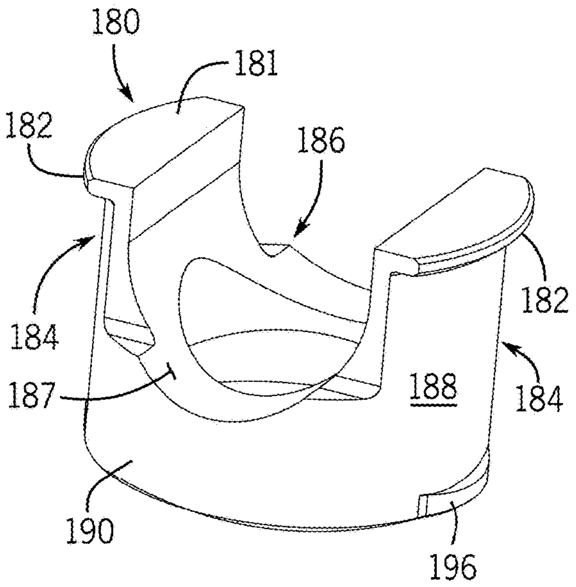
FIG. 20 is a top perspective view of the pressure insert of the multiplanar bone anchor assembly of FIG. 2.
Figure 21:
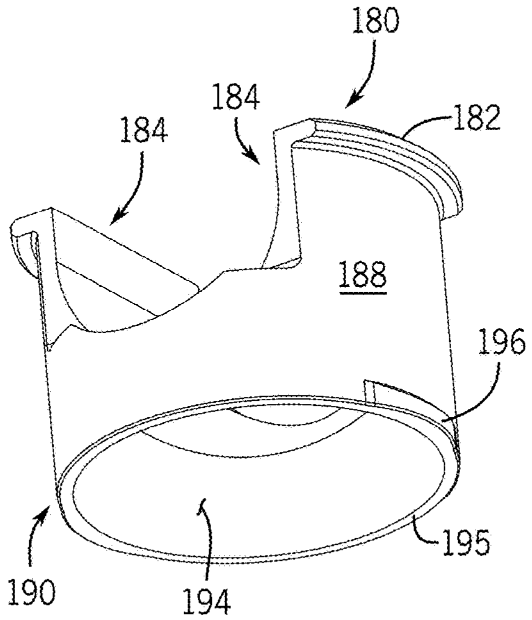
FIG. 21 is a bottom perspective view of the pressure insert of FIG. 20.
Figure 22:
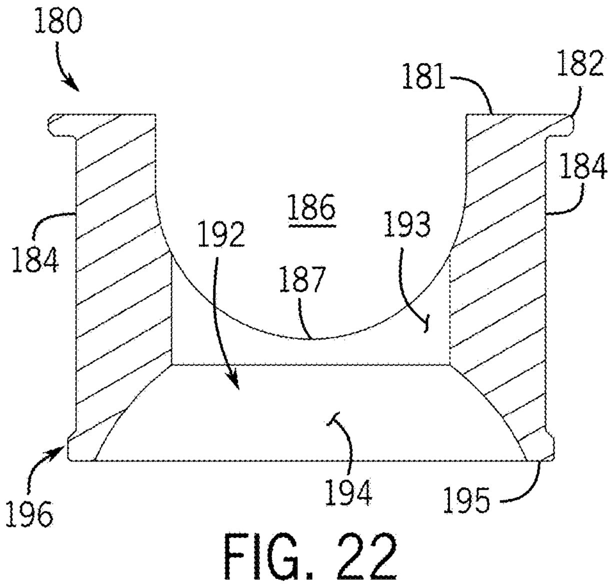
FIG. 22 is a cross-sectional side view of the pressure insert of FIG. 20.
Figure 23:
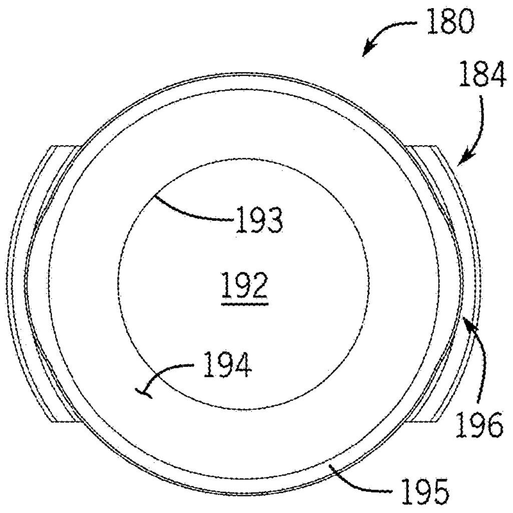
FIG. 23 is a bottom view of the pressure insert of FIG. 20.

Illustrated in FIGS. 2 and 8-11 is the multiplanar receiver 100 having a generally U-shaped appearance with a partially discontinuous substantially cylindrical inner profile and a partially cylindrical and partially faceted outer profile, although other profiles are contemplated. The multiplanar receiver 100 has a vertical centerline axis 101, or axis of rotation, that is shown in FIG. 9 that is alignable with the longitudinal axis 52 of the bone anchor 50 shown in FIG. 5, such orientation being desirable, but not required during assembly of the multiplanar receiver sub-assembly 11 with the bone anchor 50. After the multiplanar receiver sub-assembly 11 is pivotally attached to the capture portion 60, either before or after the bone anchor 50 is implanted in a vertebra, the receiver axis 101 is typically disposed at an angle with respect to the shank axis 52 as shown, for example, in FIGS. 64-65.

The multiplanar receiver 100 generally comprises a base portion 140 defining an internal cavity 134 or lower portion of a generally cylindrical central bore 120 that is centered around the receiver's vertical centerline axis 101, and a pair of upright arms 110 extending upwardly from the base 140 to form the upper portion of the receiver and to define an upwardly-open channel 106 configured for receiving the elongate rod. Each of the upright arms 110 has an interior face 104 that includes a discontinuous upper portion of the central bore 120, which may be bounded on either side by opposing vertical planar end surfaces 107 that curve downwardly into U-shaped lower saddle surfaces 108. In one aspect the opposing end surfaces 107 and saddle surfaces 108 can define the front and back ends of the upwardly open channel 106 that also opens laterally onto a front face 116 and a back face 117 of the multiplanar receiver 100, respectively. The central bore 120 can extend from top surfaces 102 of the upright arms 110 at the proximal end 103 of the receiver downwardly through both the open channel 106 and the internal cavity 134 to communicate with a bottom surface 148 of the multiplanar receiver 100 through a bottom opening 144. In addition, it is foreseen that the multiplanar receiver 100 can be configured to have a closed rod-receiving channel, in which case the top surfaces 102 and upper portions of the upright arms 110 can connect together to form a solid ring surrounding the central bore 120, and in which case one or more of its internal components can be uploaded into the central bore of the receiver through its bottom opening.

The upper or channel portion of the central bore 120 further includes a discontinuous guide and advancement structure 122 formed into the interior faces 104 of the upright arms 110, which guide and advancement structure 122 is configured to engage with a complementary structure formed into the outer side surfaces of the closure 30, as described more fully below. The guide and advancement structure 122 in the illustrated embodiment is a discontinuous helically wound thread form having a square-shaped thread 123. It will be understood, however, that the guide and advancement structure 122 could alternatively comprise an interlocking flange-like thread, a buttress thread, a modified buttress thread, a reverse angle thread, or other thread-like or non-thread-like closure mating structure for operably guiding a closure, such as closure 30, downward between the arms 110 under rotation, as well as for the closure 30 engaging directly against the elongate rod positioned within the channel 106. Additionally, the various structures and surfaces forming a helically wound guide and advancement structure 122 can also be configured to resist, to inhibit, to limit, or to preferentially allow and control some limited amount of splay of the upright arms 110 of the receiver while advancing the closure 30 downward under rotation and when torquing the closure 30 against the elongate rod to generate a downwardly-directed thrust that locks the bone anchor assembly into position.

Moving downward along the interior faces 104 of the upright arms 110, the portion of the central bore 120 located between the vertical end surfaces 107 that define the channel 106 can include a runout groove 124 immediately below the guide and advancement structure 122 that is followed, in turn, by a discontinuous upper cylindrical ledge structure 126 and a discontinuous inner recess 128 defined by a downward-facing upper arcuate surface 127 and an upward-facing lower arcuate surface 129. A partially discontinuous cylindrical surface 130 can then extend downwardly from the inner recess 128 and around and below the lower saddle surfaces 108 to an upwardly-facing circumferential ledge 132 that is located in a central portion of the internal cavity 134, or lower portion of the central bore 120. In one aspect the upwardly-facing circumferential ledge 132 can be located at the upper end of an inwardly-protruding over-travel lip structure 133, as described below. The cylindrical surface 130 can further include opposed expanded portions 131 aligned with and extending below the inner edges of the saddle surfaces 108, with the expanded portions 131 providing for ease of assembly of the pressure insert 180 into the bore 130 of the receiver, as discussed below. The circumferentially continuous portions of cylindrical surfaces 130, 131 can thus define the upper portion of the internal cavity 134 of the multiplanar receiver 100.

The lower portion off the internal cavity 134 includes a seat surface 136 that can be frictionally slidably mateable with the spherically-shaped outer surface of the ring retainer 152 and with the lower curvate section 84 of the capture portion 60 at high angles of articulation of the bone anchor 50 with respect to the multiplanar receiver 100. When formed as a spherical surface, for example, the spherical seat surface 136 can also extend from an equator plane 135 (defined as the maximum diameter of the spherically-shaped seat surface 136 in a plane perpendicular to the vertical centerline axis 101 of the multiplanar receiver 100) upwardly and inwardly along the inwardly-protruding over-travel lip structure 133 to the upwardly-facing circumferential ledge 132, as well as downwardly and inwardly from the equator plane 135 to the lower edge 143 that, together with a lowermost cylindrical or chamfered surface 145, can define the bottom opening 144 of the multiplanar receiver 100.

The spherical seat surface 136 can be continuous around the circumference of the cavity 134 except for the lower portions of opposed vertically-aligned recesses or side pockets 138 formed into cylindrical surface 130, with the opposed side pockets 138 extending downward through the ledge surface 132 into the upper portion of the spherical seat surface 136. As discussed in more detail below, the opposed side pockets 138 can be sized and shaped for receiving opposite tabs extending outward from the outer surface of the pressure insert 180 during assembly of the multiplanar receiver sub-assembly 11, so as to maintain a rotational alignment of the pressure insert 180 with respect to the multiplanar receiver 100. It is also foreseen that the multiplanar receiver 100 can be configured without the ledge surface 132 in some embodiments.

It is foreseen that the other shapes or structures for the seat surface of the central bore, which are also slidably mateable with a multiplanar shank connecting or retainer sub-assembly 150 configured to hold the bone anchor 50, are also possible, including but not limited to a non-spherical surface, a conical or tapered surface, a chamfered surface, a stepped lower structure with one or more inner edges (whether sharp or rounded), and the like, and are considered to fall within the scope of the present disclosure. It is further foreseen that the seat surface could also be in a separate lower portion or part of the receiver.

The multiplanar receiver 100 can have a partially cylindrical and partially faceted outer profile. In the illustrated embodiment, for example, the partially cylindrical portions can include curvate side outer surfaces 112 of the upright arms 110 opposite the interior faces 104 that extend downward from the top surfaces 102 of the upright arms toward a lower tapered surface 146 of the base 140 that angles inwardly to the bottom surface 148 of the multiplanar receiver 100. The multiplanar receiver 100 can further include upper curvate-extending instrument engaging grooves 114 below the top surfaces 102 of the upright arms 110 that extend horizontally across the curvate side outer surfaces 112 to the front face 116 and the back face 117 of the multiplanar receiver 100.

Likewise shown in the drawings, the faceted or planar portions of the multiplanar receiver 100 may comprise front and back outer planar faces 142 on the receiver base 140 below the open channel 106, and which can extend upwardly as narrow flats 118 on the front and back faces 116, 117 of the upright arms. The faceted or planar portions of the multiplanar receiver 100 can further include side outer planar faces (not shown) and/or tool receiving and engaging recesses (also not shown) formed into the curvate side outer surfaces 112 below the upper instrument engaging grooves 114, and which can be parallel with each other and oriented perpendicular to the front and back outer planar faces 142. In one aspect the upper instrument engaging grooves 114, the front and back outer planar faces 142, the narrow flats 118, and any other planar tool-engagement surface or recess can serve together as outer tool engagement surfaces that allow for tooling to more securely engage and hold the multiplanar receiver 100 during an initial pre-assembly with the internal components to form the multiplanar receiver sub-assembly 11, during coupling of the receiver sub-assembly to the bone anchor 50, either after or before the implantation of the body 90 of the bone anchor into a vertebra, and also during further assembly of the multiplanar receiver sub-assembly 11 with the elongate rod and the closure 30 so as to aid in torquing and counter-torquing to lock the assembly.

Furthermore, it will be appreciated that the multiplanar receiver 100 can include additional features and aspects not shown in the drawings, including but not limited to inwardly-threaded breakoff extensions extending upwardly from the tops of the upright arms for interfacing with tooling and for guiding the elongate rod and the outwardly-threaded closure into the receiver channel. It is also foreseen that other shapes and configurations for the interior and exterior surfaces of the multiplanar receiver 100, different from those shown in the drawings while providing for similar interaction and functionality of the various components of the pivotal bone anchor assembly, are also possible and considered to fall within the scope of the present disclosure, including but not limited to receivers having bottom openings with cut-out sections or slanted bottom surfaces that form oblique or expanded bottom openings, and the like, that provide for increased pivotal motion for the shank in at least one direction.

Illustrated in FIGS. 2 and 12-15 is an example of a multiplanar embodiment for the ring retainer 152 comprising an O-ring body having a curvate outer surface, such as spherical outer surface 156 extending between a top annular or edge surface 154 and a bottom annular or edge surface 158, and a center aperture 160. The center aperture 160 can be defined by inner slidable surfaces 162, 168 that are configured to loosely slidably engage with the outer slidable surfaces 68, 74 of the capture portion 60 of the bone anchor 50 when the capture portion is fully uploaded into the ring retainer 152. The ring retainer 152 can also include an internal recess 164 that extends into and circumferentially around a mid-portion of the center aperture 160, and which can be defined by an upper annular surface 165, a recess sidewall surface 166, and a lower tapered or beveled surface 167. The center aperture 160 can further include a lower chamfered surface 169 extending between the lower inner slidable surface 168 and the bottom annular or edge surface 158, and which can be complementary with the beveled lip surface 81 of the capture portion 60 of the shank 50. The ring retainer 152 can also include a slit or slot 153 extending through the thickness of the O-ring body, from the center aperture 160 through to the outer surface 156, to form an open ring retainer that is expandable so as to allow the capture ring 170 to be preloaded or positioned within the internal recess 164, and which is also compressible so as to allow the ring retainer 152 to be pressed into the spherical seat surface 136 of the cavity 134 of the multiplanar receiver 100 so as to provide for a pre-lock friction fit and alignment stability for the retainer sub-assembly 150 with respect to the multiplanar receiver 100.

As described in more detail below, the multiplanar ring retainer 152 is securable within the cavity 134 of the multiplanar receiver 100 with the spherical outer surface 156 being frictionally engaged with the spherical seat surface 136, and with the center aperture 160 being centered above the bottom opening 144 of the multiplanar receiver 100. As noted above, the spherical outer surface 156 of the ring retainer 152 can also have the same radius as the lower spherical extension 86 of the lower curvate section 84 and the upper spherical extension 66 of the upper curvate section 64, in which case the three spherical surfaces 156, 66, 86 may align with each other to form a substantially spherical capture head when the bone anchor 50 is coupled to the ring retainer 152. Moreover, the lower chamfered surface 169 of the ring retainer 152 can be adjacent to, or even contacting, the beveled lip surface 81 of the capture portion 60 (described above) when the bone anchor 50 is coupled to the ring retainer 152 (as shown in FIGS. 60-65).

With the reference to FIGS. 2 and 16-19, the pivotal bone anchor assembly 12 further includes a capture ring 170 comprising an open ring body having a slit or slot 175 that allows for expansion of the capture ring 170 during assembly of the bone anchor 50 to the multiplanar receiver sub-assembly 11. As illustrated in the drawing figures, the open ring body can have a variable height between an outwardly- and downwardly-beveled top surface 172 and an outwardly- and upwardly-beveled bottom surface 178. The open ring body can also have a variable width between a tapered outer surface 176 and a tapered inner surface 176 that is greater toward the bottom end of the capture ring 170, so as to define a non-rectangular wedge-shaped body in cross section. Moreover, the height of the capture ring, as measured along a central axis of the capture ring, can be at least twice its maximum width, as measured between the tapered inner surface 176 of the capture ring aperture 173 and a lower outer edge 177 that defines the junction between the tapered outer surface 174 and the beveled bottom surface 178. Indeed, in some aspects the height of the capture ring 170 can be three to four times the maximum width, so as to better control and direct the forces that are transferred downward from the upper portion of the capture portion of the shank to the lower portion of the ring retainer 152 and seat surface 136 of the multiplanar receiver 100.

The tapered inner surface 176 generally defines the capture ring aperture 173 that can be smaller than the center aperture 160 of the ring retainer 152 when the capture ring 170 is in a neutral or free state (i.e. neither compressed nor expanded). The tapered inner surface 176 can have a taper angle ranging between about three degrees and about nine degrees, and can be complementary with the outwardly-facing inner recessed surface 72 of the capture recess 70 described above.

Furthermore, the junction between the tapered inner surface 176 and the beveled top surface 172 can define a rounded top edge 171 of the capture ring 170, while the junction between the tapered inner surface 176 and the beveled bottom surface 178 can define a rounded bottom inner edge 179. As described below, both the rounded top edge 171 and beveled top surface 172 are configured to engage with the complementary upper step surface 71 of the capture recess 70 of the capture portion 60. At the opposite end, the rounded bottom inner edge 179 is configured to engage with the lower step surface 73 of the capture recess 70, while the beveled bottom surface 178 is configured to engage with the complementary lower beveled surface 167 of the inner recess 164 of the ring retainer 152.

With the reference to FIGS. 2 and 20-23, the pivotal bone anchor assembly 12 further includes a pressure insert 180 that can be configured to both control the movement of capture portion 60 of the shank 50 during its uploading into the multiplanar receiver sub-assembly 11, and to transfer a downwardly directed force from the elongate rod and the closure 30 to the top of the capture portion 60 of the shank 50 and to the ring retainer 152 and, thereby locking the pivotal bone anchor assembly 12 in a fixed angular and rotational position. As such, the pressure insert 180 includes an inner upward-facing rod-seating surface 187 that is engageable with the elongate rod, and a rounded concave (as shown) or tapered lower surface 194 that is engageable with the curvate outer surface 156 of the ring retainer 152 and the upper curvate section 64 of the capture portion 60 as it projects upwardly above the top annular or edge surface 154 of the ring retainer 152. Thus, in one aspect the inner upward-facing surface 187 can be a curved saddle surface that extends between two upright insert arms 184 that are formed integral with a lower insert base portion 190 and extend upward to define an insert channel 186 configured to receive the elongate rod, and with the base portion 190 and upright arms 184 together defining an cylindrical outer surface 188 sized to be slidably received within the central bore 120 of the multiplanar receiver 100. In another aspect, the concave lower surface 194 of the pressure insert can be a spherical surface that extends upward and inward from an annular lower bottom edge 195 to define a downwardly-opening concave spherical surface. The pressure insert can also include a central tool-receiving aperture 192 defined by an inner cylindrical surface 193 configured to slidably receive a drive tool (not shown) that extends downwardly through the central bore 120 to engage the internal drive socket 54 formed into the top end 53 of the universal capture portion 60.

The upright insert arms 184 can further include flanges 182 that project radially outward from the top portions of the insert upright arms 184, with the flanges having top surfaces 181 that are configured to rotate under the downward-facing upper arcuate surfaces 127 of the discontinuous recess 128 formed into the central bore 120 of the receiver, as describe above in reference to FIGS. 8-11. In the representative embodiment of the pivotal bone anchor assembly shown in FIGS. 20-23 and 44-48, for example, the pressure insert 180 can be rotatable with a tool, up to and through about a 90 degree range (approximately ¼ turn) around the vertical centerline axis 101 of the multiplanar receiver 100, with the outwardly-projecting flanges 182 rotating into a center portion of the discontinuous recess 128 so that the top surfaces 181 of flanges 182 are aligned with but spaced below the downward-facing upper arcuate surfaces 127.

The pressure insert 180 may additionally include an indexing structure configured to releasably engage with a complementary indexing structure formed into the central bore 120 of the multiplanar receiver 100, upon rotation of the pressure insert about the receiver vertical centerline axis 101, so as to inhibit further rotation of the pressure insert out of its rotated position. For example, and as shown in FIGS. 20-23 and 44-48, in one embodiment the indexing structure of the insert can comprise opposite outwardly projecting nubs or protuberances 196 located near the lower bottom edge 195 of the base portion 190 or higher up along the side of the insert that releasably engage with the opposed vertical side pockets 138 formed into the central bore 120 of the multiplanar receiver 100 upon rotation of the pressure insert 180 into its rotated position. It is foreseen that other structures can be used to hold the insert relative to the receiver, such as crimps, pegs, set screws or separate rings, to inhibit rotational and/or translational movement of the insert about the vertical axis of the receiver, and that the pressure insert could be snapped in place, or otherwise positioned, within the receiver.

Figure 24:
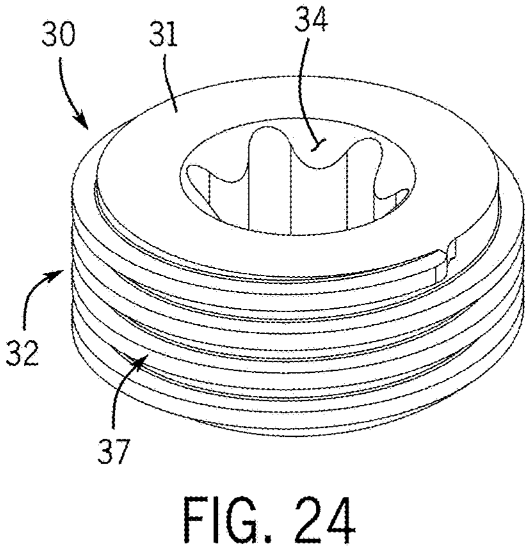
FIG. 24 is a top perspective view of the closure of the pivotal bone anchor assembly of FIG. 2.
Figure 25:
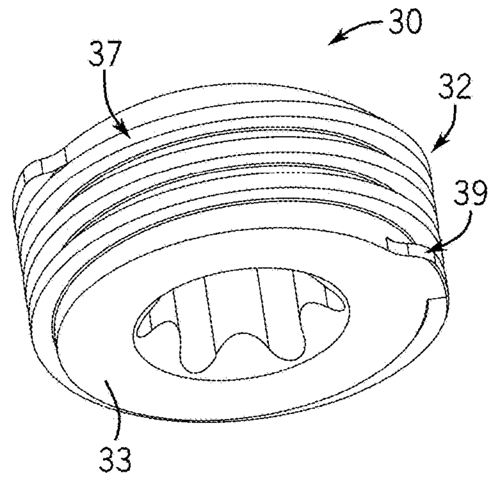
FIG. 25 is a bottom perspective view of the closure of FIG. 24.

With reference to FIGS. 2 and 24-25, the closure top or closure 30 of the pivotal bone anchor assembly 12 can comprise a substantially cylindrical body having a top surface 31, a bottom surface 33, and a continuous guide and advancement structure 37 formed into its outer surface 36, with the guide and advancement structure 37 being rotatably mateable with the complementary discontinuous guide and advancement structure 122 formed into the upper portion of the central bore 120 of the multiplanar receiver 100 that is defined by the interior faces 104 of the upright arms 110. As shown in the drawings, the continuous guide and advancement structure 37 of the closure can further include one or more start structures 39 that are specifically shaped to engage one or more lead-in structures of the discontinuous guide and advancement structure 122 of the multiplanar receiver 100 in a controlled fashion and with less tendency to cross-thread.

The closure 30 can also include a central drive structure, such as a central drive socket 34 and/or a breakoff head (not shown) formed into or attached to the top surface 31 of the cylindrical closure body, as known in the art. As shown, the central drive socket 34 can extend entirely through the body of the closure 30 to form a through-aperture, with both the top surface 31 and bottom surface 33 being annular surfaces. Alternatively, the central drive socket 34 may extend only partially down into the body of the closure and the bottom surface 33 can be a continuous solid surface across the expanse thereof (not shown), and which in some aspects may be substantially planar across the expanse of the bottom surface, or in other aspects may include downwardly extending structures, such a spike or ring, that can be pressed into the upper portion of the elongate rod to further secure the elongate rod to the pivotal bone anchor assembly. It is also foreseen that the closure can be multi-part in nature, as is known in the art.

Figure 26:
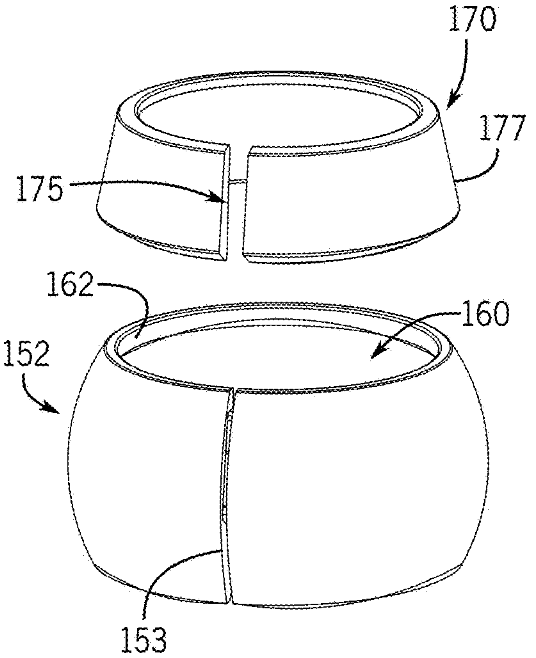
FIG. 26 is a perspective view of the ring retainer of FIG. 12 and the capture ring of FIG. 16 prior to assembly together into a multiplanar retainer sub-assembly.
Figure 27:
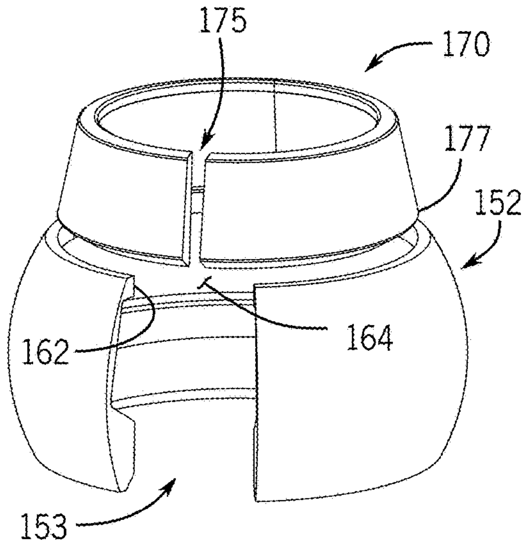
FIG. 27 is a perspective view of the ring retainer and capture ring of FIG. 26 during assembly together into the multiplanar retainer sub-assembly.

To begin assembly of the pivotal bone anchor assembly 12, the capture ring 170 can first be installed or positioned into the internal recess 164 of the ring retainer 152 to form the retainer sub-assembly 150, as shown in FIGS. 26-31. With reference to FIG. 26, to begin this assembly the capture ring 170 can be placed above the ring retainer 152 in preparation for top loading into the center aperture 160 of the ring retainer 152 (although bottom loading into the ring retainer is also contemplated). The ring retainer 152 can then be expanded and the slot 153 opened until the diameter of the center aperture 160 at the upper inner slidable surface 162 is greater than the outer diameter of the lower outer edge 177 of the capture ring 170, as shown in FIG. 27. In one aspect the capture ring 170 can also be slightly compressed so that the width of the capture ring slot 175 and the outer diameter of the lower outer edge 177 is less than what it would be in its neutral or free-standing state.

Figure 28:
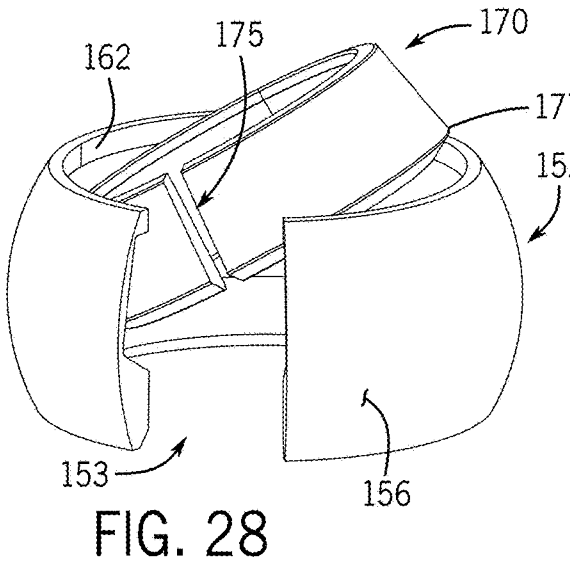
FIG. 28 is another perspective view of the ring retainer and capture ring of FIG. 26 during assembly together into the multiplanar retainer sub-assembly.
Figure 29:
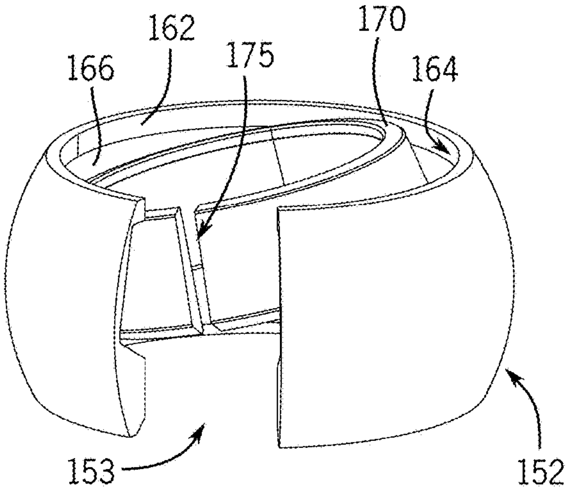
FIG. 29 is another perspective view of the ring retainer and capture ring of FIG. 26 during assembly together into the multiplanar retainer sub-assembly.
Figure 30:
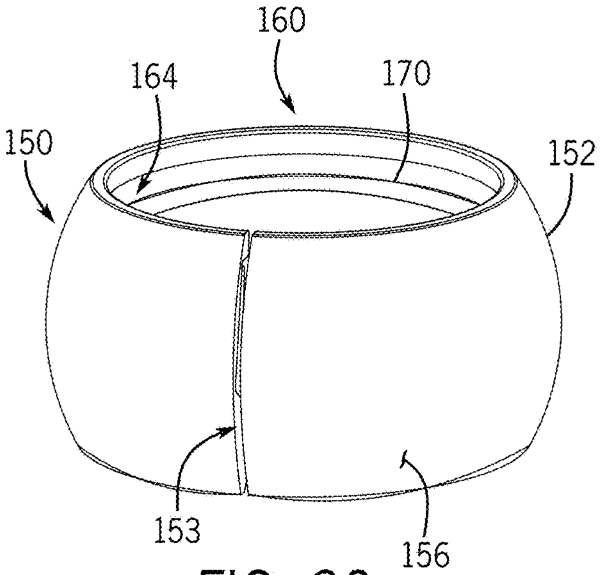
FIG. 30 is a perspective view of the ring retainer and capture ring of FIG. 26 after assembly together into the multiplanar retainer sub-assembly.
Figure 31:
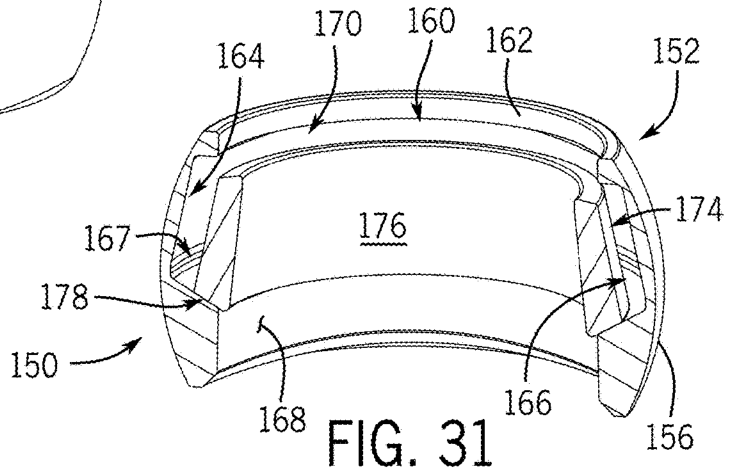
FIG. 31 is a cross-sectional perspective view of the ring retainer and capture ring of FIG. 30 after assembly together into the multiplanar retainer sub-assembly.

As shown in FIGS. 28-29, the capture ring 170 may then be tilted and inserted into the center aperture 160 of the ring retainer 152 at an angled orientation, until one side of the lower outer edge 177 contacts the inward-facing recessed surface 166 of the internal recess 164 or the adjacent portion of the beveled lower surface 167, thereby allowing the opposite side of the angled capture ring 170 to drop down into the opposite side of the internal recess 164. The ring retainer 152 can then be released to close back toward its neutral state to capture the now-horizontal capture ring 170 within its internal recess 164, as shown in FIG. 30. With reference to the cross-sectional view of FIG. 31, the capture ring 170 in its neutral or free state can project partially into the center aperture 160 of the ring retainer 152 while simultaneously providing for a space or gap between the outer surface 174 of the capture ring and the recessed sidewall surface 166 of the internal recess 164 that allows for the expansion of the capture ring 170 within the internal recess 164 during future assembly steps without the need for expansion of the ring retainer 152. In one aspect the resting engagement between beveled bottom surface 178 of the capture ring 170 and the lower tapered or beveled surface 167 of the inner recess 164 of the ring retainer can act to center the capture ring 170 within the center aperture 160 of the ring retainer 152.

It will be understood that the forced expansion of the ring retainer 152 shown in FIGS. 27-29 can result in a marginal inelastic deformation of the O-ring body of the ring retainer 152, so that the diameter of the spherical outer surface 156 in the free and neutral state is now greater than what is was before the expansion. As described below, this deformation can be advantageously employed in subsequent assembly steps to establish a compressive friction engagement between the spherical outer surface 156 of the ring retainer 152 and the spherical seat surface 136 of the multiplanar receiver 100.

Figure 32:
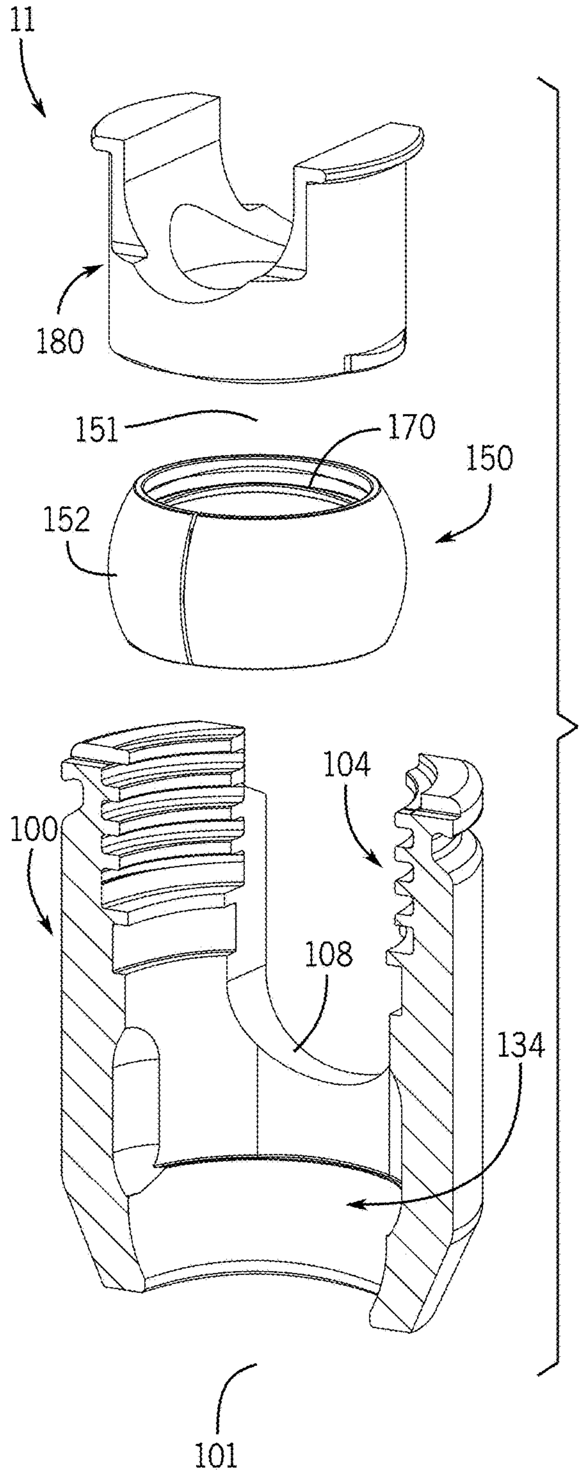
FIG. 32 is an exploded cross-sectional perspective view of the components of a multiplanar receiver sub-assembly prior to their pre-assembly into a shipping configuration with the receiver configured to house the multiplanar retainer sub-assembly.

Illustrated in FIG. 32 are the individual components of the multiplanar assembly 12 that, in many embodiments, can be pre-assembled together into a receiver sub-assembly at a factory or manufacturing facility, prior to shipping to a spine company or a hospital or surgery center and engagement with the capture portion of the bone anchor in the surgical setting. As described above, these components generally include the multiplanar receiver 100, the retainer sub-assembly 150 that incorporates the ring retainer 152 with the separate open capture ring 170 secured therein, and the pressure insert 180. In one aspect the multiplanar receiver 100, the retainer sub-assembly 150, and the insert 180 being pre-assembled into a receiver sub-assembly can be further defined as the shipping state configuration for the 'modular' bone anchor assembly, as described herein and commonly understood in the art. It will be appreciated, however, that in other embodiments the shipping state configuration can include the additional assembly of the multiplanar receiver sub-assembly together with the bone anchor at the factory or manufacturing facility or the spine company. It will also be appreciated that in yet other embodiments the individual components described above can also be pre-assembled into the receiver sub-assembly at the hospital or surgery center prior to implantation in a patient.

Figure 33:
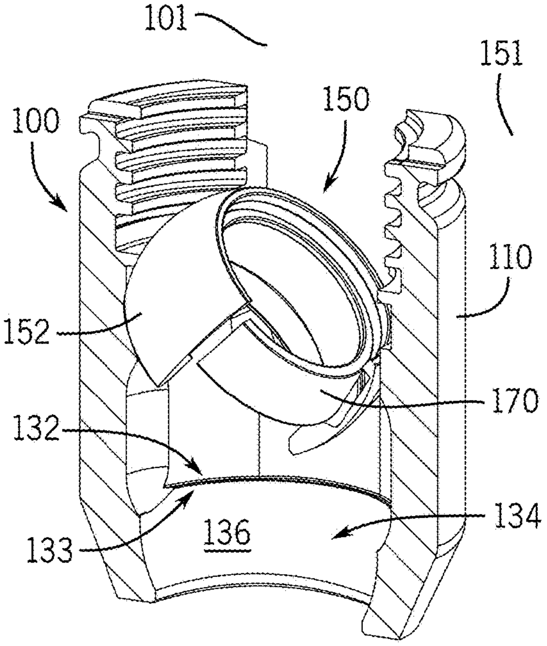
FIG. 33 is a partially cut-away front perspective view of the receiver of FIG. 32 with the multiplanar retainer sub-assembly being downloaded through the open channel of the receiver.
Figure 34:
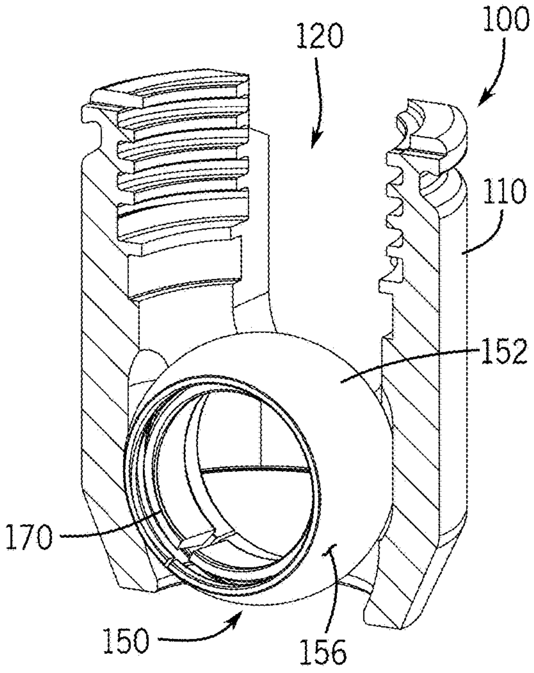
FIG. 34 is a partially cut-away front perspective view of the receiver of FIG. 33 with the multiplanar retainer sub-assembly being further downloaded into the cavity of the receiver.
Figure 35:
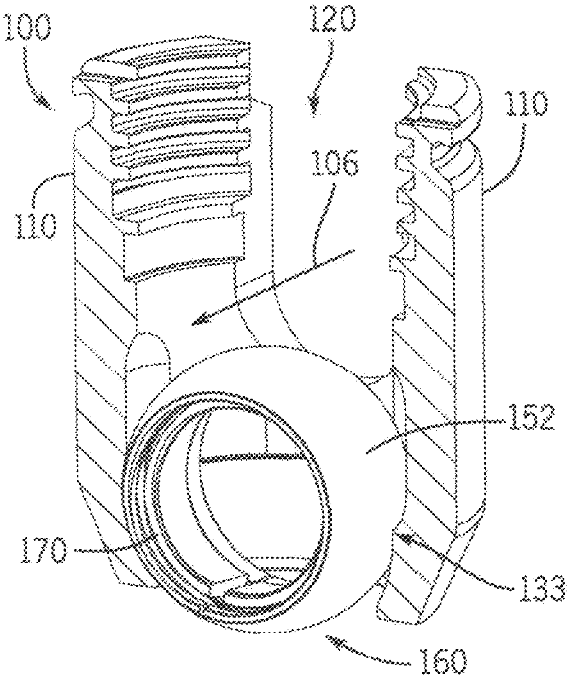
FIG. 35 is a partially cut-away front perspective view of the receiver of FIG. 34 with the vertically-oriented multiplanar retainer sub-assembly contacting the upper edge of the seat surface of the receiver.
Figure 36:
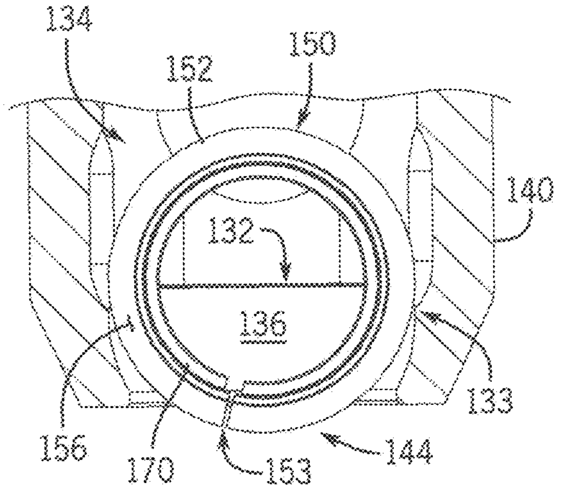
FIG. 36 is a partially cut-away front view of the receiver and multiplanar retainer sub-assembly of FIG. 35.

To begin the pre-assembly of the receiver sub-assembly 11, the capture ring 170 can first be installed into the internal recess 164 of the ring retainer 152 to form the retainer sub-assembly 150 (FIGS. 30-31), as described above. The retainer sub-assembly 150 can then be top-loaded into the multiplanar receiver 100, as shown in FIGS. 33-39. This can be achieved, for instance, by rotating the ring retainer 152 to a substantially vertical position in which the axis of rotation 151 of the retainer sub-assembly 150 is substantially perpendicular to the vertical centerline axis 101, and in which the top and bottom surfaces of the ring retainer 152 can face the interior faces 104 of the receiver arms 110 (as shown in FIG. 33) or the saddle surfaces 108 that help define the upwardly-open channel 106 (as shown in FIG. 34), or at any orientation in between. The retainer sub-assembly 150 can then be downloaded through the receiver channel 106 and into the receiver cavity 134 or lower portion of the central bore 120 until the spherical outer surface 156 of the ring retainer 152 contacts the inner edge of the ledge surface 132 located at the upper end of the inwardly-protruding overtravel lip structure 133, at two opposing points (or lines) of contact across the cavity 134 of the multiplanar receiver 100, as shown in FIGS. 35-36. In one aspect ring retainer 152 can be positioned so that the slot 153 is located on the lower side of the ring retainer in the lower portion of the cavity 134.

Figure 37:
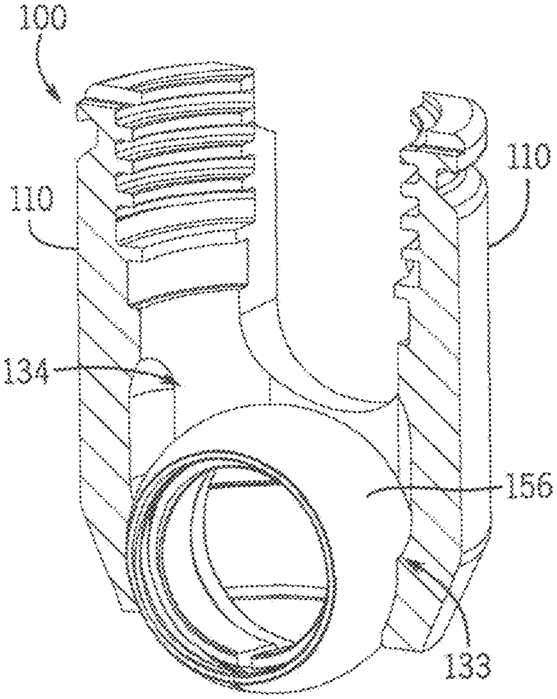
FIG. 37 is a partially cut-away front perspective view of the receiver with the multiplanar retainer sub-assembly being somewhat resiliently compressed and pushed down into a vertical partially-seated engagement with the seat surface of the receiver.
Figure 38:
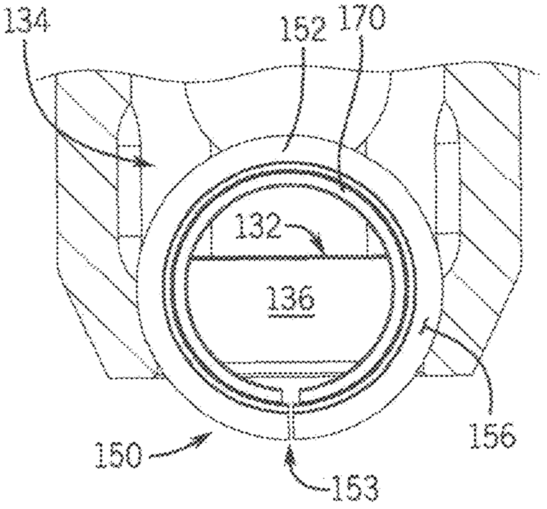
FIG. 38 is a partially cut-away front view of the receiver and multiplanar retainer sub-assembly of FIG. 37.

With the inner diameter of the spherical seat surface 136 of the cavity 134 being substantially equal to or slightly less than the outer diameter of the spherical outer surface 156 of the ring retainer 152, the diameter of the central bore 120 of the multiplanar receiver 100 at the inner edge of the ledge surface 132 will be less that the outer diameter of the spherical outer surface 156 in its neutral or free-standing state. This is because, as previous described, the spherical seat surface 136 extends upwardly and inwardly from the equator plane 135 to the ledge surface 132, thereby reducing the diameter of the spherically-shaped seat surface 136 as measured in a plane perpendicular to the vertical centerline axis 101 of the multiplanar receiver 100, such as the plane of the ledge surface 132. Thus, with the ring retainer 152 contacting the inner edge of the ledge surface 132, the retainer sub-assembly 150 can then be pushed or driven downward against the inner edge until the slot 153 closes and the O-ring body of the ring retainer 152 compresses to a smaller diameter that allows the ring retainer 152 to pass downward below the ledge surface 132 and into the lower portion of the cavity 134 defined by the spherical seat surface 136, as shown in FIGS. 37-38, after which the O-ring body of the ring retainer 152 is allowed to expand back toward its neutral or free-standing size, but with some residual slight compression for a tight fit therebetween.

Figure 39:
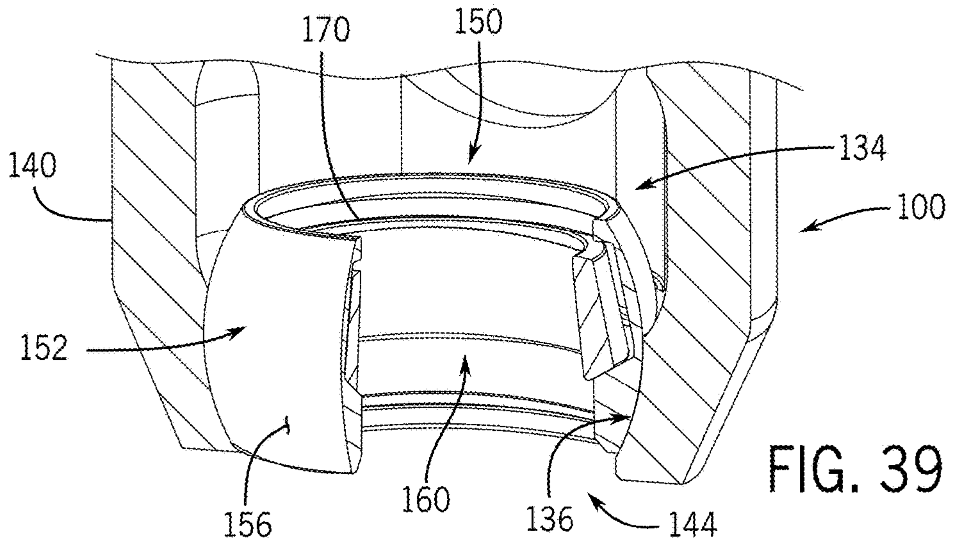
FIG. 39 is a partially cut-away front perspective view of the receiver with the multiplanar retainer sub-assembly being rotated into a horizontal fully-seated friction fit stabilizing engagement against the seat surface of the receiver.

Depending on the relative diameters and tolerances of the inner spherical seat surface 136 of the cavity 134 and the outer spherical surface 156 of the ring retainer 152, the ring retainer 152 can engage the spherical seat surface 136 of the multiplanar receiver 100, both above and below the equator plane of the cavity 134, again with a slight interference fit, thereby establishing a compressible frictional engagement between the two structures that inhibits the movement of the retainer sub-assembly 150 relative to the multiplanar receiver 100. The retainer sub-assembly 150 can now be rotated with force to a horizontal orientation, as shown in FIG. 39, with the spherical outer surface 156 of the ring retainer 152 more fully engaged with the inner spherical seat surface 136 of the cavity 134, and with the center aperture 160 of the ring retainer 152 being centered above the bottom opening 144 and co-aligned with the vertical axis 101 of the multiplanar receiver 100.

It is foreseen that other structures and interconnections between the components of the receiver sub-assembly can be also used to secure the ring retainer 152 in its pre-assembled position within the receiver cavity 134 with its center aperture 160 aligned and centered with the bottom opening 144 at the base 140 of the multiplanar receiver 100, and are considered to fall within the scope of the present disclosure, such as a downward force from a frictional engagement with the pressure insert.

Figure 40:
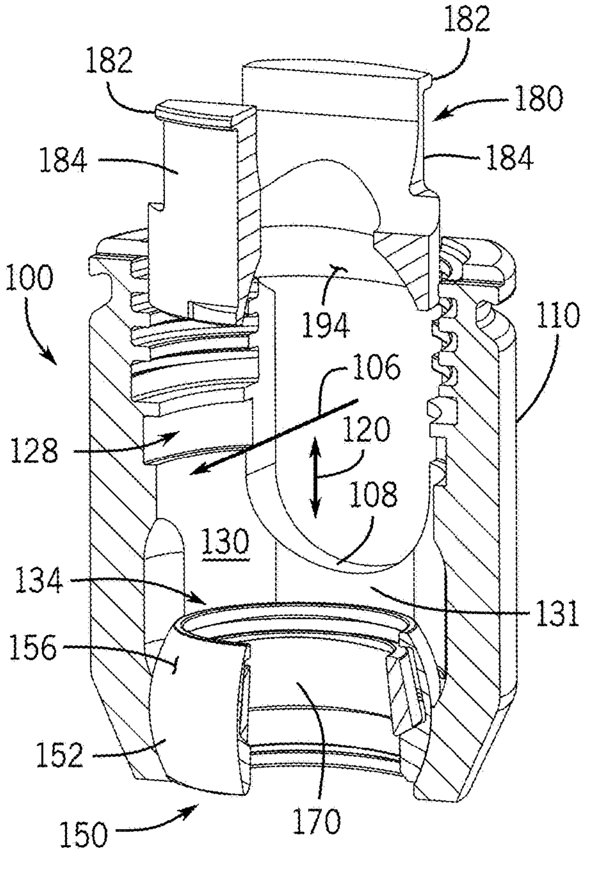
FIG. 40 is a partially cut-away front perspective view of the receiver with the seated multiplanar retainer sub-assembly and with a pressure insert being downloaded through the open channel of the receiver.
Figure 41:
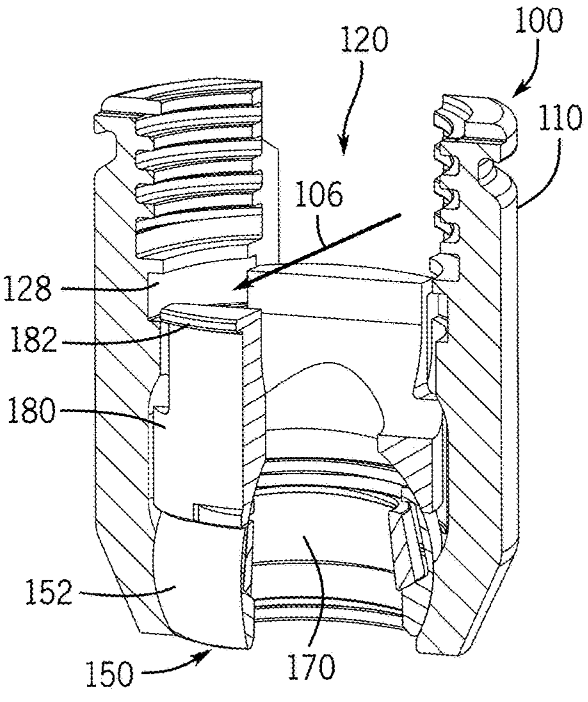
FIG. 41 is a partially cut-away front perspective view of the receiver with the seated multiplanar retainer sub-assembly, with the pressure insert being further downloaded into the cavity of the receiver to engage the ring retainer.

After the retainer sub-assembly 150 is seated within the spherical seat surface 136 of the multiplanar receiver 100, the pressure insert 180 may then be top-loaded into the central bore 120 and installed into its the shipping state position above the retainer sub-assembly 150. As shown in FIGS. 40-41, this can be achieved by positioning the pressure insert 180 above the central bore 120 of the receiver with the insert arms 184 and radially projecting flanges 182 being aligned with the receiver channel 106, and then downloading the pressure insert 180 through the receiver channel 106 until the concave lower surface 194 of the pressure insert 180 contacts the upper portion of the spherical outer surface 156 of the ring retainer 152 and the flanges 182 reach the level of the discontinuous inner recess 128 formed into the central bore 120 for this type of twist-in-place insert.

Figure 42:
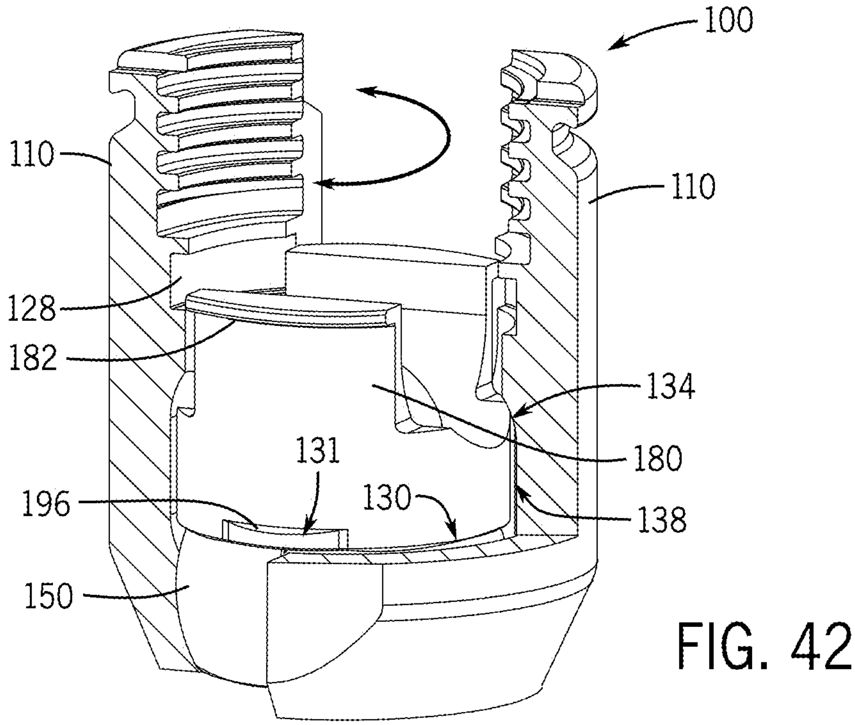
FIG. 42 is another partially cut-away front perspective view of the receiver with the seated multiplanar retainer sub-assembly and downloaded the pressure insert, schematically showing the range of engagements between the lower projection of the insert and the upper portion of the receiver cavity.
Figure 43:
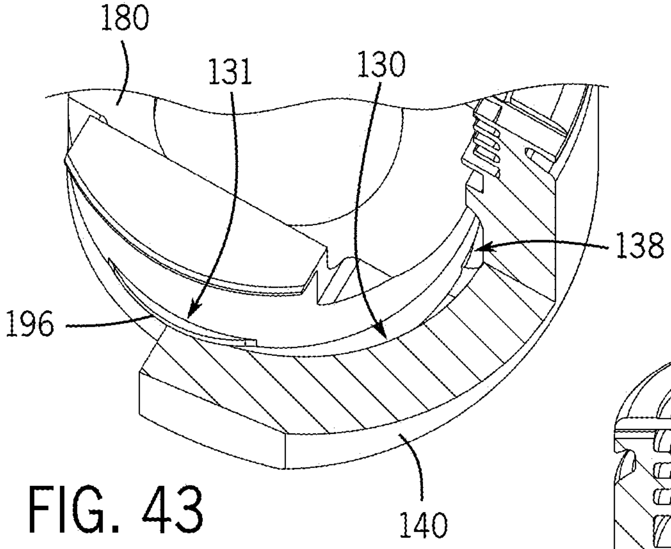
FIG. 43 is another partially cut-away front perspective view of the receiver with the seated multiplanar retainer sub-assembly and downloaded the pressure insert, prior to rotation of the pressure insert about the vertical centerline axis of the receiver.

As shown in the partially cut-away perspective views of FIGS. 42-43, during the downloading of the pressure insert 180 through the receiver channel 106 the opposite outwardly-projecting nubs or protuberances 196 of the insert will generally be aligned with the inner edges of the saddle surfaces 108 and the opposed expanded portions 131 of the substantially cylindrical surface 130 that defines the upper portion of the cavity 134 (see FIG. 40). The opposed expanded portions 131 can have a diameter that is greater than the distance between the outermost surfaces of the projecting nubs 196, thereby allowing the nubs to move downwardly passed the saddle surface 108 and freely enter the cavity 134 during the downloading of the pressure insert 180.

Figure 44:
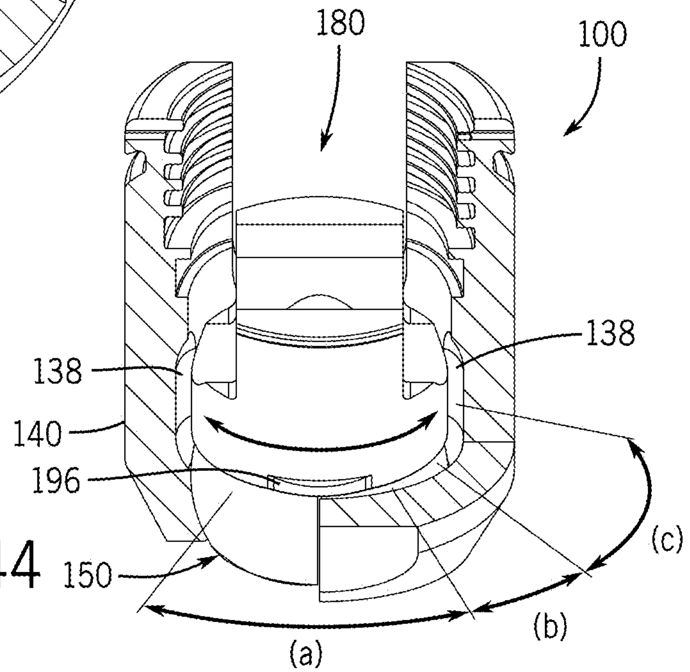
FIG. 44 is close-up partially cut-away top perspective view of the receiver, seated multiplanar retainer sub-assembly, and downloaded pressure insert of FIG. 43.

With reference to FIG. 44, the opposed expanded portions 131 of the cavity 134 can thus provide limited zones (A) of free motion for the nubs 196 when the pressure insert 180 is rotated slightly in either direction, while the non-expanded portions of the cylindrical surface 130 on either side of the expanded portions 131 can have a diameter that is slightly less than the distance between the outer surfaces of the projecting nubs, so as to create limited zones (B) with a slight interference or frictional fit between the nubs and the cylindrical surface. This interference can inhibit further rotation with pressure insert without a moment force that may be applied, for instance, with a tool. As can also be seen in FIG. 44, the opposed vertical side pockets 138 located at right angles to the opposed expanded portions 131 and centered underneath each upright arm 110 of the multiplanar receiver 100 can also provide free motion zones (C) for the nubs 196.

Figure 45:
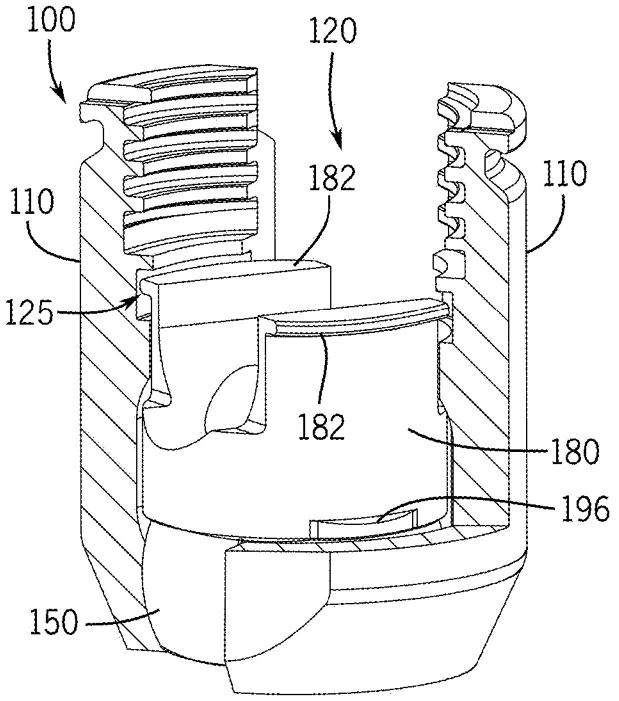
FIG. 45 is another partially cut-away front perspective view of the receiver, the seated multiplanar retainer sub-assembly, and the downloaded and partially rotated pressure insert.
Figure 46:
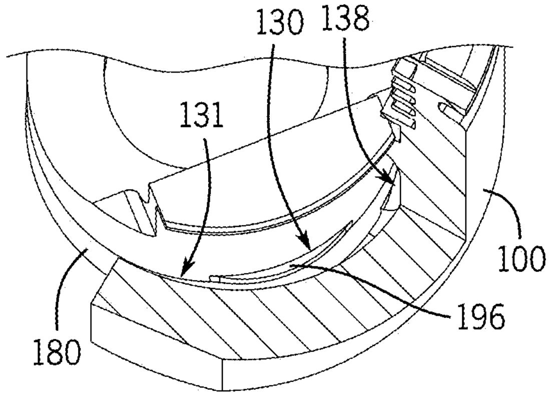
FIG. 46 is close-up partially cut-away top perspective view of the receiver, seated multiplanar retainer sub-assembly, and downloaded and partially rotated pressure insert of FIG. 45.

After reaching the initial downloaded position shown in FIGS. 41-44 in which the radially projecting flanges 182 are aligned with the channel 106 of the multiplanar receiver 100 and the nubs 196 with the opposed expanded portions 131, the pressure insert 180 may then be rotated around its longitudinal axis (which is co-linear with the vertical centerline axis 101 of the multiplanar receiver 100) so that the radially projecting flanges 182 begin to enter into the discontinuous inner recess 128 of the upright arms 110, as shown in FIG. 45. At the same time the projecting nubs 196 can become slidably frictionally engaged with the cylindrical sidewall surfaces 130 of the receiver cavity, as shown in FIG. 46. The rotation of the pressure insert 180 can continue for a full 90 degrees or quarter turn, until the projecting nubs 196 slide or snap into the opposed side pockets 138 of the cavity 134 and the radially projecting flanges 182 become positioned completely within the discontinuous inner recess 128 of the upright arms 110, thereby forming the multiplanar receiver sub-assembly 11 shown in FIG. 47. Again, other structures for holding the pressure insert 180 in alignment with the central bore 120 are also possible and considered to fall within the scope of the present disclosure, including but not limited to a reversal of the male/female relationship with an inwardly-protruding projection being formed on an inner surface of the central bore and a recess or notch being formed into the outer surface of the pressure insert.

Figure 47:
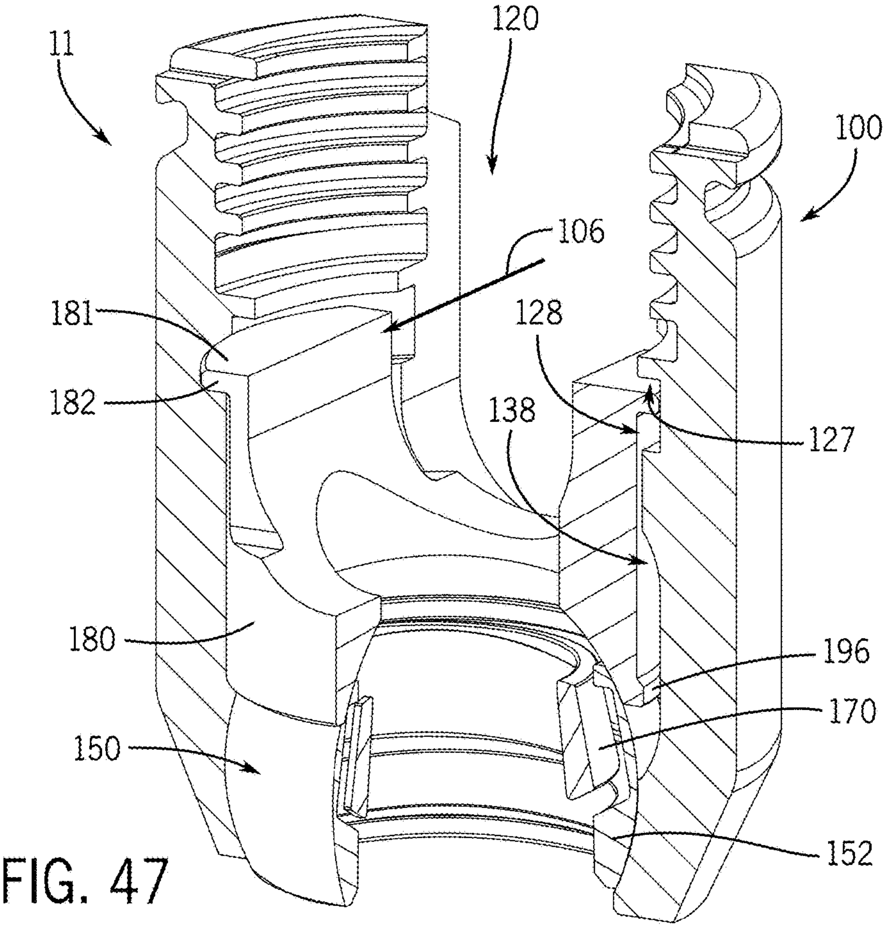
FIG. 47 is a partially cut-away front perspective view of the receiver with the seated multiplanar retainer sub-assembly and the pressure insert being fully rotated therein to form a pre-assembled multiplanar receiver sub-assembly in the shipping state.

Once the projecting nubs 196 become positioned within the opposed side pockets 138, further engagement between the projecting nubs 196 and the sides of the vertically-aligned side pockets 138 can inhibit rotation the pressure insert 180, either clockwise or counter-clockwise, out of its rotated position. At same time, further engagement between the upward-facing top surfaces 181 of the flanges 182 and the downward-facing upper arcuate surfaces 127 of the inner recess 128 can prevent the pressure insert 180 from moving back up within the central bore 120. Thus, upon the pressure insert 180 being rotated into its fully installed position within the multiplanar receiver 100 above the retainer sub-assembly 150, as shown in FIG. 47, the multiplanar receiver sub-assembly 11 of the pivotal bone anchor assembly 12 is now in its shipping state position or configuration that is configured to prevent both the pressure insert 180 and the retainer sub-assembly 150 from exiting the central bore 120 of the multiplanar receiver 100 or from getting out of alignment. With the pre-assembly of the multiplanar receiver sub-assembly 11 now complete, moreover, the multiplanar receiver sub-assembly 11 is ready for storage and/or shipping and handling, and for eventually attachment to the capture portion of a bone anchor or bone screw either prior to or during spinal surgery.

Figure 48:
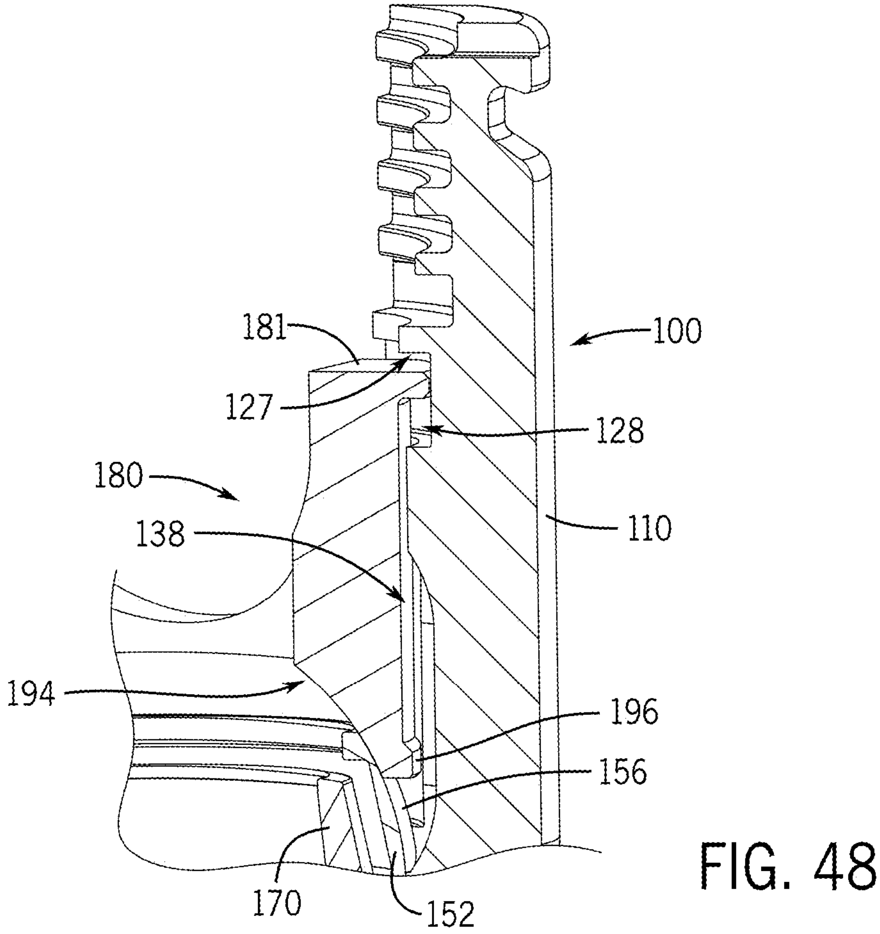
FIG. 48 is a close-up cross-sectional perspective view of the fully rotated pressure insert of FIG. 47.

With reference to FIG. 48, the upright arms 184 and projecting flanges 182 of the pressure insert 180 of the multiplanar embodiment of the pivotal bone anchor 12 can be sized and shaped so that the upward-facing top surfaces 181 of the flanges 182 are spaced a short distance below the downward-facing upper arcuate surfaces 127 of the inner recess 128 when the concave lower surface 194 is contacting the upper portion of the spherical outer surface 156 of the ring retainer 152. With the retainer sub-assembly 150 being frictionally secured within the inner spherical seat surface of the cavity, this can allow for a slight axial or vertical displacement, or looseness, of the pressure insert 180 within the multiplanar receiver 100 when the multiplanar receiver sub-assembly 11 is in the shipping state configuration shown in FIG. 47. Nevertheless, the pressure insert 180 will be maintained within the central bore 120 of the receiver in preparation for limiting the upward travel of the capture portion of the bone anchor during its assembly with the multiplanar receiver sub-assembly 11, as well as to provide the transfer and distribution of force or pressure from the closure and elongate rod to the capture portion and to the retainer sub-assembly 150 during the final assembly and locking of the pivotal bone anchor assembly 12.

Figure 49:
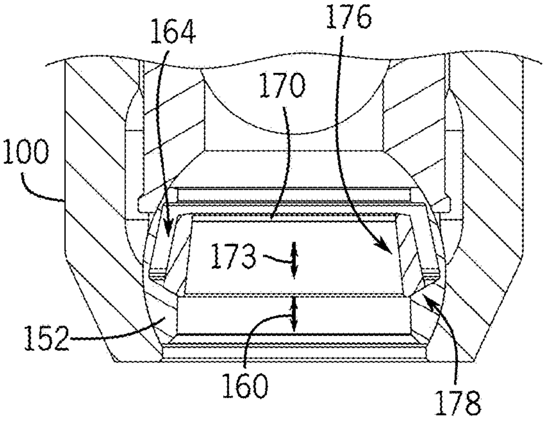
FIG. 49 is another close-up cross-sectional perspective view of the receiver, seated multiplanar retainer sub-assembly, and fully rotated pressure insert of FIG. 47, showing the capture ring in a centered position within the cavity of the ring retainer.
Figure 50:
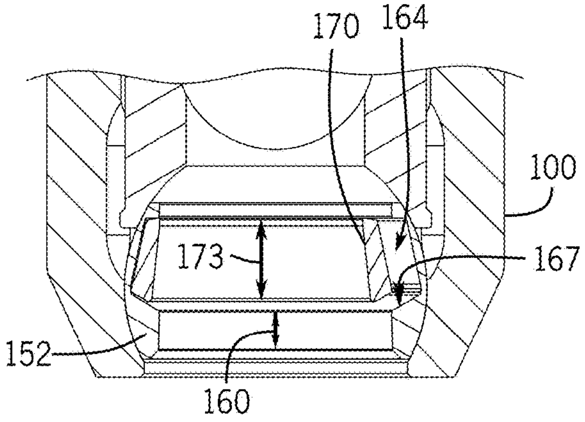
FIG. 50 is another close-up cross-sectional perspective view of the receiver, seated multiplanar retainer sub-assembly, and fully rotated pressure insert of FIG. 47, showing the capture ring in a maximum offset position within the cavity of the ring retainer.
Figure 51:
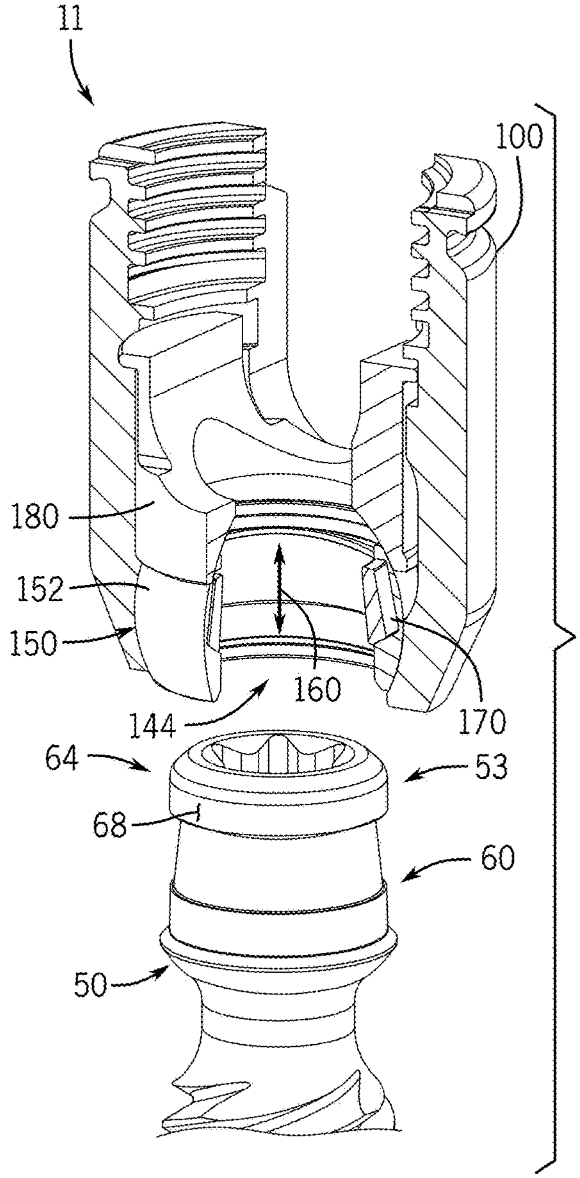
FIG. 51 is a partially cut-away front perspective view of the multiplanar receiver sub-assembly positioned above the universal capture portion of a bone anchor.

It is further appreciated that the capture ring 170 may also be slightly displaceable within the internal recess 164 of the ring retainer 152 when the multiplanar receiver sub-assembly 11 is in the shipping state configuration, as illustrated in FIGS. 49-50. For instance, the dimensions of the internal recess 164, which is large enough to allow for the capture ring 170 expand around and capture the capture portion of the bone anchor during its assembly with the multiplanar receiver sub-assembly 11, may also allow for the capture ring 170 to shift or displace laterally during shipping and handling. As such, the aperture 173 of the open capture ring 170 may not be precisely co-axial with the center aperture 160 of the ring retainer 152 at the time of uploading the capture portion 60 into the retainer sub-assembly 150. Nevertheless, the tapered shapes of the inner surface 176 and the beveled bottom surface 178 of the capture ring 170, in combination with the tapered shape of the beveled lower surface 167 of the internal recess 164 and the tapered or rounded shapes of the upper curvate section 64 and upper outer slidable surface 68 of the capture portion 60 of the bone anchor, can ensure that the capture ring 170 is smoothly and reliably self-guided onto the upper end of the capture portion 60 during the its uploading into the multiplanar receiver sub-assembly 11.

One representative embodiment for assembling the multiplanar receiver sub-assembly 11 to the capture portion 60 of the bone anchor 50 is illustrated in FIGS. 51-61. For instance, and with initial reference to FIG. 51, the multiplanar receiver sub-assembly 11 can be first positioned above the proximal end 53 of the bone anchor 50, with the center aperture 160 of the ring retainer 152, that is centered within bottom opening 144 of the multiplanar receiver 100, being generally aligned with the upper curvate section 64 and the upper outer slidable surface 68 of the capture portion 60.

Figure 52:
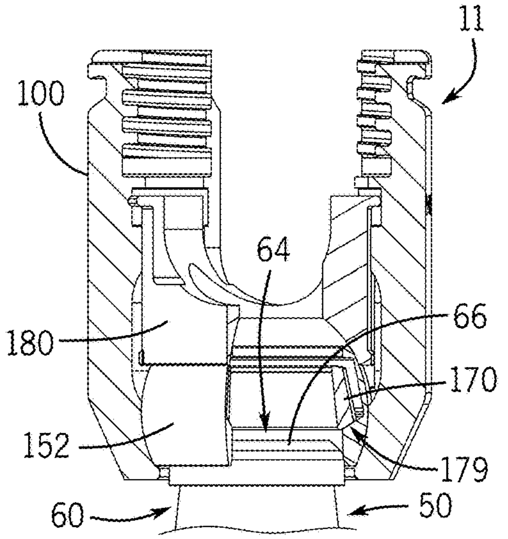
FIG. 52 is a partially cut-away front perspective view of the multiplanar receiver sub-assembly moving downward onto the universal capture portion of the bone anchor.
Figure 53:
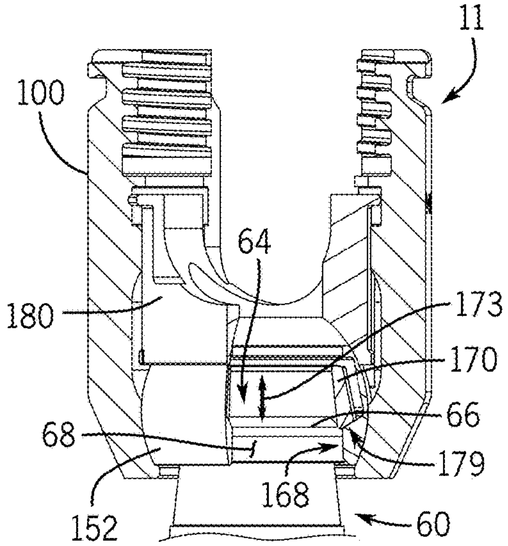
FIG. 53 is a partially cut-away front perspective view of the multiplanar receiver sub-assembly moving downward until the universal capture portion of the bone anchor engages the capture ring enclosed within the ring retainer.

With reference to FIGS. 52-53, the multiplanar receiver sub-assembly 11 is then dropped downward (or the bone anchor 50 is moved upward, depending on the frame of reference of the reader) until the top edge or upper curvate section 64 of the capture portion 60 enters the center aperture 160 of the ring retainer 152 and travels upward toward the capture ring 170 (FIG. 52). As previously described, the upper curvate section 64 can be formed with the spherical upper edge surface 66, so as to facilitate an initial slidable engagement with the lower inner slidable surface 168 of the ring retainer 152 upon entry of the upper end 53 of the capture portion 60 into the center aperture 160. This slidable engagement can function to center and align the ring retainer 152 (and hence the entire receiver sub-assembly 11 that is frictionally secured around the ring retainer 152) on the capture portion 60, so that the vertical centerline axis 101 of the multiplanar receiver 100 can become substantially co-axial with the longitudinal axis 52 of the bone anchor 50. The multiplanar receiver sub-assembly 11 continues to move downward (or the bone anchor 50 moves upward) as the upper outer slidable surface 68 of the capture portion 60 slides along the lower inner slidable surface 168 of the ring retainer 152, until the upper curvate section 64 contacts the bottom inner edge 179 of the capture ring 170 that is supported on the beveled lower surface 167 of the internal recess 164 of the ring retainer 152. This contact can serve to automatically center the capture ring 170 on the upper curvate section 64 as the spherical top edge 66 begins to move upward into the aperture 173 of the capture ring 170, as shown in FIG. 53.

As noted above, the receiver 100 of the receiver sub-assembly 11 is frictionally secured around the ring retainer 152 of the retainer sub-assembly 150, so that the placement of the center aperture 160 of the ring retainer 152 around the capture portion 60 of an implanted bone anchor 50 can naturally adjust and align the multiplanar receiver 100 with the longitudinal axis 52 of the bone anchor 50 as the capture portion 60 moves upward into the center aperture 160 of the ring retainer 152. Nevertheless, it will be appreciated that the moderate frictional engagement between the spherical outer surface 156 of the ring retainer 152 and the spherical seat surface 136 of the multiplanar receiver 100 may also allow for some pivoting and self-adjustment of the ring retainer 152 within the cavity 134 if the orientation of the receiver 100 is substantially fixed (such as by other members of a spinal construct), so that only the ring retainer 152 and retainer sub-assembly 150 become aligned with the longitudinal axis 52 of the bone anchor 50. This can provide for the coupling of the receiver sub-assembly 11 to the bone anchor 50 in a misaligned condition.

Figure 54:
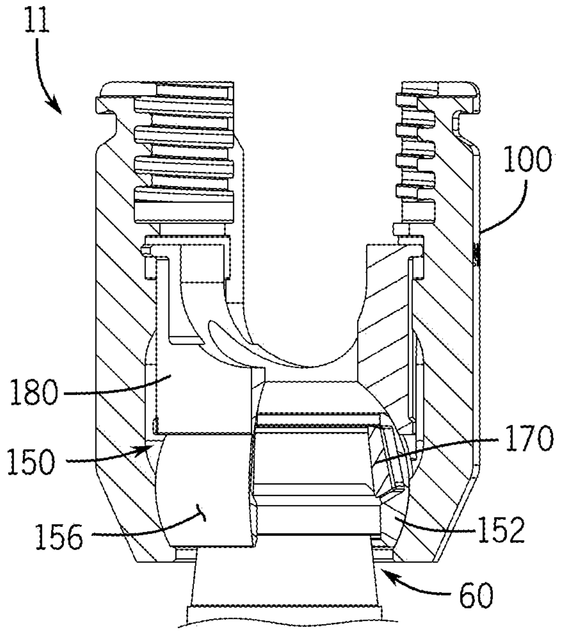
FIG. 54 is a partially cut-away front perspective view of the multiplanar receiver sub-assembly moving further downward as the universal capture portion of the bone anchor pushes the capture ring upward to engage the top surface of the recess of the ring retainer.
Figure 55:
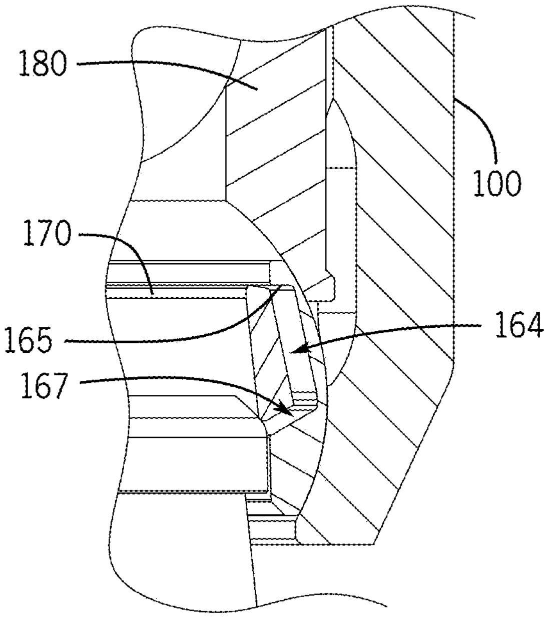
FIG. 55 is a close-up cross-sectional side view of the multiplanar receiver sub-assembly and universal capture portion of FIG. 54.

With reference to FIGS. 54-55, the capture portion 60 then pushes the capture ring 170 up off the beveled lower surface 167 of the internal recess 164 and into engagement with the upper annular surface 165 that acts as a stop surface to prevent further upward movement of the capture ring 170 within the internal recess 164.

Figure 56:
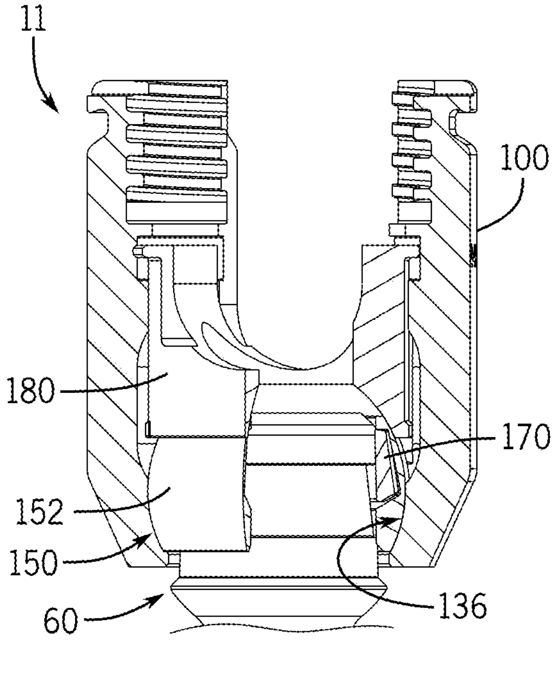
FIG. 56 is a partially cut-away front perspective view of the multiplanar receiver sub-assembly moving further downward as the universal capture portion of the bone anchor drives the capture ring outward within the recess of the ring retainer to a maximum expansion configuration.
Figure 57:
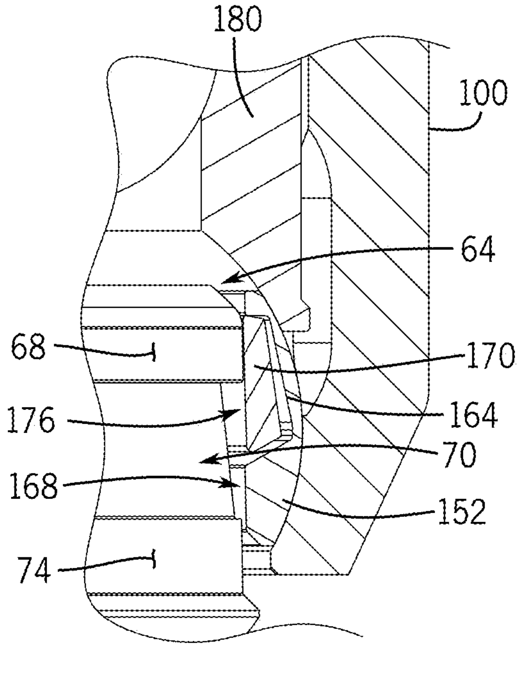
FIG. 57 is a close-up cross-sectional side view of the multiplanar receiver sub-assembly and universal capture portion of FIG. 56.

With reference to FIGS. 56-57, the multiplanar receiver sub-assembly 11 continues to move downward (or the bone anchor 50 moves upward) as the sliding engagement of the tapered inner surface 176 of the capture ring 170, first by the upper curvate section 64 of the capture portion 60 and then by the upper outer slidable surface 68, forces the capture ring 170 to gradually expand outwardly into the internal recess 164 of the ring retainer 152. Thus, the expansion of the capture ring 170 occurs while the ring retainer 152, being tightly constrained by the spherical seat surface 136 of the multiplanar receiver 100, maintains its original dimensions and does not expand outwardly. It will thus be appreciated that the expansion space for the capture ring 170, which performs the expansion/'snap on' connection function (i.e.

the retaining device function) of the retainer sub-assembly 150, is now provided within the ring retainer 152 itself, and that the cavity 134 of the central bore 120 of the multiplanar receiver 100 does not require an expansion chamber portion to provide space for the expansion of the retaining device during the uploaded of the capture portion 60 into the multiplanar receiver sub-assembly 11, as may be present in pivotal bone anchor assemblies of different design.

As can be seen in to FIGS. 56-57, the inwardly-angled shape of the tapered inner surface 176 of the capture ring 170 can cause the capture ring 170 to continue to expand as it moves downwardly across the upper outer slidable surface 68 and over the capture recess 70, until the capture ring 170 reaches the state of maximum expansion shown in the drawings. In one aspect the inwardly-angled wedge shape of the capture ring 170 may be temporarily deformed into a more vertical wedge shape as the rigid upper outer slidable surface 68 reaches the thinner upper portion of the capture ring 170 at the same time that the thicker lower portion of the capture ring 170 overhangs the capture recess 70. At about the same time, the lower inner slidable surface 168 of the ring retainer 152 can also become slidably engaged by the lower outer slidable surface 74 of the universal capture portion 60 due to the continued movement between the shank 50 and the multiplanar receiver sub-assembly 11. This lower slidable engagement can function to further align and stabilize the connection between the multiplanar receiver sub-assembly 11 and the universal capture portion 60.

Figure 58:
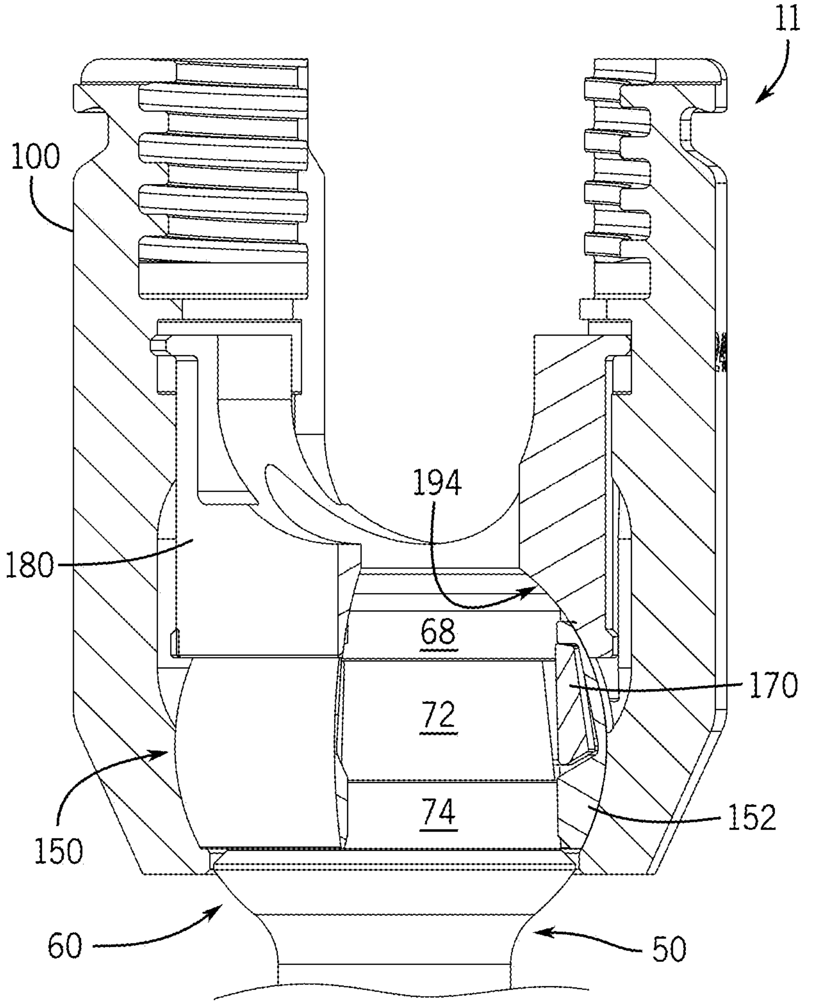
FIG. 58 is a partially cut-away front perspective view of the multiplanar receiver sub-assembly moving further downward as the universal capture portion of the bone anchor pushes further upward through the seated multiplanar retainer sub-assembly to engage the bottom surface of the pressure insert without moving the retainer sub-assembly up off of the seat surface on the receiver.
Figure 59:
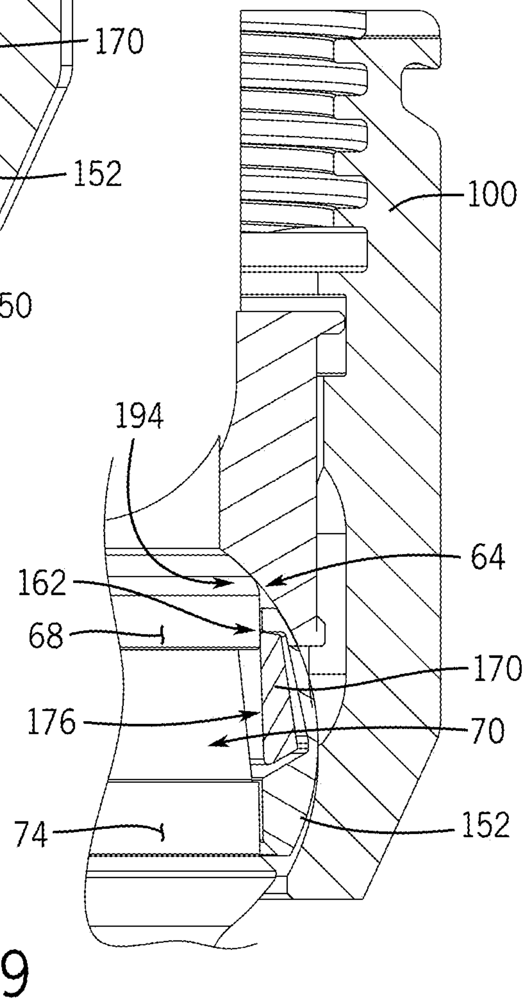
FIG. 59 is a close-up cross-sectional side view of the multiplanar receiver sub-assembly and universal capture portion of FIG. 58.

With reference to FIGS. 58-59, the multiplanar receiver sub-assembly 11 continues to move downward (or the bone anchor 50 moves upward) as the tapered inner surface 176 of the capture ring 170 continues to slide downwardly along the upper outer slidable surface 68 toward the horizontal capture recess 70. However, given that the upper inner slidable surface 162 of the ring retainer 152 is much shorter than the height of the capture ring 170, the upper curvate section 64 of the capture portion 60 can project upwards beyond the top edge or annular surface 154 of the ring retainer 152, so as to contact the concave lower surface 194 of the pressure insert 180 prior to the capture ring 170 fully reaching the capture recess 70.

Figure 60:
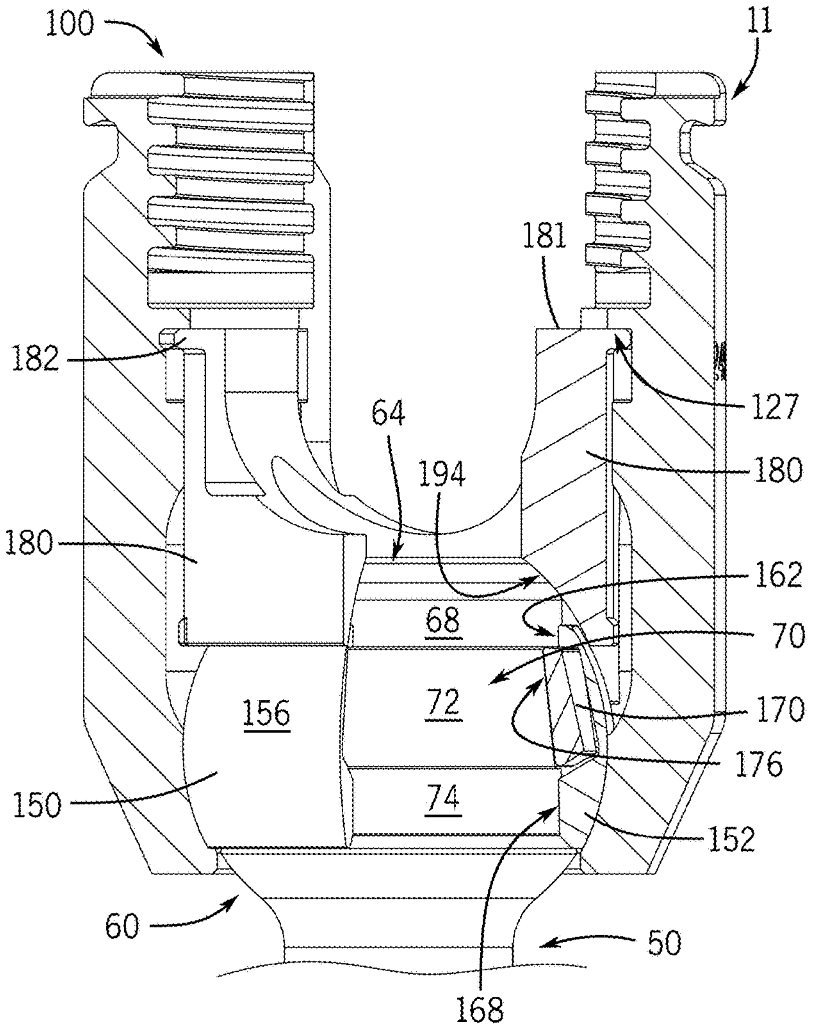
FIG. 60 is a partially cut-away front perspective view of the multiplanar receiver sub-assembly moving further downward and the insert moving upward until the capture ring snaps into the retainer recess to capture the universal capture portion within the multiplanar receiver sub-assembly.
Figure 61:
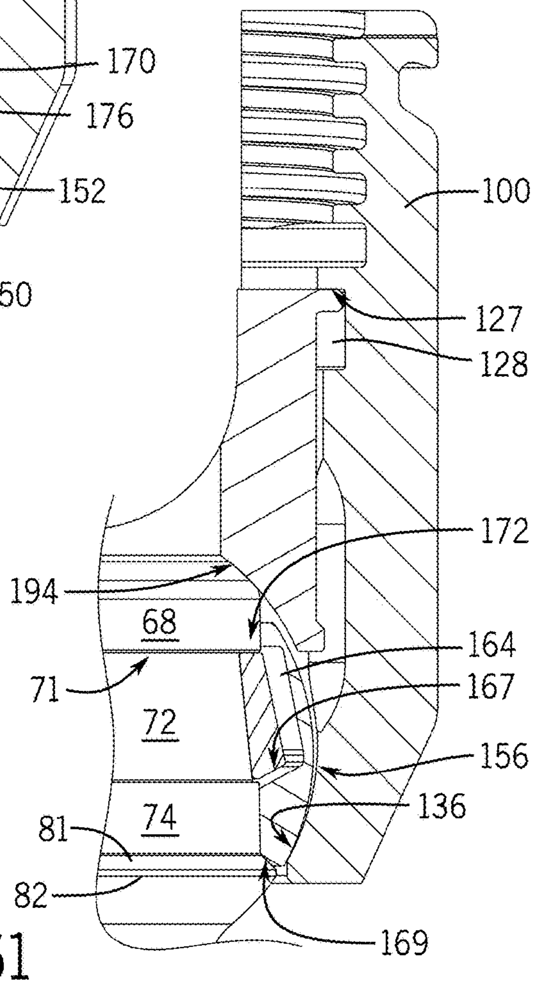
FIG. 61 is a close-up cross-sectional side view of the multiplanar receiver sub-assembly and universal capture portion of FIG. 60.

With reference to FIGS. 60-61, the multiplanar receiver sub-assembly 11 continues to move downward (or the bone anchor 50 moves upward) while the upper curvate section 64 of the capture portion 60 pushes the pressure insert 180 upwards within the central bore 120 of the multiplanar receiver 100, until the capture ring 170 eventually slides off the upper outer slidable surface 68 and snaps into the horizontal capture recess 70, thereby coupling the capture portion 60 directly to the retainer sub-assembly 150, and through the retainer sub-assembly 150 to the multiplanar receiver sub-assembly 11. In one aspect the forced expansion of the capture ring 170 shown in FIGS. 56-59 can result in a slight inelastic deformation of the metallic material forming the capture ring 170, so that the diameter of the tapered inner surface 176 of the capture ring, when the capture ring 170 snaps back into its free and neutral state, may now be greater than what is was before the expansion. Accordingly, the tapered inner surface 176 of the capture ring 170 may slip slightly downward along the tapered inner recessed surface 72 of the capture recess 70 until the two surfaces become loosely engaged with each other, so that the capture ring 170 becomes only lightly coupled to the universal capture portion 60 as it now rotates and translates with the shank 50 within the ring retainer 152. Alternatively, it is contemplated that the material properties of the open ring body of the snap capture ring 170 may be configured such that any deformation due to the expansion is avoided, and that the capture ring 170 can elastically snap into and engage the tapered inner recessed surface 72 of the capture recess 70 with a tight interference or friction fit.

Simultaneously with the snapping in of the capture ring 170 or shortly thereafter, upwardly- and outwardly-facing beveled lip surface 81 of the outer lip structure 82 at the lower end of the capture portion 60 can engage the lower chamfered surface 169 of the ring retainer 152, thereby preventing any further upward movement of the capture portion 60 relative to the ring retainer 152. This can ensure that the capture ring 170 remains in a desired position within the capture recess 70, with the beveled top surface 172 of the capture ring 170 located underneath and aligned with the complementary outwardly- and downwardly-angled upper step surface 71 of the capture recess 70, in preparation for receiving a downwardly-directed force applied by the closure in the final locked configuration.

At about the same time, the top surfaces 181 of the flange 224 at the upper end of the pressure insert 180 can engage the downward-facing upper arcuate surfaces 127 of the discontinuous recess 128, so as to prevent any further upward movement of the pressure insert 180 and the capture portion 60 relative to the multiplanar receiver 100. This engagement between the top surfaces 181 and the upper arcuate surfaces 127 can define the maximum push-through position of the shank 50 relative to the multiplanar receiver sub-assembly 11. Using these engagements between the pressure insert 180 and the multiplanar receiver 100, and between the capture portion 60 and the pressure insert 180, as a hard stop for the upward motion of the shank 50 relative to the multiplanar receiver sub-assembly 11 can ensure that the upward passage of the shank 50 does not push the retainer sub-assembly 150 up and out of its own captured position within the spherical seat surface 136 of the receiver. In addition, providing for the hard stop shortly after the capture ring 170 snaps into the horizontal capture recess 70 to complete the connection between the shank 50 and the multiplanar receiver sub-assembly 11 can provide a positive indication to the surgeon or medical professional that the coupling of the two components is now complete, while also limiting further error or complication if the surgeon pushes down on the multiplanar receiver sub-assembly 11 with too much force when attaching the multiplanar receiver sub-assembly 11 to the capture portion 60 of a shank 50 that has been implanted into the bone of a patient.

As previously described, the frictional engagement between the spherical outer surface 156 of the ring retainer 152 and the spherical seat surface 136 of the receiver, due to the frictional interference fit between the spherical surfaces that extends both above and below the equator plane 135 of the seat surface, can be sufficient to frictionally secure the ring retainer 152 in the shipping state position with the center aperture 160 of the ring retainer 152 being co-aligned with the bottom opening 144 of the multiplanar receiver 100, prior to coupling with the bone anchor 50. This same frictional engagement can also be sufficient to inhibit any pivoting motion of the combined retainer sub-assembly 150 and bone anchor relative to the multiplanar receiver 100 after their coupling together, except by an applied force such as manual manipulation. Thus, once coupled together and prior to downloading the elongate rod into the receiver channel 106 and the locking the assembly with the closure (as shown in FIGS. 62-65), the ring retainer 152 and bone anchor 50 can be pivotably frictionally secured to the multiplanar receiver 100 with a non-floppy friction fit at the interface between the spherical outer surface 156 of the retainer and the spherical seat surface 136 of the cavity of the multiplanar receiver 100.

With continued reference to FIGS. 60-61, the multiplanar receiver sub-assembly 11 is now coupled to the capture portion 60 by the capture ring 170 that is secured within both the horizontal capture recess 70 of the capture portion and the internal recess 164 of the ring retainer 152. In one aspect the average diameters of the outer slidable surfaces 68, 74 of the capture portion 60 (whether cylindrical or frusto-conical) can be less than the average diameters of the inner slidable surfaces 162, 168 that define the center aperture 160, even when the bone anchor is in its most "upward" coupled position shown in the drawings. This can result in the outer slidable surfaces 68, 74 being either spaced from or only lightly engaged with the inner slidable surfaces 162, 168 with no significant frictional or press-fit engagement being established between the two bands of slidable surfaces. As such, the lack of a strong frictional engagement between the outer slidable surfaces 68, 74 and the inner slidable surfaces 162, 168 can allow for the capture portion 60 to remain freely rotatable or lightly frictionally rotatable within the ring retainer 152 regardless of the pivotal mobility of the ring retainer 152 and shank 50 relative to the multiplanar receiver 100. It will be appreciated that this aspect of the pivotal bone anchor assembly 12 can advantageously allow for the rotatable implantation, or screwing in, of the anchor portion of a pre-assembled bone anchor assembly to a desired depth in the bone of a patient without a corresponding rotation of the multiplanar receiver sub-assembly 11. This can also advantageously allow for the multiplanar receiver sub-assembly 11 to be secured to the universal capture portion 60 by separate tooling and to be maintained in a desired alignment relative to other elements in a spinal construct throughout both the implantation and rod reduction procedures.

In this configuration, moreover, the capture portion 60 may only be secured to the multiplanar receiver sub-assembly 11 by the capture ring 170 and therefore able to travel up and down vertically within a small range defined by internal abutting engagements between the ring retainer 152, the capture ring 170, and the universal capture portion 60. As described above and shown in FIG. 61, for instance, the upwardly-facing beveled lip surface 81 of the capture portion 60 can engage the downwardly-facing lower chamfered surface 169 of the ring retainer 152 at the lower end of the assembly to define the most "upward" position of the bone anchor 50 relative to the ring retainer 152 and receiver 100 (which remain secured together). Thus, with the capture ring 170 being positioned within the capture recess 70, with the beveled top surface 172 of the capture ring 170 below the downward-facing upper step surface 71 of the capture recess 70, a small lower gap can exist between the beveled bottom surface 178 of the capture ring 170 and the complementary tapered lower surface 167 of the internal recess 164 of the ring retainer 152. A small upper gap that can also exist between the concave lower surface 194 of the pressure insert 180 and the spherical outer surface 156 of the ring retainer 152.

Figure 63:
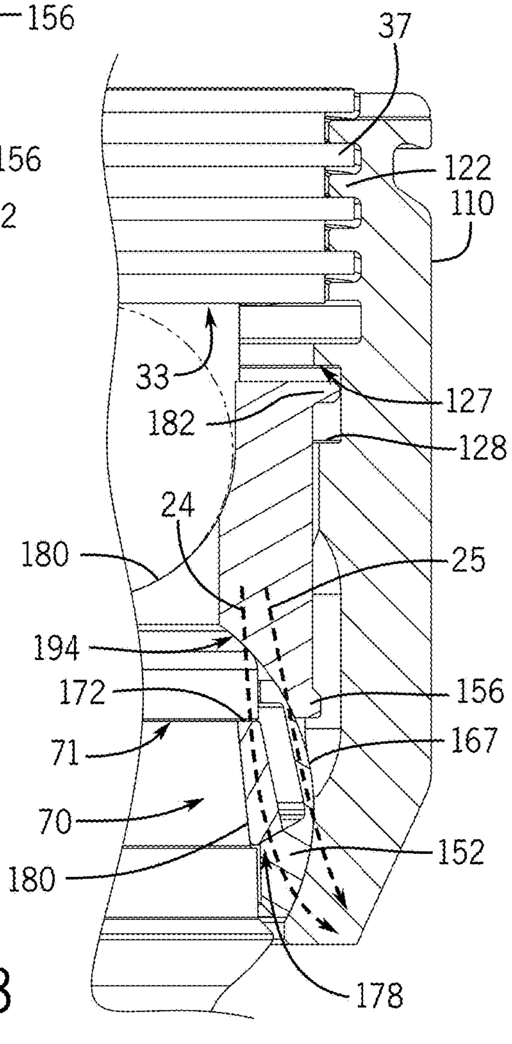
FIG. 63 is a close-up cross-sectional side view of the fully-assembled multiplanar bone anchor assembly of FIG. 62 and depicting the locking load path.

The other end of the short range of vertical travel can be defined when the upper and lower surfaces of the capture ring 170 become fulling engaged with their complementary surfaces on the capture portion 60 and the ring retainer 152, respectively, such as when the pressure insert 180 and bone anchor 50 are pushed back downwards relative to the multiplanar receiver 100 (as illustrated in FIG. 63). In particular, the bone anchor 50 can be driven downward relative to the multiplanar receiver 100 and ring retainer 152, carrying the capture ring 170 with it, until the beveled lower surface 178 of the capture ring 170 abuts the tapered lower surface 167 of the internal recess 164. If the capture ring 170 is only loosely engaged to the inner recessed surface 72 of the capture recess 70, the bone anchor 50 may continue to move downwards for a fraction of a millimeter until the downward-facing upper step surface 71 of the capture recess 70 abuts the beveled top surface 172 of the capture ring 170 to halt any further downward motion of the bone anchor, thereby defining the most "downward" coupled position of the bone anchor 50 relative to the multiplanar receiver sub-assembly 11.

As described above, the pressure insert 180 may be only loosely held within the central bore 120 of the multiplanar receiver 100 in a non-biased shipping state configuration, with allowance for a slight axial or vertical displacement bounded by the downward-facing upper arcuate surfaces 127 of the inner recess 128 and the upper portion of the spherical outer surface 156 of the ring retainer 152. As such, the force of gravity will generally cause the multiplanar receiver 100 to naturally settle downward around onto the flanges 182 of the pressure insert 180 that is supported, in turn, on the upper curvate section 64 of the vertically-oriented universal capture portion 60. Thus, unless otherwise manipulated or acted upon by another force or outside engagement, the bone anchor 50 and receiver sub-assembly 11, as initially coupled together, will typically remain in the configuration shown in FIGS. 60-61 until the components are further locked together with the elongate rod and the closure.

Nevertheless, it is foreseen that alternative biased embodiments of the pressure insert, including but not limited to pressure inserts with integral spring elements, non-integral spring elements, and like, are also possible and considered to fall within the scope of the present disclosure. It is also foreseen that both the multiplanar receiver and the multiplanar pressure insert can be reconfigured so that tooling may be used to temporarily hold the pressure insert down in a biased or even in a temporarily independent locking position within the receiver sub-assembly, until there is a final locking of the pivotal bone anchor assembly with the elongate rod and via the closure. It is further foreseen that the upright arms of the pressure insert can extend above a top of the rod and be engaged by an outer ring of the closure to provide for provisional locking of the bone anchor assembly.

Figure 62:
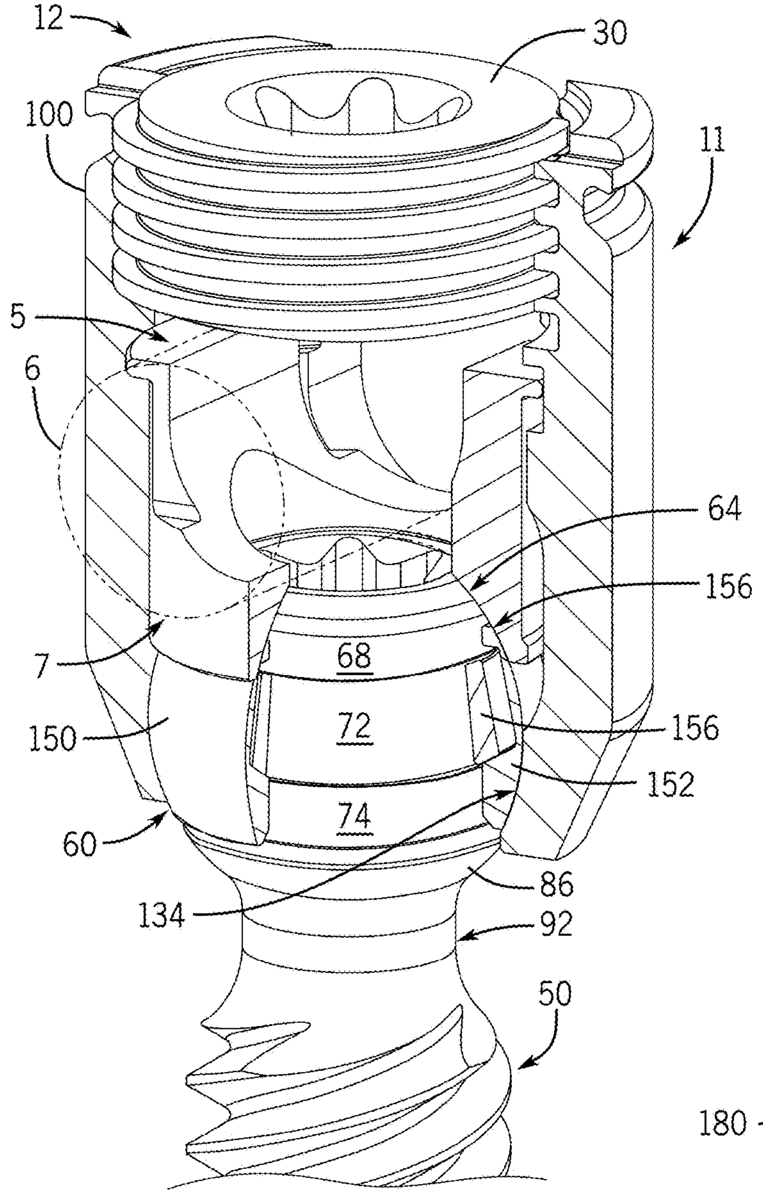
FIG. 62 is a partially cut-away front perspective view of the multiplanar bone anchor assembly, fully assembled with the elongate rod and closure and with the bone anchor in a non-articulated position relative to the receiver.

With reference to FIGS. 62-63, the final assembly of the multiplanar assembly 12 can be now completed with the addition of the elongate rod 6 and the closure 30. For instance, after a desired alignment of the multiplanar receiver sub-assembly 11 relative to the bone anchor 50 has been achieved, the elongate rod 6 can be installed (i.e. reduced) into the channel 106 of the multiplanar receiver 100 with the closure 30, and which reduction can include the use of instruments and/or breakoff extensions on the multiplanar receiver 100. After an initial placement of the elongate rod within the upper portion of the channel 106, the closure 30 can be rotatably and/or threadably installed into the upper portion of the central bore 120 of the multiplanar receiver 100, in which the continuous guide and advancement structure 37 of the closure body engages the discontinuous guide and advancement structure 122 formed into the interior faces of the upright arms 110 simultaneous with the bottom surface 33 of the closure 30 engaging the top surface 5 of the elongate rod 6 to push it downwards. The elongate rod 6 can be pushed downward into the channel until the lowermost or underside surface 7 of the elongate rod 6 engages the inner upward-facing rod-seating surface 187 of the pressure insert 180.

Further rotation and torquing of the closure 30 can then be used to drive the elongate rod 6 downward onto the pressure insert 180, which in turn can push both the pressure insert 180 and the universal capture portion 60 with the attached capture ring 170 downward relative to the ring retainer 152 and the multiplanar receiver 100. As described above, pushing this inner group of assembled components downwards relative to the outer group of assembled components (i.e. the multiplanar receiver 100 and ring retainer 152) can close the small gaps shown in FIG. 61, so that there is now surface-to-surface engagement between the beveled bottom surface 178 of the capture ring 170 and the complementary tapered lower surface 167 of the internal recess 164 of the ring retainer 152, and between the concave lower surface 194 of the pressure insert 180 and the spherical outer surface 156 of the ring retainer 152 and/or the upper curvate section 64 of the capture portion 60. Without being bound to a particular theory, it is contemplated that these engagements can serve to establish divided internal load paths between the closure 30 (that is secured within the arms 110 of the receiver) and the ring retainer 152 that drives the lower portion of the ring retainer 152 further downward and outward into the spherical seat surface 136 of the receiver cavity 134 as it tries to expand in a contained space to achieve a final locked configuration of the bone anchor assembly 12 in which the multiplanar receiver sub-assembly 11 can no longer pivot or rotate relative to the universal bone anchor 50.

For example, with specific reference to FIG. 63 showing the longitudinal axis of the bone anchor 50 being substantially aligned with the vertical centerline axis 101 of the multiplanar receiver 100, it is contemplated that a primary load path 24 can be established that extends downward from the elongate rod 6 through the pressure insert 180, the distal end of the universal capture portion 60 between the upper curvate section 64 and the upper step surface 71 of the capture recess 70, the capture ring 170, and the thick lower portion of the ring retainer 152 to the spherical seat surface 136 and base 140 of the multiplanar receiver 100. The primary load path 24 can carry a majority portion of the load created by the rotation and torquing of the closure 30 that drives the ring retainer 152 into the spherical seat surface 136 and base of the multiplanar receiver 100. Moreover, because the primary load path 24 also includes the engagement between the rounded lower surface 194 of the pressure insert 180 and the upper curvate section 64 of the capture portion 60, it will be appreciated that the capture portion 60 will also become frictionally rotationally locked with the pressure insert 180 and receiver 100 at the same time that the ring retainer 152 is frictionally pivotably locked to the spherical seat surface 136 of the multiplanar receiver 100, even though there may be no rotational frictional engagement between the upper and lower outer slidable surfaces 68, 74 of the capture portion 60 and the upper and lower inner slidable surfaces 162, 168 of the ring retainer 152, respectively.

It is further contemplated that pushing the pressure insert 180 and the capture portion 60 back downward in FIGS. 62-63 can also close the upper gap to re-engage the concave lower surface 194 of the pressure insert 180 with the upper portion of the spherical outer surface 156 of the ring retainer 152, thereby establishing a secondary load path 25. The secondary load path 25 can carry a secondary portion of the load from the closure 30 downward from the elongate rod 6 through the pressure insert 180 and the O-ring body of the ring retainer 152 between the upper and lower portions of the spherical outer surface 156, through to the spherical seat surface 136 and base 140 of the multiplanar receiver 100, which can add to the frictional pivotal locking of the ring retainer 152 to the spherical seat surface 136 of the multiplanar receiver 100.

It will be appreciated that with the capture portion 60 and receiver sub-assembly 11 being in the configuration shown in FIGS. 62-63, the secondary load path 25 that passes downward from the pressure insert 180 into the upper portion of the spherical outer surface 156 of the ring retainer 152 may also act to compress the thinner upper portion of the O-ring body of the ring retainer 152 inwardly toward the capture portion 60, thereby closing both the uppermost portion of the slit or slot 153 of the ring retainer 152 and the circumferential gap between the upper inner slidable surface 162 of the ring retainer 152 and the upper outer slidable surface 68 of the capture portion 60. If the circumferential gap between the two surfaces 68, 162 is less than half the width of the slit or slot 153 of the ring retainer 152, the upper inner slidable surface 162 may clamp around the upper outer slidable surface 68 to add to the frictional engagement that prevents further rotation of the bone anchor 50 relative to the multiplanar receiver 100. Thus, in one aspect the rotation of the bone anchor 50 in the locked configuration can be constrained both by the frictional engagement between the concave lower surface 194 of the pressure insert 180 and the upper curvate section 64 of the universal capture portion 60, and by the additional clamping of the upper inner slidable surface 162 of the ring retainer 152 about the upper outer slidable surface 68 of the universal capture portion 60.

In the same way, the primary load path 24 that passes downward through the capture ring 170 into the thick lower portion of the of the ring retainer 152, and specifically across the interface between the beveled bottom surface 178 of the capture ring and the complementary tapered lower surface 167 of the internal recess 164 of the ring retainer 152, may include a large outwardly-directed force component that serves to drive the lower portion of the O-ring body of the ring retainer 152 outwardly against the spherical seat surface 136 of the receiver cavity 134 (which component would act to open the lowermost portion of the slit or slot 153 of the ring retainer 152 if the ring retainer were not already restrained by the spherical seat surface 136). Nevertheless, this large outwardly-directed force component can operate to increase the strength of the connection between the capture portion 60 and the receiver sub-assembly by resisting and counter-acting any bending forces caused by an excessive pulling upward on the multiplanar receiver 100 after the pivotal bone anchor assembly 12 has been locked with the closure 30.

It will be further appreciated that the force or load applied to the top 7 of the elongate rod 6 by the closure 30 during final locking, and which is subsequently transferred downward through the pressure insert 180 and other components of the receiver sub-assembly to the spherical seat surface 136 and base 140 of the multiplanar receiver 100, can be quite large and sufficient to cause the elastic deflection of various portions of the components, as noted above. Moreover, in some aspects the load may also be sufficiently great to locally exceed the yield strength of the component materials at predetermined locations, so that portions of the components can slightly yield and inelastically deform to compress and bind together to become a more solidly locked assembly or unit. Even so, it is contemplated that removing the force or load applied to the rod will nevertheless generally allow reliable re-mobilization of the now-unlocked assembly.

Figure 64:
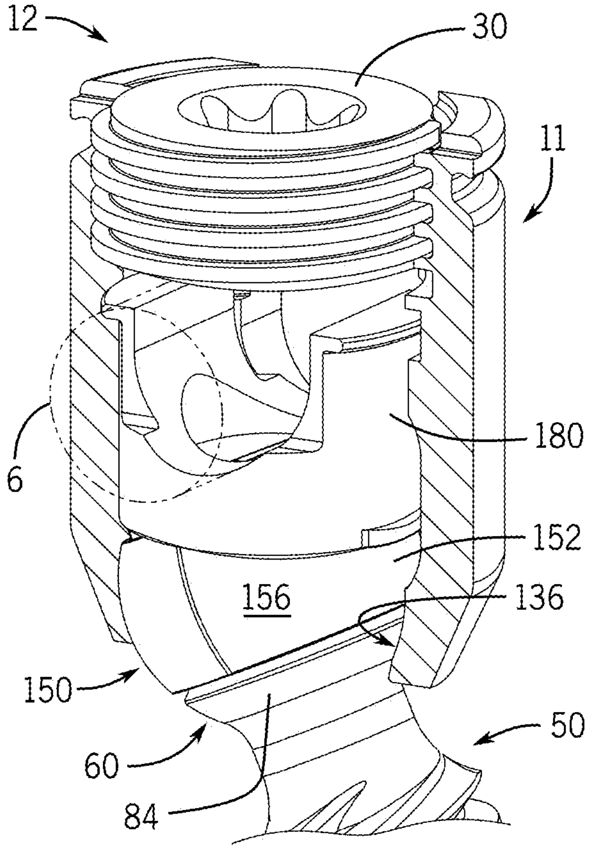
FIG. 64 is a front perspective view of the fully-assembled multiplanar bone anchor assembly of FIG. 62, with the bone anchor in an articulated position relative to the receiver.

Further to the above, it is also contemplated that the divided load paths from the pressure insert 180 down through the universal capture portion 60, capture ring 170 and ring retainer 152 can vary significantly depending on the angular alignment of the shank 50 relative to the multiplanar receiver 100 and the internal engagements between the internal components. For example, FIGS. 64-65 provide additional views of the multiplanar assembly 12 after complete assembly with the elongate rod 6 and the closure 30, and with the shank 50 being articulated relative to the multiplanar receiver sub-assembly 11. For instance, in the partially-sectioned view of FIG. 64, in which the shank 50 is articulated in the medial-lateral plane, illustrated in the foreground is the partial circumferential engagement of the lower surface of the pressure insert 180 about the upper portion of the ring retainer 152, in front of the partial circumferential engagement of the lower surface of the pressure insert 180 about the upper curvate section of the universal capture portion 60. Lower down is shown the partial circumferential engagements of both the lower curvate section 84 of the universal capture portion 60 (in the foreground) and the lower portion of the ring retainer 152 with the spherical seat surface 136 formed into the base portion of the multiplanar receiver 100 (on the opposite side of the receiver).

Further shown in the cross-sectional view of FIG. 65, in which the shank 50 is articulated in the sagittal plane, illustrated on the right side of the drawing is the partial circumferential engagement of the lower surface of the pressure insert 180 about the upper portion of the ring retainer 152, above the partial circumferential engagement of the lower curvate section 84 of the universal capture portion 60 with the spherical seat surface 136, resulting in split load path 26 that can pass through the lower portion of the universal capture portion 60. Illustrated on the left side of the drawing is the partial circumferential engagement of the lower surface 194 of the pressure insert 180 about the upper curvate section 64 of the universal capture portion 60, above the partial circumferential engagement of the lower portion of the ring retainer 152 with the spherical seat surface 136, resulting in split load path 27 that can pass from the upper portion of the universal capture portion 60 through to both the ring retainer 152 on the left side and the lower curvate section 84 on the right side of the universal capture portion 60.

Furthermore, and regardless of the articulation angle of the shank 50 relative to the receiver sub-assembly, the multiplanar assembly 12 that incorporates both the universal capture portion 60 and the retainer sub-assembly 150 comprising the ring retainer 152 with the internal capture ring 170 can provide for a superior interconnection between the shank 50 and receiver sub-assembly 11 over other types of pivotal or polyaxial bone anchor assemblies known in the art. This is in addition to the other advantages described above.

Monoplanar Bone Anchor Assembly

Figure 66:
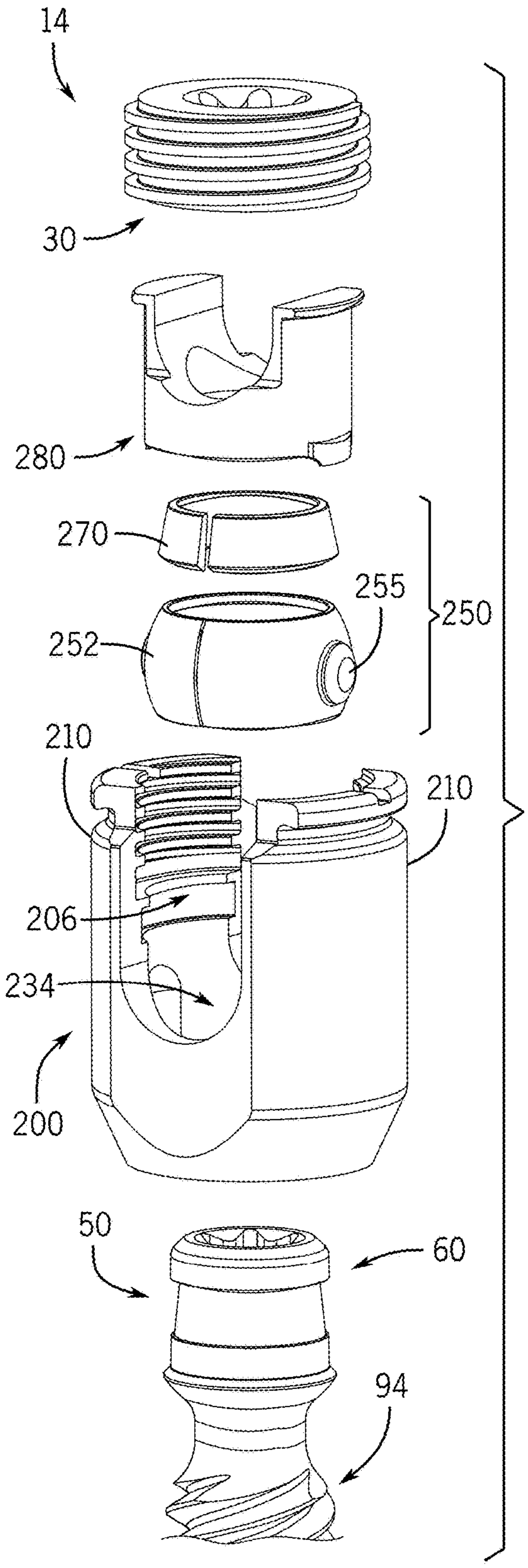
FIG. 66 is an exploded perspective view of a monoplanar embodiment of a bone anchor assembly, in accordance with the representative embodiment of the multi-component spinal fixation system shown in FIG. 1.

Referring now to FIG. 66, illustrated therein is an exploded perspective view of one representative embodiment of the monoplanar pivotal bone anchor assembly 14 that is configured, as noted above, to limit the pivotal motion of the bone anchor 50 relative to the receiver sub-assembly 13 (or vice versa) to a single plane while still providing for a 360-degree range of rotational motion around the longitudinal axis of the bone anchor. The monoplanar assembly 14 can include the same bone anchor 50 or bone screw described above, having a universal capture portion 60 or shank head and an anchor portion 94 opposite the capture portion 60 for securement or attachment to the bone of a patient. Similar to the multiplanar assembly 12 discussed above, the monoplanar assembly 14 can also include a receiver 200 that can be initially pivotably secured to the universal capture portion 60 with a number of separate internal components that have been pre-assembled into the cavity 234 and the rod channel 206 to form the receiver sub-assembly 13. These internal components can include, but are not limited to, a monoplanar pivotal or articulating retainer sub-assembly 250 that includes a monoplanar ring retainer 252 having a separate open capture ring 270 secured therein, and a pressure insert or element 280. After an elongate rod (not shown) has been positioned within the lower portion of the rod channel 206, the same closure 30 shown above (or another appropriate type of closure) can be threadably or otherwise secured into an upper portion of the rod channel to apply pressure to an upper surface of the elongate rod, thereby locking both the elongate rod and the monoplanar assembly 14 into a final locked position.

The primary difference between the multiplanar pivotal bone anchor assembly 12 previously described and the monoplanar pivotal bone anchor assembly 14 of FIG. 66 can be the replacement of the multiplanar ring retainer 152, having the substantially continuous spherical outer surface 156, with the monoplanar ring retainer 252 that further includes rounded protrusions or pegs 255 that project outwardly from opposite sides of the discontinuous spherical outer surface 256. The opposite pegs 255 are generally configured to be positioned within, and thereafter constrained by, the opposed vertical side pockets 238 formed in to the cavity 234 of the receiver 200, so that the pivotal motion of the ring retainer 252 relative to the receiver 200 is limited to a single plane defined by a pivot axis extending between the opposite pegs 255. Additionally, both the receiver 200 and the pressure insert 280 may also be configured differently in order to better interact with the opposite pegs 255 of the ring retainer 152. The remainder of the components forming the monoplanar assembly 14, such as the universal shank 50, the capture ring 270, and the closure 30, can be the same as or substantially similar to those already described, so as to more completely provide a modular spinal fixation system with all the attendant benefits thereof.

Figure 67:
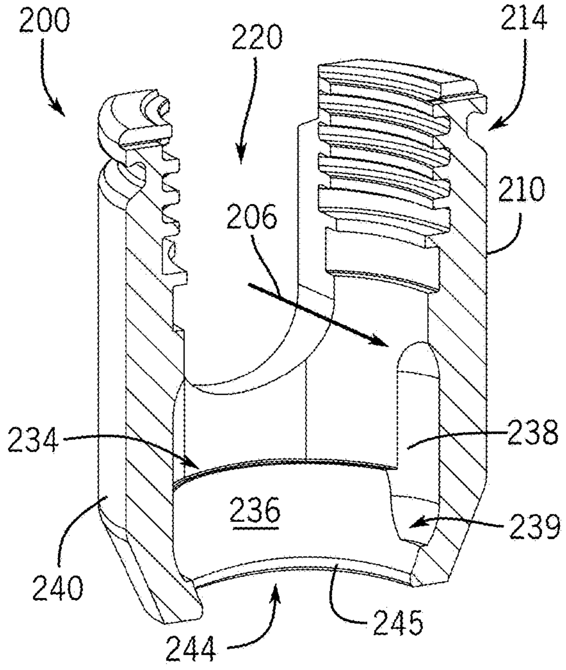
FIG. 67 is a cross-sectional perspective view of the receiver of the monoplanar bone anchor assembly of FIG. 66.
Figure 68:
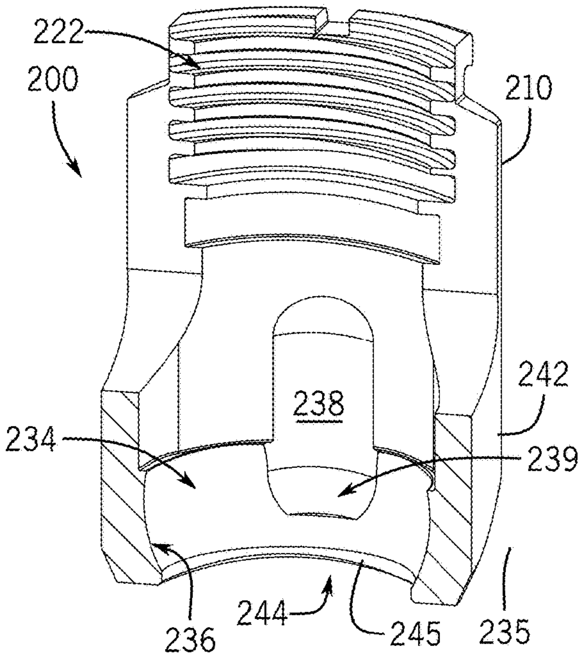
FIG. 68 is another cross-sectional perspective view of the receiver of FIG. 67.
Figure 69:
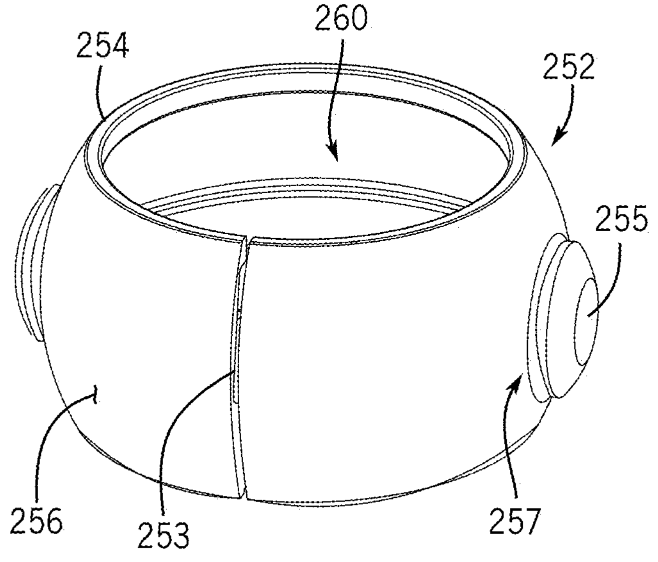
FIG. 69 is a perspective view of the ring retainer of the monoplanar bone anchor assembly of FIG. 66.
Figure 70:
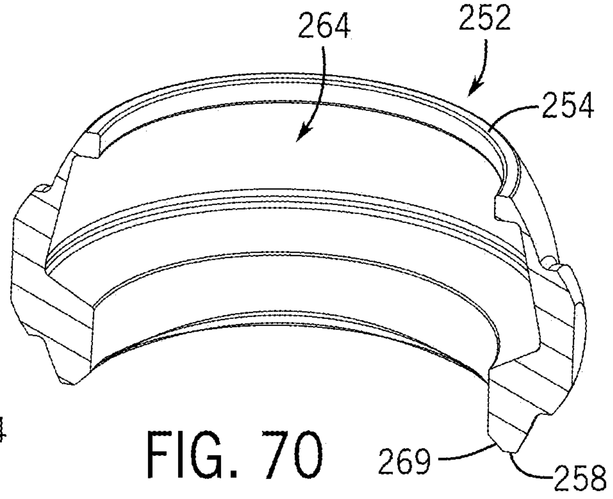
FIG. 70 is a cross-sectional perspective view of the ring retainer of FIG. 69.
Figure 71:
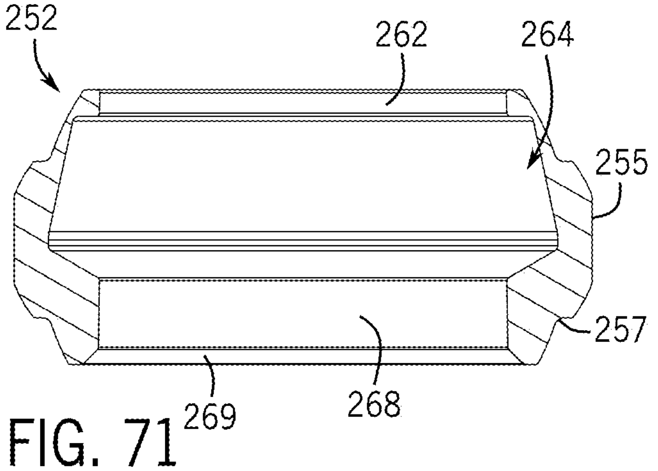
FIG. 71 is a cross-sectional side view of the ring retainer of FIG. 69.
Figure 72:
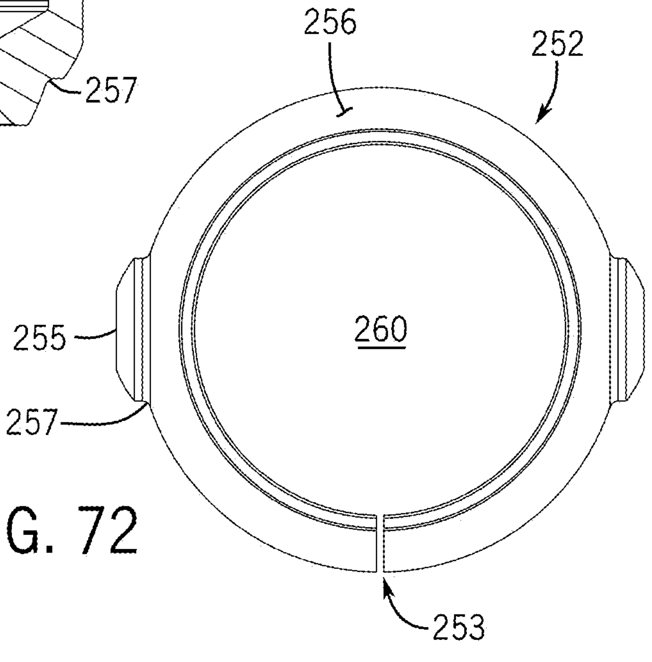
FIG. 72 is a top view of the ring retainer of FIG. 69.
Figure 73:
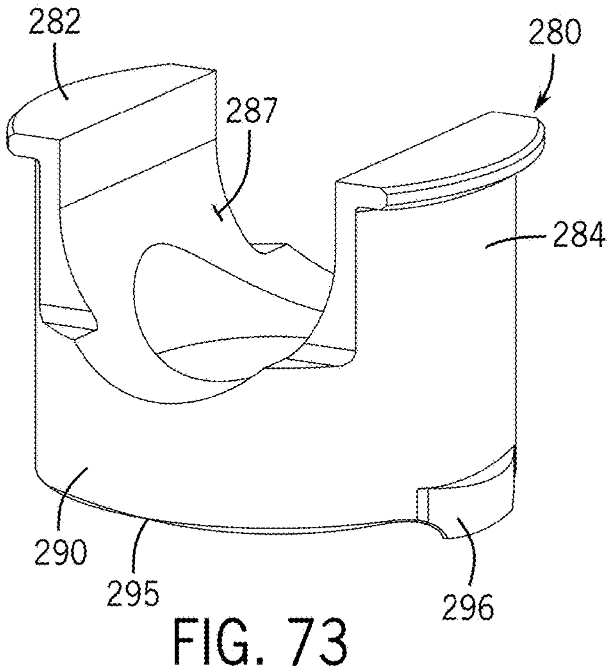
FIG. 73 is a top perspective view of the pressure insert of the monoplanar bone anchor assembly of FIG. 66.
Figure 74:
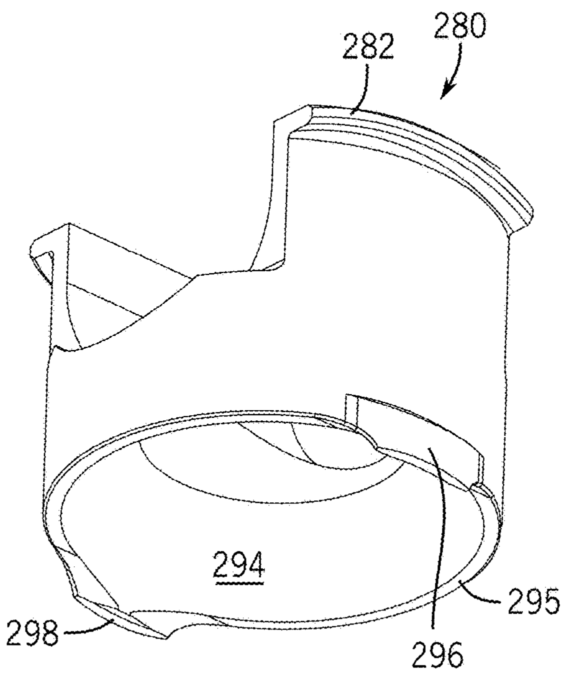
FIG. 74 is a bottom perspective view of the pressure insert of FIG. 73.
Figure 75:
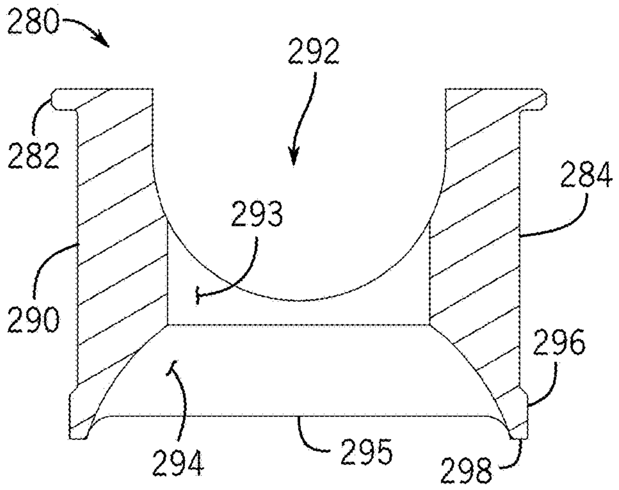
FIG. 75 is a cross-sectional side view of the pressure insert of FIG. 73.
Figure 76:
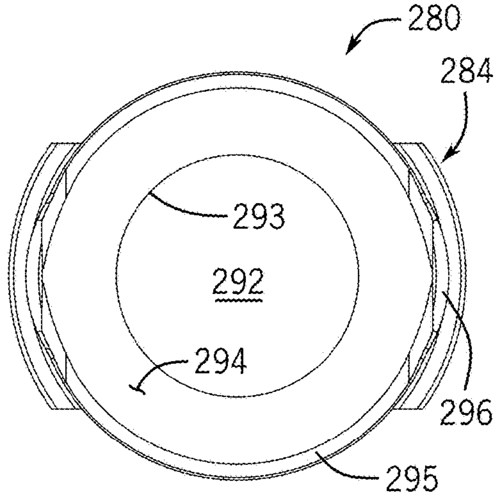
FIG. 76 is a bottom view of the pressure insert of FIG. 73.

The receiver 200 of the monoplanar assembly 14 illustrated in FIGS. 67-68 can have substantially the same construction and features of the multiplanar receiver 100 of the multiplanar assembly 12 described above, with the exception that the opposed side pockets 238 formed into the cavity 234 of the receiver 200 can extend further downward into the spherical seat surface 236 or otherwise be modified or configured to accommodate the outwardly-projecting opposite rounded pegs 255 of the ring retainer 252 (see FIG. 66). This construction can still leave a lower portion of the spherical seat surface 236 untouched and extending continuously 360-degrees around the central bore 220 between the lower ends of the opposed side pockets 238 and a lower edge 243 that can define, together with a lowermost cylindrical or chamfered surface 245, the bottom opening 244 of the receiver 200. The opposed side pockets 238 can further include curvilinear bottom surfaces 239 having an axis of curvature that is aligned with the geometric center of the spherical seat surface 236. As described in more detail below, the curvilinear bottom surfaces 239 of the opposed side pockets 238 can be configured for slidable engagement with lower portions of the opposite rounded pegs 255 of the ring retainer 252, so that the rounded pegs can rotate on the curvilinear bottom surfaces 239 of the opposed side pockets 238 at the same time that the spherical outer surface of the ring retainer slides across of the spherical seat surface 236 of the receiver cavity 234. With the spherical seat surface 236 being inwardly and downwardly curved from the equator plane 235, the opposed side pockets 238 can become deeper toward their lower ends, thereby providing the pockets with wider curvilinear bottom surfaces 239 and more resistance to pull-out forces.

The remaining structural elements of the monoplanar pivotal receiver 200, including the base 240, the upright arms 210 forming the rod channel 206, the discontinuous guide and advancement structure 222 formed into the upper portion of the central bore 220, the tool engagement structures 214, the curvate side outer surfaces 212 of the upright arms 210, the front and back outer planar faces 242 of the receiver base 240, and the like, can be the same as or substantially similar to the structural elements of the multiplanar pivotal receiver 100 described above. Again, this type of assembly is generally configured to have frictional axial independent rotation between the shank and the receiver.

With reference to FIGS. 69-72, the monoplanar ring retainer 252 includes the opposite rounded protrusions or pegs 255 projecting outwardly from the spherical outer surface 256 of the O-ring body. In one aspect each of the rounded pegs 255 can include a cylindrical base portion 257 located inwardly of the rounded outer surface, with the cylindrical base portions 257 configured for engagement by downward facing surfaces of the pressure insert 280, as described in more detail below. The remaining structural elements of the monoplanar ring retainer 252, including the top annular or edge surface 254, the bottom annular or edge surface 258, the center aperture 260 defined by inner slidable surfaces 262, 268 and the internal recess 264 that extends into and circumferentially around a mid-portion of the center aperture 260, the lower chamfered surface 269, and the slit or slot 253 extending through the thickness of the O-ring body, can be the same as or substantially similar to the structural elements of the multiplanar ring retainer 152 described above. As such, the discontinuous spherical outer surface 256 of the monoplanar ring retainer 252 can also have the same radius as the lower partial-spherical outer surface 86 of the capture portion 60, in which case the spherical surfaces 256, 86 may align with each other to form a spherically-shaped capture head (except for the opposite rounded pegs 255) when the bone anchor 50 is coupled to the monoplanar ring retainer 252. In this configuration the lower chamfered surface 269 of the monoplanar ring retainer 252 can be adjacent to, or even contacting, the beveled lip surface 81 of the capture portion 60 (described above) when the bone anchor 50 is coupled to the monoplanar ring retainer 252.

As previously noted, it is understood that the open capture ring 270 shown in the exploded perspective view of FIG. 66 can be the same as or substantially similar to the open capture ring 170 that is positionable with the multiplanar ring retainer 152 of the multiplanar assembly 12 discussed above, and can be configured with the same structure and to perform the same functions during the assembly and operation of the monoplanar assembly 14 as with the multiplanar assembly 12.

With reference to FIGS. 73-77, the monoplanar assembly 14 can further include a monoplanar pressure insert 280 that can be substantially similar to the multiplanar pressure insert 180 of the multiplanar assembly 12 discussed above, with the exception that the opposite outwardly-projecting nubs or protuberances 296 that can defined the indexing structure of the insert can project further downwardly below the concave lower surface 294 and the annular bottom edge 295 of the pressure insert 280. The nubs 296 can also include elongate bottom edge surfaces 298 below the annular bottom edge 295 that are configured to engage upper portions of the opposite rounded pegs 255 when the insert 280 is in its lowermost position contacting the ring retainer 252.

The remaining structural elements of the monoplanar pressure insert 280, including the lower insert base portion 290 having a cylindrical outer surface 288, the two upright insert arms 284 formed integral with a lower base portion 290 and having inner surfaces that define the inner upward-facing rod-seating surface 287, the flanges 282 projecting radially outward from top portions of the insert upright arms 284, and the central tool-receiving aperture 292 defined by an inner cylindrical surface 293 and configured to slidably receive a drive tool (not shown), can be the same as or substantially similar to the structural elements of the multiplanar pressure insert 180 described above.

Figure 77:
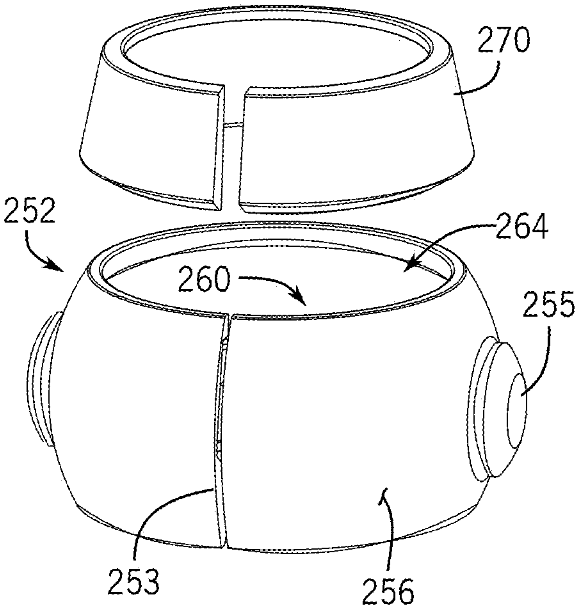
FIG. 77 is a perspective view of the ring retainer of FIG. 69 and the capture ring of FIG. 16 prior to assembly together into a monoplanar retainer sub-assembly.
Figure 78:
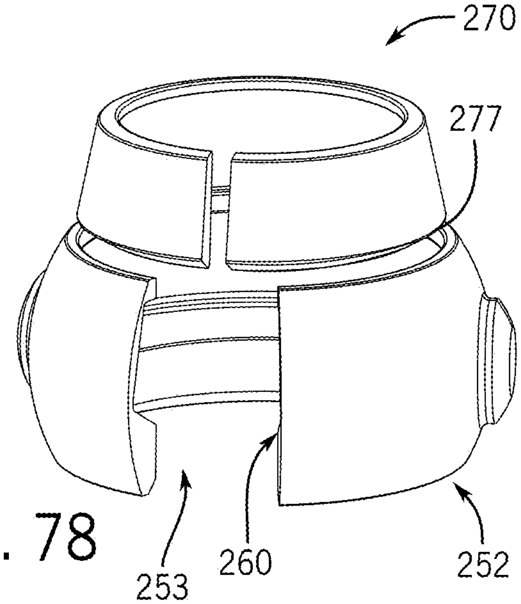
FIG. 78 is a perspective view of the ring retainer and capture ring of FIG. 77 during assembly together into the monoplanar retainer sub-assembly.

To begin assembly of the monoplanar assembly 14, the capture ring 270 can first be installed or positioned into the internal recess 264 of the ring retainer 252 to form the retainer sub-assembly 250, as shown in FIGS. 77-80. With reference to FIG. 77, to begin this assembly the capture ring 270 can be placed above the ring retainer 252 in preparation for top loading into the center aperture 260 of the ring retainer 252 (although bottom loading into the ring retainer is also contemplated). The ring retainer 252 can then be expanded and the slot 253 opened until the diameter of the center aperture 260 at the upper slidable surface 262 is greater than the outer diameter of the lower outer edge 277 of the capture ring 270, as shown in FIG. 78. In one aspect the capture ring 270 can also be slightly compressed so that the width of the capture ring slot 275 and the outer diameter of the lower outer edge 277 is less than it what it would be in its neutral or free-standing state.

Figure 79:
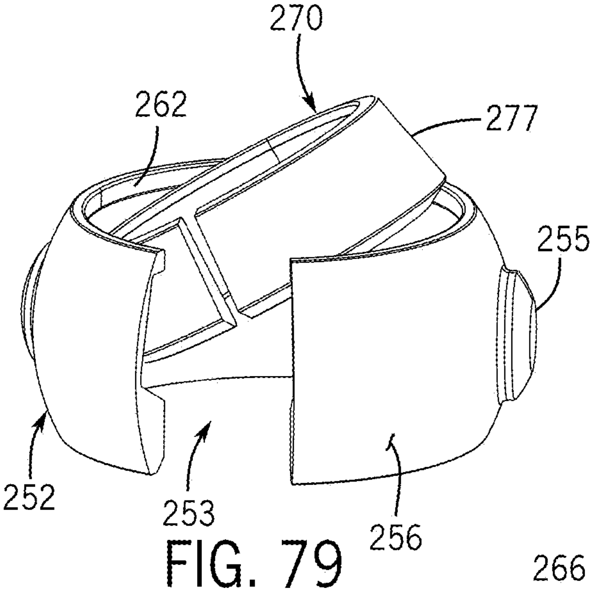
FIG. 79 is another perspective view of the ring retainer and capture ring of FIG. 77 during assembly together into the monoplanar retainer sub-assembly.
Figure 80:
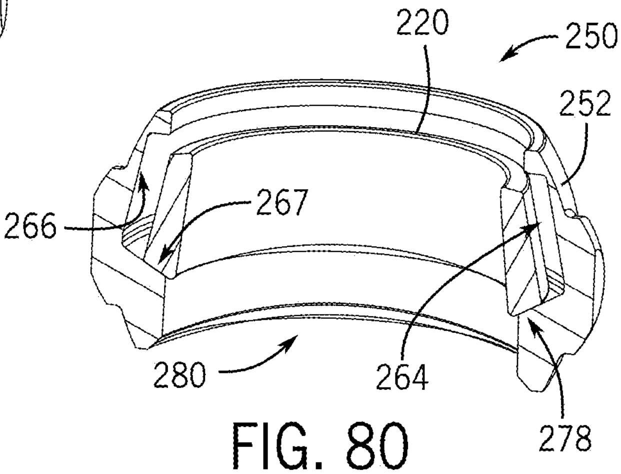
FIG. 80 is a cross-sectional perspective view of the ring retainer and capture ring of FIG. 79 after assembly together into the monoplanar retainer sub-assembly.

As shown in FIG. 79, the capture ring 270 may then be tilted and inserted into the center aperture 260 of the ring retainer 252 at an angled orientation, until one side of the lower outer edge 277 contacts the inward-facing recessed surface 266 of the internal recess 264 or the adjacent portion of the beveled lower surface 267, thereby allowing the opposite side of the angled capture ring 270 to drop down into the opposite side of the internal recess 264. The ring retainer 252 can then be released to close back toward its neutral state to capture the now-horizontal capture ring 270 within its internal recess, as shown in the cross-sectional view of FIG. 80. The capture ring 270 in its neutral or free state can project partially into the center aperture 260 of the ring retainer 252 while simultaneously providing for a space or gap between the outer surface 274 of the capture ring and the recessed sidewall surface 266 of the internal recess 264 that allows for the expansion of the capture ring 270 within the internal recess 264 during future assembly steps. In one aspect the resting engagement between beveled bottom surface 278 of the capture ring 270 and the lower tapered or beveled surface 267 of the inner recess 264 of the ring retainer can act to center the capture ring 270 within the center aperture 260 of the ring retainer 252.

It will be understood that the forced expansion of the ring retainer 252 shown in FIGS. 78-79 can result in a marginal inelastic deformation of the O-ring body of the ring retainer 252, so that the diameter of the spherical outer surface 256 in the free and neutral state is now greater than what is was before the expansion. As described below, this deformation can be advantageously employed in subsequent assembly steps to establish a compressive friction engagement between the spherical outer surface 256 of the ring retainer 252 and the spherical seat surface 236 of the receiver 200.

Figure 81:
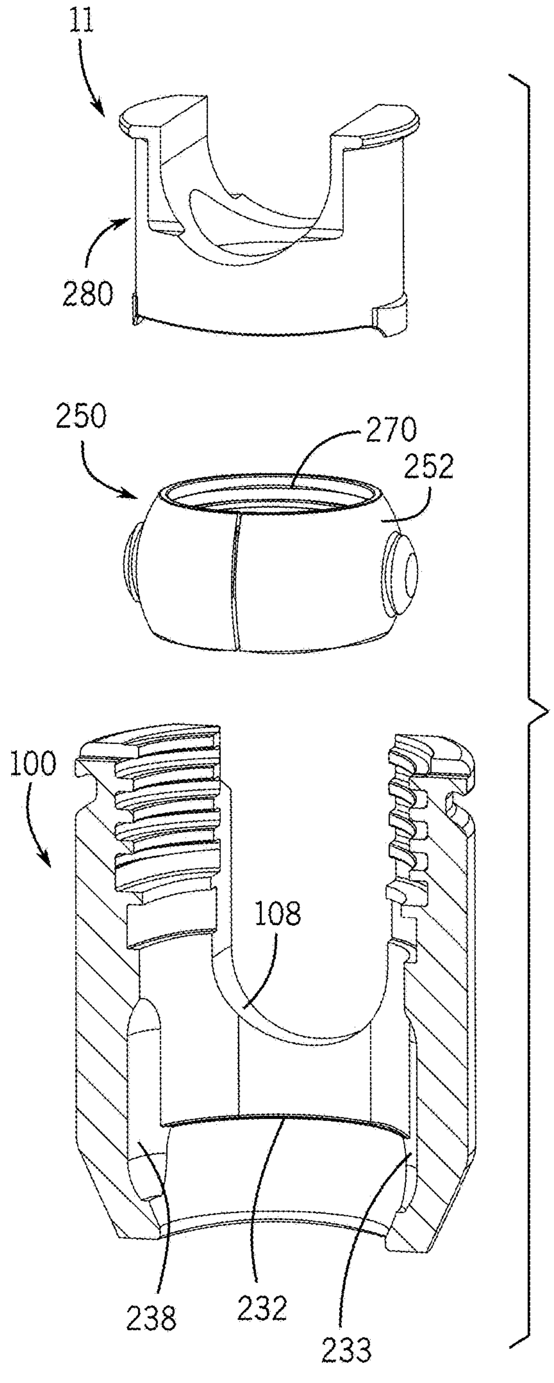
FIG. 81 is an exploded side view of the components of a monoplanar receiver sub-assembly prior to their pre-assembly into a shipping configuration.

Illustrated in FIG. 81 are the individual components of the monoplanar assembly 14 that, in many embodiments, can be pre-assembled together into a receiver sub-assembly 13 at a factory or manufacturing facility, prior to shipping to a hospital or surgery center and engagement with the capture portion of the bone anchor in the surgical setting. As noted above, these components generally include the monoplanar receiver 200, the monoplanar retainer sub-assembly 250 that includes the monoplanar ring retainer 252 with the separate open capture ring 270 secured therein, and the monoplanar pressure insert 280. In one aspect the monoplanar receiver 200, the monoplanar retainer sub-assembly 250, and the monoplanar inset 280 being pre-assembled into the monoplanar receiver sub-assembly 13 can be further defined as the shipping state configuration for the 'modular' bone anchor assembly, as described herein and commonly understood in the art. It will be appreciated, however, that in other embodiments the shipping state configuration can include the additional assembly of the monoplanar receiver sub-assembly together with the bone anchor at the factory or manufacturing facility. It will also be appreciated that in yet other embodiments the individual components described above can also be pre-assembled into the receiver sub-assembly at the hospital or surgery center prior to implantation in a patient.

Figure 82:
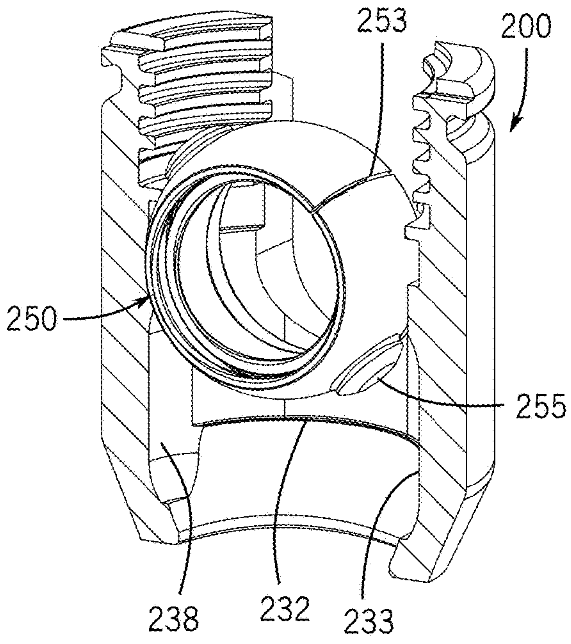
FIG. 82 is a partially cut-away front perspective view of the receiver of FIG. 81 with the monoplanar retainer sub-assembly being downloaded through the open channel of the receiver.
Figure 83:
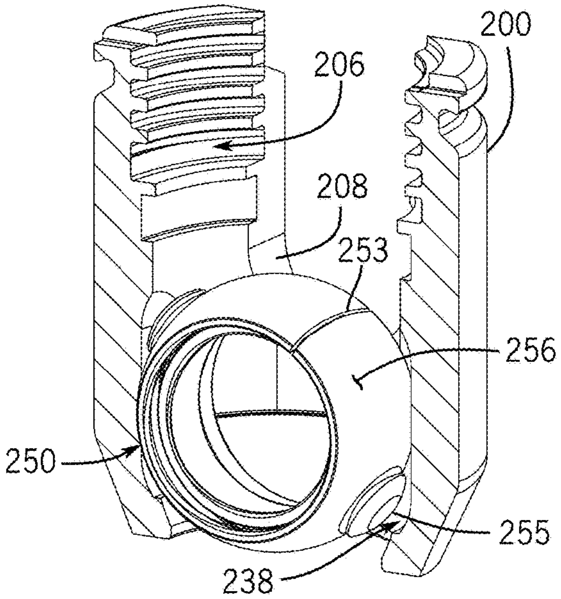
FIG. 83 is a partially cut-away front perspective view of the receiver of FIG. 61 with the monoplanar retainer sub-assembly being further downloaded into the cavity of the receiver.
Figure 84:
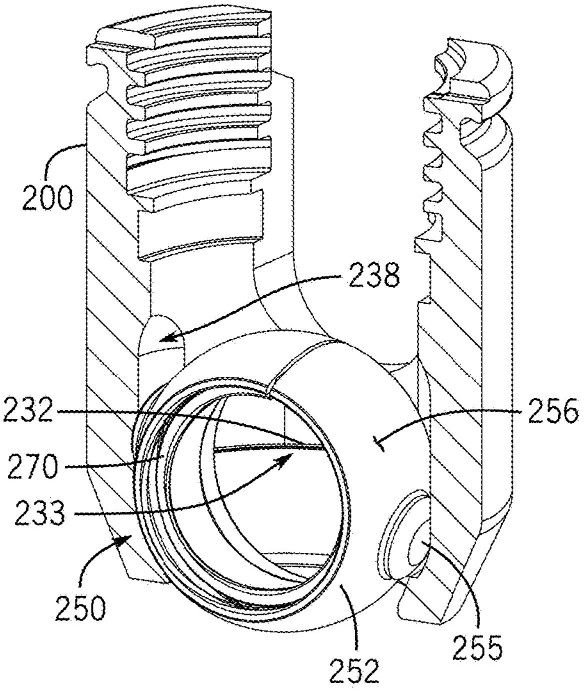
FIG. 84 is a partially cut-away front perspective view of the receiver of FIG. 83 with the vertically-oriented monoplanar retainer sub-assembly contacting the upper edge of the seat surface of the receiver.
Figure 85:
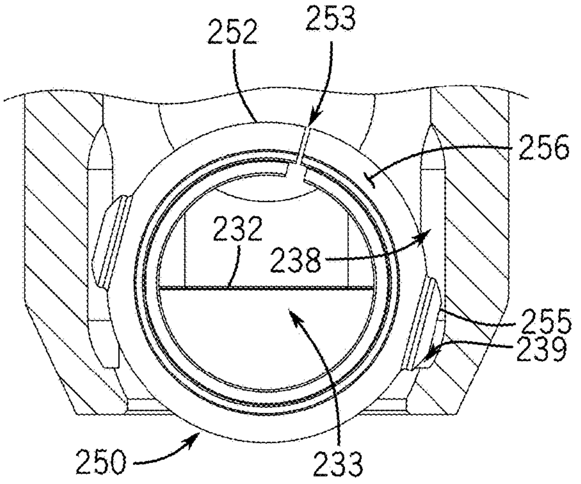
FIG. 85 is a partially cut-away front view of the receiver and monoplanar retainer sub-assembly of FIG. 84.

To begin the pre-assembly of the monoplanar receiver sub-assembly, the capture ring 270 can first be installed into the internal recess 264 of the monoplanar ring retainer 252 to form the monoplanar retainer sub-assembly 250 (see FIGS. 77-80), as described above. As shown in FIGS. 82-88, the retainer sub-assembly 250 can then be top-loaded into the receiver 200. This can be achieved, for instance, by first rotating the retainer sub-assembly 250 to a substantially vertical position in which the axis of rotation 251 of the retainer sub-assembly 250 is substantially perpendicular to the vertical centerline axis 201 of the receiver 200, the top and bottom surfaces of the ring retainer 252 face the saddle surfaces 208 that help define the upwardly-open channel 206, and one of the opposing rounded pegs 255 is aligned to enter into one of the opposed vertically-aligned side pockets 238 formed into the central bore 220, as shown in FIG. 82. The monoplanar retainer sub-assembly 250 can then be downloaded through the receiver channel 206 and into the receiver cavity 234 or lower portion of the central bore 220 until the opposite rounded peg 255 becomes adjacent to the opposite side pocket 238, as shown in FIG. 83. The monoplanar retainer sub-assembly 250 continues to move downward and can be rotated slightly until the spherical outer surface 256 of the ring retainer 252 contacts the inner edges of the ledge surfaces 232 located at the upper ends of the split overtravel lip structure 233 simultaneous with the lowest rounded peg 255 engages the curvilinear bottom surface 239 of the side pocket 238, as shown in FIGS. 84-85.

Figure 86:
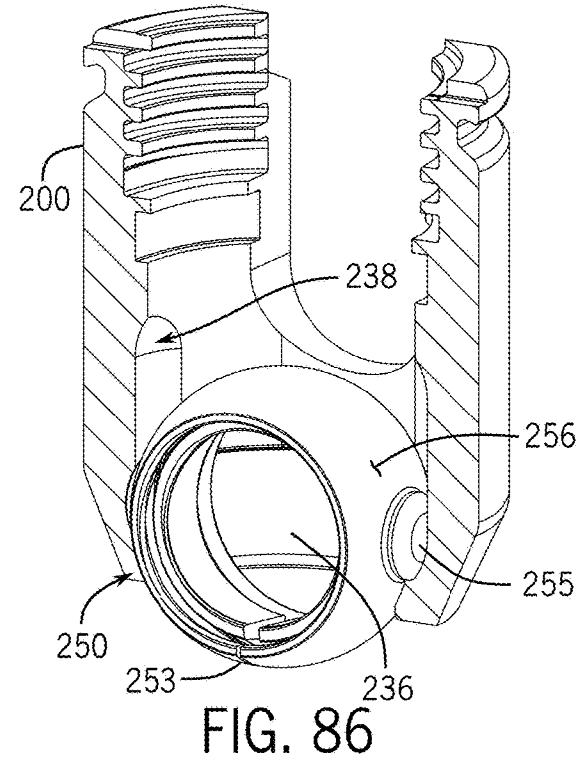
FIG. 86 is a partially cut-away front perspective view of the receiver with the monoplanar retainer sub-assembly being pressed down into a vertical partially-seated engagement with the seat surface of the receiver.
Figure 87:
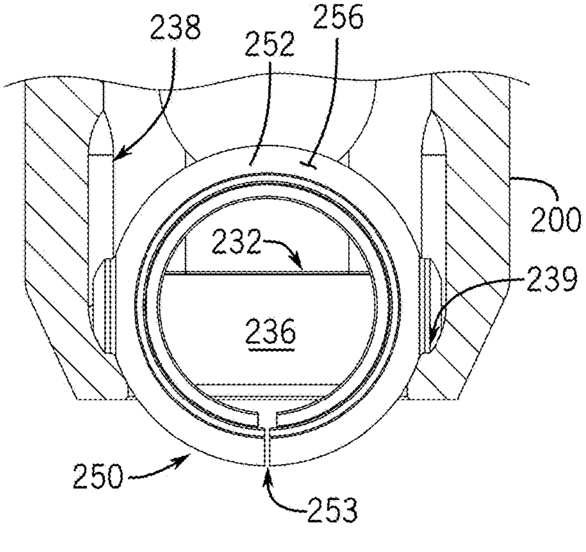
FIG. 87 is a partially cut-away front view of the receiver and monoplanar retainer sub-assembly of FIG. 86.

As previous described, the diameter of the central bore 220 of the receiver 200 at the plane defined by the ledge surfaces 232 will be less than the outer diameter of the spherical outer surface 256 of the ring retainer 252. Thus, with the monoplanar ring retainer 252 contacting the inner edges of the ledge surfaces 232, the retainer sub-assembly 250 can then be pushed or driven downward against the inner edge until the slot 253 closes and the O-ring body of the ring retainer 252 compresses to a smaller diameter that allows the ring retainer 252 to pass downward below the ledge surface 232 and into the lower portion of the cavity 234 defined by the spherical seat surface 236, as shown in FIGS. 86-87, after which the O-ring body of the monoplanar ring retainer 252 is allowed to expand back toward its neutral or free-standing size. At the same time both of the rounded pegs 255 can become engaged with the curvilinear bottom surfaces 239 of the opposed side pockets 238. It will be further appreciated that the slot 253 may be located on either the upper or the lower side of the monoplanar ring retainer 252 as it is engaged with the inner edges of the ledge surfaces 232 and is pressed into the lower portion of the cavity 234.

Figure 88:
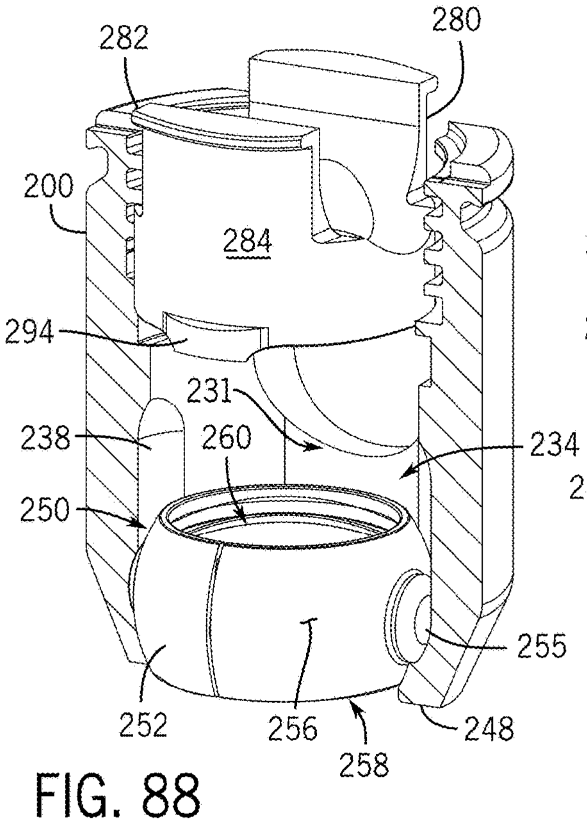
FIG. 88 is a partially cut-away front perspective view of the receiver with the seated monoplanar retainer sub-assembly, with the pressure insert being downloaded through the open channel of the receiver.

Depending on the relative diameters and tolerances of the inner spherical seat surface 236 of the cavity 234 and the outer spherical surface 256 of the monoplanar ring retainer 252, the ring retainer 252 can engage the spherical seat surface 236 of the receiver 200 with a slight interference fit, thereby establishing a compressible frictional engagement between the two structures that inhibits the movement of the retainer sub-assembly 250 relative to the receiver 200. The monoplanar retainer sub-assembly 250 can now be rotated with force to a horizontal orientation, as shown in FIG. 88, with the spherical outer surface 256 of the monoplanar ring retainer 252 more fully engaged with the inner spherical seat surface 236 of the cavity 234, and with the center aperture 260 of the ring retainer 252 being centered above the bottom opening 244 and co-aligned with the vertical axis 201 of the receiver 200. In one aspect the bottom edge surface 258 of the monoplanar ring retainer 252 can be recessed from the bottom surface 248 of the receiver 200, as shown, while in other aspects it can be substantially flush with the bottom surface 248 or even extending proud below the bottom surface.

As described above, when the opposite rounded pegs 255 of the monoplanar ring retainer 252 are positioned within the opposed side pockets 238 of the receiver 200, the pivotal motion of the ring retainer 252 relative to the receiver 200 is limited the single plane defined by the pivot axis extending between the pegs 255. Because the opposed side pockets 238 are aligned with the interior faces 204 of the upright arms 210 that define the rod receiving channel 206, as shown in the drawings, the monoplanar pivotal motion of the illustrated embodiment of the retainer sub-assembly 250 can thus be limited to the sagittal plane. It will nevertheless be appreciated that the angular location of the opposed side pockets 238 may be adjusted in either direction within the receiver cavity 234 so that the monoplanar pivotal motion of the retainer sub-assembly 250 is limited to the medial-lateral plane, or to any plane of pivotal motion located between the sagittal and medial-lateral planes.

It is further foreseen that other structures and interconnections between the components of the receiver sub-assembly can be also used to secure the ring retainer 252 in its pre-assembled position within the receiver cavity 234 with its center aperture 260 aligned and centered with the bottom opening 244 at the base 240 of the receiver 200, and are considered to fall within the scope of the present disclosure.

Figure 89:
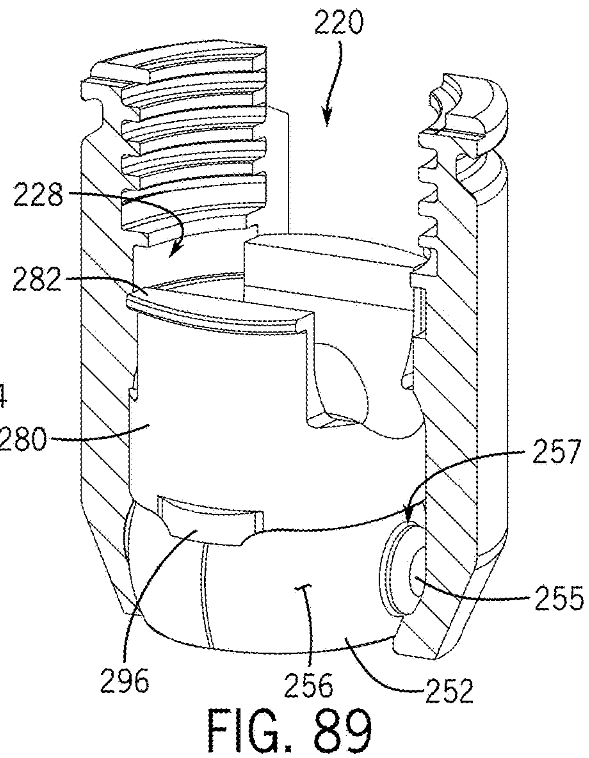
FIG. 89 is a partially cut-away front perspective view of the receiver with the seated monoplanar retainer sub-assembly, with the pressure insert being further downloaded into the cavity of the receiver to engage the ring retainer.

After the monoplanar retainer sub-assembly 250 is seated within the spherical seat surface 236 of the receiver 200, the monoplanar pressure insert 280 may then be top-loaded into the central bore 220 and installed into its the shipping state position above the retainer sub-assembly 250. As shown in FIGS. 88-89, this can be achieved by first positioning the pressure insert 280 above the central bore 220 of the receiver with the insert arms 284 and radially projecting flanges 282 being aligned with the receiver channel 206, and then downloading the pressure insert 280 through the receiver channel 206 until the concave lower surface 294 of the pressure insert 280 contacts the upper portion of the spherical outer surface 256 of the ring retainer 252 and the flanges 282 reach the level of the discontinuous inner recess 228 formed into the central bore 220 for this type of twist-in-place pressure insert.

As shown in the partially cut-away perspective views of FIGS. 88-89, during the downloading of the pressure insert 280 through the receiver channel 206 the opposite outwardly-projecting nubs or protuberances 296 of the pressure insert will generally be aligned with the inner edges of the saddle surfaces 208 and the opposed expanded portions 231 of the substantially cylindrical surface 230 that defines the upper portion of the cavity 234. As with the multiplanar embodiment discussed above, the opposed expanded portions 231 of the monoplanar receiver 200 can have a diameter that is greater than the distance between the outermost surfaces of the projecting nubs 296, thereby allowing the nubs to move downwardly passed the saddle surface 208 and freely enter the cavity 234 during the downloading of the pressure insert 280. The opposed expanded portions 231 of the cavity 234 can thus provide a limited zone of free motion for the nubs 296 when the pressure insert 280 is rotated slightly in either direction, while the non-expanded portions of the cylindrical surface 230 on either side of the expanded portions 231 can have a diameter that is slightly less than the distance between the outer surfaces of the projecting nubs, so as to create a slight interference or frictional fit between the nubs 296 and the cylindrical surface 230. This interference can inhibit further rotation with pressure insert without a moment force that may be applied, for instance, with a tool. The opposed vertical side pockets 238 located at right angles to the opposed expanded portions 231 and centered underneath each upright arm 210 of the receiver 200 can also provide free motion zones for the nubs 296.

Figure 90:
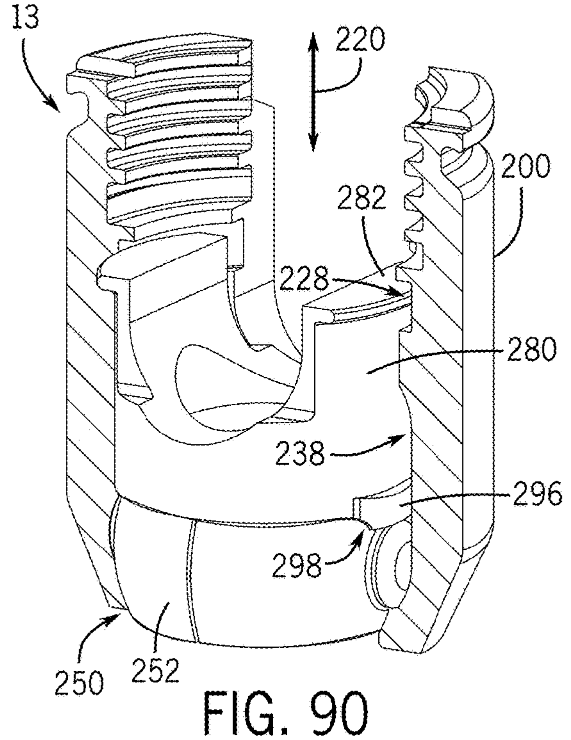
FIG. 90 is a partially cut-away front perspective view of the receiver with the seated monoplanar retainer sub-assembly and the pressure insert being fully rotated therein to form a pre-assembled monoplanar receiver sub-assembly in the shipping state position.
Figure 91:
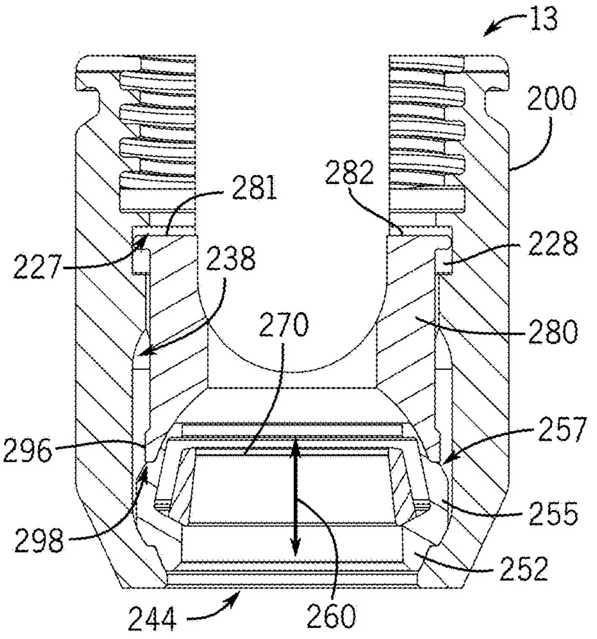
FIG. 91 is a partially cut-away front view of the receiver, pressure insert, and monoplanar retainer sub-assembly in the shipping state position of FIG. 90.

With reference to FIGS. 90-91, the monoplanar pressure insert 280 may then be rotated around its longitudinal axis (which is co-linear with the vertical centerline axis 201 of the receiver 200), so that the radially projecting flanges 282 enter into the discontinuous inner recess 228 of the upright arms 210 at the same time that that the projecting nubs 296 can become slidably frictionally engaged with the cylindrical sidewall surfaces 230 of the receiver cavity 234. The rotation of the pressure insert 280 can continue for a full 90 degrees or quarter turn, until the radially projecting flanges 282 become positioned completely within the discontinuous inner recess 228 of the upright arms 210 and the projecting nubs 296 slide or snap into the opposed side pockets 238 of the cavity 234, and with the elongate bottom edge surfaces 298 of the projecting nubs 296 resting on or slightly above the cylindrical base portion 257 of the opposite rounded pegs 255. The engagement between the elongate bottom edge surfaces 298 of the projecting nubs 296 with the cylindrical base portion 257 of the opposite rounded pegs 255 serves to hold the pegs 255 down against the curvilinear bottom surfaces 239 of the vertical pockets 238, and thereby restrain the monoplanar ring retainer 252 from lifting or twisting up out of the opposed side pockets 238 under out-of-plane side loading or bending on the shank in the monoplanar receiver sub-assembly 13.

Furthermore, once the projecting nubs 296 become positioned within the opposed side pockets 238, further engagement between the projecting nubs 296 and the sides of the vertically-aligned side pockets 138 can inhibit rotation the pressure insert 280, either clockwise or counter-clockwise, out of its rotated position. At same time, further engagement between the upward-facing top surfaces 281 of the flanges 282 and the downward-facing upper arcuate surfaces 227 of the inner recess 228 can prevent the pressure insert 280 from moving back up within the central bore 220 of the receiver 200. Thus, upon the monoplanar pressure insert 280 being rotated into its fully installed position within the receiver 200 above the monoplanar retainer sub-assembly 250, as shown in FIGS. 90-91, the pre-assembly of the monoplanar receiver sub-assembly 13 into a shipping state position or configuration, which is operable to prevent both the pressure insert 280 and the retainer sub-assembly 250 from exiting the central bore 220 of the receiver 200, is now complete. It will be appreciated that the monoplanar receiver sub-assembly 13 is now ready for storage and/or shipping and handling, and for eventually attachment to the capture portion of a bone anchor or bone screw either prior to or during spinal surgery.

With continued reference to FIGS. 90-91, in one aspect the upright arms 284 and projecting flanges 282 of the monoplanar pressure insert 280 can also be sized and shaped so that the upward-facing top surfaces 281 of the flanges 282 are spaced a short distance below the downward-facing upper arcuate surfaces 227 of the inner recess 228 when the concave lower surface 294 of the pressure insert 280 is contacting the upper portions of the ring retainer 252. With the monoplanar retainer sub-assembly 250 being frictionally secured within the inner spherical seat surface 236 of the cavity 234, this can allow for a slight limited axial or vertical displacement of the insert 280 within the receiver 200 when the monoplanar receiver sub-assembly 13 is in the shipping state configuration shown in the drawings. Nevertheless, the pressure insert 280 will be maintained within the central bore 220 of the receiver in preparation for limiting the upward travel of the capture portion of the bone anchor during its assembly with the monoplanar receiver sub-assembly 13, as well as to provide the transfer and distribution of force or pressure from the closure and elongate rod to the capture portion and to the monoplanar retainer sub-assembly 250 during the final assembly and locking of the monoplanar pivotal bone anchor assembly 14.

Again, it is foreseen that other structures for holding the monoplanar pressure insert 280 in alignment with the central bore 220 of the receiver 200 are also possible and considered to fall within the scope of the present disclosure, including but not limited to a reversal of the male/female relationship with an inwardly-protruding projection being formed on an inner surface of the central bore and a recess or notch being formed into the outer surface of the pressure insert.

Figure 92:
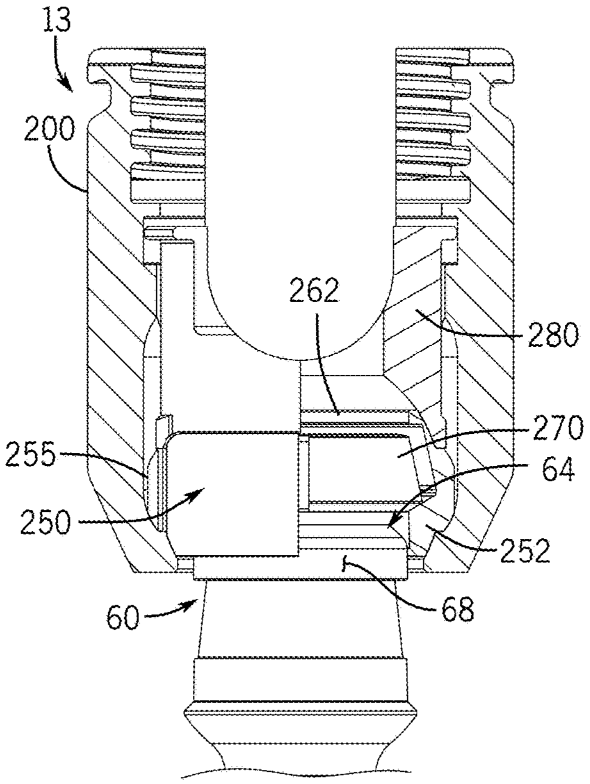
FIG. 92 is a partially cut-away front perspective view of the monoplanar receiver sub-assembly moving downward onto the universal capture portion of the bone anchor.

The assembly of the monoplanar receiver sub-assembly 13 of FIGS. 90-91 to the capture portion 60 of the bone anchor 50 can be substantially similar to the assembly of the multiplanar embodiment discussed above in reference to FIGS. 51-61. For example, and with reference to the abbreviated sequence of assembly shown in FIGS. 92-95, the monoplanar receiver sub-assembly 13 can be first positioned above the proximal end of the bone anchor 50, with the center aperture 260 of the ring retainer 252, that is centered within bottom opening 244 of the receiver 200, being generally aligned with the upper curvate section 64 and the upper outer slidable surface 68 of the capture portion 60. As shown in FIG. 92, the receiver sub-assembly 13 is then dropped downward (or the bone anchor 50 is moved upward, depending on the frame of reference of the reader) until the top edge or upper curvate section 64 of the capture portion 60 enters the center aperture 260 of the ring retainer 252 and travels upward toward the capture ring 270. The initial slidable engagement of the upper curvate section 64 and upper slidable surface 68 with the lower inner slidable surface 268 of the ring retainer 252, upon entry of the upper end of the capture portion 60 into the center aperture 260, can function to center and align the monoplanar ring retainer 252 (and hence the entire monoplanar receiver sub-assembly 13 that is frictionally secured around the monoplanar ring retainer 252) on the capture portion 60, so that the vertical centerline axis of the monoplanar receiver 200 can become substantially co-axial with the longitudinal axis of the bone anchor 50.

Figure 93:
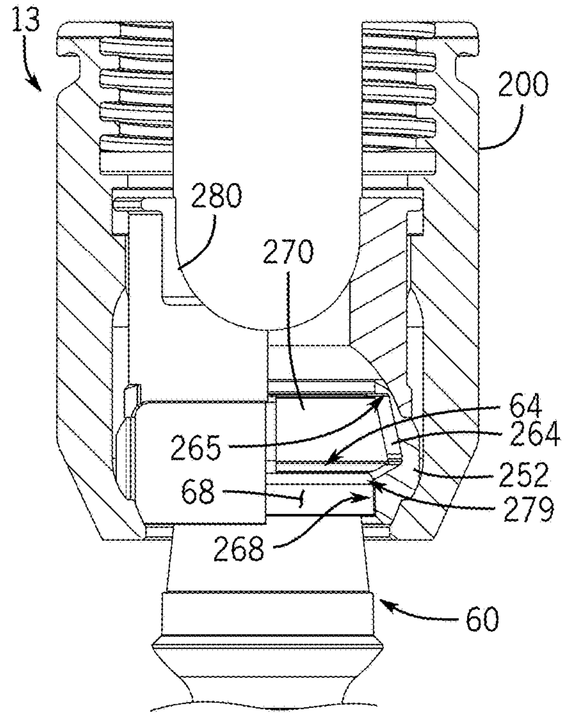
FIG. 93 is a partially cut-away front perspective view of the monoplanar receiver sub-assembly moving downward until the universal capture portion of the bone anchor engages and pushes the capture ring upward to engage the top surface of the recess of the ring retainer.

The monoplanar receiver sub-assembly 13 continues to move downward (or the bone anchor 50 moves upward) as the upper outer slidable surface 68 of the capture portion 60 slides along the lower inner slidable surface 268 of the ring retainer 252, until the upper curvate section 64 contacts the bottom inner edge 279 of the capture ring 270 that is supported on the beveled lower surface 267 of the internal recess 264 of the ring retainer 252. With reference to FIG. 93, the capture portion 60 then pushes the capture ring 270 up off the beveled lower surface 267 and into engagement with the upper annular surface 265 that acts as a stop surface to prevent further upward movement of the capture ring 270 within the internal recess 264.

Similar to the multiplanar assembly described and illustrated above, the monoplanar receiver sub-assembly 13 continues to move downward (or the bone anchor 50 moves upward) as the sliding engagement of the tapered inner surface 276 of the capture ring 270, first by the upper curvate section 64 of the capture portion 60 and then by the upper outer slidable surface 68, forces the capture ring 270 to expand outwardly into the internal recess 264 of the ring retainer 252. The inwardly-angled shape of the tapered inner surface 276 can cause the capture ring 270 to continue to expand as it moves downwardly across the upper outer slidable surface 68 and over the capture recess 70, until the capture ring 270 reaches the state of maximum expansion. At about the same time, the lower inner slidable surface 268 of the ring retainer 252 can also become slidably engaged by the lower outer slidable surface 74 of the universal capture portion 60 due to the continued movement between the shank 50 and the monoplanar receiver sub-assembly 13.

Figure 94:
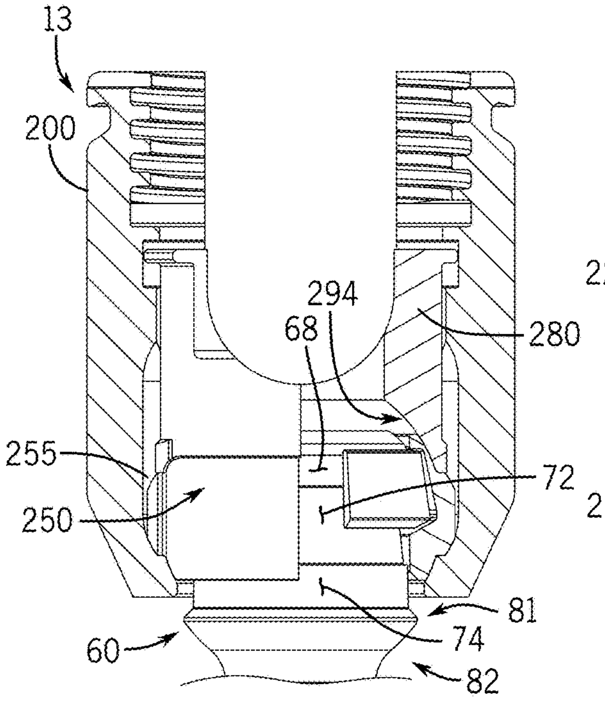
FIG. 94 is a partially cut-away front perspective view of the monoplanar receiver sub-assembly moving further downward as the universal capture portion of the bone anchor drives the capture ring outward within the recess of the ring retainer to a maximum expansion configuration.
Figure 95:
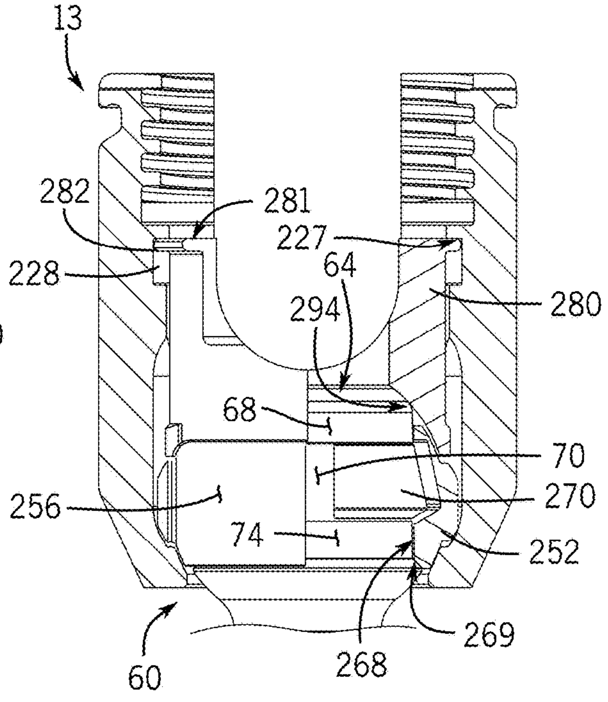
FIG. 95 is a partially cut-away front perspective view of the monoplanar receiver sub-assembly moving further downward and the insert upward until the capture ring snaps into the retainer recess to capture the universal capture portion within the monoplanar receiver sub-assembly, and with out-of-plane bending on the shank (not shown) the pegs on the monoplanar retainer would engage the insert as a stop.

With reference to FIG. 94, the monoplanar receiver sub-assembly 13 continues to move downward (or the bone anchor 50 moves upward) as the tapered inner surface 276 of the capture ring 270 continues to slide downwardly along the upper outer slidable surface 68 toward the horizontal capture recess 70. At the same time, the upper curvate section 64 of the capture portion 60 can project upwards beyond the top edge or annular surface 254 of the ring retainer 252, so as to contact the concave lower surface 294 of the pressure insert 280 prior to the capture ring 270 fully reaching the capture recess 70. With reference to FIG. 95, the upper curvate section 64 of the capture portion 60 pushes the pressure insert 280 upwards within the central bore 220 of the receiver 200, until the capture ring 270 eventually slides off the upper outer slidable surface 68 and snaps into the horizontal capture recess 70, thereby coupling the capture portion 60 directly to the monoplanar retainer sub-assembly 250, and through the monoplanar retainer sub-assembly 250 to the monoplanar receiver sub-assembly 13.

Simultaneously with the snapping in of the capture ring 270 or shortly thereafter, upwardly- and outwardly-facing beveled lip surface 81 of the outer lip structure 82 at the lower end of the capture portion 60 can engage the lower chamfered surface 269 of the monoplanar ring retainer 252, thereby preventing any further upward movement of the capture portion 60 relative to the ring retainer 252. At about the same time, the top surfaces 281 of the flange 282 at the upper end of the pressure insert 280 can engage the downward-facing upper arcuate surfaces 227 of the discontinuous recess 228, so as to prevent any further upward movement of the monoplanar pressure insert 280 and the capture portion 60 relative to the receiver 200. As with the multiplanar embodiment, this engagement between the top surfaces 281 and the upper arcuate surfaces 227 can define the maximum push-through position of the shank 50 relative to the monoplanar receiver sub-assembly 13.

As also previously described, the frictional engagement between the spherical outer surface 256 of the monoplanar ring retainer 252 and the spherical seat surface 236 of the receiver, due to the frictional interference fit between the spherical surfaces that extends both above and below the equator plane of the seat surface, can be sufficient to frictionally secure the monoplanar ring retainer 252 in the shipping state position with its center aperture 260 being co-aligned with the bottom opening 244 of the receiver 200, prior to coupling with the bone anchor 50. This same frictional engagement can also be sufficient to inhibit any pivoting motion of the combined monoplanar retainer sub-assembly 250 and bone anchor 50 relative to the receiver 200 after their coupling together, except by an applied force such as manual manipulation. Thus, once coupled together and prior to downloading the elongate rod into the receiver channel 206 and the locking the assembly with the closure, the monoplanar ring retainer 252 and bone anchor 50 can be pivotably frictionally secured to the receiver 200 with a non-floppy friction fit at the interface between the spherical outer surface 256 of the ring retainer and the spherical seat surface 236 of the cavity of the receiver 200.

With continued reference to FIG. 95, the monoplanar receiver sub-assembly 13 is now coupled to the capture portion 60 by the capture ring 270 that is secured within both the horizontal capture recess 70 of the capture portion and the internal recess 264 of the ring retainer 252. In one aspect the average diameters of the outer slidable surfaces 68, 74 of the capture portion 60 (whether cylindrical or frusto-conical) can be less than the average diameters of the inner slidable surfaces 262, 268 that define the center aperture 260, even when the bone anchor is in its most "upward" coupled position shown in the drawings. This can result in the outer slidable surfaces 68, 74 being either spaced from or only lightly engaged with the inner slidable surfaces 262, 268 with no significant frictional or press-fit engagement being established between the two bands of slidable surfaces. As such, the lack of a strong frictional engagement between the outer slidable surfaces 68, 74 and the inner slidable surfaces 262, 268 can allow for the capture portion 60 to remain freely rotatable or lightly frictionally rotatable within the ring retainer 252 regardless of the pivotal mobility of the ring retainer 252 and shank 50 relative to the receiver 200.

As described above, the pressure insert 280 may be only loosely held within the central bore 220 of the receiver 200 in a non-biased shipping state configuration, with allowance for a slight axial or vertical displacement bounded by the downward-facing upper arcuate surfaces 227 of the inner recess 228 and the upper portion of the spherical outer surface 256 of the monoplanar ring retainer 252. As such, the force of gravity will generally cause the receiver 200 to naturally settle downward around onto the flanges 282 of the pressure insert 280 that is supported, in turn, on the upper curvate section 64 of the vertically-oriented universal capture portion 60. Thus, unless otherwise manipulated or acted upon by another force or outside engagement, the bone anchor 50 and monoplanar receiver sub-assembly 13, as initially coupled together, will typically remain in the configuration shown in FIG. 95 until the components are further locked together with the elongate rod and the closure.

It is foreseen that alternative biased embodiments of the pressure insert, including but not limited to pressure inserts with integral spring elements, non-integral spring elements, and like, are also possible and considered to fall within the scope of the present disclosure. It is further foreseen that both the monoplanar receiver and the monoplanar pressure insert can be reconfigured so that tooling may be used to temporarily hold the pressure insert down in a biased or even in a temporarily locked position within the receiver sub-assembly, until there is a final locking of the pivotal bone anchor assembly with the elongate rod and via the closure.

Figure 96:
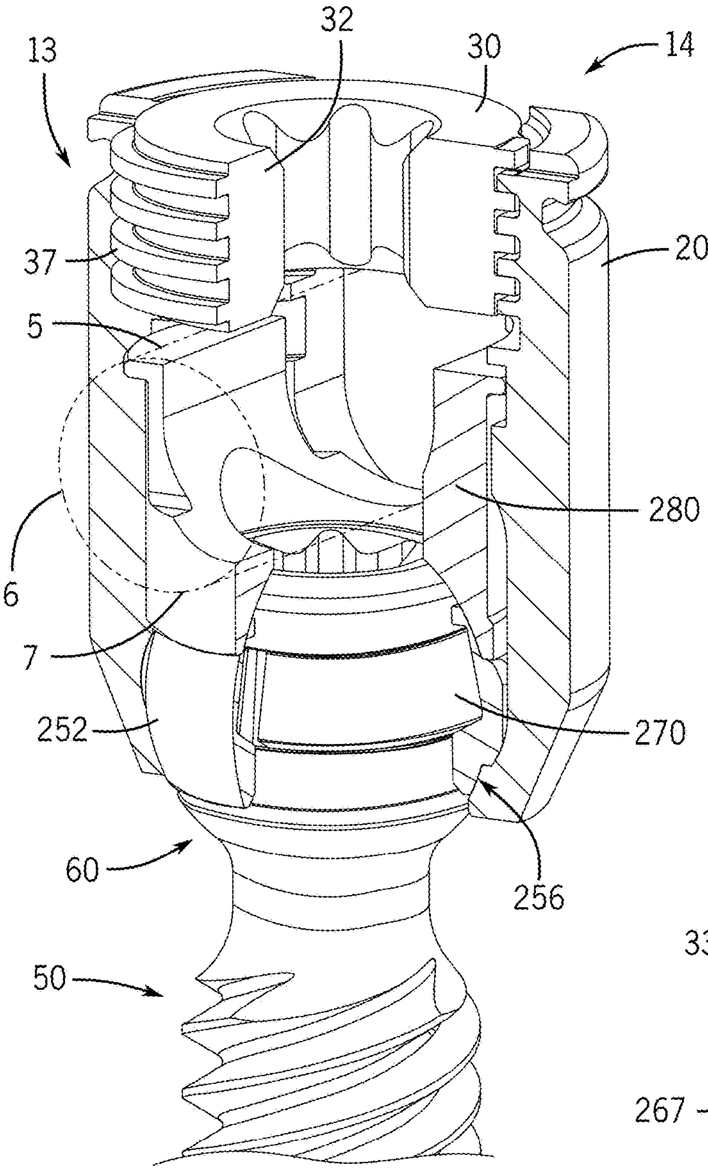
FIG. 96 is a partially cut-away front perspective view of the monoplanar bone anchor assembly, fully assembled with the elongate rod and closure and with the bone anchor in a non-articulated position relative to the receiver.
Figure 97:
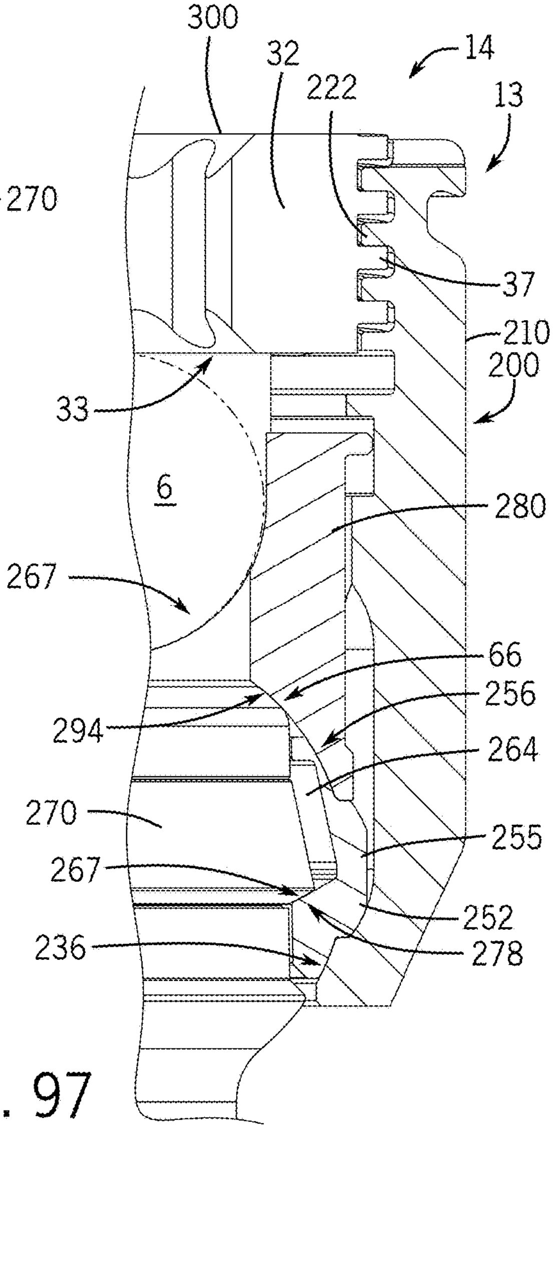
FIG. 97 is a close-up cross-sectional side view of the fully-assembled monoplanar bone anchor assembly of FIG. 96.

With reference to FIGS. 96-97, the final assembly of the monoplanar assembly 14 can be now completed with the addition of the elongate rod 6 and the closure 30. For instance, after a desired alignment of the monoplanar receiver sub-assembly 13 relative to the bone anchor 50 has been achieved, the elongate rod 6 can be installed (i.e. reduced) into the channel 206 of the receiver 200 with the closure 30, and which reduction can include the use of instruments and/or breakoff extensions on the receiver 200. After an initial placement of the elongate rod within the upper portion of the channel 206, the closure 30 can be rotatably and/or threadably installed into the upper portion of the central bore 220 of the receiver 200, in which the continuous guide and advancement structure 37 of the closure body 32 engages the discontinuous guide and advancement structure 222 formed into the interior faces of the upright arms 210 simultaneous with the bottom surface 33 of the closure 30 engaging the top surface 5 of the elongate rod 6 to push it downwards. The elongate rod 6 can be pushed downward into the channel until the lowermost or underside surface 7 of the elongate rod 6 engages the inner upward-facing rod-seating surface 287 of the monoplanar pressure insert 280.

Further rotation and torquing of the closure 30 can then be used to drive the elongate rod 6 downward onto the pressure insert 280, which in turn can push both the pressure insert 280 and the universal capture portion 60 with the attached capture ring 270 downward relative to the ring retainer 252 and the receiver 200. As with the multiplanar embodiment described above, pushing this inner group of assembled components downwards relative to the outer group of assembled components (i.e. the receiver 200 and ring retainer 252) can close the small gaps shown in FIG. 95, so that there is now surface-to-surface engagement between the beveled bottom surface 278 of the capture ring 270 and the complementary tapered lower surface 267 of the internal recess 264 of the ring retainer 252. In addition, there is surface-to-surface engagement between the concave lower surface 294 of the pressure insert 280 and the spherical outer surface 256 of the ring retainer 252, between the elongate bottom edge surfaces 298 of the projecting nubs 296 and the cylindrical base portion 257 of the opposite rounded pegs 255, and/or between the concave lower surface 294 of the pressure insert 280 and the spherical upper edge surface 66 of the capture portion 60. Without being bound to a particular theory, it is contemplated that these engagements can serve to establish divided internal load paths between the closure 30 (that is secured within the arms 210 of the receiver) and the ring retainer 252 that drives the lower portion of the ring retainer 252 further downward and outward into the spherical seat surface 236 of the receiver cavity 234 to achieve a final locked configuration of the bone anchor assembly 14 in which the receiver sub-assembly 13 can no longer pivot in the single plane or rotate relative to the universal bone anchor 50.

In one aspect, the monoplanar receiver 200 having the opposed vertically-aligned side pockets 238 formed into the cylindrical sidewall 230 of the central bore 220 and extending downward into the upper portion of the partially spherical seat surface 236 may also be used for multiplanar receiver sub-assemblies 200 without any significant decrease in performance. For instance, it is contemplated that the continuous 360-degree contact between the multiplanar ring retainer 152 and the spherical seat surface 236 of the monoplanar receiver 200 below the lower portions of the opposed side pockets 238 can avoid high-stress discontinuities while providing for a smooth continuous engagement and support for the multiplanar retainer sub-assemblies that resists pull-out at all angulation angles.

Monoaxial (Non-Pivotal) Bone Anchor Assembly

Figure 98:
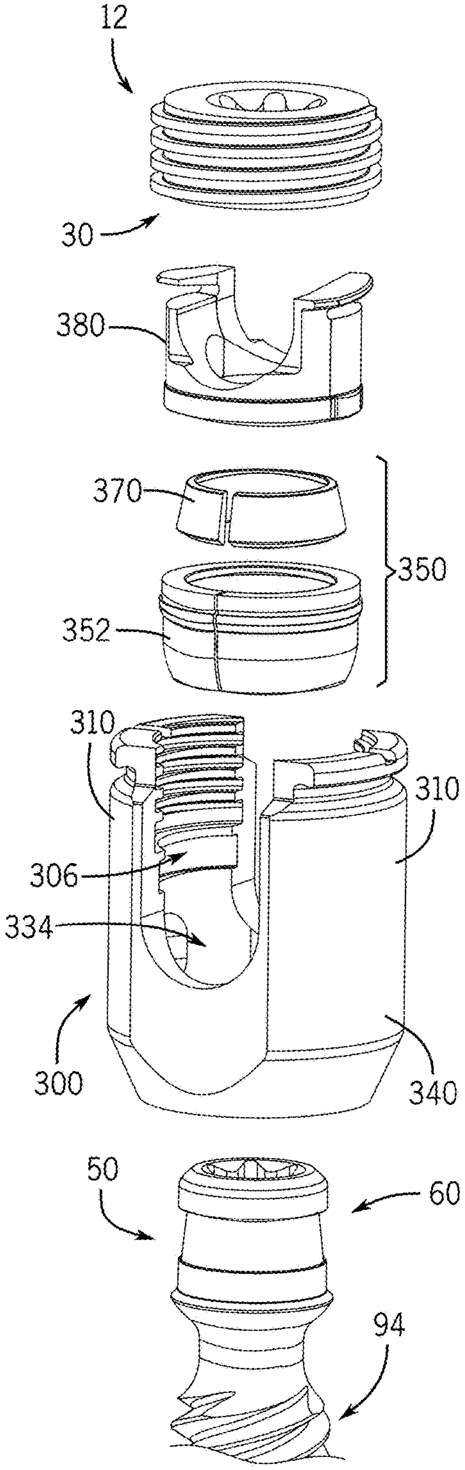
FIG. 98 is an exploded perspective view of a substantially non-pivotal but axially rotatable, or monoaxial, embodiment of a bone anchor assembly, in accordance with the representative embodiment of the multi-component spinal fixation system shown in FIG. 1.

Referring now to FIG. 98, illustrated therein is an exploded perspective view of one representative embodiment of the non-pivotal, relatively “fixed”, or monoaxial bone anchor assembly 16 that is configured, as noted above, to substantially limit pivotal motion of the bone anchor relative to the receiver sub-assembly (or vice versa) while still providing for rotational motion around a 360-degree range. The monoaxial assembly 16 can include the same bone anchor 50 or bone screw described above, having a universal capture portion 60 or shank head and an anchor portion 94 opposite the capture portion 60 for securement or attachment to the bone of a patient. Similar to the multiplanar assembly 12 and the monoplanar assembly 14 discussed above, the monoaxial assembly 16 can also include a receiver 300 that can be initially secured to the universal capture portion 60 with a number of separate internal components that have been pre-assembled into the internal cavity 324 and the rod channel 306 to form the monoaxial receiver sub-assembly 15. These internal components can include, but are not limited to, a monoaxial retainer sub-assembly 350 that includes a monoaxial ring retainer 352 having a separate open capture ring 370 secured therein, and a pressure insert or element 380. After an elongate rod (not shown) has been positioned within the lower portion of the rod channel 306, the same closure 30 shown above (or another appropriate type) can be threadably or otherwise secured into an upper portion of the rod channel 306/central bore 320 to apply pressure to an upper surface of the elongate rod, thereby locking both the elongate rod and the monoaxial assembly 16 into a final locked position.

The primary difference between the multiplanar pivotal and monoplanar pivotal bone anchor assembles previously described and the monoaxial bone anchor assembly 16 of FIG. 98 can be the replacement of the pivotal ring retainers, having spherical outer surfaces, with the monoaxial ring retainer 352 having a cylindrical upper surface with a circumferential ridge protruding outwardly from a center portion thereof, and which is engageable by complementary structures formed into the cavity of the monoaxial receiver 300, and an annular planar top surface that is engageable by an annular planar bottom surface of the monoaxial pressure insert 380. The remainder of the components forming the monoaxial assembly 16, such as the universal shank 50, the capture ring 370, and the closure 30, can be the same as or substantially similar to those already described, so as to more completely provide a modular spinal fixation system with an array of receiver sub-assemblies having all of the attendant benefits thereof.

Figure 99:
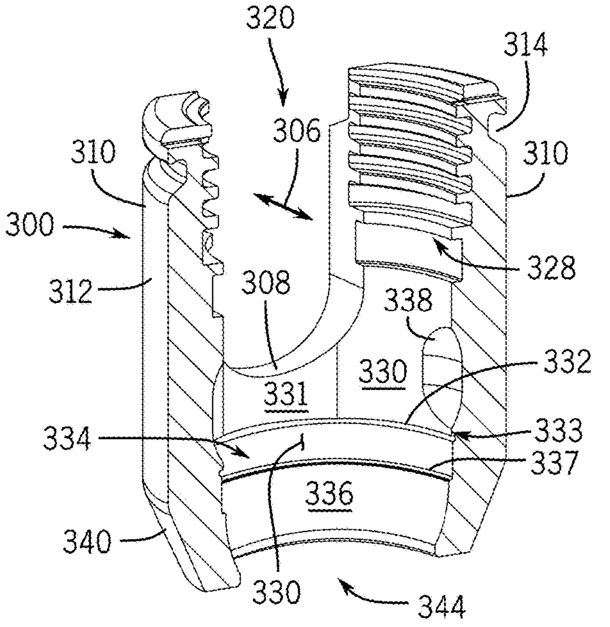
FIG. 99 is a cross-sectional perspective view of the receiver of the monoaxial bone anchor assembly of FIG. 98.
Figure 100:
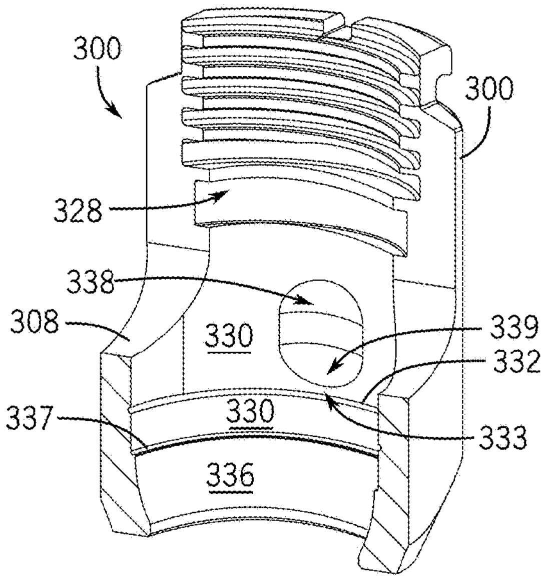
FIG. 100 is another cross-sectional perspective view of the receiver of FIG. 99.
Figure 101:
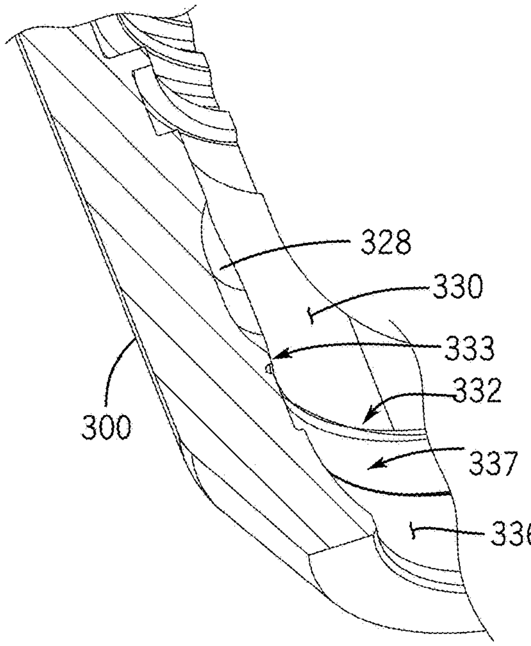
FIG. 101 is a close up perspective view of the cavity of the receiver of FIG. 99.

The receiver 300 of the monoaxial assembly 16 illustrated in FIGS. 99-101 can have much the same construction and features of the pivotal receiver embodiments 110, 200 described above, with the exception that the spherical or curvate seat surface 336 does not extend upward from the bottom opening 344 of the receiver 300 beyond the equator plane on an overtravel lip structure. Instead, the upper extent of the seat surface 336 can be defined by an upward-facing lower circumferential ledge 337 located at or below the equator plane. The lower circumferential ledge 337 can extend between the seat surface 336 and the continuous portion of the cylindrical surface 330 that defines the upper portions of the cavity 334, and which extends upward past the saddle surfaces 308 to the discontinuous inner recess 328 that receives the outwardly-projecting flanges 382 of the monoaxial pressure insert 380. An upper circumferential groove 332 can also be formed into the cylindrical surface 330 of the cavity 334 of the monoaxial receiver 300, between the lower circumferential ledge 337 and the saddle surfaces 308. In addition, the opposed side pockets 338 formed into the cavity 334 of the receiver 300 can be reduced in size, with the curvilinear bottom surfaces 339 of the side pockets 338 being moved further upward within the central bore 320 above both the lower circumferential ledge 335 and the upper circumferential groove 332. Finally, narrow arc portions of the cylindrical surface 330 located between the curvilinear bottom surfaces 339 of the side pockets 338 and the upper circumferential groove 332 can be further modified to gradually project inward into the receiver cavity as opposed inwardly-protruding arc structures 333, with the maximum extent of protrusion occurring directly below the center of the opposed side pockets 338. As described in more detail below, the opposed inwardly-protruding arc structures 333 can engage with complementary outwardly-projecting surfaces of the monoaxial ring retainer 352 to hold the ring retainer 352 in position upon downloading into the cavity 334 of the receiver 300.

It will be appreciated that with the monoaxial embodiment of the bone anchor assembly 16, it may not be necessary for the seat surface 336 of the monoaxial receiver 300 to be spherical or curvate so as to provide for pivotal motion between the receiver 300 and the bone anchor 50, and that other shapes or geometries for the seat surface 336 are also possible. The remaining structural elements of the monoaxial receiver 300, including the base 340, the upright arms 310 forming the rod channel 306, the discontinuous guide and advancement structure 322 formed into the upper portion of the central bore 320, the tool engagement structures 314, the curvate side outer surfaces 312 of the upright arms 310, the front and back outer planar faces 342 of the receiver base, and the like, can be the same as or substantially similar to the structural elements of the pivotal receivers 100, 200 described above.

Figure 102:
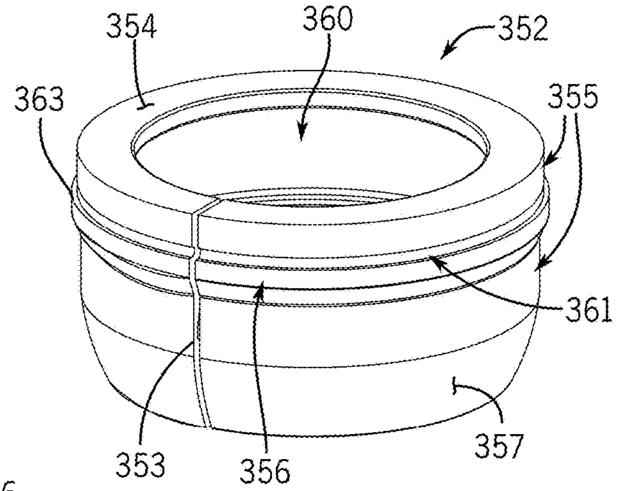
FIG. 102 is a perspective view of the ring retainer of the monoaxial bone anchor assembly of FIG. 98.
Figure 103:
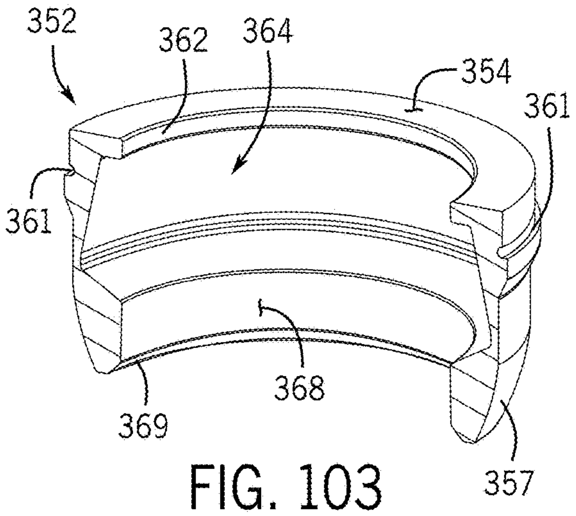
FIG. 103 is a cross-sectional perspective view of the monoaxial ring retainer of FIG. 102.
Figure 104:
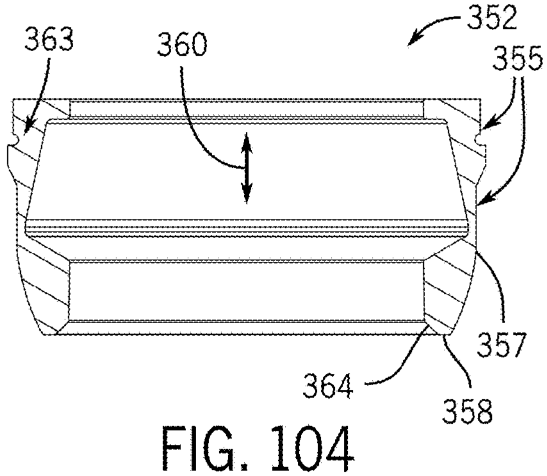
FIG. 104 is a cross-sectional side view of the monoaxial ring retainer of FIG. 102.

With reference to FIGS. 102-104, the monoaxial ring retainer 352 can include a top annular surface 354 and a bottom annular surface 358, and a spherical or curvate lower outer surface 357 adjacent the bottom annular surface 358 that is configured to engage with the seat surface 336 of the receiver 300 in a monoaxial manner. A cylindrical upper outer surface 355 can extend upward from the lower outer surface 357 to the top annular surface 354, and in one aspect can include a ridge structure 356 projecting outwardly from a mid-portion of the cylindrical upper outer surface 355. The monoaxial ring retainer 352 can further include an outer relief groove 361 immediately above the outwardly-projecting ridge structure 356 that can serve to define an upward-facing ledge surface 363 that is configured to engage with the bottom edge surfaces of the inwardly-protruding arc structures 333 of the cavity 334 of the receiver 300 upon the positioning of the monoaxial ring retainer 352 within the cavity 334.

The remaining structural elements of the monoaxial ring retainer 352, including the center aperture 360 defined by inner slidable surfaces 362, 368 and the internal recess 364 that extends into and circumferentially around a mid-portion of the center aperture 300, the lower chamfered surface 369, the slit or slot 353 extending through the thickness of the O-ring body, and the like, can be the same as or substantially similar to the structural elements of the multiplanar and monoplanar pivotal ring retainers 152, 252 described above. As such, the lower chamfered surface 369 of the monoaxial ring retainer 352 can be adjacent to, or even contacting, the beveled lip surface 81 of the capture portion 60 (described above) when the bone anchor 50 is coupled to the monoaxial ring retainer 352.

As previously noted, it is understood that the open capture ring 370 shown in the exploded perspective view of FIG. 98 can be the same as or substantially similar to the open capture rings 170, 270 that are positionable within the multiplanar and monoplanar ring retainers 152, 252 of the pivotal assemblies 12, 14 discussed above, respectively, and can be configured with the same structure and to perform the same functions during the assembly and operation of the monoaxial assembly 16 as with the pivotal assemblies 12, 14.

Figure 105:
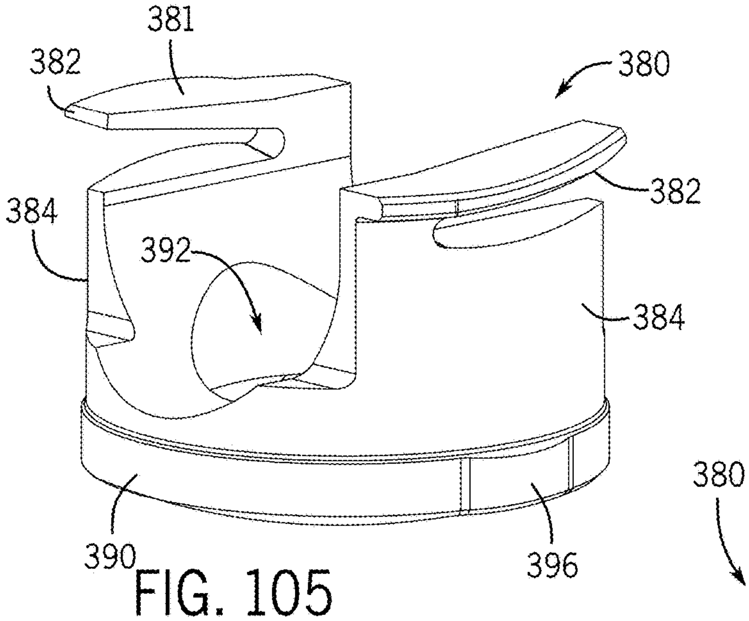
FIG. 105 is a top perspective view of the pressure insert of the monoaxial pivotal bone anchor assembly of FIG. 98.
Figure 106:
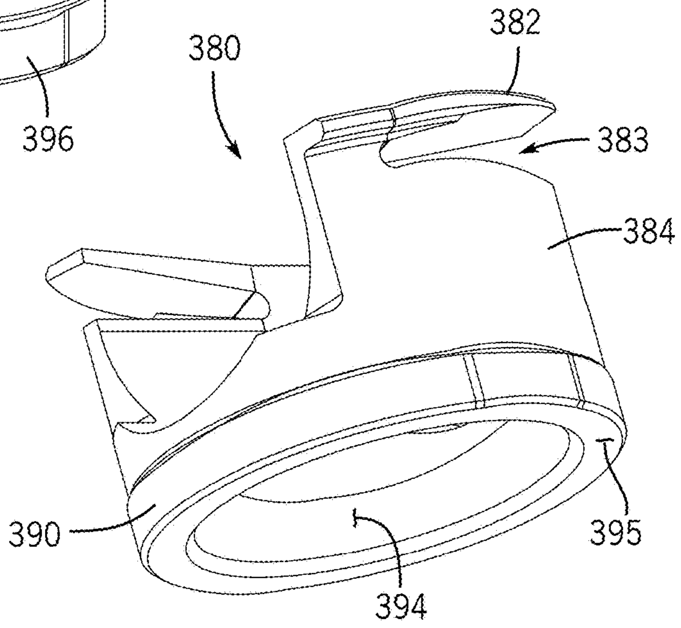
FIG. 106 is a bottom perspective view of the monoaxial pressure insert of FIG. 105.
Figure 107:
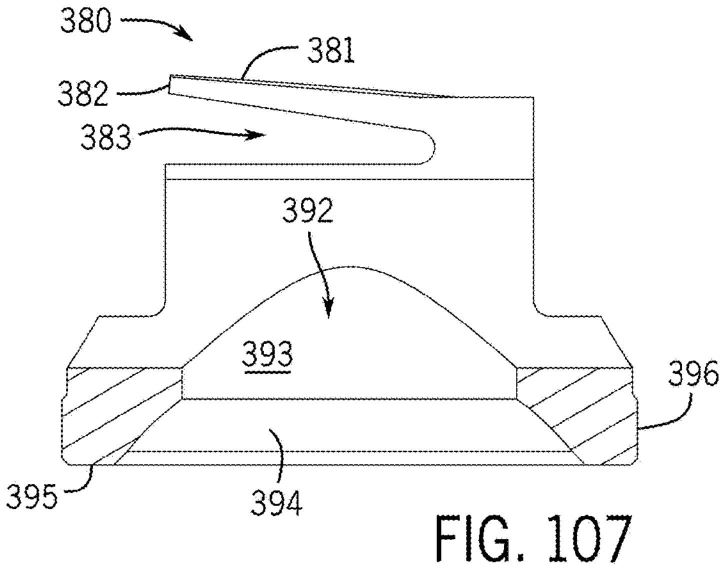
FIG. 107 is a cross-sectional side view of the monoaxial pressure insert of FIG. 105.

With reference to FIGS. 105-107, the monoaxial assembly 16 can further include a monoaxial pressure insert 380 that can be substantially similar to the pressure inserts 180, 280 of the pivotal bone anchor embodiments 12, 14 discussed above, with an exception in that the base 390 of the pressure insert 380 can be shortened and the width of the annular bottom edge can be increased to define an annular bottom surface 395 that is configured to overlap the annular top surface 354 of the monoaxial ring retainer 352, and to possibly engage with the annular top surface 354 in the final locked configuration, as discussed below. Shortening the base 390 can also raise the location of the opposite outwardly projecting nubs or protuberances 396 located near the bottom surface 395 that are configured to releasably engage with the opposed vertical side pockets 338 formed into the central bore 320 of the monoaxial receiver 300 upon rotation of the pressure insert 380 into its rotated position. Finally, the top portions of the insert upright arms 384 can also be modified to form upwardly-angled spring-like flanges 382 having top surfaces 381 that are configured to engage with the downward-facing upper arcuate surfaces 327 of the discontinuous recess 328 formed into the central bore 320 of the monoaxial receiver 300, also upon rotation of the pressure insert 380 into its rotated position, so as to provide a downwardly-directed force that biases the monoaxial pressure insert 380 against the upper curvate section 64 of the universal capture portion 60 or shank head and/or the annular top surface 354 of the monoaxial ring retainer 352. In one aspect this modification can include forming a slot 383 extending inward from the trailing edge of the insert upright arms 384 and just below the radially projecting flanges 382, and then bending the trailing end of each flange 382 upward to form the upwardly-angled spring-like structures.

The remaining structural elements of the monoaxial pressure insert 380, including the lower insert base portion 390 having a cylindrical outer surface 388, the two upright insert arms 384 formed integral with the lower base portion 290 and having inner surfaces that define the inner upward-facing rod-seating surface 387, the concave lower surface 394, the central tool-receiving aperture 392 defined by an inner cylindrical surface 393 and configured to slidably receive a drive tool (not shown), and the like, can be the same as or substantially similar to the structural elements of the pivotal pressure inserts 180, 280 described above.

Figure 108:
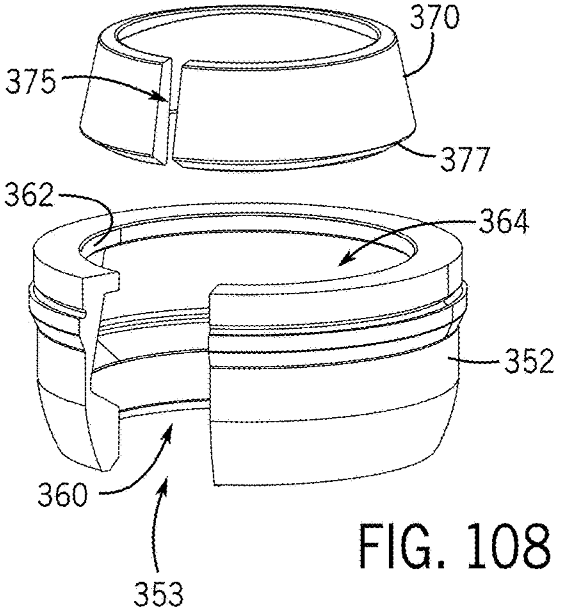
FIG. 108 is a perspective view of the monoaxial ring retainer of FIG. 102 and the capture ring of FIG. 16 prior to assembly together into a monoaxial retainer sub-assembly.
Figure 109:
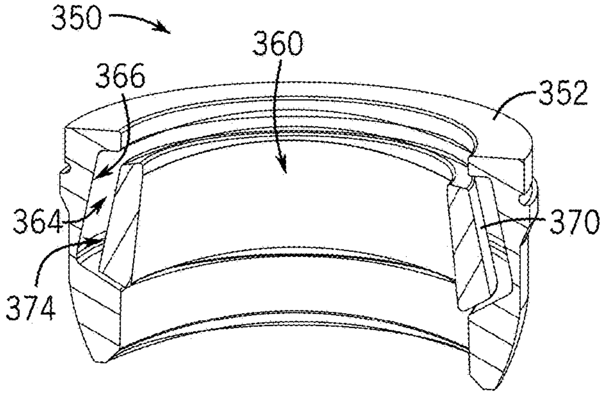
FIG. 109 is a cross-sectional perspective view of the monoaxial ring retainer and capture ring of FIG. 108 after assembly together into the monoaxial retainer sub-assembly.

To begin assembly of the monoaxial bone anchor assembly 16, the capture ring 370 can first be installed or positioned into the internal recess 364 of the monoaxial ring retainer 352 to form the retainer sub-assembly 350, as shown in FIGS. 108-109. To begin this assembly the capture ring 370 can be placed above the monoaxial ring retainer 352 in preparation for top loading into the center aperture 360 of the ring retainer 352 (although bottom loading into the ring retainer is also contemplated). The monoaxial ring retainer 352 can then be expanded and the slot 353 opened until the diameter of the center aperture 360 at the upper inner slidable surface 362 is greater than the outer diameter of the lower outer edge 377 of the capture ring 370, as shown in FIG. 108. In one aspect the capture ring 370 can also be slightly compressed so that the width of the capture ring slot 375 and the outer diameter of the lower outer edge 377 is less than it what it would be in its neutral or free-standing state.

The capture ring 370 may then be tilted and inserted into the center aperture 360 of the monoaxial ring retainer 352 at an angled orientation, as with the pivotal embodiments described above. After the positioning of the capture ring 370 within the internal recess 364, the monoaxial ring retainer 352 can be released to close back toward its neutral state to capture the now-horizontal capture ring 270, as shown in the cross-sectional view of FIG. 109. The capture ring 370 in its neutral or free state can project partially into the center aperture 360 of the ring retainer 352 while simultaneously providing for a space or gap between the outer surface 374 of the capture ring and the recessed sidewall surface 366 of the internal recess 364 that allows for the expansion of the capture ring 370 within the internal recess 364 during future assembly steps. As with the pivotal embodiments described above, in one aspect the forced expansion of the monoaxial ring retainer 352 shown in FIG. 108 can result in a marginal inelastic deformation of the O-ring body of the ring retainer 352, so that the diameters of the outer surfaces in the free and neutral state are now greater than what they were before the expansion. This deformation can be advantageously employed in subsequent assembly steps to establish a compressive friction engagement between the outer surfaces of the monoaxial ring retainer 352 and the internal surfaces of the receiver cavity 334.

Figure 110:
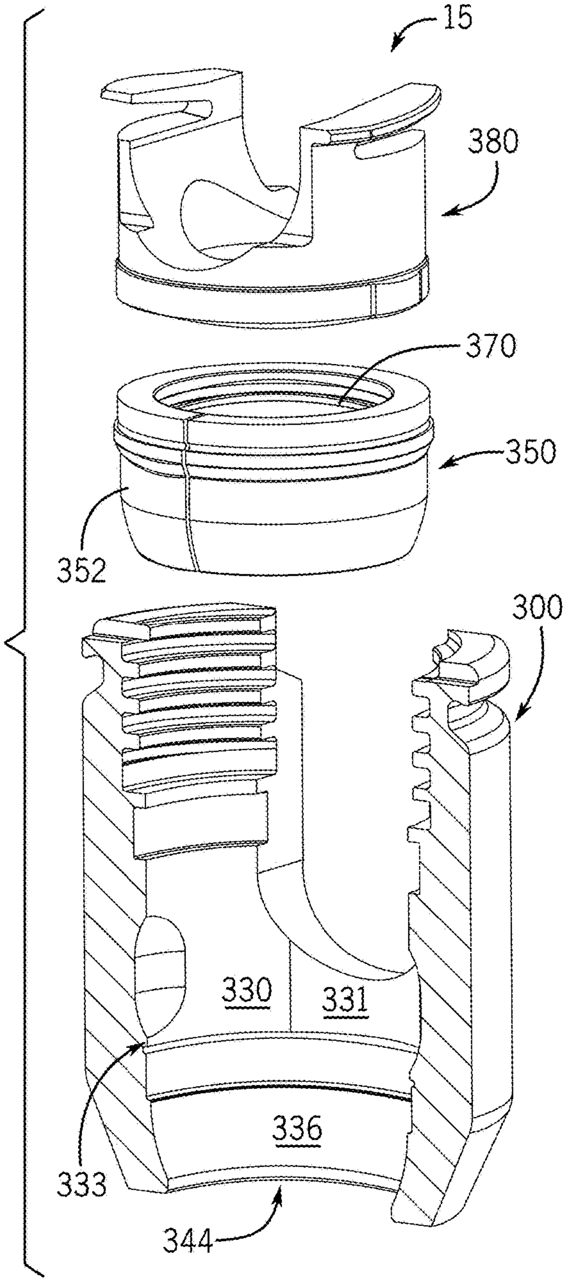
FIG. 110 is an exploded side view of the components of a monoaxial receiver sub-assembly prior to their pre-assembly into a shipping configuration.

Illustrated in FIG. 110 are the individual components of the monoaxial bone anchor assembly 16 that, in many embodiments, can be pre-assembled together into a receiver sub-assembly 15 at a factory or manufacturing facility, prior to shipping to a hospital or surgery center and engagement with the capture portion of the bone anchor in the surgical setting. As noted above, these components generally include the monoaxial receiver 300, the monoaxial retainer sub-assembly 350 that includes the monoaxial ring retainer 352 with the separate open capture ring 370 secured therein, and the monoaxial pressure insert 380. In one aspect the monoaxial receiver 300, the monoaxial retainer sub-assembly 350, and the monoaxial insert 380 being pre-assembled into the monoaxial receiver sub-assembly 15 can be further defined as the shipping state configuration for the 'modular' bone anchor assembly, as described herein and commonly understood in the art. It will be appreciated, however, that in other embodiments the shipping state configuration can include the additional assembly of the monoaxial receiver sub-assembly together with the bone anchor at the factory or manufacturing facility. It will also be appreciated that in yet other embodiments the individual components described above can also be pre-assembled into the receiver sub-assembly at the spine company, the hospital or surgery center prior to implantation in a patient.

Figure 111:
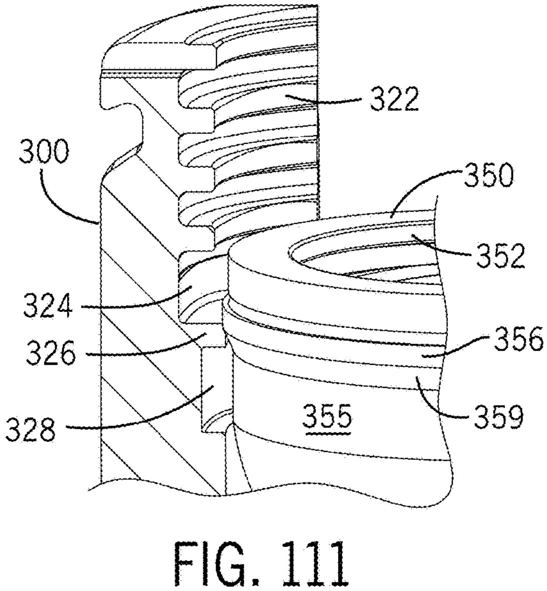
FIG. 111 is a close-up partially cut-away front perspective view of the receiver of FIG. 110 with the horizontally-oriented monoaxial retainer sub-assembly being downloaded through the channel of the receiver.

To begin the pre-assembly of the monoaxial receiver sub-assembly 15, in one aspect the monoaxial retainer sub-assembly 350 can first be top-loaded into the receiver 300 through the receiver channel 306 in a substantially horizontal orientation. The retainer sub-assembly 350 can move downward past the threads of the discontinuous guide and advance structure 322 until the outwardly-projecting circumferential ridge structure 356 of the monoaxial ring retainer 352 abuts an upper edge surface of the upper cylindrical ledge 326 located between the run-out groove 324 and the inner recess 328 of the central bore 320, as shown in FIG. 111. In this representative configuration, the upper cylindrical ledge 326 can have an inner diameter that is greater than the outer diameter of the cylindrical outer surface 355, so as to provide clearance for the lower portion of the monoaxial retainer sub-assembly 350, but slightly less than the outer diameter of the ridge structure 356. In addition, the circumferential ridge structure 356 can also include a tapered or frustoconical surface 359 extending downwardly to the cylindrical outer surface 355, and which frustoconical surface 359 can first contact the upper cylindrical ledge 326 of receiver 300 as the monoaxial retainer sub-assembly 350 is top-loaded through the receiver channel 306.

Figure 112:
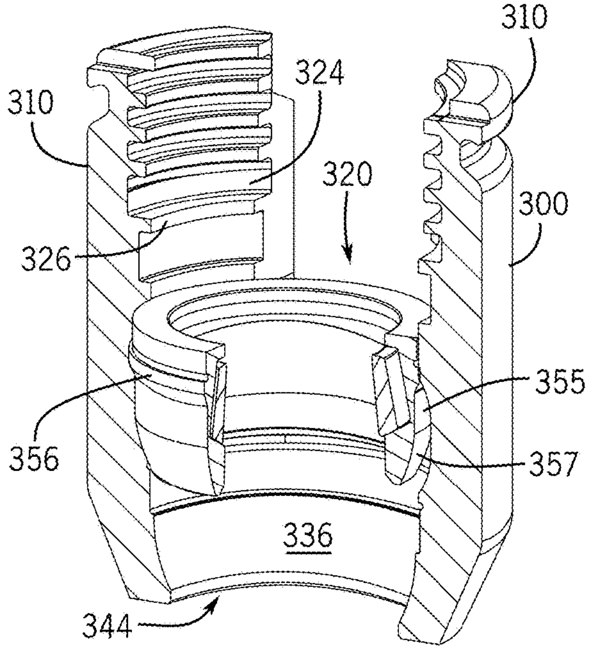
FIG. 112 is a partially cut-away front perspective view of the receiver of FIG. 111 with the monoaxial retainer sub-assembly being further downloaded through the channel of the receiver.
Figure 113:
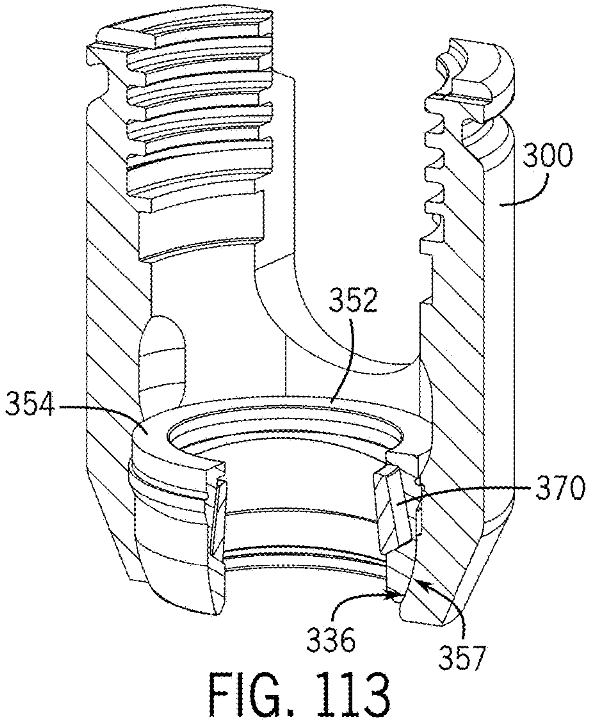
FIG. 113 is a partially cut-away front perspective view of the receiver of FIG. 112 with the monoaxial retainer sub-assembly being pressed down into engagement with the seat surface of the receiver.
Figure 114:
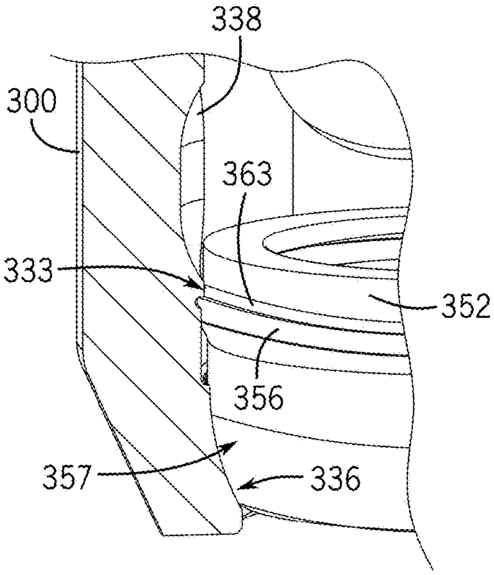
FIG. 114 is a close-up partially cut-away front perspective view of the receiver of FIG. 113 with the monoaxial retainer sub-assembly being positioned within the cavity of the receiver.

It will be appreciated that applying a downward pressure to the top of the monoaxial ring retainer 352, with the frustoconical surface 359 of the ring retainer 352 being engaged with the upper cylindrical ledge 326 of the central bore 320, can cause the ring retainer 352 to compress and close the slot 353 until the circumferential ridge structure 356 pushes past both the upper cylindrical ledge 326 and the inner recess 328 to enter the portion of the central bore 320 defined by the partially-discontinuous lower cylindrical surface 330, as shown in FIG. 112. Continued application of the downward pressure can drive the monoaxial receiver sub-assembly 15 further downward within the central bore 320 until the spherical or curvate lower outer surface 357 of the monoaxial ring retainer 352 becomes engaged with the seat surface 336 of the receiver 300 and circumferential ridge structure 356 snaps under the inwardly-protruding arc structures 333 of the cavity 334, as shown in FIGS. 113-114, after which the O-ring body of the monoaxial ring retainer 352 is allowed to expand back toward its neutral or free-standing size. At this point the bottom edge surfaces of the inwardly-protruding arc structures 333 can become overlappingly engaged with the upward-facing ledge surface 363 of the circumferential ridge structure 356, holding the monoaxial retainer sub-assembly 350 firmly in place and inhibiting any upward or reverse movement of the monoaxial ring retainer 352.

It will be further appreciated that other structures and interconnections between the components of the monoaxial receiver sub-assembly 15 can be also used to secure the monoaxial ring retainer 352 in its pre-assembled position within the receiver cavity 334 with its center aperture 360 aligned and centered with the bottom opening 344 at the base 340 of the receiver 300, and are considered to fall within the scope of the present disclosure.

After the monoaxial retainer sub-assembly 350 is positioned within the cavity 334 and against the seat surface 336 of the receiver 300, the monoaxial pressure insert 380 may then be top-loaded into the central bore 320 and installed into its the shipping state position above the retainer sub-assembly 350. As shown in FIGS. 115-118, this can be achieved by first positioning the monoaxial pressure insert 380 above the central bore 320 of the receiver with the insert arms 384 and radially projecting flanges 382 being aligned with the receiver channel 306, and then downloading the pressure insert 380 through the receiver channel 306 until the annular bottom surface 395 of the pressure insert 380 contacts the top annular surface 354 of the monoaxial ring retainer 252 and the flanges 382 reach the level of the discontinuous inner recess 328 formed into the central bore 320 for this type of twist-in-place pressure insert.

Figure 115:
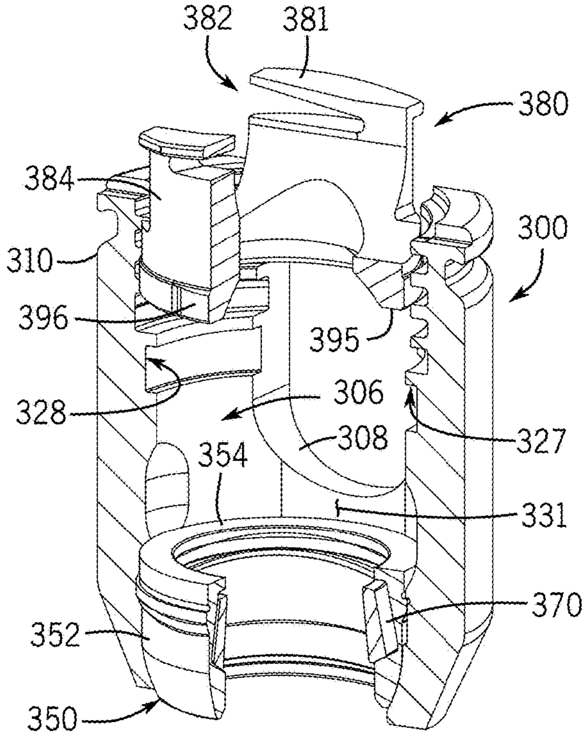
FIG. 115 is a partially cut-away front perspective view of the receiver with the seated monoaxial retainer sub-assembly, with the monoaxial pressure insert being downloaded through the open channel of the receiver.
Figure 116:
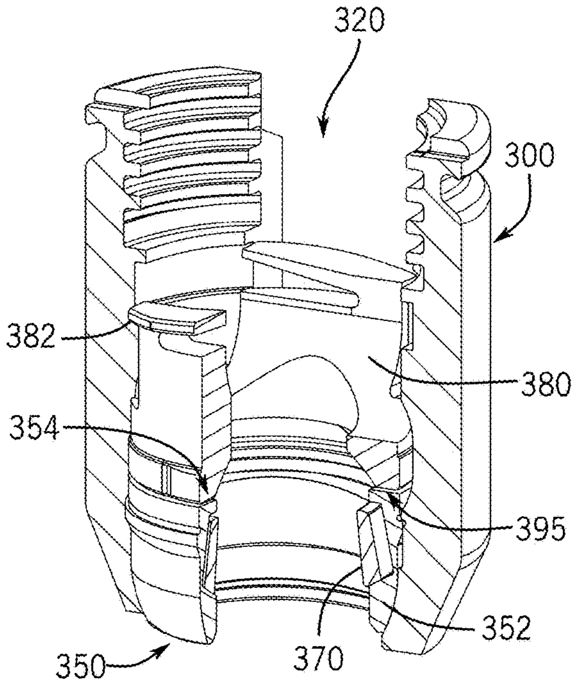
FIG. 116 is a partially cut-away front perspective view of the receiver with the seated monoaxial retainer sub-assembly, with the monoaxial pressure insert being further downloaded into the cavity of the receiver to engage the ring retainer.

As shown in the partially cut-away perspective views of FIGS. 115-116, during the downloading of the monoaxial pressure insert 380 through the receiver channel 306 the opposite outwardly-projecting nubs or protuberances 396 of the pressure insert will generally be aligned with the inner edges of the saddle surfaces 308 and the opposed expanded portions 331 of the substantially cylindrical surface 330 that defines the upper portion of the cavity 334. As with the pivotal embodiments discussed above, the opposed expanded portions 331 of the receiver cavity 334 can have a diameter that is greater than the distance between the outermost surfaces of the projecting nubs 396, thereby allowing the nubs to move downwardly passed the saddle surface 308 and freely enter the cavity 334 during the downloading of the pressure insert 380. The opposed expanded portions 331 can thus provide a limited zone of free motion for the nubs 396 when the pressure insert 380 is rotated slightly in either direction, while the non-expanded portions of the cylindrical surface 330 on either side of the expanded portions 331 can have a diameter that is equal to or slightly less than the distance between the outer surfaces of the projecting nubs, so as to create a slight interference or frictional fit between the nubs 396 and the cylindrical surface 330. This interference can inhibit further rotation with pressure insert without a moment force that may be applied, for instance, with a tool. The opposed vertical side pockets 338 located at right angles to the opposed expanded portions 331 and centered underneath each upright arm 310 of the receiver 300 can also provide free motion zones for the nubs 396.

Figure 117:
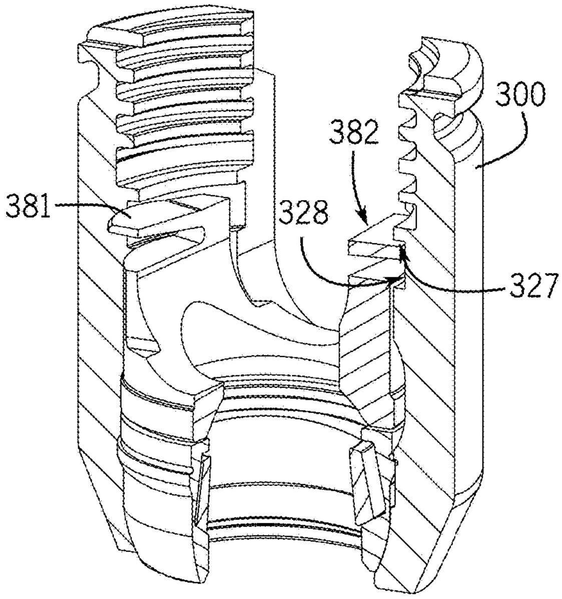
FIG. 117 is a partially cut-away front perspective view of the receiver with the seated monoaxial retainer sub-assembly and the monoaxial pressure insert being fully rotated therein to form a pre-assembled monoaxial receiver sub-assembly in the shipping state position.
Figure 118:
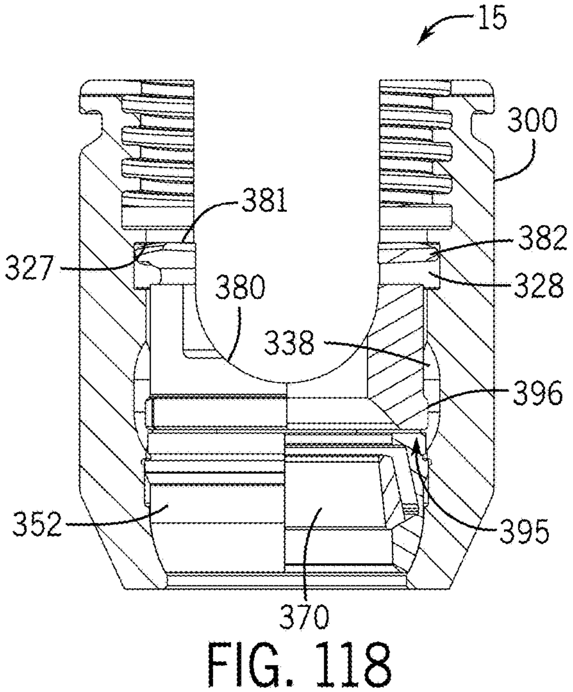
FIG. 118 is a partially cut-away front view of the pre-assembled monoaxial receiver sub-assembly in the shipping state position of FIG. 117.

With reference to FIGS. 117-118, the monoaxial pressure insert 380 may then be rotated around its longitudinal axis (which is co-linear with the vertical centerline axis 301 of the receiver 300), so that the radially projecting flanges 382 can enter into the discontinuous inner recess 328 of the upright arms 310 at the same time that that the projecting nubs 396 can become slidably frictionally engaged the cylindrical sidewall surfaces 330 of the receiver cavity 334. The rotation of the pressure insert 380 can continue for a full 90 degrees or quarter turn, until the radially projecting flanges 382 become positioned completely within the discontinuous inner recess 328 of the upright arms 310 and the projecting nubs 396 slide or snap into the opposed side pockets 338 of the cavity 334. Once the projecting nubs 396 become positioned within the opposed side pockets 338, further engagement between the projecting nubs 396 and the sides of the vertically-aligned side pockets 338 can inhibit rotation of the pressure insert 380, either clockwise or counter-clockwise, out of its rotated position.

At same time, the completion of the rotation of the monoaxial pressure insert 380 can cause the upwardly-projecting trailing end of each radially projecting flange 382 to forcefully engage the downward-facing upper arcuate surfaces 327 of the inner recess 328, thereby biasing the annular bottom surface 395 of the pressure insert 380 downward against the annular top surface 354 of the monoaxial ring retainer 352 and preventing the pressure insert 380 from moving back up within the central bore 320 of the receiver 300. In other words, in one aspect the upward-facing ramped surfaces 381 of the monoaxial pressure insert 380 can provide a spring-like camming action that converts the rotatory motion of the pressure insert 380 into a linear downward movement that generates a biasing downward pressure onto the monoaxial ring retainer 352, prior to the coupling with the universal capture portion 60 of the bone anchor and the installation of the rod and the final locking of the monoaxial assembly 16 by the closure 30.

Upon the monoaxial pressure insert 380 being rotated into its fully installed position within the receiver 300 above the monoaxial retainer sub-assembly 350, as shown in FIGS. 117-118, the pre-assembly of the monoaxial receiver sub-assembly 15 into a shipping state position or configuration, which is operable to prevent both the pressure insert 380 and the retainer sub-assembly 350 from exiting the central bore 320 of the receiver 300, is now complete. It will be appreciated that the monoaxial receiver sub-assembly 15 is now ready for storage and/or shipping and handling, and for eventually attachment to the capture portion of a bone anchor or bone screw either prior to or during spinal surgery.

Again, it is foreseen that other structures for holding the monoaxial pressure insert 380 in alignment with the central bore 320 of the receiver 300 are also possible and considered to fall within the scope of the present disclosure, including but not limited to a reversal of the male/female relationship with an inwardly-protruding projection being formed on an inner surface of the central bore and a recess or notch being formed into the outer surface of the pressure insert.

Figure 119:
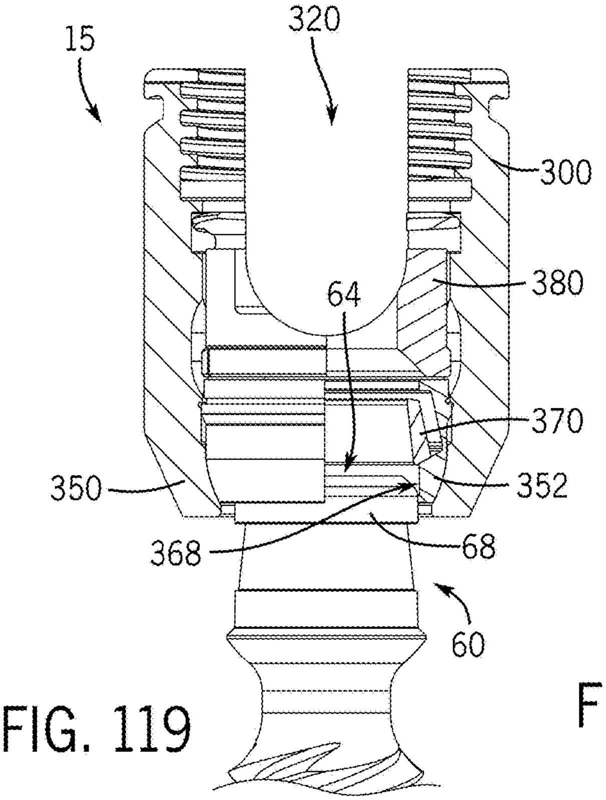
FIG. 119 is a partially cut-away front perspective view of the monoaxial receiver sub-assembly moving downward onto the universal capture portion of the bone anchor.

The assembly of the monoaxial receiver sub-assembly 15 of FIGS. 117-118 to the capture portion 60 of the bone anchor 50 can be substantially similar to the assembly of the pivotal embodiments discussed above. For example, and with reference to the abbreviated sequence of assembly shown in FIGS. 119-122, the monoaxial receiver sub-assembly 15 can be first positioned above the proximal end of the bone anchor 50, with the center aperture 360 of the ring retainer 352 (that is centered within bottom opening 344 of the receiver 300) being generally aligned with the upper curvate section 64 and the upper outer slidable surface 68 of the capture portion 60. As shown in FIG. 119, the receiver sub-assembly 15 is then dropped downward (or the bone anchor 50 is moved upward, depending on the frame of reference of the reader) until the top edge or upper curvate section 64 of the capture portion 60 enters the center aperture 360 of the ring retainer 352 and travels upward toward the capture ring 370. The initial slidable engagement of the upper curvate section 64 and the upper slidable surface 68 with the lower inner slidable surface 368 of the ring retainer 352, upon entry of the capture portion 60 into the center aperture 360, can function to center and align the monoaxial ring retainer 352 (and hence the entire monoaxial receiver sub-assembly 15 that is frictionally secured around the monoaxial ring retainer 352) on the capture portion 60, so that the vertical centerline axis 301 of the monoaxial receiver 300 can become substantially co-axial with the longitudinal axis 51 of the bone anchor 50.

Figure 120:
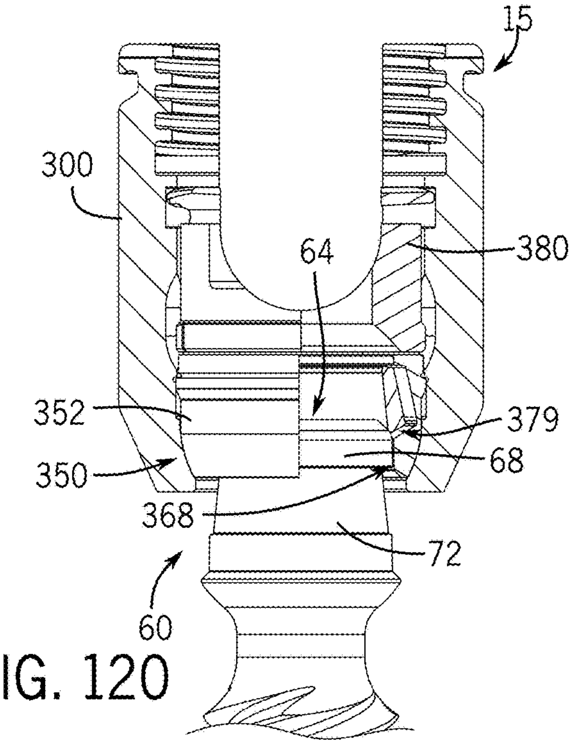

The monoaxial receiver sub-assembly 15 continues to move downward (or the bone anchor 50 moves upward) as the upper outer slidable surface 68 of the capture portion 60 slides along the lower inner slidable surface 368 of the monoaxial ring retainer 352, until the upper curvate section 64 contacts the bottom inner edge 379 of the capture ring 370 that is supported on the beveled lower surface 367 of the internal recess 364 of the ring retainer 352. With reference to FIG. 120, the capture portion 60 then pushes the capture ring 370 up off the beveled lower surface 367 and into engagement with the upper annular surface 365 that acts as a stop surface to prevent further upward movement of the capture ring 370 within the internal recess 364.

Similar to the multiplanar assembly described and illustrated above, the monoaxial the receiver sub-assembly 15 continues to move downward (or the bone anchor 50 moves upward) as the sliding engagement of the tapered inner surface 376 of the capture ring 370, first by the upper curvate section 64 of the capture portion 60 and then by the upper outer slidable surface 68, forces the capture ring 370 to expand outwardly into the internal recess 364 of the ring retainer 352. The inwardly-angled shape of the tapered inner surface 376 of the capture ring 370 can cause the capture ring 370 to continue to expand as it moves downwardly across the upper outer slidable surface 68 and over the capture recess 70, until the capture ring 370 reaches the state of maximum expansion. At about the same time, the lower inner slidable surface 368 of the ring retainer 352 can also become slidably engaged by the lower outer slidable surface 74 of the universal capture portion 60 due to the continued movement between the shank 50 and the monoaxial receiver sub-assembly 15.

Figure 121:
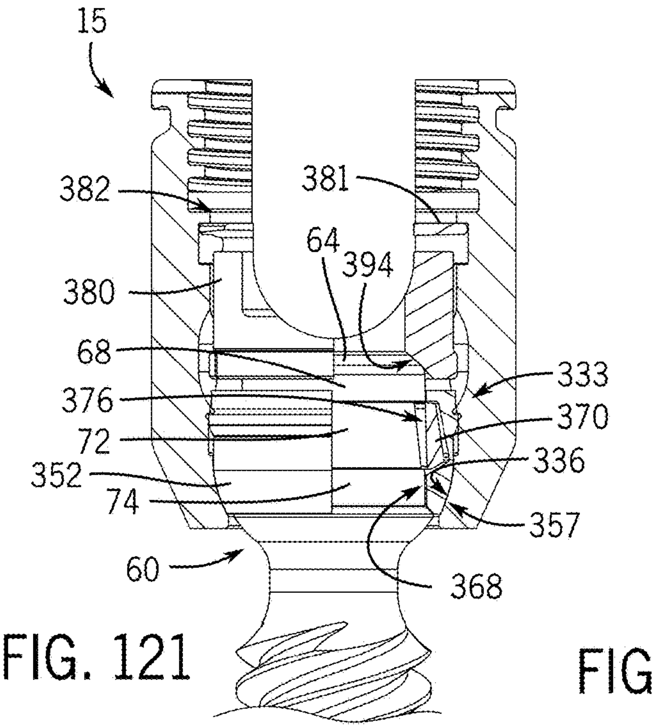

With reference to FIG. 121, the monoaxial receiver sub-assembly 15 continues to move downward (or the bone anchor 50 moves upward) as the tapered inner surface 376 of the capture ring 370 continues to slide downwardly along the upper outer slidable surface 68 toward the horizontal capture recess 70. At the same time, the upper curvate section 64 of the capture portion 60 can project upwards beyond the top annular surface 354 of the monoaxial ring retainer 352, so as to contact the concave lower surface 394 of the pressure insert 380 prior to the capture ring 370 fully reaching the capture recess 70, and pushes the base 390 of the monoaxial pressure insert 380 upwards within the central bore 320 of the receiver 300 while compressing the upwardly-angled spring-like flanges 382 of the insert upright arms 384 against the downward-facing upper arcuate surfaces 327 of the discontinuous recess 328.

Figure 122:
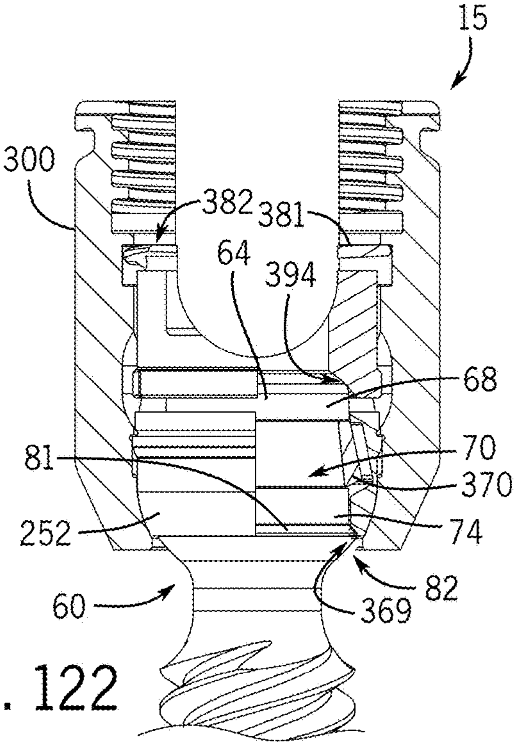

With reference to FIG. 122, the upper curvate section 64 of the capture portion 60 continues to push the monoaxial pressure insert 380 upwards within the central bore 320 of the monoaxial receiver 300, until the capture ring 370 eventually slides off the upper outer slidable surface 68 and snaps into the horizontal capture recess 70, thereby coupling the capture portion 60 directly to the monoaxial retainer sub-assembly 350, and through the monoaxial retainer sub-assembly 350 to the monoaxial receiver sub-assembly 15.

Simultaneously with the snapping in of the capture ring 370 or shortly thereafter, the upwardly- and outwardly-facing beveled lip surface 81 of the outer lip structure 82 at the lower end of the capture portion 60 can engage the lower chamfered surface 369 of the monoaxial ring retainer 352, thereby preventing any further upward movement of the capture portion 60 relative to the ring retainer 352. At about the same time, the spring-like engagement between the upwardly-angled flanges 382 of the insert upright arms 384 with the downward-facing upper arcuate surfaces 327 of the discontinuous recess 328 can create a downwardly-directed force that is sufficiently strong to inhibit any further upward movement of the capture portion 60 relative to the receiver 300. As with the multiplanar embodiment, this engagement between the top surfaces 381 and the upper arcuate surfaces 327 can define the maximum push-through position of the shank 50 relative to the monoaxial receiver sub-assembly 15.

The frictional engagement between the lower outer surface 357 of the monoaxial ring retainer 352 and the seat surface 336 of the receiver, due to the interference fit provided by the structural engagements between the upward-facing ledge surface 363 and the inwardly-protruding arc structures 333 of the cavity 334, can be sufficient to frictionally secure the monoaxial ring retainer 352 in the shipping state position with its center aperture 360 being co-aligned with the bottom opening 344 of the receiver 300, prior to coupling with the bone anchor 50. These same frictional interference engagements at both the lower and upper end portions of the ring retainer 352 can also be sufficient to inhibit any pivotal motion of the combined monoaxial retainer sub-assembly 350 and bone anchor 50 relative to the receiver 200 after their coupling together. Thus, once coupled together and prior to downloading the elongate rod into the receiver channel 306 and the locking the monoaxial assembly 16 with the closure, the monoaxial ring retainer 352 and bone anchor 50 can be frictionally secured to the receiver 300 with a rigid, monoaxial interference fit by the dual interface between the lower outer surface 357 and the upward-facing ledge surface 363 of the monoaxial ring retainer 352 with the seat surface 336 and inwardly-protruding arc structures 333 of the monoaxial receiver 300, respectively.

With continued reference to FIG. 122, the monoaxial receiver sub-assembly 15 is now coupled to the capture portion 60 by the capture ring 370 that is secured within both the horizontal capture recess 70 of the capture portion and the internal recess 364 of the ring retainer 352. In one aspect the average diameters of the outer slidable surfaces 68, 74 of the capture portion 60 (whether cylindrical or frusto-conical) can be less than the average diameters of the inner slidable surfaces 362, 368 that define the center aperture 360, even when the bone anchor is in its most "upward" coupled position shown in the drawings. This can result in the outer slidable surfaces 68, 74 being either spaced from or only lightly engaged with the inner slidable surfaces 362, 368 with no significant frictional or press-fit engagement being established between the two circular bands of slidable surfaces. As such, the lack of a strong frictional engagement between the outer slidable surfaces 68, 74 and the inner slidable surfaces 362, 368 can allow for the capture portion 60 to remain rotatable within the monoaxial ring retainer 352 regardless of the inability of the ring retainer 352 and shank 50 to pivot relative to the receiver 300.

As described above, in one aspect the monoaxial pressure insert 380 can be secured within the central bore 320 of the receiver 300 in a biased shipping state configuration, with the annular bottom surface 395 pressing downward against the annular top surface 354 of the monoaxial ring retainer 352. During the uploading of the capture portion 60 of the shank 50 through the ring retainer 352, the upper curvate section 64 of the capture portion 60 can project upwards through the central through-aperture 360 so as to contact the concave lower surface 394 of the pressure insert 380 and push the base 390 of the monoaxial pressure insert 380 upwards off the top annular surface 354. The upward movement of the base 390 of the pressure insert 390 relative to the top surfaces 381 of the upwardly-angled spring-like flanges 382 that are pressed against the immovable upper arcuate surfaces 327 of the discontinuous recess 328 can increase the downwardly-directed biasing force on the upper curvate section 64 of the capture portion 60, thereby establishing a biased frictional engagement between the concave lower surface 394 of the pressure insert 380 and the upper curvate section 64 of the capture portion 60 that can resist the rotational movement of the shank 50 relative to the non-rotating ring retainer 352 and receiver 300.

As described in more detail below, alternative biased embodiments of the monoaxial pressure insert, including but not limited to pressure inserts with integral spring elements, non-integral spring elements, and like, are also possible and considered to fall within the scope of the present disclosure. In addition, it is foreseen that both the monoaxial receiver and the monoaxial pressure insert can be reconfigured so that tooling may be used to temporarily hold the monoaxial pressure insert down in a biased or even in a temporarily locked position within the monoaxial receiver sub-assembly, until there is a final locking of the monoaxial bone anchor assembly with the elongate rod via the closure.

Figure 123:
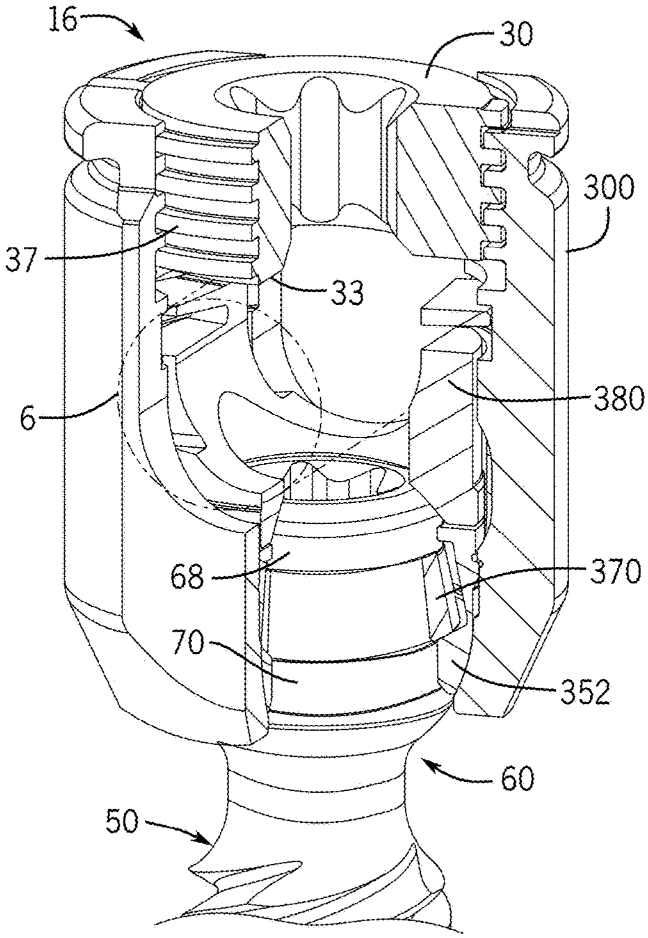
Figure 124:
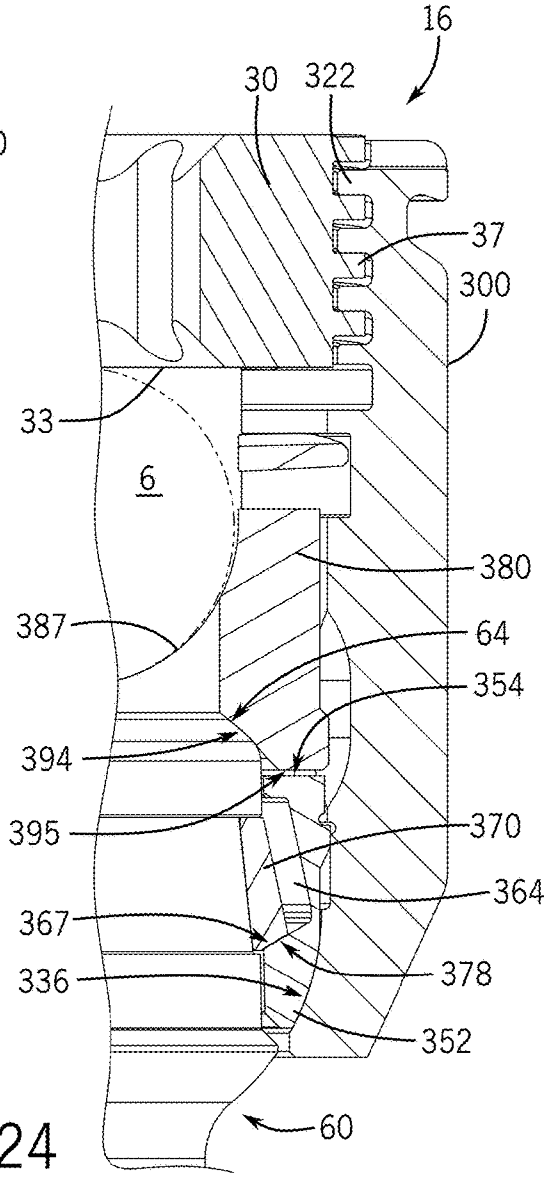

With reference to FIGS. 123-124, the final assembly of the monoaxial assembly 16 can be now completed with the addition of the elongate rod 6 and the closure 30. For instance, after a desired alignment of the monoaxial receiver sub-assembly 15 relative to the bone anchor 50 has been achieved, the elongate rod 6 can be installed (i.e. reduced) into the channel 306 of the monoaxial receiver 300 with the closure 30, and which reduction can include the use of instruments and/or breakoff extensions on the receiver 300. After an initial placement of the elongate rod within the upper portion of the channel 306, the closure 30 can be rotatably and/or threadably installed into the upper portion of the central bore 320 of the receiver 300, in which the continuous guide and advancement structure 37 of the closure body engages the discontinuous guide and advancement structure 322 formed into the interior faces of the upright arms 310 simultaneous with the bottom surface 33 of the closure 30 engaging the top surface 5 of the elongate rod 6 to push it downwards. The elongate rod 6 can be pushed downward into the channel until the lowermost or underside surface 7 of the elongate rod 6 engages the inner upward-facing rod-seating surface 387 of the monoaxial pressure insert 380.

Further rotation and torquing of the closure 30 can then be used to drive the elongate rod 6 downward onto the pressure insert 380, which in turn can push both the monoaxial pressure insert 380 and the universal capture portion 60 with the attached capture ring 370 downward relative to the monoaxial ring retainer 352 and the monoaxial receiver 300. As with the pivotal embodiments described above, pushing this inner group of assembled components downwards relative to the outer group of assembled components (i.e. the receiver 300 and ring retainer 352) can close the small gaps shown in FIG. 122, so that there is now surface-to-surface engagement between the beveled bottom surface 378 of the capture ring 370 and the complementary tapered lower surface 367 of the internal recess 364 of the monoaxial ring retainer 352. In addition, there is surface-to-surface engagement at least between the concave lower surface 394 of the monoaxial pressure insert 380 and the upper curvate section 64 of the capture portion 60, and also possibly between the annular bottom surface 395 of the pressure insert 380 and the top annular surface 354 of the monoaxial ring retainer 352. Without being bound to a particular theory, it is contemplated that these engagements can serve to establish divided internal load paths between the closure 30 (that is secured within the arms 310 of the receiver) and the monoaxial ring retainer 352 that drives the lower portion of the ring retainer 352 further downward and outward into the spherical or curvate seat surface 336 of the receiver cavity 334 to achieve a final locked configuration of the monoaxial bone anchor assembly 16 in which the receiver sub-assembly 15 can no longer rotate relative to the universal bone anchor 50.

Spinal Fixation System with Bone Debris Clearance

Illustrated in FIG. 125 is another representative spinal fixation system 410 in which the universal shank head or capture portion of the shank or bone anchor described above, configured for bottom loading into an array of modular receiver and retainer sub-assemblies having different functionalities, can be further modified to form a shank or bone anchor 450 with a universal shank head or capture portion 460 having both modularity and bone debris clearance capabilities. In particular, the type of universal shank head 460 shown in FIG. 125 is configured to be cleared of bone debris and soft tissue simultaneous with the process or motion of being "snapped" into, or otherwise connected, and captured by either a multiplanar pivotal and independently axially rotatable receiver subassembly 411, a uniplanar pivotal and independently axially rotatable receiver subassembly 413, or an independently axially rotatable but non-pivotal (i.e. monoaxial) receiver sub-assembly 415, each of which can include a pre-lock friction fit feature. It will be appreciated that where features and aspects of the spinal fixation system 410 are common with those of the spinal fixation system 10 described above, and with similar structures and functionality, the detailed disclosure above can be applied to the corresponding components shown and described below and also to the spinal fixation system as a whole, so as to avoid unnecessary duplication and repetition.

With continued reference to FIG. 125, the representative embodiment of the multiplanar receiver sub-assembly 411 with bone debris clearance can be combined with a bone screw 450 having the universal shank head 460 to form a multiplanar bone anchor assembly 412 further described in reference to FIGS. 126-181. Similarly, the representative embodiment of the uniplanar receiver sub-assembly 413 shown in FIG. 125 can be combined with the same universal bone screw 450 to form a uniplanar bone anchor assembly 414 further described in reference to FIGS. 182-199. Likewise, the representative embodiment of the non-pivotal or monoaxial receiver sub-assembly shown in FIG. 125 can be combined with the same universal bone screw 450 to form a monoaxial bone anchor assembly 416 further described in reference to FIGS. 199-221.

Multiplanar Bone Anchor Assembly with Bone Debris Clearance

Referring now in more detail to the drawing figures, FIG. 126 is an exploded perspective view of one representative embodiment of a multiplanar pivotal bone anchor assembly 412 with bone debris clearance that includes a bone anchor 450, such as a shank, having a universal shank head or capture portion 460 and an anchor portion 494 opposite the capture portion 460 for securement within or attachment to the bone of a patient. The multiplanar assembly 412 also includes a receiver 500 or housing having a base portion 540 defining an internal cavity 534 or lower portion of a central bore 520 that is configured to accommodate a multiplanar articulating retainer sub-assembly 550 (generally comprising three parts) that is couplable to the capture portion 460, and a pair of upright arms 510 defining an open rod channel 506 configured for receiving the elongate rod. The receiver 500 can be initially pivotably secured to the capture portion 460 with a number of separate internal components that have been pre-assembled into the internal cavity 534 and the rod channel 506 to form the multiplanar receiver sub-assembly 411. These internal components can include, but are not limited to, the pivoting or articulating retainer sub-assembly 550 that includes a ring retainer 552 having a separate open capture ring 570 and a separate open cleaning or 'bone sweep' ring 440 secured therein (as described in more detail below), and a pressure insert 580, also known as a saddle, crown, cap, bushing, spacer or compression element. In one aspect the ring retainer 552 can be an open ring retainer, with a closed ring retainer also being contemplated and considered to fall within the scope of the present disclosure. After an elongate rod (not shown) has been positioned within the lower portion of the rod channel 506, a closure 430 can be threadably or otherwise secured into an upper portion of the rod channel 506 to apply pressure to an upper surface of the rod, such as by direct contact, thereby locking both the elongate rod and the multiplanar assembly 41 into a final locked position. As discussed in more detail below, in one aspect the separate open capture ring 570 can be common to each embodiment of receiver sub-assembly shown in FIG. 125.

The addition of the open bone sweep ring 440 to the retainer sub-assembly 550, the reduction in the height of the open capture ring 470, and the modification of the internal structures of the open ring retainer 452 to accommodate both the open capture ring 470 and the open bone sweep ring 440, are some of the significant differences between the multiplanar bone anchor assembly 412 and the previous embodiment of the multiplanar assembly described above.

As shown in the exploded assembly view of FIG. 126 and isolated views of FIGS. 127-131, the bone anchor 450 has a capture portion 460, or type of universal shank head, at an upper or proximal end 453, and a body 490 extending distally from the capture portion 460 with an attachment or anchor portion 494 at a distal end 497 configured for fixation to the bone of a patient. The reduction in height of the horizontal capture recess 470 extending into and circumferentially around a mid-portion of the capture portion 460, and the addition of a plurality of open, vertically aligned debris storage pockets 476 arranged circumferentially around the capture portion below the horizontal capture recess 470, are some of the significant differences between the universal shank head 460 and the previous embodiment of the universal shank head described above.

Other aspects of the bone anchor 450, including but not limited to the shank body 490 extending distally from the capture portion 460 with an attachment or anchor portion 494 at a distal end 497 configured for fixation to the bone of a patient, the narrow neck portion 92 extending longitudinally between the anchor portion 94 and the capture portion 460, an annular horizontally-planar top surface 462 that surrounds an internal drive feature or drive socket 454, the upper curvate section 464 and lower curvate section 484 of the capture portion 460 that further include upper and lower spherical surfaces 466, 486 that together define upper and lower spherical extensions, respectively, of the spherical outer surface 556 of the ring retainer 552, and an upper outer slidable surface 468 can be substantially similar in form and function to the previous embodiment of the bone anchor described above. However, the lower outer slidable surface of the earlier-described capture portion can be replaced by raised top surfaces 477 of pocket walls 478 that define and separate the individual debris storage pockets 476 located immediately below the capture recess.

Illustrated in FIGS. 132-135 is the multiplanar receiver 500 having a generally U-shaped appearance with a partially discontinuous substantially cylindrical inner profile and a partially cylindrical and partially faceted outer profile, although other profiles are contemplated. In one aspect the receiver 500 of the multiplanar bone anchor assembly 412 can be substantially similar in form and function to the previous embodiment of the multiplanar receiver described above, including but not limited to a base portion 540 defining the internal cavity 534 or lower portion of a central bore 520, a pair of upright arms 510 extending upwardly from the base 540 to define the upwardly-open channel 506 for receiving the elongate rod, each of the upright arms 110 having an interior face 104 that includes a discontinuous guide and advancement structure 522 configured to engage with a complementary structure formed into the outer side surfaces of the closure 430, and a runout groove 524 immediately below the guide and advancement structure 522 that is followed, in turn, by a discontinuous upper cylindrical ledge structure 526 and a discontinuous inner recess 528 defined by a downward-facing upper arcuate surface 527 and an upward-facing lower arcuate surface 529. The multiplanar receiver 500 can further include the internal cavity 534 includes a seat surface 536 that can be frictionally slidably mateable with the spherically-shaped outer surface of the ring retainer 552, and which can extend upwardly and inwardly along the inwardly-protruding overtravel lip structure 533 to the upwardly-facing circumferential ledge 532, as well as downwardly and inwardly from the equator plane to the lower edge 543 that, together with a lowermost cylindrical or chamfered surface 545, can define the bottom opening 544 of the multiplanar receiver 500. The multiplanar receiver 500 can also include the opposed side pockets 538 formed into cylindrical surface 530, with the opposed side pockets 538 extending downward through the ledge surface 532 into the upper portion of the spherical seat surface 536.

Illustrated in FIGS. 136-138 is the multiplanar open ring retainer 552 having a curvate outer surface 556, such as a spherical surface, extending between a top annular or edge surface 554 and a bottom edge 558 or annular surface, and a center aperture 560. The size, profile, and outer surfaces of the multiplanar open ring retainer 552 can be substantially similar in form and function to those of the previous embodiment of the multiplanar open ring retainer described above. However, the inner surfaces that define the center aperture 560 of the open ring retainer can be modified from the previous version to include multiple internal recesses 564, 566 that are configured to accommodate both the open capture ring 570 and the open bone sweep ring 440, respectively. In one aspect the lower internal recess 566 for the bone sweep ring 440 may include a step structure 567 having a sharp edge or corner that is configured to engage with a complementary circular outer recess formed into the outer side surface of the bone sweep ring 440, thereby centralizing and stabilizing the bone sweep ring 440 within the center aperture 560 of the multiplanar open ring retainer 552 in the "as shipped" configuration (such as when the receiver sub-assemblies together with the bone anchors, rods, closures, and/or special tooling, etc., are packaged and shipped in trays from the manufacturer and prior to their implantation and/or complete assembly.

The multiplanar open ring retainer 552 can also include an upper inner slidable surface 562 configured to interface with the outer surfaces of the capture portion 460 of the shank 450 as described in the previous embodiment. However, the single, somewhat longer lower inner slidable surface of the previous embodiment can be replaced with a central inner slidable surface 565 and a somewhat shorter lower inner slidable surface 568 and lower chamfered surface 569 that become positioned adjacent the raised top surfaces 477 of pocket walls 478 that define and separate the individual debris storage pockets 476, as illustrated below (see FIGS. 178-181).

Illustrated in FIGS. 139-141 is the open bone sweep ring 440 comprising an open ring body having a slit or slot 441 that allows for expansion and compression of the bone sweep ring 440 during assembly of the bone anchor 450 to the receiver sub-assembly 411, and which is configured for positioning into the lower internal recess 566 of the open ring retainer 552 prior to the retainer sub-assembly 550 being loaded into the receiver 500. As described in more detail below, the inner surface 446 of the bone sweep ring 440 can be tapered to define a frustoconical central aperture 443 having its narrowest diameter 447 proximate the upper end, so as to provide a cleaning or sweeping function that substantially scrapes clean the horizontal capture recess 470 of the capture portion 460 during assembly of the bone anchor 450 to any of the various types of receiver sub-assemblies. The outer surface 444 of the open bone sweep ring 440 can also include a circular outer recess or groove 445 configured for engagement with the step structure 567 formed into the lower internal recess 566 of the open ring retainer 552 discussed above.

Illustrated in FIGS. 142-144 is the capture ring 570 comprising an open ring body having a slit or slot 575 that allows for expansion of the capture ring 570 during assembly of the bone anchor 450 to the multiplanar receiver sub-assembly 411, and which is configured for positioning into the upper internal recess 564 of the ring retainer 552 prior to the retainer sub-assembly 550 being loaded into the receiver 500. Although shorter in height than the previous embodiments described above, the capture ring 570 can otherwise be substantially similar in form and function to those same above-described embodiments.

Illustrated in FIGS. 145-150 is the multiplanar pressure insert 580, which can be configured to control the position of the retainer sub-assembly 550 and/or the rotational movement of the capture portion 460 of the shank 450 both during and after its uploading into the multiplanar receiver sub-assembly 411. For example, the pressure insert 580 can also include U-shaped non-integral axially-biasing spring elements or clips 598 secured within complementary recesses 585 formed into the upper ends of the upright insert arms 584 behind shortened leading-edge flanges 582. As described in more detail below, upon installation of the multi-piece pressure insert 580 into the receiver 500, the shortened flanges 582 and clips 598 can become positioned within the discontinuous inner recess 528 of the upright arms 520 of the receiver 500, with the top surfaces 597 of the axially-biasing clips 598 configured to engage with the downward-facing upper arcuate surfaces 527 of the discontinuous recess 528 to as to provide an axially-directed (relative to the vertical centerline axis of the receiver) spring-like biasing force to the upper portion of the retainer sub-assembly 550 and/or to the upper spherical surface 466 of the capture portion 460 of the shank 450. In one aspect the axially-biasing clips 598 can include guide apertures 599 that are configured for positioning around guide posts 583 extending upward from upper surfaces of the insert arms 584 behind the leading-edge flanges 582. The interaction between the inner surfaces of the guide apertures 599 and the outer surfaces of the guide posts 583 can establish a secure connection and proper alignment of the axially-biasing clips 598 to the upper ends of the upright insert arms 584.

Other aspects of the pressure insert 580 of the multiplanar bone anchor assembly 412, such as the inner upward-facing rod-seating surface 587, the central tool-receiving aperture

592, the cylindrical outer surface 588 sized to fit within the central bore 520, and the opposite outwardly projecting nubs or protuberances 596 located near the lower bottom edge 595 of the base portion 590 of the pressure insert 580, can be substantially similar in form and function to the previous embodiment of the multiplanar pressure insert described above. Nevertheless, and as described in more detail below in reference to FIGS. 220-238, alternative designs for the pressure insert that provide additional variation on the functionality described above, and which can be interchangeable with the illustrated pressure insert 580, are also possible and considered to fall within the scope of the present disclosure.

Illustrated in FIGS. 151-152 is the closure top 430 or closure of the multiplanar bone anchor assembly 412 that can comprise a substantially cylindrical body 432 having a top surface 431, a bottom surface 433, and a continuous guide and advancement structure 437 formed into its cylindrical side outer surface 436, with the continuous guide and advancement structure 437 being rotatably mateable with the complementary discontinuous guide and advancement structure 522 formed into the upper portion of the central bore 520 of the multiplanar receiver 500. In one aspect the closure top 430 of the present disclosure can be substantially similar in form and function to the previous embodiment of the closure top described above. Nevertheless, and as described in more detail below in reference to FIG. 238, other designs for the closure top that provide additional variation on the functionality described above, and which can be interchangeable with the illustrated closure top 430, are also possible and considered to fall within the scope of the present disclosure.

To begin assembly of the multiplanar bone anchor assembly 412 shown in FIG. 126, both the capture ring 570 and the bone sweep ring 440 can first be installed or positioned into the internal recesses 564, 566 of the ring retainer 552 to form the multiplanar retainer sub-assembly 550, as shown in FIGS. 152-156. With reference to FIG. 152, to begin this assembly the capture ring 570 can be placed above the ring retainer 552 in preparation for top loading into the center aperture 560 of the open ring retainer 552, which is expanded and its slot 553 opened until the diameter of the center aperture 560 at the upper inner slidable surface 562 is greater than the outer diameter of the lower outer edge 577 of the capture ring 570. In one aspect the capture ring 570 can also be slightly compressed so that the width of the capture ring slot 575 and the outer diameter of the lower outer edge 577 is less than what it would be in its neutral or free-standing state. The capture ring 570 may then be tilted and inserted into the center aperture 560 of the open ring retainer 552 at an angled orientation, as shown in FIG. 154, until it enters the upper internal recess 564. The bone sweep ring 440 can be uploaded into the center aperture 560 using a similar process (not shown) until it enters the lower internal recess 566 of the open ring retainer 552. The ring retainer 560 can then be released to close back toward its neutral state to capture the now-horizontal capture ring 570 and bone sweep ring 440 within its internal recesses 564, 566, as shown in FIGS. 155-156.

With particular reference to the cross-sectional view of FIG. 156, the bone sweep ring 440 can be centralized and stabilized within the center aperture 560 of the multiplanar open ring retainer 552 by the engagement with the short step surface 567 formed into the lower end of the lower internal recess 566, the upper edge of which can defined the sharp corner that partially projects into the lower internal recess 566 to become engaged by the circular outer recess or groove 445 formed into the outer side surface 444 of the open bone sweep ring 440. Nevertheless, it is understood that other aspects of the assembly of the multiplanar retainer sub-assembly 550 can be substantially similar to those of the previous embodiment of the multiplanar retainer sub-assembly described above, including the understanding that the forced expansion of the open ring retainer 552 during the pre-assembly steps can result in a marginal inelastic deformation of the body of the open ring retainer 552, so that the diameter of the spherical outer surface 556 in the free and neutral state may now be greater than what is was before the expansion. This deformation can be advantageously employed in subsequent assembly steps to establish a compressive frictional engagement between the spherical outer surface 556 of the open ring retainer 552 and the spherical seat surface 536 of the multiplanar receiver 500.

With reference to FIGS. 157-165, illustrated therein is the assembly of the individual components of the multiplanar assembly 412 that, in many embodiments, can be pre-assembled together into the multiplanar assembly receiver sub-assembly 411 at a factory or manufacturing facility, prior to shipping to a spine company or a hospital or surgery center and engagement with the capture portion 460 of the bone anchor 50 in the surgical setting. The steps or movements for pre-assembling the multiplanar receiver sub-assembly 411 into the shipping state configuration shown in FIGS. 164-165 can be substantially similar to those steps or movements in the pre-assembly of the previous embodiment of the multiplanar receiver sub-assembly described above, with the exception that the resiliently axially-biased version of the multiplanar pressure insert 580 can be secured within the central bore 520 of the multiplanar receiver 500 in a biased shipping state configuration, with the concave lower surface 594 of the pressure insert 580 pressing downward against the upper portion of the spherical outer surface 556 of the multiplanar open ring retainer 552 to further stabilize or inhibit motion of the open ring retainer 552 relative to the receiver 500. This can be in addition to the compressive frictional engagement between the inner spherical seat surface 536 of the cavity 534 and the outer spherical surface 556 of the open ring retainer 552 that is provided by the slight interference fit between the two surfaces that is already configured to inhibit any pivotal movement of the retainer sub-assembly relative 550 to the receiver 500, as also disclosed above.

With reference to FIGS. 166-177, illustrated therein is the assembly of the multiplanar receiver sub-assembly 411 to the universal shank head or capture portion 460 of the bone anchor 450. In one aspect the steps or movements for attaching the multiplanar receiver sub-assembly 411 to the universal capture portion 460 can be substantially similar to those steps or movements of the previous embodiment of the multiplanar receiver sub-assembly described above, especially with regards to interactions between capture ring 570 and the capture portion 460 of the bone anchor 450. Also illustrated therein are additional interactions between the multiplanar version of the resiliently axially biased pressure insert 580 and the internal recesses 528 of the central bore 520 of the receiver 500, and between the bone sweep ring 440 and the capture portion 460 throughout the various steps or movements that serve to clear the horizontal capture recess 470 of any bone debris or soft tissue that might interfere with the capture ring 570.

In particular, as shown in FIGS. 167-168, the bone sweep ring 440 can be engaged and pushed upward and expanded within the lower internal recess 566 of the open ring retainer 552 by the upper curvate section 464 of the capture portion 460, prior to the upper curvate section 464 contacting the bottom inner edge 579 of the capture ring 570 that is supported within the upper internal recess 564 of the open ring retainer 552. As the capture portion 460 then engages and pushes the capture ring 570 up off the beveled lower surface of the upper internal recess 564 and into engagement with the upper annular surface of the upper internal recess 564, as shown in FIG. 169, the upper inner edge 447 of the bone sweep ring 440 can scrape downward along the upper outer slidable surface 468 of the capture portion 460 to substantially remove any debris or organic matter that might otherwise be carried upward toward the inner surface 576 of the capture ring 570.

With reference to FIGS. 170-171, the upper inner edge 447 of the bone sweep ring 440 can continue to scrape downward along the upper outer slidable surface 468 of the capture portion 460 as the capture portion 460 continues to push upward into the multiplanar receiver sub-assembly 411, until the upper inner edge 447 reaches and snaps inward into the horizontal capture recess 470. As shown in FIG. 172, the upper inner edge 447 of the bone sweep ring 440 can then scrape downward against the tapered inner recessed surface 472 of the capture recess 470, pushing any bone debris and soft tissue in its path downward into the vertically aligned debris storage pockets 476 that are arranged circumferentially around the capture portion 460 below the capture recess 470, thereby leaving behind a substantially clean tapered inner recessed surface 472 for the capture ring 570 to engage.

With reference to FIGS. 173-175, the upper inner edge 447 of the bone sweep ring 440 can continue to scrape downward along the tapered inner recessed surface 472 of the capture recess 470 until it reaches the level of the debris storage pockets 476, at which point the bone sweep ring 440 can expand slightly and the upper inner edge 447 can then scrape downward across the plurality of raised top surfaces 477 of the pocket walls 478 that define and separate the individual debris storage pockets 476. By the time the capture ring 570 snaps into the horizontal capture recess 470 to secure the multiplanar receiver sub-assembly 411 to the capture portion 460 of the bone anchor 450, as shown in FIGS. 176-177, the upper inner edge 447 of the bone sweep ring 440 is spaced below the lower end 473 of the capture recess 470. In this position the tapered inner surface 446 of the bone sweep ring 440, the lower portion of the lower interior recess 566 of the open ring retainer 552, and the outwardly-facing debris storage pockets 476 can together define a debris storage volume that can substantially confine the bone debris and soft tissue that was pushed downward from the upper outer slidable surface 468 and capture recess 470 of the capture portion 460, even in situations where the multiplanar receiver sub-assembly 412 is subsequently articulated and/or rotated by the surgeon following in-situ insertion assemblies.

With continued reference to FIGS. 176-177, and as discussed above, in one aspect the resiliently axially biased pressure insert 580 can be secured within the central bore 520 of the receiver 500 in a biased shipping state configuration, with the concave lower surface 594 pressing downward against the upper portion of the spherical outer surface 556 of the multiplanar open ring retainer 552. During the uploading of the capture portion 460 of the shank 450 through the multiplanar open ring retainer 552, the upper curvate section 464 of the capture portion 460 can project upwards through the central through-aperture 560 so as to contact the concave lower surface 594 of the pressure insert 580 and push the body of the multiplanar pressure insert 580 upwards off the spherical outer surface 556 of the multiplanar open ring retainer 552. The upward movement of the body of the pressure insert 580 relative to the top surfaces 597 of the two upwardly-angled resilient or spring-like axially biasing clips 598 that are pressed against the immovable upper arcuate surfaces 527 of the discontinuous recess 528 can increase the downwardly-directed biasing force on the upper curvate section 464 of the capture portion 460, thereby establishing an axially biased pre-lock frictional engagement between the concave lower surface 594 of the pressure insert 580 and the upper curvate section 464 of the capture portion 460 that can frictionally resist the rotational movement of the open ring retainer 552 and receiver 500 relative to the longitudinal axis 452 of the non-rotating shank 450 that can be fixed or anchored to patient bone.

With reference to FIGS. 178-181, the final assembly of the multiplanar bone anchor assembly 412 can be now completed with the addition of the elongate rod 6 and the closure 430. It is understood that the steps for completing the assembly and the features and aspects of the completely assembled and locked multiplanar bone anchor assembly 412 can be substantially similar to those steps, features, and aspects of the previous embodiment of the multiplanar bone anchor assembly described above, especially with regards to the internal engagements between the components of the retainer sub-assembly 550, the pressure insert 580, and the capture portion of the bone anchor 460 that result in the capture portion 460 becoming frictionally rotationally locked by the pressure insert 580 at the same time that the open ring retainer 552 is frictionally pivotably locked between the pressure insert 580 and the spherical seat surface 536 of the receiver 500. Notably, and regardless of the articulation angle of the shank relative to the receiver sub-assembly (see FIGS. 180-181), the multiplanar bone anchor assembly 412 that incorporates both the universal shank head 460 and the multiplanar retainer sub-assembly 450 (comprising the multiplanar open ring retainer 452 with the internal capture ring 470 and the bone sweep ring 440) can provide for a more reliable and superior interconnection between the shank 450 and the multiplanar receiver sub-assembly 411 over other types of pivotal or polyaxial bone anchor assemblies known in the art, in addition to the other advantages described above.

Monoplanar Bone Anchor Assembly with Bone Debris Clearance

Referring now to FIG. 182, illustrated therein is an exploded perspective view of one representative embodiment of the monoplanar pivotal bone anchor assembly 414 that is configured, as noted above, to limit the pivotal motion of the bone anchor 450 relative to the receiver sub-assembly 413 (or vice versa) to a single plane while still providing for a 360-degree range of pre-lock frictional rotational motion around the longitudinal axis 452 of the bone anchor 450. The monoplanar assembly 414 can include the same bone anchor 450 or bone screw described above, having a universal capture portion 460 or shank head and an anchor portion 494 opposite the capture portion 460 for securement or attachment to the bone of a patient. Similar to the multiplanar assembly 412 discussed above, the monoplanar assembly 412 can also include a monoplanar receiver 600 that can be initially pivotably secured to the universal shank head 460 with a number of separate internal components that have been pre-assembled into the internal cavity 634 and the rod channel 606 to form the monoplanar receiver sub-assembly 413. These internal components can include, but are not limited to, a monoplanar retainer sub-assembly 650 that includes a monoplanar open ring retainer 652 having the same open capture ring 470 and open bone sweep ring 440 secured therein, and a monoplanar pressure insert 880. After an elongate rod (not shown) has been positioned within the lower portion of the rod channel 606, the same closure 430 shown above (or any another appropriate type of closure) can be threadably or otherwise secured into an upper portion of the central bore 620 to apply pressure to an upper surface of the elongate rod, thereby locking both the elongate rod and the monoplanar assembly 414 into a final locked position.

Similar to the embodiments without bone debris clearance described above, the primary difference between the multiplanar pivotal bone anchor assembly 412 of FIG. 126 and the monoplanar pivotal bone anchor assembly 414 of FIG. 182 can be the replacement of the multiplanar open ring retainer 552, having the substantially continuous spherical outer surface 556, with the monoplanar open ring retainer 652 that further includes rounded protrusions or pegs 655 that project outwardly from opposite sides of the discontinuous spherical outer surface 656. The opposite pegs 655 are generally configured to be positioned within, and thereafter constrained by, the opposed vertical side pockets 638 formed in to the cavity 634 of the monoplanar receiver 600, so that the pivotal motion of the monoplanar open ring retainer 652 relative to the monoplanar receiver 600 is limited to a single plane defined by a pivot axis extending between the opposite pegs 655. Additionally, both the monoplanar receiver 600 and the monoplanar pressure insert 680 may also be configured differently than their multiplanar counterparts in order to better interact with the opposite pegs 655 of the monoplanar open ring retainer 652. The remainder of the components forming the monoplanar assembly 414, such as the bone screw 450 with the universal shank head 460, the bone sweep ring 440, the capture ring 570, and the closure 430, can be the same as or substantially similar to those already described, so as to more completely provide a modular spinal fixation system 410 with all the attendant benefits thereof.

Accordingly, it is understood that the structures and functions of the various components forming the monoplanar assembly with bone debris clearance 414, as illustrated in FIGS. 182-199, may be substantially similar in form and function to the corresponding components of the monoplanar assembly without bone debris clearance 14 described above, combined with the further modifications for the addition of the bone sweep ring 440 to the monoplanar retainer sub-assembly 600 and a monoplanar version 680 of the resiliently axially biased pressure insert (as discussed above in reference to the embodiment of the multiplanar assembly 412). It is further understood that the steps or movements for pre-assembling the monoplanar receiver sub-assembly 413 into the shipping state configuration (shown in FIGS. 190-195), for attaching the monoplanar receiver sub-assembly 413 to the capture portion 460 of the bone anchor 450 (shown in FIGS. 196-197), and for completing the final assembly of the monoplanar bone anchor assembly 414 with the rod 6 and closure 430 (shown in FIGS. 198-199), can be substantially similar to those of the previous the monoplanar assembly 14 described above, combined with the additional interactions between the bone sweep ring 440 and the capture portion 460 that clear the horizontal capture recess 470 prior to engagement by the capture ring 570 (as also discussed above in reference to the multiplanar assembly 412).

Monoaxial Bone Anchor Assembly with Bone Debris Clearance

Referring now to FIG. 200, illustrated therein is an exploded perspective view of one representative embodiment of the monoaxial or 'non-pivotal but rotatable' bone anchor assembly 416 that is configured, as noted above, to substantially limit pivotal motion of the bone anchor relative to the receiver sub-assembly (or vice versa) while still providing for pre-lock frictional rotational motion around a 360-degree range. The monoaxial assembly 416 can include the same bone anchor or bone screw 450 described above, having a universal shank head 460 or capture portion and an anchor portion 494 opposite the capture portion for securement or attachment to the bone of a patient. Similar to the multiplanar assembly 412 and the monoplanar assembly 414 discussed above, the monoaxial assembly 416 can also include a monoaxial receiver 700 that can be initially secured to the capture portion 460 with a number of separate internal components that have been pre-assembled into the internal cavity 734 and the rod channel 706 to form the monoaxial receiver sub-assembly 415. These internal components can include, but are not limited to, a monoaxial retainer sub-assembly 750 that includes a monoaxial open ring retainer 752 having the same open capture ring 570 and open bone sweep ring 440 secured therein, and a monoaxial resiliently axially biased pressure insert 780. After an elongate rod (not shown) has been positioned within the lower portion of the rod channel 706, the same closure 430 shown above (or another appropriate type) can be threadably or otherwise secured into an upper portion of the central bore 420 to apply pressure to an upper surface of the elongate rod, thereby locking both the elongate rod and the monoaxial assembly 416 into a final locked position.

The primary difference between the embodiments of the multiplanar assemblies and the monoplanar assemblies described above and the monoaxial bone anchor assembly 416 of FIG. 200 can be the replacement of the pivotal ring retainers, having mostly spherical outer surfaces, with the monoaxial open ring retainer 752 having an cylindrical upper outer surface 755 adjacent an annular planar top surface 754, a spherical or curvate lower outer surface 357 adjacent a bottom annular surface 758, and a ridge structure 756 projecting outwardly from a mid-portion of the cylindrical upper outer surface 755. The ridge structure 756 can be engageable with complementary structures formed into the cavity 734 of the monoaxial receiver 700, while the annular planar top surface 754 can be engageable by an annular planar bottom surface 795 of the monoaxial version of the resiliently axially biased pressure insert 780. The remainder of the components forming the monoaxial assembly 416, such as the bone screw 450 with the universal shank head 460, the bone sweep ring 440, the capture ring 570, and the closure 430, can be the same as or substantially similar to those already described, so as to more completely provide the modular spinal fixation system 410 with an array or constellation of receiver sub-assemblies having all of the attendant benefits thereof.

Accordingly, it is understood that the structures and functions of the various components forming the monoaxial assembly with bone debris clearance 416, as illustrated in FIGS. 200-221, may be substantially similar in form and function to the corresponding components of the monoplanar assembly without bone debris clearance 16 described above, combined with the further modifications for the addition of the bone sweep ring 440 to the monoplanar retainer sub-assembly 700 and a monoplanar version 780 of the resiliently axially biased pressure insert (as discussed above in reference to the embodiment of the multiplanar assembly with bone debris clearance 412). It is further understood that the steps or movements for pre-assembling the monoaxial receiver sub-assembly 415 into the shipping state configuration (shown in FIGS. 207-217), for attaching the monoaxial receiver sub-assembly 415 to the capture portion 460 of the bone anchor 450 (shown in FIGS. 218-219), and for completing the final assembly of the monoaxial bone anchor assembly 416 with the rod 6 and closure 430 (shown in FIGS. 220-221), can be substantially similar to those of the previous the monoaxial assembly 16 described above, combined with the additional interactions between the bone sweep ring 440 and the capture portion 460 that clear the horizontal capture recess 470 of the bone anchor 450 prior to engagement by the capture ring 570 (as also discussed above in reference to the multiplanar assembly 412).

Additional Pressure Insert Embodiments

With reference to FIGS. 222-223, illustrated therein is another representative embodiment of a multiplanar pressure insert 800 that could be used with either of the above-referenced multiplanar assemblies or that could be modified, as previously described, for use with any of the above-referenced monoplanar or monoaxial assemblies. In particular, the multi-piece pressure insert 800 can include a different type of U-shaped non-integral axially-biasing clip 808 that is secured within the complementary recesses 805 formed into the upper ends of the upright insert arms 804. As with the previous embodiments, the axially-biasing clips 808 can become positioned within the discontinuous inner recess of the upright arms of the receiver (not shown) so as to provide a downwardly-directed biasing force on the capture portion of the bone anchor (also not shown), thereby establishing a biased frictional engagement between the concave lower surface of the pressure insert and the upper curvate section of the capture portion that can resist the rotational movement of the capture portion relative to the non-rotating ring retainer and receiver. Unlike the guide aperture of the previous axially-biasing clip embodiments, the separate axially-biasing clip 808 of FIGS. 222-223 can include a notched tip 809 that interacts with a vertical guide structure 803 formed into the frontside of a shortened trailing-edge flange 806, so as to establish the secure connection and proper alignment of the axially-biasing clips 808 to the upper ends of the upright insert arms 804.

Illustrated in FIG. 224 is another representative embodiment of a pressure insert 810 that could be modified for use with any of the above-referenced multiplanar, monoplanar, or monoaxial assemblies. In particular, the upper ends of the upright insert arms 814 and the axially-biasing clip 818 of the multi-piece pressure insert 810 can be configured so that pressure insert 810 is rotated clockwise rather than counterclockwise upon assembly into the central bore of the receiver.

Illustrated in FIGS. 225-226 is another representative embodiment of a pressure insert 820 that could be modified for use with any of the above-referenced multiplanar, monoplanar, or monoaxial assemblies. In particular, multi-piece pressure insert 820 includes a different type of U-shaped non-integral axially-biasing clip 828 secured within complementary recesses 825 formed into the upper end surfaces of the upright insert arms 824. In the illustrated embodiment, the radially-aligned axially-biasing clips 828 can become positioned within the discontinuous inner recess of the upright arms of the receiver so as to provide a downwardly-directed biasing force on the capture portion of the bone anchor (not shown), thereby establishing a biased frictional engagement between the concave lower surface 826 of the pressure insert and the upper curvate section of the capture portion that can resist the rotational movement of the shank relative to the non-rotating ring retainer and receiver. In one aspect the upper portions of the axially-biasing clips 828 can clip onto inwardly-protruding arcuate ridges of the central bore of the receiver, as shown in FIG. 228.

Illustrated in FIGS. 229-232 is yet another representative embodiment of a pressure insert 830 that could be modified for use with any of the above-referenced multiplanar, monoplanar, or monoaxial assemblies. In particular, the multi-piece pressure insert 830 includes yet another type of U-shaped non-integral axially-biasing clip 838 secured within complementary recesses 835 formed into the upper end surfaces of the upright insert arms 834. As with previous embodiments of the resiliently axially-biased pressure inserts, the radially-aligned axially-biasing clips 838 can become positioned within the discontinuous inner recess of the upright arms of the receiver so as to provide a downwardly-directed biasing force on the capture portion of the bone anchor (not shown) and thereby establish a biased frictional engagement between the concave lower surface 836 of the pressure insert and the upper curvate section of the capture portion that can resist the rotational movement of the shank relative to the non-rotating ring retainer and receiver. In one aspect the upper portions of the axially-biasing clips 838 can clip into through-apertures formed into the upright arms of the receiver, as shown in FIG. 232.

Illustrated in FIG. 233 is another representative embodiment of a pressure insert 840 that could be modified for use with any of the above-referenced multiplanar, monoplanar, or monoaxial assemblies. In particular, the upward-facing top surfaces 841 of the flanges 842 extending outward from the upper ends of the insert upright arms 844 can include opposite ramped portions 843 that can generate a constant axially-directed biasing force to the top of the capture portion of the bone anchor (not shown) upon installation pressure insert into the receiver. The axially-directed biasing force can be the result of a camming action between the downward-facing surface formed into the central bore of the receiver and the ramped upward-facing surface 843 of the pressure insert as it is rotated into its final position. In one aspect this design can provide a cam-lock friction fit to the receiver sub-assembly prior to final assembly with the elongate rod and the closure.

Illustrated in FIG. 234 is another similar embodiment of the pressure insert 850 that can provide the same function, but in which the upper ends of the insert upright arms 854 extend upwardly above the top surface of the elongate rod for engagement by the closure top and the flanges 852, in turn, extend laterally outward from the cylindrical outer surfaces 856 of the insert upright arms 844. Nevertheless, as with the embodiment of the pressure insert 840 shown in FIG. 233, the upward-facing top surfaces 851 of the flanges 852 can also include opposite ramped portions 853 that can generate the constant axially-directed biasing force to the top of the capture portion of the bone anchor (not shown) upon installation pressure insert 850 into the receiver, so as to provide the cam-lock friction fit to the receiver sub-assembly prior to final assembly with the elongate rod and the closure.

Illustrated in FIGS. 235-237 is another representative embodiment of a pressure insert 860 that could be modified for use with any of the above-referenced multiplanar, monoplanar, or monoaxial assemblies. In particular, the pressure insert 860 can have a hybrid insert rod channel or saddle 866 that is configured to receive rods of differing size. For example, in one aspect the center portion 865 of the insert rod channel 866 can have a radius of curvature configured to closely receive and center a 4.5 mm rod, while the upper outer portions 867 of the insert rod channel 866 can have a radius of curvature configured to closely receive and center a 5.0 mm rod. Other configurations for the different radii of curvature, such as for larger or smaller rods, are also contemplated and configured to fall within the scope of the present disclosure.

Illustrated in FIG. 238 are additional alternative combinations for using a single pressure insert 880 with a set of interchangeable closures 870, 876 that may be used with the modular spinal fixation system with bone debris clearance 410 described above. For instance, it is foreseen that a set of closures configured for interchangeable use with any of the above-referenced multiplanar, monoplanar, or monoaxial assemblies can, in one aspect, also be configured to provide a screw lock only, in which the outer ring portion 872 of a multi-piece closure 870 is placed into engagement with the top surfaces 881 of insert upright arms 884 of the pressure insert 880 that can extend above the top surface 5 of the elongate rod 6, as shown in FIG. 238(*a*). Alternatively, a screw and rod lock can be provided by the same multi-piece closure 870 and pressure insert 880, in which inner plug or set screw portion 874 of the multi-piece closure 870 is placed into engagement with the top surface 5 of the elongate rod 6 at the same time that outer ring portion 872 of the multi-piece closure 870 is placed into engagement with the top surfaces 881 of insert upright arms 884, as shown in FIG. 238(*b*). Finally, a full lock can be provided with a single-piece closure 876 having a bottom surface 878 with a downwardly projecting center portion 877 that is configured to engage the top surface 5 of the elongate rod 6 at the same time that a circumferential outer ring portion 879 engages with the top surfaces 881 of insert upright arms 884, as shown in FIG. 238(*c*).

As indicated above, the invention has been described herein in terms of preferred embodiments and methodologies considered by the inventor to represent the best mode of carrying out the invention. It will be understood by the skilled artisan, however, that a wide range of additions, deletions, and modifications, both subtle and gross, may be made to the illustrated representative embodiments of the spinal fixation systems and their attendant pivotal and non-pivotal bone anchor assemblies without departing from the spirit and scope of the invention. As such, these and other revisions might be made by those of skill in the art without departing from the spirit and scope of the invention that is constrained only by the following claims.

What is claimed is:

1. A bone anchor assembly for securing an elongate rod to a bone of a patient with a closure, the bone anchor assembly comprising:

a bone anchor comprising a longitudinal axis, a capture portion, and an anchor portion opposite the capture portion configured for fixation to the bone, the capture portion including an upper slidable outer surface, a lower slidable outer surface, and a capture recess between the upper slidable outer surface and the lower slidable outer surface;

a receiver comprising a base defining a lower portion of a central bore centered around a vertical centerline axis and communicating with a bottom of the receiver through a bottom opening, and an upper portion having a channel configured to receive the elongate rod, the central bore extending upward through the channel to a top of the receiver and including a seat surface adjacent the bottom opening; and a retainer sub-assembly positionable into the lower portion of the central bore of the receiver proximate the bottom opening, the retainer sub-assembly comprising:

a ring retainer comprising an annular bottom surface, an outer surface, and a center aperture configured to receive the capture portion of the bone anchor; the center aperture including a lower internal recess and an upper internal recess;

an open sweep ring positionable within the lower internal recess of the ring retainer and configured to sweep the capture recess of bone debris upon the uploading of the capture portion through the center aperture of the ring retainer; and an open capture ring positionable within the upper internal recess of the ring retainer and configured to snap into in the swept capture recess of the bone anchor to capture and hold the capture portion of the bone anchor to the ring retainer;

wherein the outer surface of the ring retainer is configured for frictional engagement with the seat surface of the central bore to secure the retainer sub-assembly and the captured bone anchor to the receiver.

2. The bone anchor assembly of claim 1, wherein the upper slidable outer surface and the lower slidable outer surface are frustoconical.

3. The bone anchor assembly of claim 1, wherein the lower slidable outer surface further comprises a discontinuous surface defined by raised top surfaces of a plurality of pocket walls, with the plurality of pocket walls defining a plurality of debris storage pockets configured to receive the bone debris swept from the capture recess.

4. The bone anchor assembly of claim 3, wherein the plurality of debris storage pockets are equally spaced around the circumference of the capture portion of the bone anchor immediately below and in communication with the capture recess.

5. The bone anchor assembly of claim 1, wherein engagements between the open capture ring, the ring retainer, and the capture recess of the capture structure are configured to provide for rotatable motion of the captured bone anchor relative to the ring retainer and the receiver.

6. The bone anchor assembly of claim 1, wherein the seat surface of the central bore is a partial spherical seat surface and the outer surface of the ring retainer is a partial spherical outer surface complementary with the partial spherical seat surface and configured to provide for pivotal motion of the captured bone anchor with respect to the receiver.

7. The bone anchor assembly of claim 6, wherein the partial spherical seat surface of the central bore extends upward from the bottom opening of the receiver to a circumferential ledge that defines an upper end of an overtravel lip structure formed into the central bore of the receiver above an equator line of the partial spherical seat surface.

8. The bone anchor assembly of claim 6, wherein the ring retainer further comprises an open O-ring body having a slit or slot extending through a thickness thereof from a top annular surface to a bottom annular surface, and wherein the partial spherical outer surface of the ring retainer is configured to be compressed against the overtravel lip structure of the central bore during a downloading of the retainer sub-assembly into the partial spherical seat surface through an upper portion of the central bore.

9. The bone anchor assembly of claim 8, wherein the partial spherical outer surface of the ring retainer is configured for compressive frictional engagement by the partial spherical seat surface of the central bore to provide a non-floppy pivotal friction fit that inhibits pivotal motion between the captured bone anchor and the receiver prior to downloading the elongate rod into the channel of the receiver and locking the receiver sub-assembly with the closure.

10. The bone anchor assembly of claim 6, wherein the capture portion of the bone anchor further comprises an upper spherical extension and a lower spherical extension configured to align with the partial spherical outer surface of the ring retainer so as to form a substantially spherical capture head when the ring retainer is coupled to the captured bone anchor via the open capture ring.

11. The bone anchor assembly of claim 10, wherein the lower spherical extension of the capture portion of the captured bone anchor is slidably mateable with the spherical seat surface of the receiver.

12. The bone anchor assembly of claim 1, wherein the capture recess of the capture portion of the bone anchor includes a tapered inner recessed surface that is complementary with a tapered inner surface of the open capture ring.

13. The bone anchor assembly of claim 1 and further comprising a pressure insert configured for positioning within the central bore of the receiver, the pressure insert having an upper surface engageable with the elongate rod and a concave lower surface engageable with an upper curvate section of the capture portion of the bone anchor upon the uploading of the capture portion through the bottom opening of the receiver and into the retainer sub-assembly.

14. The bone anchor assembly of claim 13, wherein the pressure insert includes a first indexing structure configured to releasably engage with a complementary second indexing structure formed into the central bore of the receiver, upon rotation of the pressure insert about the vertical centerline axis of the receiver, so as to maintain the pressure insert in a rotated position.

15. The bone anchor assembly of claim 13, wherein at least one exterior surface of the pressure insert is configured to releasably engage with at least one interior surface of the central bore to apply a downward pressure to the upper curvate section of the capture portion to provide an axial rotation friction fit between the captured bone anchor and the receiver prior to downloading the elongate rod into the channel of the receiver and locking the receiver sub-assembly with the closure.

16. The bone anchor assembly of claim 15, wherein the at least one exterior surface of the pressure insert is an upward-facing surface and the at least one interior surface of the central bore is a downward-facing surface, and wherein the pressure insert is rotatable with a tool about the vertical centerline axis of the receiver, with the upward-facing surface entering into a biased frictional engagement with the downward-facing surface so as to apply the downward pressure to the upper curvate section of the capture portion.

17. The bone anchor assembly of claim 15 and further comprising the elongate rod and a closure, wherein the closure is configured for positioning entirely within the central bore of the above the elongate rod and in engagement with the upper portion of the receiver to apply a downward pressure toward a top of the elongate rod, so as to secure the elongate rod to the bone of the patient.

18. The bone anchor assembly of claim 1, wherein the bone anchor assembly is a multiplanar pivoting retainer sub-assembly.

19. A retainer sub-assembly for securing a bone anchor to a receiver of a bone anchor assembly, the bone anchor having a capture portion with a horizontal capture recess and an anchor portion opposite the capture portion, the receiver having a central bore with a seat surface proximate a bottom opening and a channel for receiving a rod, the retainer sub-assembly comprising:

a ring retainer comprising an annular bottom surface, an outer surface, and a center aperture configured to receive the capture portion of the bone anchor; the center aperture including a lower internal recess and an upper internal recess;

an open sweep ring positionable within the lower internal recess of the ring retainer and configured to sweep the capture recess of bone debris upon the uploading of the capture portion through the center aperture of the ring retainer; and an open capture ring positionable within the upper internal recess of the ring retainer and configured to snap into the swept capture recess of the bone anchor to capture and hold the capture portion of the bone anchor to the ring retainer, wherein the outer surface of the ring retainer is configured for frictional engagement with the seat surface of the central bore to secure the retainer sub-assembly and the captured bone anchor to the receiver.

20. The retainer sub-assembly of claim 19, wherein engagements between the open capture ring, the ring retainer, and the capture recess of the capture structure are configured to provide for rotatable motion of the captured bone anchor relative to the ring retainer and the receiver.

21. The retainer sub-assembly of claim 19, wherein the seat surface of the central bore is a partial spherical seat surface and the outer surface of the ring retainer is a partial spherical outer surface complementary with the partial spherical seat surface and configured to provide for pivotal motion of the captured bone anchor with respect to the receiver.

* * * * *